(12) United States Patent
Pryzdial et al.

(10) Patent No.: US 7,666,990 B2
(45) Date of Patent: Feb. 23, 2010

(54) AMINO ACID-SUBSTITUTED COAGULATION FACTOR V

(75) Inventors: Edward L. G. Pryzdial, Vancouver (CA); Abed Zeibdawi, Nepean (CA); Jean Grundy, Ottawa (CA)

(73) Assignee: Canadian Blood Services (CA)

( * ) Notice: Subject to any disclaimer, the term of this patent is extended or adjusted under 35 U.S.C. 154(b) by 0 days.

(21) Appl. No.: 11/337,979

(22) Filed: Jan. 23, 2006

(65) Prior Publication Data

US 2006/0241039 A1 Oct. 26, 2006

Related U.S. Application Data

(63) Continuation of application No. PCT/CA2004/001089, filed on Jul. 23, 2004.

(60) Provisional application No. 60/489,124, filed on Jul. 23, 2003.

(51) Int. Cl.
*C07K 14/00* (2006.01)
(52) U.S. Cl. .................... 530/350; 530/300
(58) Field of Classification Search .............. None
See application file for complete search history.

(56) References Cited

U.S. PATENT DOCUMENTS

2007/0083334 A1* 4/2007 Mintz et al. .............. 702/19

FOREIGN PATENT DOCUMENTS

EP  0 761 686 A2  3/1997

OTHER PUBLICATIONS

Wells, Biochemistry, vol. 29, pp. 8509-8517, 1990.*
Seffernick et al., J. Bacteriology, vol. 183, pp. 2405-2410, 2001.*
Cripe et al. Biochemistry vol. 31, 1992, pp. 3777-3785.*
Sorenson, Kristoffer W. et al.; Biochemistry; 43(19):5803-5810 (May 18, 2004).
Yang, Tony L. et al.; Blood; 91(12):4593-4599 (Jun. 15, 1998).
Zeibdawi, Abed R. et al.; Biochemical Journal; 377(1):141-148 (Jan. 2004).
Zeibdawi, Abed R. et al.; Journal of Biological Chemistry; 276(23):19929-19936 (Jun. 8, 2001).
Adams, Ty E. et al., PNAS, 101(24):8918-8923 (2004). "The crystal structure of activated protein C-inactivated bovine factor Va: Implications for cofactor function."

* cited by examiner

*Primary Examiner*—Hope A Robinson
(74) *Attorney, Agent, or Firm*—Nixon Peabody LLP

(57) ABSTRACT

There is provided FV derivatives that reduce blood clotting activity, by reducing thrombin generation, when compared to wild-type FV. In particular, the FV of the present invention comprises single-point and multi-point mutations, encompassed by aspartic acid 79 to glutamic acid 119 of the wild type sequence (SEQ ID NO:2). The derivatives can be used to treat patient with conditions necessitating reduced clotting activity.

8 Claims, 5 Drawing Sheets

Figure 4

SEQUENCE LISTING

<160> NUMBER OF SEQ ID NOS: 30

<210> SEQ ID NO 1
<211> LENGTH: 4150
<212> TYPE: DNA
<213> ORGANISM: Homo sapiens
<220> FEATURE:
<221> NAME/KEY: CDS
<222> LOCATION: (1)..(4005)

<400> SEQUENCE: 1

```
gca cag cta agg cag ttc tac gtg gct gct cag ggc atc agt tgg agc      48
Ala Gln Leu Arg Gln Phe Tyr Val Ala Ala Gln Gly Ile Ser Trp Ser
 1               5                  10                  15 tac cga cct gag ccc aca aac tca agt ttg aat ctt tct gta act tcc      96
Tyr Arg Pro Glu Pro Thr Asn Ser Ser Leu Asn Leu Ser Val Thr Ser
                20                  25                  30 ttt aag aaa att gtc tac aga gag tat gaa cca tat ttt aag aaa gaa     144
Phe Lys Lys Ile Val Tyr Arg Glu Tyr Glu Pro Tyr Phe Lys Lys Glu
            35                  40                  45 aaa cca caa tct acc att tca gga ctt ctt ggg cct act tta tat gct     192
Lys Pro Gln Ser Thr Ile Ser Gly Leu Leu Gly Pro Thr Leu Tyr Ala
        50                  55                  60
```

-continued

| | |
|---|---|
| gaa gtc gga gac atc ata aaa gtt cac ttt aaa aat aag gca gat aag<br>Glu Val Gly Asp Ile Ile Lys Val His Phe Lys Asn Lys Ala Asp Lys<br>65                          70                        75                        80 | 240 |
| ccc ttg agc atc cat cct caa gga att agg tac agt aaa tta tca gaa<br>Pro Leu Ser Ile His Pro Gln Gly Ile Arg Tyr Ser Lys Leu Ser Glu<br>                      85                        90                        95 | 288 |
| ggt gct tct tac ctt gac cac aca ttc cct gca gag aag atg gac gac<br>Gly Ala Ser Tyr Leu Asp His Thr Phe Pro Ala Glu Lys Met Asp Asp<br>                100                      105                 110 | 336 |
| gct gtg gct cca ggc cga gaa tac acc tat gaa tgg agt atc agt gag<br>Ala Val Ala Pro Gly Arg Glu Tyr Thr Tyr Glu Trp Ser Ile Ser Glu<br>         115                        120                        125 | 384 |
| gac agt gga ccc acc cat gat gac cct cca tgc ctc aca cac atc tat<br>Asp Ser Gly Pro Thr His Asp Asp Pro Pro Cys Leu Thr His Ile Tyr<br>130                         135                        140 | 432 |
| tac tcc cat gaa aat ctg atc gag gat ttc aac tct ggg ctg att ggg<br>Tyr Ser His Glu Asn Leu Ile Glu Asp Phe Asn Ser Gly Leu Ile Gly<br>145                        150                        155                160 | 480 |
| ccc ctg ctt atc tgt aaa aaa ggg acc cta act gag ggt ggg aca cag<br>Pro Leu Leu Ile Cys Lys Lys Gly Thr Leu Thr Glu Gly Gly Thr Gln<br>                      165                        170                 175 | 528 |
| aag acg ttt gac aag caa atc gta cta ctt ttt gct gtg ttt gat gaa<br>Lys Thr Phe Asp Lys Gln Ile Val Leu Leu Phe Ala Val Phe Asp Glu<br>         180                        185                        190 | 576 |
| agc aag agc tgg agc cag tca tca tcc cta atg tac aca gtc aat gga<br>Ser Lys Ser Trp Ser Gln Ser Ser Ser Leu Met Tyr Thr Val Asn Gly<br>195                         200                        205 | 624 |
| tat gtg aat ggg aca atg cca gat ata aca gtt tgt gcc cat gac cac<br>Tyr Val Asn Gly Thr Met Pro Asp Ile Thr Val Cys Ala His Asp His<br>         210                        215                        220 | 672 |
| atc agc tgg cat ctg ctg gga atg agc tcg ggg cca gaa tta ttc tcc<br>Ile Ser Trp His Leu Leu Gly Met Ser Ser Gly Pro Glu Leu Phe Ser<br>225                        230                        235                240 | 720 |
| att cat ttc aac ggc cag gtc ctg gag cag aac cat cat aag gtc tca<br>Ile His Phe Asn Gly Gln Val Leu Glu Gln Asn His His Lys Val Ser<br>                      245                        250                        255 | 768 |
| gcc atc acc ctt gtc agt gct aca tcc act acc gca aat atg act gtg<br>Ala Ile Thr Leu Val Ser Ala Thr Ser Thr Thr Ala Asn Met Thr Val<br>         260                        265                        270 | 816 |
| ggc cca gag gga aag tgg atc ata tct tct ctc acc cca aaa cat ttg<br>Gly Pro Glu Gly Lys Trp Ile Ile Ser Ser Leu Thr Pro Lys His Leu<br>275                         280                        285 | 864 |
| caa gct ggg atg cag gct tac att gac att aaa aac tgc cca aag aaa<br>Gln Ala Gly Met Gln Ala Tyr Ile Asp Ile Lys Asn Cys Pro Lys Lys<br>         290                        295                        300 | 912 |
| acc agg aat ctt aag aaa ata act cgt gag cag agg cgg cac atg aag<br>Thr Arg Asn Leu Lys Lys Ile Thr Arg Glu Gln Arg Arg His Met Lys<br>305                         310                        315                320 | 960 |
| agg tgg gaa tac ttc att gct gca gag gaa gtc att tgg gac tat gca<br>Arg Trp Glu Tyr Phe Ile Ala Ala Glu Glu Val Ile Trp Asp Tyr Ala<br>                      325                        330                        335 | 1008 |
| cct gta ata cca gcg aat atg gac aaa aaa tac agg tct cag cat ttg<br>Pro Val Ile Pro Ala Asn Met Asp Lys Lys Tyr Arg Ser Gln His Leu<br>         340                        345                        350 | 1056 |
| gat aat ttc tca aac caa att gga aaa cat tat aag aaa gtt atg tac<br>Asp Asn Phe Ser Asn Gln Ile Gly Lys His Tyr Lys Lys Val Met Tyr<br>355                        360                        365 | 1104 |
| aca cag tac gaa gat gag tcc ttc acc aaa cat aca gtg aat ccc aat<br>Thr Gln Tyr Glu Asp Glu Ser Phe Thr Lys His Thr Val Asn Pro Asn | 1152 |

-continued

```
            370                 375                 380
atg aaa gaa gat ggg att ttg ggt cct att atc aga gcc cag gtc aga     1200
Met Lys Glu Asp Gly Ile Leu Gly Pro Ile Ile Arg Ala Gln Val Arg
385                 390                 395                 400 gac aca ctc aaa atc gtg ttc aaa aat atg gcc agc cgc ccc tat agc     1248
Asp Thr Leu Lys Ile Val Phe Lys Asn Met Ala Ser Arg Pro Tyr Ser
                405                 410                 415 att tac cct cat gga gtg acc ttc tcg cct tat gaa gat gaa gtc aac     1296
Ile Tyr Pro His Gly Val Thr Phe Ser Pro Tyr Glu Asp Glu Val Asn
            420                 425                 430 tct tct ttc acc tca ggc agg aac aac acc atg atc aga gca gtt caa     1344
Ser Ser Phe Thr Ser Gly Arg Asn Asn Thr Met Ile Arg Ala Val Gln
            435                 440                 445 cca ggg gaa acc tat act tat aag tgg aac atc tta gag ttt gat gaa     1392
Pro Gly Glu Thr Tyr Thr Tyr Lys Trp Asn Ile Leu Glu Phe Asp Glu
            450                 455                 460 ccc aca gaa aat gat gcc cag tgc tta aca aga cca tac tac agt gac     1440
Pro Thr Glu Asn Asp Ala Gln Cys Leu Thr Arg Pro Tyr Tyr Ser Asp
465                 470                 475                 480 gtg gac atc atg aga gac atc gcc tct ggg cta ata gga cta ctt cta     1488
Val Asp Ile Met Arg Asp Ile Ala Ser Gly Leu Ile Gly Leu Leu Leu
                485                 490                 495 atc tgt aag agc aga tcc ctg gac agg cga gga ata cag agg gca gca     1536
Ile Cys Lys Ser Arg Ser Leu Asp Arg Arg Gly Ile Gln Arg Ala Ala
                500                 505                 510 gac atc gaa cag cag gct gtg ttt gct gtg ttt gat gag aac aaa agc     1584
Asp Ile Glu Gln Gln Ala Val Phe Ala Val Phe Asp Glu Asn Lys Ser
            515                 520                 525 tgg tac ctt gag gac aac atc aac aag ttt tgt gaa aat cct gat gag     1632
Trp Tyr Leu Glu Asp Asn Ile Asn Lys Phe Cys Glu Asn Pro Asp Glu
530                 535                 540 gtg aaa cgt gat gac ccc aag ttt tat gaa tca aac atc atg agc act     1680
Val Lys Arg Asp Asp Pro Lys Phe Tyr Glu Ser Asn Ile Met Ser Thr
545                 550                 555                 560 atc aat ggc tat gtg cct gag agc ata act act ctt gga ttc tgc ttt     1728
Ile Asn Gly Tyr Val Pro Glu Ser Ile Thr Thr Leu Gly Phe Cys Phe
                565                 570                 575 gat gac act gtc cag tgg cac ttc tgt agt gtg ggg acc cag aat gaa     1776
Asp Asp Thr Val Gln Trp His Phe Cys Ser Val Gly Thr Gln Asn Glu
            580                 585                 590 att ttg acc atc cac ttc act ggg cac tca ttc atc tat gga aag agg     1824
Ile Leu Thr Ile His Phe Thr Gly His Ser Phe Ile Tyr Gly Lys Arg
            595                 600                 605 cat gag gac acc ttg acc ctc ttc ccc atg cgt gga gaa tct gtg acg     1872
His Glu Asp Thr Leu Thr Leu Phe Pro Met Arg Gly Glu Ser Val Thr
610                 615                 620 gtc aca atg gat aat gtt gga act tgg atg tta act tcc atg aat tct     1920
Val Thr Met Asp Asn Val Gly Thr Trp Met Leu Thr Ser Met Asn Ser
625                 630                 635                 640 agt cca aga agc aaa aag ctg agg ctg aaa ttc agg gat gtt aaa tgt     1968
Ser Pro Arg Ser Lys Lys Leu Arg Leu Lys Phe Arg Asp Val Lys Cys
                645                 650                 655 atc cca gat gat gat gaa gac tca tat gag att ttt gaa cct cca gaa     2016
Ile Pro Asp Asp Asp Glu Asp Ser Tyr Glu Ile Phe Glu Pro Pro Glu
            660                 665                 670 tct aca gtc atg gct aca cgg aaa atg cat gat cgt tta gaa cct gaa     2064
Ser Thr Val Met Ala Thr Arg Lys Met His Asp Arg Leu Glu Pro Glu
            675                 680                 685 gat gaa gag agt gat gct gac tat gat tac cag aac aga ctg gct gca     2112
```

-continued

```
                Asp Glu Glu Ser Asp Ala Asp Tyr Asp Tyr Gln Asn Arg Leu Ala Ala
                        690                 695                 700 gca tta gga att agg agg gaa aca gat att gaa gac tct gat gat att          2160
Ala Leu Gly Ile Arg Arg Glu Thr Asp Ile Glu Asp Ser Asp Asp Ile
705                 710                 715                 720 cca gaa gat acc aca tat aag aaa gta gtt ttt cga aag tac ctc gac          2208
Pro Glu Asp Thr Thr Tyr Lys Lys Val Val Phe Arg Lys Tyr Leu Asp
                725                 730                 735 agc act ttt acc aaa cgt gat cct cga ggg gag tat gaa gag cat ctc          2256
Ser Thr Phe Thr Lys Arg Asp Pro Arg Gly Glu Tyr Glu Glu His Leu
            740                 745                 750 gga att ctt ggt cct att atc aga gct gaa gtg gat gat gtt atc caa          2304
Gly Ile Leu Gly Pro Ile Ile Arg Ala Glu Val Asp Asp Val Ile Gln
        755                 760                 765 gtt cgt ttt aaa aat tta gca tcc aga ccg tat tct cta cat gcc cat          2352
Val Arg Phe Lys Asn Leu Ala Ser Arg Pro Tyr Ser Leu His Ala His
    770                 775                 780 gga ctt tcc tat gaa aaa tca tca gag gga aag act tat gaa gat gac          2400
Gly Leu Ser Tyr Glu Lys Ser Ser Glu Gly Lys Thr Tyr Glu Asp Asp
785                 790                 795                 800 tct cct gaa tgg ttt aag gaa gat aat gct gtt cag cca aat agc agt          2448
Ser Pro Glu Trp Phe Lys Glu Asp Asn Ala Val Gln Pro Asn Ser Ser
                805                 810                 815 tat acc tac gta tgg cat gcc act gag cga tca ggg cca gaa agt cct          2496
Tyr Thr Tyr Val Trp His Ala Thr Glu Arg Ser Gly Pro Glu Ser Pro
                820                 825                 830 ggc tct gcc tgt cgg gct tgg gcc tac tac tca gct gtg aac cca gaa          2544
Gly Ser Ala Cys Arg Ala Trp Ala Tyr Tyr Ser Ala Val Asn Pro Glu
            835                 840                 845 aaa gat att cac tca ggc ttg ata ggt ccc ctc cta atc tgc caa aaa          2592
Lys Asp Ile His Ser Gly Leu Ile Gly Pro Leu Leu Ile Cys Gln Lys
        850                 855                 860 gga ata cta cat aag gac agc aac atg cct gtg gac atg aga gaa ttt          2640
Gly Ile Leu His Lys Asp Ser Asn Met Pro Val Asp Met Arg Glu Phe
865                 870                 875                 880 gtc tta cta ttt atg acc ttt gat gaa aag aag agc tgg tac tat gaa          2688
Val Leu Leu Phe Met Thr Phe Asp Glu Lys Lys Ser Trp Tyr Tyr Glu
                885                 890                 895 aag aag tcc cga agt tct tgg aga ctc aca tcc tca gaa atg aaa aaa          2736
Lys Lys Ser Arg Ser Ser Trp Arg Leu Thr Ser Ser Glu Met Lys Lys
                900                 905                 910 tcc cat gag ttt cac gcc att aat ggg atg atc tac agc ttg cct ggc          2784
Ser His Glu Phe His Ala Ile Asn Gly Met Ile Tyr Ser Leu Pro Gly
            915                 920                 925 ctg aaa atg tat gag caa gag tgg gtg agg tta cac ctg ctg aac ata          2832
Leu Lys Met Tyr Glu Gln Glu Trp Val Arg Leu His Leu Leu Asn Ile
        930                 935                 940 ggc ggc tcc caa gac att cac gtg gtt cac ttt cac ggc cag acc ttg          2880
Gly Gly Ser Gln Asp Ile His Val Val His Phe His Gly Gln Thr Leu
945                 950                 955                 960 ctg gaa aat ggc aat aaa cag cac cag tta ggg gtc tgg ccc ctt ctg          2928
Leu Glu Asn Gly Asn Lys Gln His Gln Leu Gly Val Trp Pro Leu Leu
                965                 970                 975 cct ggt tca ttt aaa act ctt gaa atg aag gca tca aaa cct ggc tgg          2976
Pro Gly Ser Phe Lys Thr Leu Glu Met Lys Ala Ser Lys Pro Gly Trp
                980                 985                 990 tgg ctc cta aac aca gag gtt gga gaa aac cag aga gca ggg atg caa          3024
Trp Leu Leu Asn Thr Glu Val Gly Glu Asn Gln Arg Ala Gly Met Gln
                995                 1000                1005
```

```
acg cca ttt ctt atc atg gac aga gac tgt agg atg cca atg gga cta      3072
Thr Pro Phe Leu Ile Met Asp Arg Asp Cys Arg Met Pro Met Gly Leu
    1010                1015                1020 agc act ggt atc ata tct gat tca cag atc aag gct tca gag ttt ctg      3120
Ser Thr Gly Ile Ile Ser Asp Ser Gln Ile Lys Ala Ser Glu Phe Leu
1025                1030                1035                1040 ggt tac tgg gag ccc aga tta gca aga tta aac aat ggt gga tct tat      3168
Gly Tyr Trp Glu Pro Arg Leu Ala Arg Leu Asn Asn Gly Gly Ser Tyr
                1045                1050                1055 aat gct tgg agt gta gaa aaa ctt gca gca gaa ttt gcc tct aaa cct      3216
Asn Ala Trp Ser Val Glu Lys Leu Ala Ala Glu Phe Ala Ser Lys Pro
            1060                1065                1070 tgg atc cag gtg gac atg caa aag gaa gtc ata atc aca ggg atc cag      3264
Trp Ile Gln Val Asp Met Gln Lys Glu Val Ile Ile Thr Gly Ile Gln
        1075                1080                1085 acc caa ggt gcc aaa cac tac ctg aag tcc tgc tat acc aca gag ttc      3312
Thr Gln Gly Ala Lys His Tyr Leu Lys Ser Cys Tyr Thr Thr Glu Phe
    1090                1095                1100 tat gta gct tac agt tcc aac cag atc aac tgg cag atc ttc aaa ggg      3360
Tyr Val Ala Tyr Ser Ser Asn Gln Ile Asn Trp Gln Ile Phe Lys Gly
1105                1110                1115                1120 aac agc aca agg aat gtg atg tat ttt aat ggc aat tca gat gcc tct      3408
Asn Ser Thr Arg Asn Val Met Tyr Phe Asn Gly Asn Ser Asp Ala Ser
                1125                1130                1135 aca ata aaa gag aat cag ttt gac cca cct att gtg gct aga tat att      3456
Thr Ile Lys Glu Asn Gln Phe Asp Pro Pro Ile Val Ala Arg Tyr Ile
            1140                1145                1150 agg atc tct cca act cga gcc tat aac aga cct acc ctt cga ttg gaa      3504
Arg Ile Ser Pro Thr Arg Ala Tyr Asn Arg Pro Thr Leu Arg Leu Glu
        1155                1160                1165 ctg caa ggt tgt gag gta aat gga tgt tcc aca ccc ctg ggt atg gaa      3552
Leu Gln Gly Cys Glu Val Asn Gly Cys Ser Thr Pro Leu Gly Met Glu
    1170                1175                1180 aat gga aag ata gaa aac aag caa atc aca gct tct tcg ttt aag aaa      3600
Asn Gly Lys Ile Glu Asn Lys Gln Ile Thr Ala Ser Ser Phe Lys Lys
1185                1190                1195                1200 tct tgg tgg gga gat tac tgg gaa ccc ttc cgt gcc cgt ctg aat gcc      3648
Ser Trp Trp Gly Asp Tyr Trp Glu Pro Phe Arg Ala Arg Leu Asn Ala
                1205                1210                1215 cag gga cgt gtg aat gcc tgg caa gcc aag gca aac aac aat aag cag      3696
Gln Gly Arg Val Asn Ala Trp Gln Ala Lys Ala Asn Asn Asn Lys Gln
            1220                1225                1230 tgg cta gaa att gat cta ctc aag atc aag aag ata acg gca att ata      3744
Trp Leu Glu Ile Asp Leu Leu Lys Ile Lys Lys Ile Thr Ala Ile Ile
        1235                1240                1245 aca cag ggc tgc aag tct ctg tcc tct gaa atg tat gta aag agc tat      3792
Thr Gln Gly Cys Lys Ser Leu Ser Ser Glu Met Tyr Val Lys Ser Tyr
    1250                1255                1260 acc atc cac tac agt gag cag gga gtg gaa tgg aaa cca tac agg ctg      3840
Thr Ile His Tyr Ser Glu Gln Gly Val Glu Trp Lys Pro Tyr Arg Leu
1265                1270                1275                1280 aaa tcc tcc atg gtg gac aag att ttt gaa gga aat act aat acc aaa      3888
Lys Ser Ser Met Val Asp Lys Ile Phe Glu Gly Asn Thr Asn Thr Lys
                1285                1290                1295 gga cat gtg aag aac ttt ttc aac ccc cca atc att tcc agg ttt atc      3936
Gly His Val Lys Asn Phe Phe Asn Pro Pro Ile Ile Ser Arg Phe Ile
            1300                1305                1310 cgt gtc att cct aaa aca tgg aat caa agt att gca ctt cgc ctg gaa      3984
Arg Val Ile Pro Lys Thr Trp Asn Gln Ser Ile Ala Leu Arg Leu Glu
        1315                1320                1325
```

```
ctc ttt ggc tgt gat att tac tagaattgaa cattcaaaaa ccctggaag          4035
Leu Phe Gly Cys Asp Ile Tyr
    1330                1335 agactcttta agacctcaaa ccatttagaa tgggcaatgt attttacgct gtgttaaatg    4095
ttaacagttt tccactattt ctctttcttt tctattagtg aataaaattt tatac         4150

<210> SEQ ID NO 2
<211> LENGTH: 1335
<212> TYPE: PRT
<213> ORGANISM: Homo sapiens

<400> SEQUENCE: 2

Ala Gln Leu Arg Gln Phe Tyr Val Ala Ala Gln Gly Ile Ser Trp Ser
  1               5                  10                  15

Tyr Arg Pro Glu Pro Thr Asn Ser Ser Leu Asn Leu Ser Val Thr Ser
                 20                  25                  30

Phe Lys Lys Ile Val Tyr Arg Glu Tyr Glu Pro Tyr Phe Lys Lys Glu
             35                  40                  45

Lys Pro Gln Ser Thr Ile Ser Gly Leu Leu Gly Pro Thr Leu Tyr Ala
         50                  55                  60

Glu Val Gly Asp Ile Ile Lys Val His Phe Lys Asn Lys Ala Asp Lys
 65                  70                  75                  80

Pro Leu Ser Ile His Pro Gln Gly Ile Arg Tyr Ser Lys Leu Ser Glu
                 85                  90                  95

Gly Ala Ser Tyr Leu Asp His Thr Phe Pro Ala Glu Lys Met Asp Asp
                100                 105                 110

Ala Val Ala Pro Gly Arg Glu Tyr Thr Tyr Glu Trp Ser Ile Ser Glu
            115                 120                 125

Asp Ser Gly Pro Thr His Asp Asp Pro Pro Cys Leu Thr His Ile Tyr
        130                 135                 140

Tyr Ser His Glu Asn Leu Ile Glu Asp Phe Asn Ser Gly Leu Ile Gly
145                 150                 155                 160

Pro Leu Leu Ile Cys Lys Lys Gly Thr Leu Thr Glu Gly Gly Thr Gln
                165                 170                 175

Lys Thr Phe Asp Lys Gln Ile Val Leu Leu Phe Ala Val Phe Asp Glu
            180                 185                 190

Ser Lys Ser Trp Ser Gln Ser Ser Leu Met Tyr Thr Val Asn Gly
        195                 200                 205

Tyr Val Asn Gly Thr Met Pro Asp Ile Thr Val Cys Ala His Asp His
    210                 215                 220

Ile Ser Trp His Leu Leu Gly Met Ser Ser Gly Pro Glu Leu Phe Ser
225                 230                 235                 240

Ile His Phe Asn Gly Gln Val Leu Glu Gln Asn His His Lys Val Ser
                245                 250                 255

Ala Ile Thr Leu Val Ser Ala Thr Ser Thr Thr Ala Asn Met Thr Val
            260                 265                 270

Gly Pro Glu Gly Lys Trp Ile Ile Ser Ser Leu Thr Pro Lys His Leu
        275                 280                 285

Gln Ala Gly Met Gln Ala Tyr Ile Asp Ile Lys Asn Cys Pro Lys Lys
    290                 295                 300

Thr Arg Asn Leu Lys Lys Ile Thr Arg Glu Gln Arg Arg His Met Lys
305                 310                 315                 320

Arg Trp Glu Tyr Phe Ile Ala Ala Glu Glu Val Ile Trp Asp Tyr Ala
                325                 330                 335
```

-continued

Pro Val Ile Pro Ala Asn Met Asp Lys Lys Tyr Arg Ser Gln His Leu
        340                 345                 350

Asp Asn Phe Ser Asn Gln Ile Gly Lys His Tyr Lys Val Met Tyr
            355                 360                 365

Thr Gln Tyr Glu Asp Glu Ser Phe Thr Lys His Thr Val Asn Pro Asn
        370                 375                 380

Met Lys Glu Asp Gly Ile Leu Gly Pro Ile Ile Arg Ala Gln Val Arg
385                 390                 395                 400

Asp Thr Leu Lys Ile Val Phe Lys Asn Met Ala Ser Arg Pro Tyr Ser
                405                 410                 415

Ile Tyr Pro His Gly Val Thr Phe Ser Pro Tyr Glu Asp Glu Val Asn
            420                 425                 430

Ser Ser Phe Thr Ser Gly Arg Asn Asn Thr Met Ile Arg Ala Val Gln
            435                 440                 445

Pro Gly Glu Thr Tyr Thr Tyr Lys Trp Asn Ile Leu Glu Phe Asp Glu
    450                 455                 460

Pro Thr Glu Asn Asp Ala Gln Cys Leu Thr Arg Pro Tyr Tyr Ser Asp
465                 470                 475                 480

Val Asp Ile Met Arg Asp Ile Ala Ser Gly Leu Ile Gly Leu Leu Leu
                485                 490                 495

Ile Cys Lys Ser Arg Ser Leu Asp Arg Arg Gly Ile Gln Arg Ala Ala
            500                 505                 510

Asp Ile Glu Gln Gln Ala Val Phe Ala Val Phe Asp Glu Asn Lys Ser
        515                 520                 525

Trp Tyr Leu Glu Asp Asn Ile Asn Lys Phe Cys Glu Asn Pro Asp Glu
    530                 535                 540

Val Lys Arg Asp Asp Pro Lys Phe Tyr Glu Ser Asn Ile Met Ser Thr
545                 550                 555                 560

Ile Asn Gly Tyr Val Pro Glu Ser Ile Thr Thr Leu Gly Phe Cys Phe
                565                 570                 575

Asp Asp Thr Val Gln Trp His Phe Cys Ser Val Gly Thr Gln Asn Glu
            580                 585                 590

Ile Leu Thr Ile His Phe Thr Gly His Ser Phe Ile Tyr Gly Lys Arg
        595                 600                 605

His Glu Asp Thr Leu Thr Leu Phe Pro Met Arg Gly Glu Ser Val Thr
    610                 615                 620

Val Thr Met Asp Asn Val Gly Thr Trp Met Leu Thr Ser Met Asn Ser
625                 630                 635                 640

Ser Pro Arg Ser Lys Lys Leu Arg Leu Lys Phe Arg Asp Val Lys Cys
                645                 650                 655

Ile Pro Asp Asp Asp Glu Asp Ser Tyr Glu Ile Phe Glu Pro Pro Glu
            660                 665                 670

Ser Thr Val Met Ala Thr Arg Lys Met His Asp Arg Leu Glu Pro Glu
        675                 680                 685

Asp Glu Glu Ser Asp Ala Asp Tyr Asp Tyr Gln Asn Arg Leu Ala Ala
    690                 695                 700

Ala Leu Gly Ile Arg Arg Glu Thr Asp Ile Glu Asp Ser Asp Asp Ile
705                 710                 715                 720

Pro Glu Asp Thr Thr Tyr Lys Lys Val Val Phe Arg Lys Tyr Leu Asp
                725                 730                 735

Ser Thr Phe Thr Lys Arg Asp Pro Arg Gly Glu Tyr Glu Glu His Leu
            740                 745                 750

```
Gly Ile Leu Gly Pro Ile Ile Arg Ala Glu Val Asp Val Ile Gln
        755                 760                 765

Val Arg Phe Lys Asn Leu Ala Ser Arg Pro Tyr Ser Leu His Ala His
        770                 775                 780

Gly Leu Ser Tyr Glu Lys Ser Ser Glu Gly Lys Thr Tyr Glu Asp Asp
785                 790                 795                 800

Ser Pro Glu Trp Phe Lys Glu Asp Asn Ala Val Gln Pro Asn Ser Ser
                805                 810                 815

Tyr Thr Tyr Val Trp His Ala Thr Glu Arg Ser Gly Pro Glu Ser Pro
                820                 825                 830

Gly Ser Ala Cys Arg Ala Trp Ala Tyr Tyr Ser Ala Val Asn Pro Glu
                835                 840                 845

Lys Asp Ile His Ser Gly Leu Ile Gly Pro Leu Leu Ile Cys Gln Lys
850                 855                 860

Gly Ile Leu His Lys Asp Ser Asn Met Pro Val Asp Met Arg Glu Phe
865                 870                 875                 880

Val Leu Leu Phe Met Thr Phe Asp Glu Lys Lys Ser Trp Tyr Tyr Glu
                885                 890                 895

Lys Lys Ser Arg Ser Ser Trp Arg Leu Thr Ser Ser Glu Met Lys Lys
                900                 905                 910

Ser His Glu Phe His Ala Ile Asn Gly Met Ile Tyr Ser Leu Pro Gly
                915                 920                 925

Leu Lys Met Tyr Glu Gln Glu Trp Val Arg Leu His Leu Leu Asn Ile
        930                 935                 940

Gly Gly Ser Gln Asp Ile His Val Val His Phe His Gly Gln Thr Leu
945                 950                 955                 960

Leu Glu Asn Gly Asn Lys Gln His Gln Leu Gly Val Trp Pro Leu Leu
                965                 970                 975

Pro Gly Ser Phe Lys Thr Leu Glu Met Lys Ala Ser Lys Pro Gly Trp
                980                 985                 990

Trp Leu Leu Asn Thr Glu Val Gly Glu Asn Gln Arg Ala Gly Met Gln
        995                 1000                1005

Thr Pro Phe Leu Ile Met Asp Arg Asp Cys Arg Met Pro Met Gly Leu
    1010                1015                1020

Ser Thr Gly Ile Ile Ser Asp Ser Gln Ile Lys Ala Ser Glu Phe Leu
1025                1030                1035                1040

Gly Tyr Trp Glu Pro Arg Leu Ala Arg Leu Asn Asn Gly Gly Ser Tyr
            1045                1050                1055

Asn Ala Trp Ser Val Glu Lys Leu Ala Ala Glu Phe Ala Ser Lys Pro
            1060                1065                1070

Trp Ile Gln Val Asp Met Gln Lys Glu Val Ile Ile Thr Gly Ile Gln
        1075                1080                1085

Thr Gln Gly Ala Lys His Tyr Leu Lys Ser Cys Tyr Thr Thr Glu Phe
    1090                1095                1100

Tyr Val Ala Tyr Ser Ser Asn Gln Ile Asn Trp Gln Ile Phe Lys Gly
1105                1110                1115                1120

Asn Ser Thr Arg Asn Val Met Tyr Phe Asn Gly Asn Ser Asp Ala Ser
                1125                1130                1135

Thr Ile Lys Glu Asn Gln Phe Asp Pro Pro Ile Val Ala Arg Tyr Ile
            1140                1145                1150

Arg Ile Ser Pro Thr Arg Ala Tyr Asn Arg Pro Thr Leu Arg Leu Glu
        1155                1160                1165

Leu Gln Gly Cys Glu Val Asn Gly Cys Ser Thr Pro Leu Gly Met Glu
```

```
                1170                1175                1180
Asn Gly Lys Ile Glu Asn Lys Gln Ile Thr Ala Ser Ser Phe Lys Lys
1185                1190                1195                1200

Ser Trp Trp Gly Asp Tyr Trp Glu Pro Phe Arg Ala Arg Leu Asn Ala
            1205                1210                1215

Gln Gly Arg Val Asn Ala Trp Gln Ala Lys Ala Asn Asn Lys Gln
        1220                1225                1230

Trp Leu Glu Ile Asp Leu Leu Lys Ile Lys Lys Ile Thr Ala Ile Ile
    1235                1240                1245

Thr Gln Gly Cys Lys Ser Leu Ser Ser Glu Met Tyr Val Lys Ser Tyr
1250                1255                1260

Thr Ile His Tyr Ser Glu Gln Gly Val Glu Trp Lys Pro Tyr Arg Leu
1265                1270                1275                1280

Lys Ser Ser Met Val Asp Lys Ile Phe Glu Gly Asn Thr Asn Thr Lys
                1285                1290                1295

Gly His Val Lys Asn Phe Phe Asn Pro Pro Ile Ile Ser Arg Phe Ile
            1300                1305                1310

Arg Val Ile Pro Lys Thr Trp Asn Gln Ser Ile Ala Leu Arg Leu Glu
        1315                1320                1325

Leu Phe Gly Cys Asp Ile Tyr
    1330                1335

<210> SEQ ID NO 3
<211> LENGTH: 4150
<212> TYPE: DNA
<213> ORGANISM: Homo sapiens
<220> FEATURE:
<221> NAME/KEY: CDS
<222> LOCATION: (1)..(4005)

<400> SEQUENCE: 3 gca cag cta agg cag ttc tac gtg gct gct cag ggc atc agt tgg agc      48
Ala Gln Leu Arg Gln Phe Tyr Val Ala Ala Gln Gly Ile Ser Trp Ser
  1               5                  10                  15 tac cga cct gag ccc aca aac tca agt ttg aat ctt tct gta act tcc     96
Tyr Arg Pro Glu Pro Thr Asn Ser Ser Leu Asn Leu Ser Val Thr Ser
             20                  25                  30 ttt aag aaa att gtc tac aga gag tat gaa cca tat ttt aag aaa gaa    144
Phe Lys Lys Ile Val Tyr Arg Glu Tyr Glu Pro Tyr Phe Lys Lys Glu
         35                  40                  45 aaa cca caa tct acc att tca gga ctt ctt ggg cct act tta tat gct    192
Lys Pro Gln Ser Thr Ile Ser Gly Leu Leu Gly Pro Thr Leu Tyr Ala
     50                  55                  60 gaa gtc gga gac atc ata aaa gtt cac ttt aaa aat aag gca gat aag    240
Glu Val Gly Asp Ile Ile Lys Val His Phe Lys Asn Lys Ala Asp Lys
 65                  70                  75                  80 ccc ttg agc atc cat cct caa gga att agg tac agt aaa tta tca gaa    288
Pro Leu Ser Ile His Pro Gln Gly Ile Arg Tyr Ser Lys Leu Ser Glu
                 85                  90                  95 ggt gct tct tac ctt gac cac aca ttc cct gca gag aag atg gac gac    336
Gly Ala Ser Tyr Leu Asp His Thr Phe Pro Ala Glu Lys Met Asp Asp
            100                 105                 110 gct gtg gct cca ggc cga gca tac acc tat gaa tgg agt atc agt gag    384
Ala Val Ala Pro Gly Arg Ala Tyr Thr Tyr Glu Trp Ser Ile Ser Glu
        115                 120                 125 gac agt gga ccc acc cat gat gac cct cca tgc ctc aca cac atc tat    432
Asp Ser Gly Pro Thr His Asp Asp Pro Pro Cys Leu Thr His Ile Tyr
    130                 135                 140
```

-continued

| | | |
|---|---|---|
| tac tcc cat gaa aat ctg atc gag gat ttc aac tct ggg ctg att ggg<br>Tyr Ser His Glu Asn Leu Ile Glu Asp Phe Asn Ser Gly Leu Ile Gly<br>145                        150                   155                  160 | 480 |
| ccc ctg ctt atc tgt aaa aaa ggg acc cta act gag ggt ggg aca cag<br>Pro Leu Leu Ile Cys Lys Lys Gly Thr Leu Thr Glu Gly Gly Thr Gln<br>                   165                  170                  175 | 528 |
| aag acg ttt gac aag caa atc gtg cta cta ttt gct gtg ttt gat gaa<br>Lys Thr Phe Asp Lys Gln Ile Val Leu Leu Phe Ala Val Phe Asp Glu<br>               180                  185                  190 | 576 |
| agc aag agc tgg agc cag tca tca tcc cta atg tac aca gtc aat gga<br>Ser Lys Ser Trp Ser Gln Ser Ser Ser Leu Met Tyr Thr Val Asn Gly<br>           195                  200                  205 | 624 |
| tat gtg aat ggg aca atg cca gat ata aca gtt tgt gcc cat gac cac<br>Tyr Val Asn Gly Thr Met Pro Asp Ile Thr Val Cys Ala His Asp His<br>210                        215                   220 | 672 |
| atc agc tgg cat ctg ctg gga atg agc tcg ggg cca gaa tta ttc tcc<br>Ile Ser Trp His Leu Leu Gly Met Ser Ser Gly Pro Glu Leu Phe Ser<br>225                        230                   235                  240 | 720 |
| att cat ttc aac ggc cag gtc ctg gag cag aac cat cat aag gtc tca<br>Ile His Phe Asn Gly Gln Val Leu Glu Gln Asn His His Lys Val Ser<br>                   245                  250                  255 | 768 |
| gcc atc acc ctt gtc agt gct aca tcc act acc gca aat atg act gtg<br>Ala Ile Thr Leu Val Ser Ala Thr Ser Thr Thr Ala Asn Met Thr Val<br>           260                  265                  270 | 816 |
| ggc cca gag gga aag tgg atc ata tct tct ctc acc cca aaa cat ttg<br>Gly Pro Glu Gly Lys Trp Ile Ile Ser Ser Leu Thr Pro Lys His Leu<br>275                        280                   285 | 864 |
| caa gct ggg atg cag gct tac att gac att aaa aac tgc cca aag aaa<br>Gln Ala Gly Met Gln Ala Tyr Ile Asp Ile Lys Asn Cys Pro Lys Lys<br>               290                  295                  300 | 912 |
| acc agg aat ctt aag aaa ata act cgt gag cag agg cgg cac atg aag<br>Thr Arg Asn Leu Lys Lys Ile Thr Arg Glu Gln Arg Arg His Met Lys<br>305                        310                   315                  320 | 960 |
| agg tgg gaa tac ttc att gct gca gag gaa gtc att tgg gac tat gca<br>Arg Trp Glu Tyr Phe Ile Ala Ala Glu Glu Val Ile Trp Asp Tyr Ala<br>                   325                  330                  335 | 1008 |
| cct gta ata cca gcg aat atg gac aaa aaa tac agg tct cag cat ttg<br>Pro Val Ile Pro Ala Asn Met Asp Lys Lys Tyr Arg Ser Gln His Leu<br>                     340                  345                  350 | 1056 |
| gat aat ttc tca aac caa att gga aaa cat tat aag aaa gtt atg tac<br>Asp Asn Phe Ser Asn Gln Ile Gly Lys His Tyr Lys Lys Val Met Tyr<br>           355                  360                  365 | 1104 |
| aca cag tac gaa gat gag tcc ttc acc aaa cat aca gtg aat ccc aat<br>Thr Gln Tyr Glu Asp Glu Ser Phe Thr Lys His Thr Val Asn Pro Asn<br>370                        375                   380 | 1152 |
| atg aaa gaa gat ggg att ttg ggt cct att atc aga gcc cag gtc aga<br>Met Lys Glu Asp Gly Ile Leu Gly Pro Ile Ile Arg Ala Gln Val Arg<br>385                        390                   395                  400 | 1200 |
| gac aca ctc aaa atc gtg ttc aaa aat atg gcc agc cgc ccc tat agc<br>Asp Thr Leu Lys Ile Val Phe Lys Asn Met Ala Ser Arg Pro Tyr Ser<br>                   405                  410                  415 | 1248 |
| att tac cct cat gga gtg acc ttc tcg cct tat gaa gat gaa gtc aac<br>Ile Tyr Pro His Gly Val Thr Phe Ser Pro Tyr Glu Asp Glu Val Asn<br>               420                  425                  430 | 1296 |
| tct tct ttc acc tca ggc agg aac aac acc atg atc aga gca gtt caa<br>Ser Ser Phe Thr Ser Gly Arg Asn Asn Thr Met Ile Arg Ala Val Gln<br>           435                  440                  445 | 1344 |
| cca ggg gaa acc tat act tat aag tgg aac atc tta gag ttt gat gaa<br>Pro Gly Glu Thr Tyr Thr Tyr Lys Trp Asn Ile Leu Glu Phe Asp Glu<br>450                        455                   460 | 1392 |

```
ccc aca gaa aat gat gcc cag tgc tta aca aga cca tac tac agt gac      1440
Pro Thr Glu Asn Asp Ala Gln Cys Leu Thr Arg Pro Tyr Tyr Ser Asp
465                 470                 475                 480 gtg gac atc atg aga gac atc gcc tct ggg cta ata gga cta ctt cta      1488
Val Asp Ile Met Arg Asp Ile Ala Ser Gly Leu Ile Gly Leu Leu Leu
            485                 490                 495 atc tgt aag agc aga tcc ctg gac agg cga gga ata cag agg gca gca      1536
Ile Cys Lys Ser Arg Ser Leu Asp Arg Arg Gly Ile Gln Arg Ala Ala
        500                 505                 510 gac atc gaa cag cag gct gtg ttt gct gtg ttt gat gag aac aaa agc      1584
Asp Ile Glu Gln Gln Ala Val Phe Ala Val Phe Asp Glu Asn Lys Ser
    515                 520                 525 tgg tac ctt gag gac aac atc aac aag ttt tgt gaa aat cct gat gag      1632
Trp Tyr Leu Glu Asp Asn Ile Asn Lys Phe Cys Glu Asn Pro Asp Glu
530                 535                 540 gtg aaa cgt gat gac ccc aag ttt tat gaa tca aac atc atg agc act      1680
Val Lys Arg Asp Asp Pro Lys Phe Tyr Glu Ser Asn Ile Met Ser Thr
545                 550                 555                 560 atc aat ggc tat gtg cct gag agc ata act act ctt gga ttc tgc ttt      1728
Ile Asn Gly Tyr Val Pro Glu Ser Ile Thr Thr Leu Gly Phe Cys Phe
            565                 570                 575 gat gac act gtc cag tgg cac ttc tgt agt gtg ggg acc cag aat gaa      1776
Asp Asp Thr Val Gln Trp His Phe Cys Ser Val Gly Thr Gln Asn Glu
        580                 585                 590 att ttg acc atc cac ttc act ggg cac tca ttc atc tat gga aag agg      1824
Ile Leu Thr Ile His Phe Thr Gly His Ser Phe Ile Tyr Gly Lys Arg
    595                 600                 605 cat gag gac acc ttg acc ctc ttc ccc atg cgt gga gaa tct gtg acg      1872
His Glu Asp Thr Leu Thr Leu Phe Pro Met Arg Gly Glu Ser Val Thr
610                 615                 620 gtc aca atg gat aat gtt gga act tgg atg tta act tcc atg aat tct      1920
Val Thr Met Asp Asn Val Gly Thr Trp Met Leu Thr Ser Met Asn Ser
625                 630                 635                 640 agt cca aga agc aaa aag ctg agg ctg aaa ttc agg gat gtt aaa tgt      1968
Ser Pro Arg Ser Lys Lys Leu Arg Leu Lys Phe Arg Asp Val Lys Cys
            645                 650                 655 atc cca gat gat gat gaa gac tca tat gag att ttt gaa cct cca gaa      2016
Ile Pro Asp Asp Asp Glu Asp Ser Tyr Glu Ile Phe Glu Pro Pro Glu
        660                 665                 670 tct aca gtc atg gct aca cgg aaa atg cat gat cgt tta gaa cct gaa      2064
Ser Thr Val Met Ala Thr Arg Lys Met His Asp Arg Leu Glu Pro Glu
    675                 680                 685 gat gaa gag agt gat gct gac tat gat tac cag aac aga ctg gct gca      2112
Asp Glu Glu Ser Asp Ala Asp Tyr Asp Tyr Gln Asn Arg Leu Ala Ala
690                 695                 700 gca tta gga att agg agg gaa aca gat att gaa gac tct gat gat att      2160
Ala Leu Gly Ile Arg Arg Glu Thr Asp Ile Glu Asp Ser Asp Asp Ile
705                 710                 715                 720 cca gaa gat acc aca tat aag aaa gta gtt ttt cga aag tac ctc gac      2208
Pro Glu Asp Thr Thr Tyr Lys Lys Val Val Phe Arg Lys Tyr Leu Asp
            725                 730                 735 agc act ttt acc aaa cgt gat cct cga ggg gag tat gaa gag cat ctc      2256
Ser Thr Phe Thr Lys Arg Asp Pro Arg Gly Glu Tyr Glu Glu His Leu
        740                 745                 750 gga att ctt ggt cct att atc aga gct gaa gtg gat gat gtt atc caa      2304
Gly Ile Leu Gly Pro Ile Ile Arg Ala Glu Val Asp Asp Val Ile Gln
    755                 760                 765 gtt cgt ttt aaa aat tta gca tcc aga ccg tat tct cta cat gcc cat      2352
Val Arg Phe Lys Asn Leu Ala Ser Arg Pro Tyr Ser Leu His Ala His
```

-continued

| | | | | | | | | | | | | | | | | |
|---|---|---|---|---|---|---|---|---|---|---|---|---|---|---|---|---|
| | | 770 | | | | 775 | | | | | 780 | | | | | |
| gga | ctt | tcc | tat | gaa | aaa | tca | tca | gag | gga | aag | act | tat | gaa | gat | gac | 2400 |
| Gly | Leu | Ser | Tyr | Glu | Lys | Ser | Ser | Glu | Gly | Lys | Thr | Tyr | Glu | Asp | Asp | |
| 785 | | | | 790 | | | | | 795 | | | | | 800 | | |
| tct | cct | gaa | tgg | ttt | aag | gaa | gat | aat | gct | gtt | cag | cca | aat | agc | agt | 2448 |
| Ser | Pro | Glu | Trp | Phe | Lys | Glu | Asp | Asn | Ala | Val | Gln | Pro | Asn | Ser | Ser | |
| | | | | | 805 | | | | 810 | | | | | 815 | | |
| tat | acc | tac | gta | tgg | cat | gcc | act | gag | cga | tca | ggg | cca | gaa | agt | cct | 2496 |
| Tyr | Thr | Tyr | Val | Trp | His | Ala | Thr | Glu | Arg | Ser | Gly | Pro | Glu | Ser | Pro | |
| | | | 820 | | | | 825 | | | | 830 | | | | | |
| ggc | tct | gcc | tgt | cgg | gct | tgg | gcc | tac | tac | tca | gct | gtg | aac | cca | gaa | 2544 |
| Gly | Ser | Ala | Cys | Arg | Ala | Trp | Ala | Tyr | Tyr | Ser | Ala | Val | Asn | Pro | Glu | |
| | | 835 | | | | | 840 | | | | | 845 | | | | |
| aaa | gat | att | cac | tca | ggc | ttg | ata | ggt | ccc | ctc | cta | atc | tgc | caa | aaa | 2592 |
| Lys | Asp | Ile | His | Ser | Gly | Leu | Ile | Gly | Pro | Leu | Leu | Ile | Cys | Gln | Lys | |
| | 850 | | | | | 855 | | | | | 860 | | | | | |
| gga | ata | cta | cat | aag | gac | agc | aac | atg | cct | gtg | gac | atg | aga | gaa | ttt | 2640 |
| Gly | Ile | Leu | His | Lys | Asp | Ser | Asn | Met | Pro | Val | Asp | Met | Arg | Glu | Phe | |
| 865 | | | | 870 | | | | | 875 | | | | | 880 | | |
| gtc | tta | cta | ttt | atg | acc | ttt | gat | gaa | aag | aag | agc | tgg | tac | tat | gaa | 2688 |
| Val | Leu | Leu | Phe | Met | Thr | Phe | Asp | Glu | Lys | Lys | Ser | Trp | Tyr | Tyr | Glu | |
| | | | | 885 | | | | 890 | | | | | 895 | | | |
| aag | aag | tcc | cga | agt | tct | tgg | aga | ctc | aca | tcc | tca | gaa | atg | aaa | aaa | 2736 |
| Lys | Lys | Ser | Arg | Ser | Ser | Trp | Arg | Leu | Thr | Ser | Ser | Glu | Met | Lys | Lys | |
| | | | 900 | | | | | 905 | | | | | 910 | | | |
| tcc | cat | gag | ttt | cac | gcc | att | aat | ggg | atg | atc | tac | agc | ttg | cct | ggc | 2784 |
| Ser | His | Glu | Phe | His | Ala | Ile | Asn | Gly | Met | Ile | Tyr | Ser | Leu | Pro | Gly | |
| | | 915 | | | | | 920 | | | | | 925 | | | | |
| ctg | aaa | atg | tat | gag | caa | gag | tgg | gtg | agg | tta | cac | ctg | ctg | aac | ata | 2832 |
| Leu | Lys | Met | Tyr | Glu | Gln | Glu | Trp | Val | Arg | Leu | His | Leu | Leu | Asn | Ile | |
| | 930 | | | | | 935 | | | | | 940 | | | | | |
| ggc | ggc | tcc | caa | gac | att | cac | gtg | gtt | cac | ttt | cac | ggc | cag | acc | ttg | 2880 |
| Gly | Gly | Ser | Gln | Asp | Ile | His | Val | Val | His | Phe | His | Gly | Gln | Thr | Leu | |
| 945 | | | | 950 | | | | | 955 | | | | | 960 | | |
| ctg | gaa | aat | ggc | aat | aaa | cag | cac | cag | tta | ggg | gtc | tgg | ccc | ctt | ctg | 2928 |
| Leu | Glu | Asn | Gly | Asn | Lys | Gln | His | Gln | Leu | Gly | Val | Trp | Pro | Leu | Leu | |
| | | | | 965 | | | | 970 | | | | | 975 | | | |
| cct | ggt | tca | ttt | aaa | act | ctt | gaa | atg | aag | gca | tca | aaa | cct | ggc | tgg | 2976 |
| Pro | Gly | Ser | Phe | Lys | Thr | Leu | Glu | Met | Lys | Ala | Ser | Lys | Pro | Gly | Trp | |
| | | | 980 | | | | | 985 | | | | | 990 | | | |
| tgg | ctc | cta | aac | aca | gag | gtt | gga | gaa | aac | cag | aga | gca | ggg | atg | caa | 3024 |
| Trp | Leu | Leu | Asn | Thr | Glu | Val | Gly | Glu | Asn | Gln | Arg | Ala | Gly | Met | Gln | |
| | | 995 | | | | | 1000 | | | | | 1005 | | | | |
| acg | cca | ttt | ctt | atc | atg | gac | aga | gac | tgt | agg | atg | cca | atg | gga | cta | 3072 |
| Thr | Pro | Phe | Leu | Ile | Met | Asp | Arg | Asp | Cys | Arg | Met | Pro | Met | Gly | Leu | |
| | 1010 | | | | | 1015 | | | | | 1020 | | | | | |
| agc | act | ggt | atc | ata | tct | gat | tca | cag | atc | aag | gct | tca | gag | ttt | ctg | 3120 |
| Ser | Thr | Gly | Ile | Ile | Ser | Asp | Ser | Gln | Ile | Lys | Ala | Ser | Glu | Phe | Leu | |
| 1025 | | | | 1030 | | | | | 1035 | | | | | 1040 | | |
| ggt | tac | tgg | gag | ccc | aga | tta | gca | aga | tta | aac | aat | ggt | gga | tct | tat | 3168 |
| Gly | Tyr | Trp | Glu | Pro | Arg | Leu | Ala | Arg | Leu | Asn | Asn | Gly | Gly | Ser | Tyr | |
| | | | | 1045 | | | | | 1050 | | | | | 1055 | | |
| aat | gct | tgg | agt | gta | gaa | aaa | ctt | gca | gca | gaa | ttt | gcc | tct | aaa | cct | 3216 |
| Asn | Ala | Trp | Ser | Val | Glu | Lys | Leu | Ala | Ala | Glu | Phe | Ala | Ser | Lys | Pro | |
| | | | | 1060 | | | | | 1065 | | | | | 1070 | | |
| tgg | atc | cag | gtg | gac | atg | caa | aag | gaa | gtc | ata | atc | aca | ggg | atc | cag | 3264 |
| Trp | Ile | Gln | Val | Asp | Met | Gln | Lys | Glu | Val | Ile | Ile | Thr | Gly | Ile | Gln | |
| | | | 1075 | | | | | 1080 | | | | | 1085 | | | |
| acc | caa | ggt | gcc | aaa | cac | tac | ctg | aag | tcc | tgc | tat | acc | aca | gag | ttc | 3312 |

```
Thr Gln Gly Ala Lys His Tyr Leu Lys Ser Cys Tyr Thr Thr Glu Phe
    1090                1095                1100 tat gta gct tac agt tcc aac cag atc aac tgg cag atc ttc aaa ggg      3360
Tyr Val Ala Tyr Ser Ser Asn Gln Ile Asn Trp Gln Ile Phe Lys Gly
1105                1110                1115                1120 aac agc aca agg aat gtg atg tat ttt aat ggc aat tca gat gcc tct      3408
Asn Ser Thr Arg Asn Val Met Tyr Phe Asn Gly Asn Ser Asp Ala Ser
                1125                1130                1135 aca ata aaa gag aat cag ttt gac cca cct att gtg gct aga tat att      3456
Thr Ile Lys Glu Asn Gln Phe Asp Pro Pro Ile Val Ala Arg Tyr Ile
        1140                1145                1150 agg atc tct cca act cga gcc tat aac aga cct acc ctt cga ttg gaa      3504
Arg Ile Ser Pro Thr Arg Ala Tyr Asn Arg Pro Thr Leu Arg Leu Glu
    1155                1160                1165 ctg caa ggt tgt gag gta aat gga tgt tcc aca ccc ctg ggt atg gaa      3552
Leu Gln Gly Cys Glu Val Asn Gly Cys Ser Thr Pro Leu Gly Met Glu
1170                1175                1180 aat gga aag ata gaa aac aag caa atc aca gct tct tcg ttt aag aaa      3600
Asn Gly Lys Ile Glu Asn Lys Gln Ile Thr Ala Ser Ser Phe Lys Lys
1185                1190                1195                1200 tct tgg tgg gga gat tac tgg gaa ccc ttc cgt gcc cgt ctg aat gcc      3648
Ser Trp Trp Gly Asp Tyr Trp Glu Pro Phe Arg Ala Arg Leu Asn Ala
                1205                1210                1215 cag gga cgt gtg aat gcc tgg caa gcc aag gca aac aac aat aag cag      3696
Gln Gly Arg Val Asn Ala Trp Gln Ala Lys Ala Asn Asn Asn Lys Gln
        1220                1225                1230 tgg cta gaa att gat cta ctc aag atc aag aag ata acg gca att ata      3744
Trp Leu Glu Ile Asp Leu Leu Lys Ile Lys Lys Ile Thr Ala Ile Ile
    1235                1240                1245 aca cag ggc tgc aag tct ctg tcc tct gaa atg tat gta aag agc tat      3792
Thr Gln Gly Cys Lys Ser Leu Ser Ser Glu Met Tyr Val Lys Ser Tyr
1250                1255                1260 acc atc cac tac agt gag cag gga gtg gaa tgg aaa cca tac agg ctg      3840
Thr Ile His Tyr Ser Glu Gln Gly Val Glu Trp Lys Pro Tyr Arg Leu
1265                1270                1275                1280 aaa tcc tcc atg gtg gac aag att ttt gaa gga aat act aat acc aaa      3888
Lys Ser Ser Met Val Asp Lys Ile Phe Glu Gly Asn Thr Asn Thr Lys
                1285                1290                1295 gga cat gtg aag aac ttt ttc aac ccc cca atc att tcc agg ttt atc      3936
Gly His Val Lys Asn Phe Phe Asn Pro Pro Ile Ile Ser Arg Phe Ile
        1300                1305                1310 cgt gtc att cct aaa aca tgg aat caa agt att gca ctt cgc ctg gaa      3984
Arg Val Ile Pro Lys Thr Trp Asn Gln Ser Ile Ala Leu Arg Leu Glu
    1315                1320                1325 ctc ttt ggc tgt gat att tac tagaattgaa cattcaaaaa cccctggaag         4035
Leu Phe Gly Cys Asp Ile Tyr
    1330                1335 agactcttta agacctcaaa ccatttagaa tgggcaatgt attttacgct gtgttaaatg    4095
ttaacagttt tccactattt ctctttcttt tctattagtg aataaatttt tatac         4150

<210> SEQ ID NO 4
<211> LENGTH: 1335
<212> TYPE: PRT
<213> ORGANISM: Homo sapiens

<400> SEQUENCE: 4

Ala Gln Leu Arg Gln Phe Tyr Val Ala Ala Gln Gly Ile Ser Trp Ser
  1               5                  10                  15

Tyr Arg Pro Glu Pro Thr Asn Ser Ser Leu Asn Leu Ser Val Thr Ser
```

```
                    20                  25                  30
Phe Lys Lys Ile Val Tyr Arg Glu Tyr Glu Pro Tyr Phe Lys Lys Glu
             35                  40                  45

Lys Pro Gln Ser Thr Ile Ser Gly Leu Leu Gly Pro Thr Leu Tyr Ala
     50                  55                  60

Glu Val Gly Asp Ile Ile Lys Val His Phe Lys Asn Lys Ala Asp Lys
 65                  70                  75                  80

Pro Leu Ser Ile His Pro Gln Gly Ile Arg Tyr Ser Lys Leu Ser Glu
                 85                  90                  95

Gly Ala Ser Tyr Leu Asp His Thr Phe Pro Ala Glu Lys Met Asp Asp
             100                 105                 110

Ala Val Ala Pro Gly Arg Ala Tyr Thr Tyr Glu Trp Ser Ile Ser Glu
             115                 120                 125

Asp Ser Gly Pro Thr His Asp Asp Pro Cys Leu Thr His Ile Tyr
             130                 135                 140

Tyr Ser His Glu Asn Leu Ile Glu Asp Phe Asn Ser Gly Leu Ile Gly
145                 150                 155                 160

Pro Leu Leu Ile Cys Lys Lys Gly Thr Leu Thr Glu Gly Gly Thr Gln
                 165                 170                 175

Lys Thr Phe Asp Lys Gln Ile Val Leu Leu Phe Ala Val Phe Asp Glu
             180                 185                 190

Ser Lys Ser Trp Ser Gln Ser Ser Ser Leu Met Tyr Thr Val Asn Gly
             195                 200                 205

Tyr Val Asn Gly Thr Met Pro Asp Ile Thr Val Cys Ala His Asp His
210                 215                 220

Ile Ser Trp His Leu Leu Gly Met Ser Ser Gly Pro Glu Leu Phe Ser
225                 230                 235                 240

Ile His Phe Asn Gly Gln Val Leu Glu Gln Asn His His Lys Val Ser
                 245                 250                 255

Ala Ile Thr Leu Val Ser Ala Thr Ser Thr Thr Ala Asn Met Thr Val
             260                 265                 270

Gly Pro Glu Gly Lys Trp Ile Ile Ser Ser Leu Thr Pro Lys His Leu
             275                 280                 285

Gln Ala Gly Met Gln Ala Tyr Ile Asp Ile Lys Asn Cys Pro Lys Lys
             290                 295                 300

Thr Arg Asn Leu Lys Lys Ile Thr Arg Glu Gln Arg His Met Lys
305                 310                 315                 320

Arg Trp Glu Tyr Phe Ile Ala Ala Glu Glu Val Ile Trp Asp Tyr Ala
                 325                 330                 335

Pro Val Ile Pro Ala Asn Met Asp Lys Lys Tyr Arg Ser Gln His Leu
             340                 345                 350

Asp Asn Phe Ser Asn Gln Ile Gly Lys His Tyr Lys Lys Val Met Tyr
             355                 360                 365

Thr Gln Tyr Glu Asp Glu Ser Phe Thr Lys His Thr Val Asn Pro Asn
             370                 375                 380

Met Lys Glu Asp Gly Ile Leu Gly Pro Ile Ile Arg Ala Gln Val Arg
385                 390                 395                 400

Asp Thr Leu Lys Ile Val Phe Lys Asn Met Ala Ser Arg Pro Tyr Ser
                 405                 410                 415

Ile Tyr Pro His Gly Val Thr Phe Ser Pro Tyr Glu Asp Glu Val Asn
             420                 425                 430

Ser Ser Phe Thr Ser Gly Arg Asn Asn Thr Met Ile Arg Ala Val Gln
             435                 440                 445
```

```
Pro Gly Glu Thr Tyr Thr Tyr Lys Trp Asn Ile Leu Glu Phe Asp Glu
    450                 455                 460

Pro Thr Glu Asn Asp Ala Gln Cys Leu Thr Arg Pro Tyr Tyr Ser Asp
465                 470                 475                 480

Val Asp Ile Met Arg Asp Ile Ala Ser Gly Leu Ile Gly Leu Leu Leu
                485                 490                 495

Ile Cys Lys Ser Arg Ser Leu Asp Arg Arg Gly Ile Gln Arg Ala Ala
                500                 505                 510

Asp Ile Glu Gln Gln Ala Val Phe Ala Val Phe Asp Glu Asn Lys Ser
            515                 520                 525

Trp Tyr Leu Glu Asp Asn Ile Asn Lys Phe Cys Glu Asn Pro Asp Glu
            530                 535                 540

Val Lys Arg Asp Asp Pro Lys Phe Tyr Glu Ser Asn Ile Met Ser Thr
545                 550                 555                 560

Ile Asn Gly Tyr Val Pro Glu Ser Ile Thr Thr Leu Gly Phe Cys Phe
                565                 570                 575

Asp Asp Thr Val Gln Trp His Phe Cys Ser Val Gly Thr Gln Asn Glu
            580                 585                 590

Ile Leu Thr Ile His Phe Thr Gly His Ser Phe Ile Tyr Gly Lys Arg
            595                 600                 605

His Glu Asp Thr Leu Thr Leu Phe Pro Met Arg Gly Glu Ser Val Thr
    610                 615                 620

Val Thr Met Asp Asn Val Gly Thr Trp Met Leu Thr Ser Met Asn Ser
625                 630                 635                 640

Ser Pro Arg Ser Lys Lys Leu Arg Leu Lys Phe Arg Asp Val Lys Cys
                645                 650                 655

Ile Pro Asp Asp Asp Glu Asp Ser Tyr Glu Ile Phe Glu Pro Pro Glu
                660                 665                 670

Ser Thr Val Met Ala Thr Arg Lys Met His Asp Arg Leu Glu Pro Glu
            675                 680                 685

Asp Glu Glu Ser Asp Ala Asp Tyr Asp Tyr Gln Asn Arg Leu Ala Ala
    690                 695                 700

Ala Leu Gly Ile Arg Arg Glu Thr Asp Ile Glu Asp Ser Asp Asp Ile
705                 710                 715                 720

Pro Glu Asp Thr Thr Tyr Lys Lys Val Val Phe Arg Lys Tyr Leu Asp
                725                 730                 735

Ser Thr Phe Thr Lys Arg Asp Pro Arg Gly Glu Tyr Glu Glu His Leu
            740                 745                 750

Gly Ile Leu Gly Pro Ile Ile Arg Ala Glu Val Asp Asp Val Ile Gln
            755                 760                 765

Val Arg Phe Lys Asn Leu Ala Ser Arg Pro Tyr Ser Leu His Ala His
    770                 775                 780

Gly Leu Ser Tyr Glu Lys Ser Ser Glu Gly Lys Thr Tyr Glu Asp Asp
785                 790                 795                 800

Ser Pro Glu Trp Phe Lys Glu Asp Asn Ala Val Gln Pro Asn Ser Ser
                805                 810                 815

Tyr Thr Tyr Val Trp His Ala Thr Glu Arg Ser Gly Pro Glu Ser Pro
            820                 825                 830

Gly Ser Ala Cys Arg Ala Trp Ala Tyr Tyr Ser Ala Val Asn Pro Glu
            835                 840                 845

Lys Asp Ile His Ser Gly Leu Ile Gly Pro Leu Leu Ile Cys Gln Lys
    850                 855                 860
```

```
Gly Ile Leu His Lys Asp Ser Asn Met Pro Val Asp Met Arg Glu Phe
865                 870                 875                 880

Val Leu Leu Phe Met Thr Phe Asp Glu Lys Lys Ser Trp Tyr Tyr Glu
            885                 890                 895

Lys Lys Ser Arg Ser Ser Trp Arg Leu Thr Ser Ser Glu Met Lys Lys
        900                 905                 910

Ser His Glu Phe His Ala Ile Asn Gly Met Ile Tyr Ser Leu Pro Gly
    915                 920                 925

Leu Lys Met Tyr Glu Gln Glu Trp Val Arg Leu His Leu Leu Asn Ile
    930                 935                 940

Gly Gly Ser Gln Asp Ile His Val Val His Phe His Gly Gln Thr Leu
945                 950                 955                 960

Leu Glu Asn Gly Asn Lys Gln His Gln Leu Gly Val Trp Pro Leu Leu
            965                 970                 975

Pro Gly Ser Phe Lys Thr Leu Glu Met Lys Ala Ser Lys Pro Gly Trp
        980                 985                 990

Trp Leu Leu Asn Thr Glu Val Gly Glu Asn Gln Arg Ala Gly Met Gln
    995                 1000                1005

Thr Pro Phe Leu Ile Met Asp Arg Asp Cys Arg Met Pro Met Gly Leu
    1010                1015                1020

Ser Thr Gly Ile Ile Ser Asp Ser Gln Ile Lys Ala Ser Glu Phe Leu
1025                1030                1035                1040

Gly Tyr Trp Glu Pro Arg Leu Ala Arg Leu Asn Asn Gly Gly Ser Tyr
            1045                1050                1055

Asn Ala Trp Ser Val Glu Lys Leu Ala Ala Glu Phe Ala Ser Lys Pro
            1060                1065                1070

Trp Ile Gln Val Asp Met Gln Lys Glu Val Ile Ile Thr Gly Ile Gln
            1075                1080                1085

Thr Gln Gly Ala Lys His Tyr Leu Lys Ser Cys Tyr Thr Thr Glu Phe
    1090                1095                1100

Tyr Val Ala Tyr Ser Ser Asn Gln Ile Asn Trp Gln Ile Phe Lys Gly
1105                1110                1115                1120

Asn Ser Thr Arg Asn Val Met Tyr Phe Asn Gly Asn Ser Asp Ala Ser
            1125                1130                1135

Thr Ile Lys Glu Asn Gln Phe Asp Pro Pro Ile Val Ala Arg Tyr Ile
        1140                1145                1150

Arg Ile Ser Pro Thr Arg Ala Tyr Asn Arg Pro Thr Leu Arg Leu Glu
    1155                1160                1165

Leu Gln Gly Cys Glu Val Asn Gly Cys Ser Thr Pro Leu Gly Met Glu
    1170                1175                1180

Asn Gly Lys Ile Glu Asn Lys Gln Ile Thr Ala Ser Ser Phe Lys Lys
1185                1190                1195                1200

Ser Trp Trp Gly Asp Tyr Trp Glu Pro Phe Arg Ala Arg Leu Asn Ala
        1205                1210                1215

Gln Gly Arg Val Asn Ala Trp Gln Ala Lys Ala Asn Asn Asn Lys Gln
    1220                1225                1230

Trp Leu Glu Ile Asp Leu Leu Lys Ile Lys Lys Ile Thr Ala Ile Ile
    1235                1240                1245

Thr Gln Gly Cys Lys Ser Leu Ser Ser Glu Met Tyr Val Lys Ser Tyr
    1250                1255                1260

Thr Ile His Tyr Ser Glu Gln Gly Val Glu Trp Lys Pro Tyr Arg Leu
1265                1270                1275                1280

Lys Ser Ser Met Val Asp Lys Ile Phe Glu Gly Asn Thr Asn Thr Lys
```

-continued

```
                        1285                    1290                    1295
Gly His Val Lys Asn Phe Phe Asn Pro Pro Ile Ile Ser Arg Phe Ile
                1300                    1305                    1310

Arg Val Ile Pro Lys Thr Trp Asn Gln Ser Ile Ala Leu Arg Leu Glu
        1315                    1320                    1325

Leu Phe Gly Cys Asp Ile Tyr
    1330                1335

<210> SEQ ID NO 5
<211> LENGTH: 4150
<212> TYPE: DNA
<213> ORGANISM: Homo sapiens
<220> FEATURE:
<221> NAME/KEY: CDS
<222> LOCATION: (1)..(4005)

<400> SEQUENCE: 5 gca cag cta agg cag ttc tac gtg gct gct cag ggc atc agt tgg agc       48
Ala Gln Leu Arg Gln Phe Tyr Val Ala Ala Gln Gly Ile Ser Trp Ser
  1               5                  10                  15 tac cga cct gag ccc aca aac tca agt ttg aat ctt tct gta act tcc       96
Tyr Arg Pro Glu Pro Thr Asn Ser Ser Leu Asn Leu Ser Val Thr Ser
             20                  25                  30 ttt aag aaa att gtc tac aga gag tat gaa cca tat ttt aag aaa gaa      144
Phe Lys Lys Ile Val Tyr Arg Glu Tyr Glu Pro Tyr Phe Lys Lys Glu
         35                  40                  45 aaa cca caa tct acc att tca gga ctt ctt ggg cct act tta tat gct      192
Lys Pro Gln Ser Thr Ile Ser Gly Leu Leu Gly Pro Thr Leu Tyr Ala
     50                  55                  60 gaa gtc gga gac atc ata aaa gtt cac ttt aaa aat aag gca gct aag      240
Glu Val Gly Asp Ile Ile Lys Val His Phe Lys Asn Lys Ala Ala Lys
 65                  70                  75                  80 ccc ttg agc atc cat cct caa gga att agg tac agt aaa tta tca gaa      288
Pro Leu Ser Ile His Pro Gln Gly Ile Arg Tyr Ser Lys Leu Ser Glu
                 85                  90                  95 ggt gct tct tac ctt gac cac aca ttc cct gca gag aag atg gac gac      336
Gly Ala Ser Tyr Leu Asp His Thr Phe Pro Ala Glu Lys Met Asp Asp
            100                 105                 110 gct gtg gct cca ggc cga gaa tac acc tat gaa tgg agt atc agt gag      384
Ala Val Ala Pro Gly Arg Glu Tyr Thr Tyr Glu Trp Ser Ile Ser Glu
        115                 120                 125 gac agt gga ccc acc cat gat gac cct cca tgc ctc aca cac atc tat      432
Asp Ser Gly Pro Thr His Asp Asp Pro Pro Cys Leu Thr His Ile Tyr
    130                 135                 140 tac tcc cat gaa aat ctg atc gag gat ttc aac tct ggg ctg att ggg      480
Tyr Ser His Glu Asn Leu Ile Glu Asp Phe Asn Ser Gly Leu Ile Gly
145                 150                 155                 160 ccc ctg ctt atc tgt aaa aaa ggg acc cta act gag ggt ggg aca cag      528
Pro Leu Leu Ile Cys Lys Lys Gly Thr Leu Thr Glu Gly Gly Thr Gln
                165                 170                 175 aag acg ttt gac aag caa atc gtg cta cta ttt gct gtg ttt gat gaa      576
Lys Thr Phe Asp Lys Gln Ile Val Leu Leu Phe Ala Val Phe Asp Glu
            180                 185                 190 agc aag agc tgg agc cag tca tca tcc cta atg tac aca gtc aat gga      624
Ser Lys Ser Trp Ser Gln Ser Ser Ser Leu Met Tyr Thr Val Asn Gly
        195                 200                 205 tat gtg aat ggg aca atg cca gat ata aca gtt tgt gcc cat gac cac      672
Tyr Val Asn Gly Thr Met Pro Asp Ile Thr Val Cys Ala His Asp His
    210                 215                 220 atc agc tgg cat ctg ctg gga atg agc tcg ggg cca gaa tta ttc tcc      720
```

```
                Ile Ser Trp His Leu Leu Gly Met Ser Ser Gly Pro Glu Leu Phe Ser
                225                 230                 235                 240 att cat ttc aac ggc cag gtc ctg gag cag aac cat cat aag gtc tca            768
Ile His Phe Asn Gly Gln Val Leu Glu Gln Asn His His Lys Val Ser
                245                 250                 255 gcc atc acc ctt gtc agt gct aca tcc act acc gca aat atg act gtg            816
Ala Ile Thr Leu Val Ser Ala Thr Ser Thr Thr Ala Asn Met Thr Val
                260                 265                 270 ggc cca gag gga aag tgg ata ata tct tct ctc acc cca aaa cat ttg            864
Gly Pro Glu Gly Lys Trp Ile Ile Ser Ser Leu Thr Pro Lys His Leu
                275                 280                 285 caa gct ggg atg cag gct tac att gac att aaa aac tgc cca aag aaa            912
Gln Ala Gly Met Gln Ala Tyr Ile Asp Ile Lys Asn Cys Pro Lys Lys
                290                 295                 300 acc agg aat ctt aag aaa ata act cgt gag cag agg cgg cac atg aag            960
Thr Arg Asn Leu Lys Lys Ile Thr Arg Glu Gln Arg Arg His Met Lys
305                 310                 315                 320 agg tgg gaa tac ttc att gct gca gag gaa gtc att tgg gac tat gca           1008
Arg Trp Glu Tyr Phe Ile Ala Ala Glu Glu Val Ile Trp Asp Tyr Ala
                325                 330                 335 cct gta ata cca gcg aat atg gac aaa aaa tac agg tct cag cat ttg           1056
Pro Val Ile Pro Ala Asn Met Asp Lys Lys Tyr Arg Ser Gln His Leu
                340                 345                 350 gat aat ttc tca aac caa att gga aaa cat tat aag aaa gtt atg tac           1104
Asp Asn Phe Ser Asn Gln Ile Gly Lys His Tyr Lys Lys Val Met Tyr
                355                 360                 365 aca cag tac gaa gat gag tcc ttc acc aaa cat aca gtg aat ccc aat           1152
Thr Gln Tyr Glu Asp Glu Ser Phe Thr Lys His Thr Val Asn Pro Asn
370                 375                 380 atg aaa gaa gat ggg att ttg ggt cct att atc aga gcc cag gtc aga           1200
Met Lys Glu Asp Gly Ile Leu Gly Pro Ile Ile Arg Ala Gln Val Arg
385                 390                 395                 400 gac aca ctc aaa atc gtg ttc aaa aat atg gcc agc cgc ccc tat agc           1248
Asp Thr Leu Lys Ile Val Phe Lys Asn Met Ala Ser Arg Pro Tyr Ser
                405                 410                 415 att tac cct cat gga gtg acc ttc tcg cct tat gaa gat gaa gtc aac           1296
Ile Tyr Pro His Gly Val Thr Phe Ser Pro Tyr Glu Asp Glu Val Asn
                420                 425                 430 tct tct ttc acc tca ggc agg aac aac acc atg atc aga gca gtt caa           1344
Ser Ser Phe Thr Ser Gly Arg Asn Asn Thr Met Ile Arg Ala Val Gln
                435                 440                 445 cca ggg gaa acc tat act tat aag tgg aac atc tta gag ttt gat gaa           1392
Pro Gly Glu Thr Tyr Thr Tyr Lys Trp Asn Ile Leu Glu Phe Asp Glu
                450                 455                 460 ccc aca gaa aat gat gcc cag tgc tta aca aga cca tac tac agt gac           1440
Pro Thr Glu Asn Asp Ala Gln Cys Leu Thr Arg Pro Tyr Tyr Ser Asp
465                 470                 475                 480 gtg gac atc atg aga gac atc gcc tct ggg cta ata gga cta ctt cta           1488
Val Asp Ile Met Arg Asp Ile Ala Ser Gly Leu Ile Gly Leu Leu Leu
                485                 490                 495 atc tgt aag agc aga tcc ctg gac agg cga gga ata cag agg gca gca           1536
Ile Cys Lys Ser Arg Ser Leu Asp Arg Arg Gly Ile Gln Arg Ala Ala
                500                 505                 510 gac atc gaa cag cag gct gtg ttt gct gtg ttt gat gag aac aaa agc           1584
Asp Ile Glu Gln Gln Ala Val Phe Ala Val Phe Asp Glu Asn Lys Ser
                515                 520                 525 tgg tac ctt gag gac aac atc aac aag ttt tgt gaa aat cct gat gag           1632
Trp Tyr Leu Glu Asp Asn Ile Asn Lys Phe Cys Glu Asn Pro Asp Glu
                530                 535                 540
```

-continued

| | | |
|---|---|---|
| gtg aaa cgt gat gac ccc aag ttt tat gaa tca aac atc atg agc act<br>Val Lys Arg Asp Asp Pro Lys Phe Tyr Glu Ser Asn Ile Met Ser Thr<br>545                    550                    555                    560 | 1680 |
| atc aat ggc tat gtg cct gag agc ata act act ctt gga ttc tgc ttt<br>Ile Asn Gly Tyr Val Pro Glu Ser Ile Thr Thr Leu Gly Phe Cys Phe<br>                  565                    570                    575 | 1728 |
| gat gac act gtc cag tgg cac ttc tgt agt gtg ggg acc cag aat gaa<br>Asp Asp Thr Val Gln Trp His Phe Cys Ser Val Gly Thr Gln Asn Glu<br>            580                    585                    590 | 1776 |
| att ttg acc atc cac ttc act ggg cac tca ttc atc tat gga aag agg<br>Ile Leu Thr Ile His Phe Thr Gly His Ser Phe Ile Tyr Gly Lys Arg<br>          595                    600                    605 | 1824 |
| cat gag gac acc ttg acc ctc ttc ccc atg cgt gga gaa tct gtg acg<br>His Glu Asp Thr Leu Thr Leu Phe Pro Met Arg Gly Glu Ser Val Thr<br>610                    615                    620 | 1872 |
| gtc aca atg gat aat gtt gga act tgg atg tta act tcc atg aat tct<br>Val Thr Met Asp Asn Val Gly Thr Trp Met Leu Thr Ser Met Asn Ser<br>625                    630                    635                    640 | 1920 |
| agt cca aga agc aaa aag ctg agg ctg aaa ttc agg gat gtt aaa tgt<br>Ser Pro Arg Ser Lys Lys Leu Arg Leu Lys Phe Arg Asp Val Lys Cys<br>                  645                    650                    655 | 1968 |
| atc cca gat gat gat gaa gac tca tat gag att ttt gaa cct cca gaa<br>Ile Pro Asp Asp Asp Glu Asp Ser Tyr Glu Ile Phe Glu Pro Pro Glu<br>            660                    665                    670 | 2016 |
| tct aca gtc atg gct aca cgg aaa atg cat gat cgt tta gaa cct gaa<br>Ser Thr Val Met Ala Thr Arg Lys Met His Asp Arg Leu Glu Pro Glu<br>          675                    680                    685 | 2064 |
| gat gaa gag agt gat gct gac tat gat tac cag aac aga ctg gct gca<br>Asp Glu Glu Ser Asp Ala Asp Tyr Asp Tyr Gln Asn Arg Leu Ala Ala<br>690                    695                    700 | 2112 |
| gca tta gga att agg agg gaa aca gat att gaa gac tct gat gat att<br>Ala Leu Gly Ile Arg Arg Glu Thr Asp Ile Glu Asp Ser Asp Asp Ile<br>705                    710                    715                    720 | 2160 |
| cca gaa gat acc aca tat aag aaa gta gtt ttt cga aag tac ctc gac<br>Pro Glu Asp Thr Thr Tyr Lys Lys Val Val Phe Arg Lys Tyr Leu Asp<br>                  725                    730                    735 | 2208 |
| agc act ttt acc aaa cgt gat cct cga ggg gag tat gaa gag cat ctc<br>Ser Thr Phe Thr Lys Arg Asp Pro Arg Gly Glu Tyr Glu Glu His Leu<br>            740                    745                    750 | 2256 |
| gga att ctt ggt cct att atc aga gct gaa gtg gat gat gtt atc caa<br>Gly Ile Leu Gly Pro Ile Ile Arg Ala Glu Val Asp Asp Val Ile Gln<br>          755                    760                    765 | 2304 |
| gtt cgt ttt aaa aat tta gca tcc aga ccg tat tct cta cat gcc cat<br>Val Arg Phe Lys Asn Leu Ala Ser Arg Pro Tyr Ser Leu His Ala His<br>770                    775                    780 | 2352 |
| gga ctt tcc tat gaa aaa tca tca gag gga aag act tat gaa gat gac<br>Gly Leu Ser Tyr Glu Lys Ser Ser Glu Gly Lys Thr Tyr Glu Asp Asp<br>785                    790                    795                    800 | 2400 |
| tct cct gaa tgg ttt aag gaa gat aat gct gtt cag cca aat agc agt<br>Ser Pro Glu Trp Phe Lys Glu Asp Asn Ala Val Gln Pro Asn Ser Ser<br>                  805                    810                    815 | 2448 |
| tat acc tac gta tgg cat gcc act gag cga tca ggg cca gaa agt cct<br>Tyr Thr Tyr Val Trp His Ala Thr Glu Arg Ser Gly Pro Glu Ser Pro<br>            820                    825                    830 | 2496 |
| ggc tct gcc tgt cgg gct tgg gcc tac tac tca gct gtg aac cca gaa<br>Gly Ser Ala Cys Arg Ala Trp Ala Tyr Tyr Ser Ala Val Asn Pro Glu<br>          835                    840                    845 | 2544 |
| aaa gat att cac tca ggc ttg ata ggt ccc ctc cta atc tgc caa aaa<br>Lys Asp Ile His Ser Gly Leu Ile Gly Pro Leu Leu Ile Cys Gln Lys<br>850                    855                    860 | 2592 |

| | |
|---|---|
| gga ata cta cat aag gac agc aac atg cct gtg gac atg aga gaa ttt<br>Gly Ile Leu His Lys Asp Ser Asn Met Pro Val Asp Met Arg Glu Phe<br>865     870     875     880 | 2640 |
| gtc tta cta ttt atg acc ttt gat gaa aag aag agc tgg tac tat gaa<br>Val Leu Leu Phe Met Thr Phe Asp Glu Lys Lys Ser Trp Tyr Tyr Glu<br>     885     890     895 | 2688 |
| aag aag tcc cga agt tct tgg aga ctc aca tcc tca gaa atg aaa aaa<br>Lys Lys Ser Arg Ser Ser Trp Arg Leu Thr Ser Ser Glu Met Lys Lys<br>900     905     910 | 2736 |
| tcc cat gag ttt cac gcc att aat ggg atg atc tac agc ttg cct ggc<br>Ser His Glu Phe His Ala Ile Asn Gly Met Ile Tyr Ser Leu Pro Gly<br>915     920     925 | 2784 |
| ctg aaa atg tat gag caa gag tgg gtg agg tta cac ctg ctg aac ata<br>Leu Lys Met Tyr Glu Gln Glu Trp Val Arg Leu His Leu Leu Asn Ile<br>930     935     940 | 2832 |
| ggc ggc tcc caa gac att cac gtg gtt cac ttt cac ggc cag acc ttg<br>Gly Gly Ser Gln Asp Ile His Val Val His Phe His Gly Gln Thr Leu<br>945     950     955     960 | 2880 |
| ctg gaa aat ggc aat aaa cag cac cag tta ggg gtc tgg ccc ctt ctg<br>Leu Glu Asn Gly Asn Lys Gln His Gln Leu Gly Val Trp Pro Leu Leu<br>     965     970     975 | 2928 |
| cct ggt tca ttt aaa act ctt gaa atg aag gca tca aaa cct ggc tgg<br>Pro Gly Ser Phe Lys Thr Leu Glu Met Lys Ala Ser Lys Pro Gly Trp<br>980     985     990 | 2976 |
| tgg ctc cta aac aca gag gtt gga gaa aac cag aga gca ggg atg caa<br>Trp Leu Leu Asn Thr Glu Val Gly Glu Asn Gln Arg Ala Gly Met Gln<br>995     1000     1005 | 3024 |
| acg cca ttt ctt atc atg gac aga gac tgt agg atg cca atg gga cta<br>Thr Pro Phe Leu Ile Met Asp Arg Asp Cys Arg Met Pro Met Gly Leu<br>1010     1015     1020 | 3072 |
| agc act ggt atc ata tct gat tca cag atc aag gct tca gag ttt ctg<br>Ser Thr Gly Ile Ile Ser Asp Ser Gln Ile Lys Ala Ser Glu Phe Leu<br>1025     1030     1035     1040 | 3120 |
| ggt tac tgg gag ccc aga tta gca aga tta aac aat ggt gga tct tat<br>Gly Tyr Trp Glu Pro Arg Leu Ala Arg Leu Asn Asn Gly Gly Ser Tyr<br>     1045     1050     1055 | 3168 |
| aat gct tgg agt gta gaa aaa ctt gca gca gaa ttt gcc tct aaa cct<br>Asn Ala Trp Ser Val Glu Lys Leu Ala Ala Glu Phe Ala Ser Lys Pro<br>1060     1065     1070 | 3216 |
| tgg atc cag gtg gac atg caa aag gaa gtc ata atc aca ggg atc cag<br>Trp Ile Gln Val Asp Met Gln Lys Glu Val Ile Ile Thr Gly Ile Gln<br>1075     1080     1085 | 3264 |
| acc caa ggt gcc aaa cac tac ctg aag tcc tgc tat acc aca gag ttc<br>Thr Gln Gly Ala Lys His Tyr Leu Lys Ser Cys Tyr Thr Thr Glu Phe<br>1090     1095     1100 | 3312 |
| tat gta gct tac agt tcc aac cag atc aac tgg cag atc ttc aaa ggg<br>Tyr Val Ala Tyr Ser Ser Asn Gln Ile Asn Trp Gln Ile Phe Lys Gly<br>1105     1110     1115     1120 | 3360 |
| aac agc aca agg aat gtg atg tat ttt aat ggc aat tca gat gcc tct<br>Asn Ser Thr Arg Asn Val Met Tyr Phe Asn Gly Asn Ser Asp Ala Ser<br>     1125     1130     1135 | 3408 |
| aca ata aaa gag aat cag ttt gac cca cct att gtg gct aga tat att<br>Thr Ile Lys Glu Asn Gln Phe Asp Pro Pro Ile Val Ala Arg Tyr Ile<br>1140     1145     1150 | 3456 |
| agg atc tct cca act cga gcc tat aac aga cct acc ctt cga ttg gaa<br>Arg Ile Ser Pro Thr Arg Ala Tyr Asn Arg Pro Thr Leu Arg Leu Glu<br>1155     1160     1165 | 3504 |
| ctg caa ggt tgt gag gta aat gga tgt tcc aca ccc ctg ggt atg gaa<br>Leu Gln Gly Cys Glu Val Asn Gly Cys Ser Thr Pro Leu Gly Met Glu | 3552 |

```
                                      -continued
    1170              1175              1180
aat gga aag ata gaa aac aag caa atc aca gct tct tcg ttt aag aaa      3600
Asn Gly Lys Ile Glu Asn Lys Gln Ile Thr Ala Ser Ser Phe Lys Lys
1185              1190              1195              1200 tct tgg tgg gga gat tac tgg gaa ccc ttc cgt gcc cgt ctg aat gcc      3648
Ser Trp Trp Gly Asp Tyr Trp Glu Pro Phe Arg Ala Arg Leu Asn Ala
             1205              1210              1215 cag gga cgt gtg aat gcc tgg caa gcc aag gca aac aac aat aag cag      3696
Gln Gly Arg Val Asn Ala Trp Gln Ala Lys Ala Asn Asn Asn Lys Gln
        1220              1225              1230 tgg cta gaa att gat cta ctc aag atc aag aag ata acg gca att ata      3744
Trp Leu Glu Ile Asp Leu Leu Lys Ile Lys Lys Ile Thr Ala Ile Ile
    1235              1240              1245 aca cag ggc tgc aag tct ctg tcc tct gaa atg tat gta aag agc tat      3792
Thr Gln Gly Cys Lys Ser Leu Ser Ser Glu Met Tyr Val Lys Ser Tyr
    1250              1255              1260 acc atc cac tac agt gag cag gga gtg gaa tgg aaa cca tac agg ctg      3840
Thr Ile His Tyr Ser Glu Gln Gly Val Glu Trp Lys Pro Tyr Arg Leu
1265              1270              1275              1280 aaa tcc tcc atg gtg gac aag att ttt gaa gga aat act aat acc aaa      3888
Lys Ser Ser Met Val Asp Lys Ile Phe Glu Gly Asn Thr Asn Thr Lys
             1285              1290              1295 gga cat gtg aag aac ttt ttc aac ccc cca atc att tcc agg ttt atc      3936
Gly His Val Lys Asn Phe Phe Asn Pro Pro Ile Ile Ser Arg Phe Ile
        1300              1305              1310 cgt gtc att cct aaa aca tgg aat caa agt att gca ctt cgc ctg gaa      3984
Arg Val Ile Pro Lys Thr Trp Asn Gln Ser Ile Ala Leu Arg Leu Glu
    1315              1320              1325 ctc ttt ggc tgt gat att tac tagaattgaa cattcaaaaa ccctggaag          4035
Leu Phe Gly Cys Asp Ile Tyr
    1330              1335 agactcttta agacctcaaa ccatttagaa tgggcaatgt attttacgct gtgttaaatg    4095
ttaacagttt tccactattt ctctttcttt tctattagtg aataaaattt tatac          4150

<210> SEQ ID NO 6
<211> LENGTH: 1335
<212> TYPE: PRT
<213> ORGANISM: Homo sapiens

<400> SEQUENCE: 6

Ala Gln Leu Arg Gln Phe Tyr Val Ala Ala Gln Gly Ile Ser Trp Ser
  1               5                  10                  15

Tyr Arg Pro Glu Pro Thr Asn Ser Ser Leu Asn Leu Ser Val Thr Ser
                 20                  25                  30

Phe Lys Lys Ile Val Tyr Arg Glu Tyr Glu Pro Tyr Phe Lys Lys Glu
             35                  40                  45

Lys Pro Gln Ser Thr Ile Ser Gly Leu Leu Gly Pro Thr Leu Tyr Ala
         50                  55                  60

Glu Val Gly Asp Ile Ile Lys Val His Phe Lys Asn Lys Ala Ala Lys
 65                  70                  75                  80

Pro Leu Ser Ile His Pro Gln Gly Ile Arg Tyr Ser Lys Leu Ser Glu
                 85                  90                  95

Gly Ala Ser Tyr Leu Asp His Thr Phe Pro Ala Glu Lys Met Asp Asp
            100                 105                 110

Ala Val Ala Pro Gly Arg Glu Tyr Thr Tyr Glu Trp Ser Ile Ser Glu
        115                 120                 125

Asp Ser Gly Pro Thr His Asp Asp Pro Pro Cys Leu Thr His Ile Tyr
```

```
            130                 135                 140
Tyr Ser His Glu Asn Leu Ile Glu Asp Phe Asn Ser Gly Leu Ile Gly
145                 150                 155                 160

Pro Leu Ile Cys Lys Lys Gly Thr Leu Thr Glu Gly Gly Thr Gln
            165                 170                 175

Lys Thr Phe Asp Lys Gln Ile Val Leu Leu Phe Ala Val Phe Asp Glu
                180                 185                 190

Ser Lys Ser Trp Ser Gln Ser Ser Leu Met Tyr Thr Val Asn Gly
            195                 200                 205

Tyr Val Asn Gly Thr Met Pro Asp Ile Thr Val Cys Ala His Asp His
210                 215                 220

Ile Ser Trp His Leu Leu Gly Met Ser Ser Gly Pro Glu Leu Phe Ser
225                 230                 235                 240

Ile His Phe Asn Gly Gln Val Leu Glu Gln Asn His His Lys Val Ser
                245                 250                 255

Ala Ile Thr Leu Val Ser Ala Thr Ser Thr Thr Ala Asn Met Thr Val
                260                 265                 270

Gly Pro Glu Gly Lys Trp Ile Ile Ser Ser Leu Thr Pro Lys His Leu
            275                 280                 285

Gln Ala Gly Met Gln Ala Tyr Ile Asp Ile Lys Asn Cys Pro Lys Lys
            290                 295                 300

Thr Arg Asn Leu Lys Lys Ile Thr Arg Glu Gln Arg His Met Lys
305                 310                 315                 320

Arg Trp Glu Tyr Phe Ile Ala Ala Glu Glu Val Ile Trp Asp Tyr Ala
                325                 330                 335

Pro Val Ile Pro Ala Asn Met Asp Lys Lys Tyr Arg Ser Gln His Leu
            340                 345                 350

Asp Asn Phe Ser Asn Gln Ile Gly Lys His Tyr Lys Lys Val Met Tyr
                355                 360                 365

Thr Gln Tyr Glu Asp Glu Ser Phe Thr Lys His Thr Val Asn Pro Asn
            370                 375                 380

Met Lys Glu Asp Gly Ile Leu Gly Pro Ile Ile Arg Ala Gln Val Arg
385                 390                 395                 400

Asp Thr Leu Lys Ile Val Phe Lys Asn Met Ala Ser Arg Pro Tyr Ser
                405                 410                 415

Ile Tyr Pro His Gly Val Thr Phe Ser Pro Tyr Glu Asp Glu Val Asn
            420                 425                 430

Ser Ser Phe Thr Ser Gly Arg Asn Asn Thr Met Ile Arg Ala Val Gln
            435                 440                 445

Pro Gly Glu Thr Tyr Thr Tyr Lys Trp Asn Ile Leu Glu Phe Asp Glu
450                 455                 460

Pro Thr Glu Asn Asp Ala Gln Cys Leu Thr Arg Pro Tyr Tyr Ser Asp
465                 470                 475                 480

Val Asp Ile Met Arg Asp Ile Ala Ser Gly Leu Ile Gly Leu Leu Leu
                485                 490                 495

Ile Cys Lys Ser Arg Ser Leu Asp Arg Arg Gly Ile Gln Arg Ala Ala
            500                 505                 510

Asp Ile Glu Gln Gln Ala Val Phe Ala Val Phe Asp Glu Asn Lys Ser
            515                 520                 525

Trp Tyr Leu Glu Asp Asn Ile Asn Lys Phe Cys Glu Asn Pro Asp Glu
            530                 535                 540

Val Lys Arg Asp Asp Pro Lys Phe Tyr Glu Ser Asn Ile Met Ser Thr
545                 550                 555                 560
```

-continued

```
Ile Asn Gly Tyr Val Pro Glu Ser Ile Thr Thr Leu Gly Phe Cys Phe
                565                 570                 575

Asp Asp Thr Val Gln Trp His Phe Cys Ser Val Gly Thr Gln Asn Glu
            580                 585                 590

Ile Leu Thr Ile His Phe Thr Gly His Ser Phe Ile Tyr Gly Lys Arg
        595                 600                 605

His Glu Asp Thr Leu Thr Leu Phe Pro Met Arg Gly Glu Ser Val Thr
    610                 615                 620

Val Thr Met Asp Asn Val Gly Thr Trp Met Leu Thr Ser Met Asn Ser
625                 630                 635                 640

Ser Pro Arg Ser Lys Lys Leu Arg Leu Lys Phe Arg Asp Val Lys Cys
                645                 650                 655

Ile Pro Asp Asp Asp Glu Asp Ser Tyr Glu Ile Phe Glu Pro Pro Glu
            660                 665                 670

Ser Thr Val Met Ala Thr Arg Lys Met His Asp Arg Leu Glu Pro Glu
        675                 680                 685

Asp Glu Glu Ser Asp Ala Asp Tyr Asp Tyr Gln Asn Arg Leu Ala Ala
    690                 695                 700

Ala Leu Gly Ile Arg Arg Glu Thr Asp Ile Glu Asp Ser Asp Asp Ile
705                 710                 715                 720

Pro Glu Asp Thr Thr Tyr Lys Lys Val Val Phe Arg Lys Tyr Leu Asp
                725                 730                 735

Ser Thr Phe Thr Lys Arg Asp Pro Arg Gly Glu Tyr Glu Glu His Leu
            740                 745                 750

Gly Ile Leu Gly Pro Ile Ile Arg Ala Glu Val Asp Asp Val Ile Gln
        755                 760                 765

Val Arg Phe Lys Asn Leu Ala Ser Arg Pro Tyr Ser Leu His Ala His
    770                 775                 780

Gly Leu Ser Tyr Glu Lys Ser Ser Glu Gly Lys Thr Tyr Glu Asp Asp
785                 790                 795                 800

Ser Pro Glu Trp Phe Lys Glu Asp Asn Ala Val Gln Pro Asn Ser Ser
                805                 810                 815

Tyr Thr Tyr Val Trp His Ala Thr Glu Arg Ser Gly Pro Glu Ser Pro
            820                 825                 830

Gly Ser Ala Cys Arg Ala Trp Ala Tyr Tyr Ser Ala Val Asn Pro Glu
        835                 840                 845

Lys Asp Ile His Ser Gly Leu Ile Gly Pro Leu Leu Ile Cys Gln Lys
    850                 855                 860

Gly Ile Leu His Lys Asp Ser Asn Met Pro Val Asp Met Arg Glu Phe
865                 870                 875                 880

Val Leu Leu Phe Met Thr Phe Asp Glu Lys Lys Ser Trp Tyr Tyr Glu
                885                 890                 895

Lys Lys Ser Arg Ser Ser Trp Arg Leu Thr Ser Ser Glu Met Lys Lys
            900                 905                 910

Ser His Glu Phe His Ala Ile Asn Gly Met Ile Tyr Ser Leu Pro Gly
        915                 920                 925

Leu Lys Met Tyr Glu Gln Glu Trp Val Arg Leu His Leu Leu Asn Ile
    930                 935                 940

Gly Gly Ser Gln Asp Ile His Val Val His Phe His Gly Gln Thr Leu
945                 950                 955                 960

Leu Glu Asn Gly Asn Lys Gln His Gln Leu Gly Val Trp Pro Leu Leu
                965                 970                 975
```

```
Pro Gly Ser Phe Lys Thr Leu Glu Met Lys Ala Ser Lys Pro Gly Trp
            980                 985                 990

Trp Leu Leu Asn Thr Glu Val Gly Glu Asn Gln Arg Ala Gly Met Gln
        995                 1000                1005

Thr Pro Phe Leu Ile Met Asp Arg Asp Cys Arg Met Pro Met Gly Leu
    1010                1015                1020

Ser Thr Gly Ile Ile Ser Asp Ser Gln Ile Lys Ala Ser Glu Phe Leu
1025                1030                1035                1040

Gly Tyr Trp Glu Pro Arg Leu Ala Arg Leu Asn Asn Gly Gly Ser Tyr
                1045                1050                1055

Asn Ala Trp Ser Val Glu Lys Leu Ala Ala Glu Phe Ala Ser Lys Pro
            1060                1065                1070

Trp Ile Gln Val Asp Met Gln Lys Glu Val Ile Ile Thr Gly Ile Gln
        1075                1080                1085

Thr Gln Gly Ala Lys His Tyr Leu Lys Ser Cys Tyr Thr Thr Glu Phe
    1090                1095                1100

Tyr Val Ala Tyr Ser Ser Asn Gln Ile Asn Trp Gln Ile Phe Lys Gly
1105                1110                1115                1120

Asn Ser Thr Arg Asn Val Met Tyr Phe Asn Gly Asn Ser Asp Ala Ser
                1125                1130                1135

Thr Ile Lys Glu Asn Gln Phe Asp Pro Pro Ile Val Ala Arg Tyr Ile
            1140                1145                1150

Arg Ile Ser Pro Thr Arg Ala Tyr Asn Arg Pro Thr Leu Arg Leu Glu
        1155                1160                1165

Leu Gln Gly Cys Glu Val Asn Gly Cys Ser Thr Pro Leu Gly Met Glu
    1170                1175                1180

Asn Gly Lys Ile Glu Asn Lys Gln Ile Thr Ala Ser Ser Phe Lys Lys
1185                1190                1195                1200

Ser Trp Trp Gly Asp Tyr Trp Glu Pro Phe Arg Ala Arg Leu Asn Ala
                1205                1210                1215

Gln Gly Arg Val Asn Ala Trp Gln Ala Lys Ala Asn Asn Asn Lys Gln
            1220                1225                1230

Trp Leu Glu Ile Asp Leu Leu Lys Ile Lys Lys Ile Thr Ala Ile Ile
        1235                1240                1245

Thr Gln Gly Cys Lys Ser Leu Ser Ser Glu Met Tyr Val Lys Ser Tyr
    1250                1255                1260

Thr Ile His Tyr Ser Glu Gln Gly Val Glu Trp Lys Pro Tyr Arg Leu
1265                1270                1275                1280

Lys Ser Ser Met Val Asp Lys Ile Phe Glu Gly Asn Thr Asn Thr Lys
                1285                1290                1295

Gly His Val Lys Asn Phe Phe Asn Pro Pro Ile Ile Ser Arg Phe Ile
            1300                1305                1310

Arg Val Ile Pro Lys Thr Trp Asn Gln Ser Ile Ala Leu Arg Leu Glu
        1315                1320                1325

Leu Phe Gly Cys Asp Ile Tyr
    1330                1335

<210> SEQ ID NO 7
<211> LENGTH: 4150
<212> TYPE: DNA
<213> ORGANISM: Homo sapiens
<220> FEATURE:
<221> NAME/KEY: CDS
<222> LOCATION: (1)..(4005)

<400> SEQUENCE: 7
```

-continued

| | | |
|---|---|---|
| gca cag cta agg cag ttc tac gtg gct gct cag ggc atc agt tgg agc<br>Ala Gln Leu Arg Gln Phe Tyr Val Ala Ala Gln Gly Ile Ser Trp Ser<br>1               5                   10                  15 | | 48 |
| tac cga cct gag ccc aca aac tca agt ttg aat ctt tct gta act tcc<br>Tyr Arg Pro Glu Pro Thr Asn Ser Ser Leu Asn Leu Ser Val Thr Ser<br>            20                  25                  30 | | 96 |
| ttt aag aaa att gtc tac aga gag tat gaa cca tat ttt aag aaa gaa<br>Phe Lys Lys Ile Val Tyr Arg Glu Tyr Glu Pro Tyr Phe Lys Lys Glu<br>        35                  40                  45 | | 144 |
| aaa cca caa tct acc att tca gga ctt ctt ggg cct act tta tat gct<br>Lys Pro Gln Ser Thr Ile Ser Gly Leu Leu Gly Pro Thr Leu Tyr Ala<br>    50                  55                  60 | | 192 |
| gaa gtc gga gac atc ata aaa gtt cac ttt aaa aat aag gca gat aag<br>Glu Val Gly Asp Ile Ile Lys Val His Phe Lys Asn Lys Ala Asp Lys<br>65                  70                  75                  80 | | 240 |
| ccc ttg agc atc cat cct caa gga att agg tac agt aaa tta tca gaa<br>Pro Leu Ser Ile His Pro Gln Gly Ile Arg Tyr Ser Lys Leu Ser Glu<br>                85                  90                  95 | | 288 |
| ggt gct tct gcc ctt gac cac aca ttc cct gca gag aag atg gac gac<br>Gly Ala Ser Ala Leu Asp His Thr Phe Pro Ala Glu Lys Met Asp Asp<br>            100                 105                 110 | | 336 |
| gct gtg gct cca ggc cga gaa tac acc tat gaa tgg agt atc agt gag<br>Ala Val Ala Pro Gly Arg Glu Tyr Thr Tyr Glu Trp Ser Ile Ser Glu<br>        115                 120                 125 | | 384 |
| gac agt gga ccc acc cat gat gac cct cca tgc ctc aca cac atc tat<br>Asp Ser Gly Pro Thr His Asp Asp Pro Pro Cys Leu Thr His Ile Tyr<br>    130                 135                 140 | | 432 |
| tac tcc cat gaa aat ctg atc gag gat ttc aac tct ggg ctg att ggg<br>Tyr Ser His Glu Asn Leu Ile Glu Asp Phe Asn Ser Gly Leu Ile Gly<br>145                 150                 155                 160 | | 480 |
| ccc ctg ctt atc tgt aaa aaa ggg acc cta act gag ggt ggg aca cag<br>Pro Leu Leu Ile Cys Lys Lys Gly Thr Leu Thr Glu Gly Gly Thr Gln<br>                165                 170                 175 | | 528 |
| aag acg ttt gac aag caa atc gtg cta cta ttt gct gtg ttt gat gaa<br>Lys Thr Phe Asp Lys Gln Ile Val Leu Leu Phe Ala Val Phe Asp Glu<br>            180                 185                 190 | | 576 |
| agc aag agc tgg agc cag tca tca tcc cta atg tac aca gtc aat gga<br>Ser Lys Ser Trp Ser Gln Ser Ser Ser Leu Met Tyr Thr Val Asn Gly<br>        195                 200                 205 | | 624 |
| tat gtg aat ggg aca atg cca gat ata aca gtt tgt gcc cat gac cac<br>Tyr Val Asn Gly Thr Met Pro Asp Ile Thr Val Cys Ala His Asp His<br>    210                 215                 220 | | 672 |
| atc agc tgg cat ctg ctg gga atg agc tcg ggg cca gaa tta ttc tcc<br>Ile Ser Trp His Leu Leu Gly Met Ser Ser Gly Pro Glu Leu Phe Ser<br>225                 230                 235                 240 | | 720 |
| att cat ttc aac ggc cag gtc ctg gag cag aac cat cat aag gtc tca<br>Ile His Phe Asn Gly Gln Val Leu Glu Gln Asn His His Lys Val Ser<br>                245                 250                 255 | | 768 |
| gcc atc acc ctt gtc agt gct aca tcc act acc gca aat atg act gtg<br>Ala Ile Thr Leu Val Ser Ala Thr Ser Thr Thr Ala Asn Met Thr Val<br>            260                 265                 270 | | 816 |
| ggc cca gag gga aag tgg atc ata tct tct ctc acc cca aaa cat ttg<br>Gly Pro Glu Gly Lys Trp Ile Ile Ser Ser Leu Thr Pro Lys His Leu<br>        275                 280                 285 | | 864 |
| caa gct ggg atg cag gct tac att gac att aaa aac tgc cca aag aaa<br>Gln Ala Gly Met Gln Ala Tyr Ile Asp Ile Lys Asn Cys Pro Lys Lys<br>    290                 295                 300 | | 912 |
| acc agg aat ctt aag aaa ata act cgt gag cag agg cgg cac atg aag<br>Thr Arg Asn Leu Lys Lys Ile Thr Arg Glu Gln Arg Arg His Met Lys | | 960 |

-continued

| | | | | | | | | | | | | | | |
|---|---|---|---|---|---|---|---|---|---|---|---|---|---|---|
| 305 | | | | 310 | | | | 315 | | | | 320 | | |

```
agg tgg gaa tac ttc att gct gca gag gaa gtc att tgg gac tat gca    1008
Arg Trp Glu Tyr Phe Ile Ala Ala Glu Glu Val Ile Trp Asp Tyr Ala
                325                 330                 335 cct gta ata cca gcg aat atg gac aaa aaa tac agg tct cag cat ttg    1056
Pro Val Ile Pro Ala Asn Met Asp Lys Lys Tyr Arg Ser Gln His Leu
            340                 345                 350 gat aat ttc tca aac caa att gga aaa cat tat aag aaa gtt atg tac    1104
Asp Asn Phe Ser Asn Gln Ile Gly Lys His Tyr Lys Lys Val Met Tyr
        355                 360                 365 aca cag tac gaa gat gag tcc ttc acc aaa cat aca gtg aat ccc aat    1152
Thr Gln Tyr Glu Asp Glu Ser Phe Thr Lys His Thr Val Asn Pro Asn
    370                 375                 380 atg aaa gaa gat ggg att ttg ggt cct att atc aga gcc cag gtc aga    1200
Met Lys Glu Asp Gly Ile Leu Gly Pro Ile Ile Arg Ala Gln Val Arg
385                 390                 395                 400 gac aca ctc aaa atc gtg ttc aaa aat atg gcc agc cgc ccc tat agc    1248
Asp Thr Leu Lys Ile Val Phe Lys Asn Met Ala Ser Arg Pro Tyr Ser
                405                 410                 415 att tac cct cat gga gtg acc ttc tcg cct tat gaa gat gaa gtc aac    1296
Ile Tyr Pro His Gly Val Thr Phe Ser Pro Tyr Glu Asp Glu Val Asn
            420                 425                 430 tct tct ttc acc tca ggc agg aac aac acc atg atc aga gca gtt caa    1344
Ser Ser Phe Thr Ser Gly Arg Asn Asn Thr Met Ile Arg Ala Val Gln
        435                 440                 445 cca ggg gaa acc tat act tat aag tgg aac atc tta gag ttt gat gaa    1392
Pro Gly Glu Thr Tyr Thr Tyr Lys Trp Asn Ile Leu Glu Phe Asp Glu
    450                 455                 460 ccc aca gaa aat gat gcc cag tgc tta aca aga cca tac tac agt gac    1440
Pro Thr Glu Asn Asp Ala Gln Cys Leu Thr Arg Pro Tyr Tyr Ser Asp
465                 470                 475                 480 gtg gac atc atg aga gac atc gcc tct ggg cta ata gga cta ctt cta    1488
Val Asp Ile Met Arg Asp Ile Ala Ser Gly Leu Ile Gly Leu Leu Leu
                485                 490                 495 atc tgt aag agc aga tcc ctg gac agg cga gga ata cag agg gca gca    1536
Ile Cys Lys Ser Arg Ser Leu Asp Arg Arg Gly Ile Gln Arg Ala Ala
            500                 505                 510 gac atc gaa cag cag gct gtg ttt gct gtg ttt gat gag aac aaa agc    1584
Asp Ile Glu Gln Gln Ala Val Phe Ala Val Phe Asp Glu Asn Lys Ser
        515                 520                 525 tgg tac ctt gag gac aac atc aac aag ttt tgt gaa aat cct gat gag    1632
Trp Tyr Leu Glu Asp Asn Ile Asn Lys Phe Cys Glu Asn Pro Asp Glu
    530                 535                 540 gtg aaa cgt gat gac ccc aag ttt tat gaa tca aac atc atg agc act    1680
Val Lys Arg Asp Asp Pro Lys Phe Tyr Glu Ser Asn Ile Met Ser Thr
545                 550                 555                 560 atc aat ggc tat gtg cct gag agc ata act act ctt gga ttc tgc ttt    1728
Ile Asn Gly Tyr Val Pro Glu Ser Ile Thr Thr Leu Gly Phe Cys Phe
                565                 570                 575 gat gac act gtc cag tgg cac ttc tgt agt gtg ggg acc cag aat gaa    1776
Asp Asp Thr Val Gln Trp His Phe Cys Ser Val Gly Thr Gln Asn Glu
            580                 585                 590 att ttg acc atc cac ttc act ggg cac tca ttc atc tat gga aag agg    1824
Ile Leu Thr Ile His Phe Thr Gly His Ser Phe Ile Tyr Gly Lys Arg
        595                 600                 605 cat gag gac acc ttg acc ctc ttc ccc atg cgt gga gaa tct gtg acg    1872
His Glu Asp Thr Leu Thr Leu Phe Pro Met Arg Gly Glu Ser Val Thr
    610                 615                 620 gtc aca atg gat aat gtt gga act tgg atg tta act tcc atg aat tct    1920
```

```
Val Thr Met Asp Asn Val Gly Thr Trp Met Leu Thr Ser Met Asn Ser
625                 630                 635                 640 agt cca aga agc aaa aag ctg agg ctg aaa ttc agg gat gtt aaa tgt    1968
Ser Pro Arg Ser Lys Lys Leu Arg Leu Lys Phe Arg Asp Val Lys Cys
                645                 650                 655 atc cca gat gat gat gaa gac tca tat gag att ttt gaa cct cca gaa    2016
Ile Pro Asp Asp Asp Glu Asp Ser Tyr Glu Ile Phe Glu Pro Pro Glu
            660                 665                 670 tct aca gtc atg gct aca cgg aaa atg cat gat cgt tta gaa cct gaa    2064
Ser Thr Val Met Ala Thr Arg Lys Met His Asp Arg Leu Glu Pro Glu
        675                 680                 685 gat gaa gag agt gat gct gac tat gat tac cag aac aga ctg gct gca    2112
Asp Glu Glu Ser Asp Ala Asp Tyr Asp Tyr Gln Asn Arg Leu Ala Ala
    690                 695                 700 gca tta gga att agg agg gaa aca gat att gaa gac tct gat gat att    2160
Ala Leu Gly Ile Arg Arg Glu Thr Asp Ile Glu Asp Ser Asp Asp Ile
705                 710                 715                 720 cca gaa gat acc aca tat aag aaa gta gtt ttt cga aag tac ctc gac    2208
Pro Glu Asp Thr Thr Tyr Lys Lys Val Val Phe Arg Lys Tyr Leu Asp
                725                 730                 735 agc act ttt acc aaa cgt gat cct cga ggg gag tat gaa gag cat ctc    2256
Ser Thr Phe Thr Lys Arg Asp Pro Arg Gly Glu Tyr Glu Glu His Leu
            740                 745                 750 gga att ctt ggt cct atc atc aga gct gaa gtg gat gat gtt atc caa    2304
Gly Ile Leu Gly Pro Ile Ile Arg Ala Glu Val Asp Asp Val Ile Gln
        755                 760                 765 gtt cgt ttt aaa aat tta gca tcc aga ccg tat tct cta cat gcc cat    2352
Val Arg Phe Lys Asn Leu Ala Ser Arg Pro Tyr Ser Leu His Ala His
    770                 775                 780 gga ctt tcc tat gaa aaa tca tca gag gga aag act tat gaa gat gac    2400
Gly Leu Ser Tyr Glu Lys Ser Ser Glu Gly Lys Thr Tyr Glu Asp Asp
785                 790                 795                 800 tct cct gaa tgg ttt aag gaa gat aat gct gtt cag cca aat agc agt    2448
Ser Pro Glu Trp Phe Lys Glu Asp Asn Ala Val Gln Pro Asn Ser Ser
                805                 810                 815 tat acc tac gta tgg cat gcc act gag cga tca ggg cca gaa agt cct    2496
Tyr Thr Tyr Val Trp His Ala Thr Glu Arg Ser Gly Pro Glu Ser Pro
            820                 825                 830 ggc tct gcc tgt cgg gct tgg gcc tac tac tca gct gtg aac cca gaa    2544
Gly Ser Ala Cys Arg Ala Trp Ala Tyr Tyr Ser Ala Val Asn Pro Glu
        835                 840                 845 aaa gat att cac tca ggc ttg ata ggt ccc ctc cta atc tgc caa aaa    2592
Lys Asp Ile His Ser Gly Leu Ile Gly Pro Leu Leu Ile Cys Gln Lys
    850                 855                 860 gga ata cta cat aag gac agc aac atg cct gtg gac atg aga gaa ttt    2640
Gly Ile Leu His Lys Asp Ser Asn Met Pro Val Asp Met Arg Glu Phe
865                 870                 875                 880 gtc tta cta ttt atg acc ttt gat gaa aag aag agc tgg tac tat gaa    2688
Val Leu Leu Phe Met Thr Phe Asp Glu Lys Lys Ser Trp Tyr Tyr Glu
                885                 890                 895 aag aag tcc cga agt tct tgg aga ctc aca tcc tca gaa atg aaa aaa    2736
Lys Lys Ser Arg Ser Ser Trp Arg Leu Thr Ser Ser Glu Met Lys Lys
            900                 905                 910 tcc cat gag ttt cac gcc att aat ggg atg atc tac agc ttg cct ggc    2784
Ser His Glu Phe His Ala Ile Asn Gly Met Ile Tyr Ser Leu Pro Gly
        915                 920                 925 ctg aaa atg tat gag caa gag tgg gtg agg tta cac ctg ctg aac ata    2832
Leu Lys Met Tyr Glu Gln Glu Trp Val Arg Leu His Leu Leu Asn Ile
    930                 935                 940
```

-continued

```
ggc ggc tcc caa gac att cac gtg gtt cac ttt cac ggc cag acc ttg    2880
Gly Gly Ser Gln Asp Ile His Val Val His Phe His Gly Gln Thr Leu
945                 950                 955                 960 ctg gaa aat ggc aat aaa cag cac cag tta ggg gtc tgg ccc ctt ctg    2928
Leu Glu Asn Gly Asn Lys Gln His Gln Leu Gly Val Trp Pro Leu Leu
            965                 970                 975 cct ggt tca ttt aaa act ctt gaa atg aag gca tca aaa cct ggc tgg    2976
Pro Gly Ser Phe Lys Thr Leu Glu Met Lys Ala Ser Lys Pro Gly Trp
        980                 985                 990 tgg ctc cta aac aca gag gtt gga gaa aac cag aga gca ggg atg caa    3024
Trp Leu Leu Asn Thr Glu Val Gly Glu Asn Gln Arg Ala Gly Met Gln
    995                 1000                1005 acg cca ttt ctt atc atg gac aga gac tgt agg atg cca atg gga cta    3072
Thr Pro Phe Leu Ile Met Asp Arg Asp Cys Arg Met Pro Met Gly Leu
  1010                1015                1020 agc act ggt atc ata tct gat tca cag atc aag gct tca gag ttt ctg    3120
Ser Thr Gly Ile Ile Ser Asp Ser Gln Ile Lys Ala Ser Glu Phe Leu
1025                1030                1035                1040 ggt tac tgg gag ccc aga tta gca aga tta aac aat ggt gga tct tat    3168
Gly Tyr Trp Glu Pro Arg Leu Ala Arg Leu Asn Asn Gly Gly Ser Tyr
            1045                1050                1055 aat gct tgg agt gta gaa aaa ctt gca gca gaa ttt gcc tct aaa cct    3216
Asn Ala Trp Ser Val Glu Lys Leu Ala Ala Glu Phe Ala Ser Lys Pro
        1060                1065                1070 tgg atc cag gtg gac atg caa aag gaa gtc ata atc aca ggg atc cag    3264
Trp Ile Gln Val Asp Met Gln Lys Glu Val Ile Ile Thr Gly Ile Gln
    1075                1080                1085 acc caa ggt gcc aaa cac tac ctg aag tcc tgc tat acc aca gag ttc    3312
Thr Gln Gly Ala Lys His Tyr Leu Lys Ser Cys Tyr Thr Thr Glu Phe
  1090                1095                1100 tat gta gct tac agt tcc aac cag atc aac tgg cag atc ttc aaa ggg    3360
Tyr Val Ala Tyr Ser Ser Asn Gln Ile Asn Trp Gln Ile Phe Lys Gly
1105                1110                1115                1120 aac agc aca agg aat gtg atg tat ttt aat ggc aat tca gat gcc tct    3408
Asn Ser Thr Arg Asn Val Met Tyr Phe Asn Gly Asn Ser Asp Ala Ser
            1125                1130                1135 aca ata aaa gag aat cag ttt gac cca cct att gtg gct aga tat att    3456
Thr Ile Lys Glu Asn Gln Phe Asp Pro Pro Ile Val Ala Arg Tyr Ile
        1140                1145                1150 agg atc tct cca act cga gcc tat aac aga cct acc ctt cga ttg gaa    3504
Arg Ile Ser Pro Thr Arg Ala Tyr Asn Arg Pro Thr Leu Arg Leu Glu
    1155                1160                1165 ctg caa ggt tgt gag gta aat gga tgt tcc aca ccc ctg ggt atg gaa    3552
Leu Gln Gly Cys Glu Val Asn Gly Cys Ser Thr Pro Leu Gly Met Glu
  1170                1175                1180 aat gga aag ata gaa aac aag caa atc aca gct tct tcg ttt aag aaa    3600
Asn Gly Lys Ile Glu Asn Lys Gln Ile Thr Ala Ser Ser Phe Lys Lys
1185                1190                1195                1200 tct tgg tgg gga gat tac tgg gaa ccc ttc cgt gcc cgt ctg aat gcc    3648
Ser Trp Trp Gly Asp Tyr Trp Glu Pro Phe Arg Ala Arg Leu Asn Ala
            1205                1210                1215 cag gga cgt gtg aat gcc tgg caa gcc aag gca aac aac aat aag cag    3696
Gln Gly Arg Val Asn Ala Trp Gln Ala Lys Ala Asn Asn Asn Lys Gln
        1220                1225                1230 tgg cta gaa att gat cta ctc aag atc aag aag ata acg gca att ata    3744
Trp Leu Glu Ile Asp Leu Leu Lys Ile Lys Lys Ile Thr Ala Ile Ile
    1235                1240                1245 aca cag ggc tgc aag tct ctg tcc tct gaa atg tat gta aag agc tat    3792
Thr Gln Gly Cys Lys Ser Leu Ser Ser Glu Met Tyr Val Lys Ser Tyr
  1250                1255                1260
```

```
acc atc cac tac agt gag cag gga gtg gaa tgg aaa cca tac agg ctg    3840
Thr Ile His Tyr Ser Glu Gln Gly Val Glu Trp Lys Pro Tyr Arg Leu
1265                1270                1275                1280 aaa tcc tcc atg gtg gac aag att ttt gaa gga aat act aat acc aaa    3888
Lys Ser Ser Met Val Asp Lys Ile Phe Glu Gly Asn Thr Asn Thr Lys
                1285                1290                1295 gga cat gtg aag aac ttt ttc aac ccc cca atc att tcc agg ttt atc    3936
Gly His Val Lys Asn Phe Phe Asn Pro Pro Ile Ile Ser Arg Phe Ile
            1300                1305                1310 cgt gtc att cct aaa aca tgg aat caa agt att gca ctt cgc ctg gaa    3984
Arg Val Ile Pro Lys Thr Trp Asn Gln Ser Ile Ala Leu Arg Leu Glu
        1315                1320                1325 ctc ttt ggc tgt gat att tac tagaattgaa cattcaaaaa ccctggaag        4035
Leu Phe Gly Cys Asp Ile Tyr
    1330                1335 agactcttta agacctcaaa ccatttagaa tgggcaatgt attttacgct gtgttaaatg  4095
ttaacagttt tccactattt ctctttcttt tctattagtg aataaattt tatac        4150

<210> SEQ ID NO 8
<211> LENGTH: 1335
<212> TYPE: PRT
<213> ORGANISM: Homo sapiens

<400> SEQUENCE: 8

Ala Gln Leu Arg Gln Phe Tyr Val Ala Ala Gln Gly Ile Ser Trp Ser
1               5                   10                  15

Tyr Arg Pro Glu Pro Thr Asn Ser Ser Leu Asn Leu Ser Val Thr Ser
            20                  25                  30

Phe Lys Lys Ile Val Tyr Arg Glu Tyr Glu Pro Tyr Phe Lys Lys Glu
        35                  40                  45

Lys Pro Gln Ser Thr Ile Ser Gly Leu Leu Gly Pro Thr Leu Tyr Ala
    50                  55                  60

Glu Val Gly Asp Ile Ile Lys Val His Phe Lys Asn Lys Ala Asp Lys
65                  70                  75                  80

Pro Leu Ser Ile His Pro Gln Gly Ile Arg Tyr Ser Lys Leu Ser Glu
                85                  90                  95

Gly Ala Ser Ala Leu Asp His Thr Phe Pro Ala Glu Lys Met Asp Asp
            100                 105                 110

Ala Val Ala Pro Gly Arg Glu Tyr Thr Tyr Glu Trp Ser Ile Ser Glu
        115                 120                 125

Asp Ser Gly Pro Thr His Asp Asp Pro Pro Cys Leu Thr His Ile Tyr
    130                 135                 140

Tyr Ser His Glu Asn Leu Ile Glu Asp Phe Asn Ser Gly Leu Ile Gly
145                 150                 155                 160

Pro Leu Leu Ile Cys Lys Lys Gly Thr Leu Thr Glu Gly Gly Thr Gln
                165                 170                 175

Lys Thr Phe Asp Lys Gln Ile Val Leu Leu Phe Ala Val Phe Asp Glu
            180                 185                 190

Ser Lys Ser Trp Ser Gln Ser Ser Ser Leu Met Tyr Thr Val Asn Gly
        195                 200                 205

Tyr Val Asn Gly Thr Met Pro Asp Ile Thr Val Cys Ala His Asp His
    210                 215                 220

Ile Ser Trp His Leu Leu Gly Met Ser Ser Gly Pro Glu Leu Phe Ser
225                 230                 235                 240

Ile His Phe Asn Gly Gln Val Leu Glu Gln Asn His His Lys Val Ser
```

-continued

```
                245                 250                 255
Ala Ile Thr Leu Val Ser Ala Thr Ser Thr Thr Ala Asn Met Thr Val
                    260                 265                 270

Gly Pro Glu Gly Lys Trp Ile Ile Ser Ser Leu Thr Pro Lys His Leu
        275                 280                 285

Gln Ala Gly Met Gln Ala Tyr Ile Asp Ile Lys Asn Cys Pro Lys Lys
    290                 295                 300

Thr Arg Asn Leu Lys Lys Ile Thr Arg Glu Gln Arg His Met Lys
305                 310                 315                 320

Arg Trp Glu Tyr Phe Ile Ala Ala Glu Val Ile Trp Asp Tyr Ala
                325                 330                 335

Pro Val Ile Pro Ala Asn Met Asp Lys Lys Tyr Arg Ser Gln His Leu
                    340                 345                 350

Asp Asn Phe Ser Asn Gln Ile Gly Lys His Tyr Lys Val Met Tyr
            355                 360                 365

Thr Gln Tyr Glu Asp Glu Ser Phe Thr Lys His Thr Val Asn Pro Asn
    370                 375                 380

Met Lys Glu Asp Gly Ile Leu Gly Pro Ile Ile Arg Ala Gln Val Arg
385                 390                 395                 400

Asp Thr Leu Lys Ile Val Phe Lys Asn Met Ala Ser Arg Pro Tyr Ser
                405                 410                 415

Ile Tyr Pro His Gly Val Thr Phe Ser Pro Tyr Glu Asp Glu Val Asn
                420                 425                 430

Ser Ser Phe Thr Ser Gly Arg Asn Asn Thr Met Ile Arg Ala Val Gln
            435                 440                 445

Pro Gly Glu Thr Tyr Thr Tyr Lys Trp Asn Ile Leu Glu Phe Asp Glu
    450                 455                 460

Pro Thr Glu Asn Asp Ala Gln Cys Leu Thr Arg Pro Tyr Tyr Ser Asp
465                 470                 475                 480

Val Asp Ile Met Arg Asp Ile Ala Ser Gly Leu Ile Gly Leu Leu Leu
                485                 490                 495

Ile Cys Lys Ser Arg Ser Leu Asp Arg Arg Gly Ile Gln Arg Ala Ala
                500                 505                 510

Asp Ile Glu Gln Gln Ala Val Phe Ala Val Phe Asp Glu Asn Lys Ser
    515                 520                 525

Trp Tyr Leu Glu Asp Asn Ile Asn Lys Phe Cys Glu Asn Pro Asp Glu
    530                 535                 540

Val Lys Arg Asp Asp Pro Lys Phe Tyr Glu Ser Asn Ile Met Ser Thr
545                 550                 555                 560

Ile Asn Gly Tyr Val Pro Glu Ser Ile Thr Thr Leu Gly Phe Cys Phe
                565                 570                 575

Asp Asp Thr Val Gln Trp His Phe Cys Ser Val Gly Thr Gln Asn Glu
            580                 585                 590

Ile Leu Thr Ile His Phe Thr Gly His Ser Phe Ile Tyr Gly Lys Arg
        595                 600                 605

His Glu Asp Thr Leu Thr Leu Phe Pro Met Arg Gly Glu Ser Val Thr
    610                 615                 620

Val Thr Met Asp Asn Val Gly Thr Trp Met Leu Thr Ser Met Asn Ser
625                 630                 635                 640

Ser Pro Arg Ser Lys Lys Leu Arg Leu Lys Phe Arg Asp Val Lys Cys
                645                 650                 655

Ile Pro Asp Asp Asp Glu Asp Ser Tyr Glu Ile Phe Glu Pro Pro Glu
                660                 665                 670
```

-continued

```
Ser Thr Val Met Ala Thr Arg Lys Met His Asp Arg Leu Glu Pro Glu
        675                 680                 685

Asp Glu Glu Ser Asp Ala Asp Tyr Asp Tyr Gln Asn Arg Leu Ala Ala
        690                 695                 700

Ala Leu Gly Ile Arg Arg Glu Thr Asp Ile Glu Asp Ser Asp Asp Ile
705                 710                 715                 720

Pro Glu Asp Thr Thr Tyr Lys Lys Val Val Phe Arg Lys Tyr Leu Asp
                725                 730                 735

Ser Thr Phe Thr Lys Arg Asp Pro Arg Gly Glu Tyr Glu His Leu
            740                 745                 750

Gly Ile Leu Gly Pro Ile Ile Arg Ala Glu Val Asp Val Ile Gln
        755                 760                 765

Val Arg Phe Lys Asn Leu Ala Ser Arg Pro Tyr Ser Leu His Ala His
    770                 775                 780

Gly Leu Ser Tyr Glu Lys Ser Ser Glu Gly Lys Thr Tyr Glu Asp Asp
785                 790                 795                 800

Ser Pro Glu Trp Phe Lys Glu Asp Asn Ala Val Gln Pro Asn Ser Ser
                805                 810                 815

Tyr Thr Tyr Val Trp His Ala Thr Glu Arg Ser Gly Pro Glu Ser Pro
            820                 825                 830

Gly Ser Ala Cys Arg Ala Trp Ala Tyr Tyr Ser Ala Val Asn Pro Glu
        835                 840                 845

Lys Asp Ile His Ser Gly Leu Ile Gly Pro Leu Leu Ile Cys Gln Lys
    850                 855                 860

Gly Ile Leu His Lys Asp Ser Asn Met Pro Val Asp Met Arg Glu Phe
865                 870                 875                 880

Val Leu Leu Phe Met Thr Phe Asp Glu Lys Lys Ser Trp Tyr Tyr Glu
                885                 890                 895

Lys Lys Ser Arg Ser Ser Trp Arg Leu Thr Ser Ser Glu Met Lys Lys
            900                 905                 910

Ser His Glu Phe His Ala Ile Asn Gly Met Ile Tyr Ser Leu Pro Gly
        915                 920                 925

Leu Lys Met Tyr Glu Gln Glu Trp Val Arg Leu His Leu Leu Asn Ile
    930                 935                 940

Gly Gly Ser Gln Asp Ile His Val Val His Phe His Gly Gln Thr Leu
945                 950                 955                 960

Leu Glu Asn Gly Asn Lys Gln His Gln Leu Gly Val Trp Pro Leu Leu
                965                 970                 975

Pro Gly Ser Phe Lys Thr Leu Glu Met Lys Ala Ser Lys Pro Gly Trp
            980                 985                 990

Trp Leu Leu Asn Thr Glu Val Gly Glu Asn Gln Arg Ala Gly Met Gln
        995                 1000                1005

Thr Pro Phe Leu Ile Met Asp Arg Asp Cys Arg Met Pro Met Gly Leu
    1010                1015                1020

Ser Thr Gly Ile Ile Ser Asp Ser Gln Ile Lys Ala Ser Glu Phe Leu
1025                1030                1035                1040

Gly Tyr Trp Glu Pro Arg Leu Ala Arg Leu Asn Asn Gly Gly Ser Tyr
                1045                1050                1055

Asn Ala Trp Ser Val Glu Lys Leu Ala Ala Glu Phe Ala Ser Lys Pro
            1060                1065                1070

Trp Ile Gln Val Asp Met Gln Lys Glu Val Ile Ile Thr Gly Ile Gln
        1075                1080                1085
```

```
Thr Gln Gly Ala Lys His Tyr Leu Lys Ser Cys Tyr Thr Thr Glu Phe
    1090                1095                1100

Tyr Val Ala Tyr Ser Ser Asn Gln Ile Asn Trp Gln Ile Phe Lys Gly
1105                1110                1115                1120

Asn Ser Thr Arg Asn Val Met Tyr Phe Asn Gly Asn Ser Asp Ala Ser
                1125                1130                1135

Thr Ile Lys Glu Asn Gln Phe Asp Pro Pro Ile Val Ala Arg Tyr Ile
        1140                1145                1150

Arg Ile Ser Pro Thr Arg Ala Tyr Asn Arg Pro Thr Leu Arg Leu Glu
    1155                1160                1165

Leu Gln Gly Cys Glu Val Asn Gly Cys Ser Thr Pro Leu Gly Met Glu
1170                1175                1180

Asn Gly Lys Ile Glu Asn Lys Gln Ile Thr Ala Ser Ser Phe Lys Lys
1185                1190                1195                1200

Ser Trp Trp Gly Asp Tyr Trp Glu Pro Phe Arg Ala Arg Leu Asn Ala
                1205                1210                1215

Gln Gly Arg Val Asn Ala Trp Gln Ala Lys Ala Asn Asn Asn Lys Gln
        1220                1225                1230

Trp Leu Glu Ile Asp Leu Leu Lys Ile Lys Lys Ile Thr Ala Ile Ile
    1235                1240                1245

Thr Gln Gly Cys Lys Ser Leu Ser Ser Glu Met Tyr Val Lys Ser Tyr
1250                1255                1260

Thr Ile His Tyr Ser Glu Gln Gly Val Glu Trp Lys Pro Tyr Arg Leu
1265                1270                1275                1280

Lys Ser Ser Met Val Asp Lys Ile Phe Glu Gly Asn Thr Asn Thr Lys
                1285                1290                1295

Gly His Val Lys Asn Phe Phe Asn Pro Pro Ile Ile Ser Arg Phe Ile
        1300                1305                1310

Arg Val Ile Pro Lys Thr Trp Asn Gln Ser Ile Ala Leu Arg Leu Glu
    1315                1320                1325

Leu Phe Gly Cys Asp Ile Tyr
1330                1335

<210> SEQ ID NO 9
<211> LENGTH: 4150
<212> TYPE: DNA
<213> ORGANISM: Homo sapiens
<220> FEATURE:
<221> NAME/KEY: CDS
<222> LOCATION: (1)..(4005)

<400> SEQUENCE: 9 gca cag cta agg cag ttc tac gtg gct gct cag ggc atc agt tgg agc      48
Ala Gln Leu Arg Gln Phe Tyr Val Ala Ala Gln Gly Ile Ser Trp Ser
  1               5                  10                  15 tac cga cct gag ccc aca aac tca agt ttg aat ctt tct gta act tcc      96
Tyr Arg Pro Glu Pro Thr Asn Ser Ser Leu Asn Leu Ser Val Thr Ser
                 20                  25                  30 ttt aag aaa att gtc tac aga gag tat gaa cca tat ttt aag aaa gaa     144
Phe Lys Lys Ile Val Tyr Arg Glu Tyr Glu Pro Tyr Phe Lys Lys Glu
             35                  40                  45 aaa cca caa tct acc att tca gga ctt ctt ggg cct act tta tat gct     192
Lys Pro Gln Ser Thr Ile Ser Gly Leu Leu Gly Pro Thr Leu Tyr Ala
         50                  55                  60 gaa gtc gga gac atc ata aaa gtt cac ttt aaa aat aag gca gat aag     240
Glu Val Gly Asp Ile Ile Lys Val His Phe Lys Asn Lys Ala Asp Lys
 65                  70                  75                  80
```

```
ccc ttg agc atc cat cct caa gga att agg tac agt aaa tta tca gaa      288
Pro Leu Ser Ile His Pro Gln Gly Ile Arg Tyr Ser Lys Leu Ser Glu
             85                  90                  95 ggt gct tct tac ctt gac cac aca ttc cct gcg gag aag atg gac gcc      336
Gly Ala Ser Tyr Leu Asp His Thr Phe Pro Ala Glu Lys Met Asp Ala
        100                 105                 110 gct gtg gct cca ggc cga gaa tac acc tat gaa tgg agt atc agt gag      384
Ala Val Ala Pro Gly Arg Glu Tyr Thr Tyr Glu Trp Ser Ile Ser Glu
    115                 120                 125 gac agt gga ccc acc cat gat gac cct cca tgc ctc aca cac atc tat      432
Asp Ser Gly Pro Thr His Asp Asp Pro Pro Cys Leu Thr His Ile Tyr
130                 135                 140 tac tcc cat gaa aat ctg atc gag gat ttc aac tct ggg ctg att ggg      480
Tyr Ser His Glu Asn Leu Ile Glu Asp Phe Asn Ser Gly Leu Ile Gly
145                 150                 155                 160 ccc ctg ctt atc tgt aaa aaa ggg acc cta act gag ggt ggg aca cag      528
Pro Leu Leu Ile Cys Lys Lys Gly Thr Leu Thr Glu Gly Gly Thr Gln
                165                 170                 175 aag acg ttt gac aag caa atc gtg cta cta ttt gct gtg ttt gat gaa      576
Lys Thr Phe Asp Lys Gln Ile Val Leu Leu Phe Ala Val Phe Asp Glu
            180                 185                 190 agc aag agc tgg agc cag tca tca tcc cta atg tac aca gtc aat gga      624
Ser Lys Ser Trp Ser Gln Ser Ser Ser Leu Met Tyr Thr Val Asn Gly
        195                 200                 205 tat gtg aat ggg aca atg cca gat ata aca gtt tgt gcc cat gac cac      672
Tyr Val Asn Gly Thr Met Pro Asp Ile Thr Val Cys Ala His Asp His
    210                 215                 220 atc agc tgg cat ctg ctg gga atg agc tcg ggg cca gaa tta ttc tcc      720
Ile Ser Trp His Leu Leu Gly Met Ser Ser Gly Pro Glu Leu Phe Ser
225                 230                 235                 240 att cat ttc aac ggc cag gtc ctg gag cag aac cat cat aag gtc tca      768
Ile His Phe Asn Gly Gln Val Leu Glu Gln Asn His His Lys Val Ser
                245                 250                 255 gcc atc acc ctt gtc agt gct aca tcc act acc gca aat atg act gtg      816
Ala Ile Thr Leu Val Ser Ala Thr Ser Thr Thr Ala Asn Met Thr Val
            260                 265                 270 ggc cca gag gga aag tgg atc ata tct tct ctc acc cca aaa cat ttg      864
Gly Pro Glu Gly Lys Trp Ile Ile Ser Ser Leu Thr Pro Lys His Leu
        275                 280                 285 caa gct ggg atg cag gct tac att gac att aaa aac tgc cca aag aaa      912
Gln Ala Gly Met Gln Ala Tyr Ile Asp Ile Lys Asn Cys Pro Lys Lys
    290                 295                 300 acc agg aat ctt aag aaa ata act cgt gag cag agg cgg cac atg aag      960
Thr Arg Asn Leu Lys Lys Ile Thr Arg Glu Gln Arg Arg His Met Lys
305                 310                 315                 320 agg tgg gaa tac ttc att gct gca gag gaa gtc att tgg gac tat gca     1008
Arg Trp Glu Tyr Phe Ile Ala Ala Glu Glu Val Ile Trp Asp Tyr Ala
                325                 330                 335 cct gta ata cca gcg aat atg gac aaa aaa tac agg tct cag cat ttg     1056
Pro Val Ile Pro Ala Asn Met Asp Lys Lys Tyr Arg Ser Gln His Leu
            340                 345                 350 gat aat ttc tca aac caa att gga aaa cat tat aag aaa gtt atg tac     1104
Asp Asn Phe Ser Asn Gln Ile Gly Lys His Tyr Lys Lys Val Met Tyr
        355                 360                 365 aca cag tac gaa gat gag tcc ttc acc aaa cat aca gtg aat ccc aat     1152
Thr Gln Tyr Glu Asp Glu Ser Phe Thr Lys His Thr Val Asn Pro Asn
    370                 375                 380 atg aaa gaa gat ggg att ttg ggt cct att atc aga gcc cag gtc aga     1200
Met Lys Glu Asp Gly Ile Leu Gly Pro Ile Ile Arg Ala Gln Val Arg
385                 390                 395                 400
```

-continued

| | |
|---|---|
| gac aca ctc aaa atc gtg ttc aaa aat atg gcc agc cgc ccc tat agc<br>Asp Thr Leu Lys Ile Val Phe Lys Asn Met Ala Ser Arg Pro Tyr Ser<br>405 410 415 | 1248 |
| att tac cct cat gga gtg acc ttc tcg cct tat gaa gat gaa gtc aac<br>Ile Tyr Pro His Gly Val Thr Phe Ser Pro Tyr Glu Asp Glu Val Asn<br>420 425 430 | 1296 |
| tct tct ttc acc tca ggc agg aac aac acc atg atc aga gca gtt caa<br>Ser Ser Phe Thr Ser Gly Arg Asn Asn Thr Met Ile Arg Ala Val Gln<br>435 440 445 | 1344 |
| cca ggg gaa acc tat act tat aag tgg aac atc tta gag ttt gat gaa<br>Pro Gly Glu Thr Tyr Thr Tyr Lys Trp Asn Ile Leu Glu Phe Asp Glu<br>450 455 460 | 1392 |
| ccc aca gaa aat gat gcc cag tgc tta aca aga cca tac tac agt gac<br>Pro Thr Glu Asn Asp Ala Gln Cys Leu Thr Arg Pro Tyr Tyr Ser Asp<br>465 470 475 480 | 1440 |
| gtg gac atc atg aga gac atc gcc tct ggg cta ata gga cta ctt cta<br>Val Asp Ile Met Arg Asp Ile Ala Ser Gly Leu Ile Gly Leu Leu Leu<br>485 490 495 | 1488 |
| atc tgt aag agc aga tcc ctg gac agg cga gga ata cag agg gca gca<br>Ile Cys Lys Ser Arg Ser Leu Asp Arg Arg Gly Ile Gln Arg Ala Ala<br>500 505 510 | 1536 |
| gac atc gaa cag cag gct gtg ttt gct gtg ttt gat gag aac aaa agc<br>Asp Ile Glu Gln Gln Ala Val Phe Ala Val Phe Asp Glu Asn Lys Ser<br>515 520 525 | 1584 |
| tgg tac ctt gag gac aac atc aac aag ttt tgt gaa aat cct gat gag<br>Trp Tyr Leu Glu Asp Asn Ile Asn Lys Phe Cys Glu Asn Pro Asp Glu<br>530 535 540 | 1632 |
| gtg aaa cgt gat gac ccc aag ttt tat gaa tca aac atc atg agc act<br>Val Lys Arg Asp Asp Pro Lys Phe Tyr Glu Ser Asn Ile Met Ser Thr<br>545 550 555 560 | 1680 |
| atc aat ggc tat gtg cct gag agc ata act act ctt gga ttc tgc ttt<br>Ile Asn Gly Tyr Val Pro Glu Ser Ile Thr Thr Leu Gly Phe Cys Phe<br>565 570 575 | 1728 |
| gat gac act gtc cag tgg cac ttc tgt agt gtg ggg acc cag aat gaa<br>Asp Asp Thr Val Gln Trp His Phe Cys Ser Val Gly Thr Gln Asn Glu<br>580 585 590 | 1776 |
| att ttg acc atc cac ttc act ggg cac tca ttc atc tat gga aag agg<br>Ile Leu Thr Ile His Phe Thr Gly His Ser Phe Ile Tyr Gly Lys Arg<br>595 600 605 | 1824 |
| cat gag gac acc ttg acc ctc ttc ccc atg cgt gga gaa tct gtg acg<br>His Glu Asp Thr Leu Thr Leu Phe Pro Met Arg Gly Glu Ser Val Thr<br>610 615 620 | 1872 |
| gtc aca atg gat aat gtt gga act tgg atg tta act tcc atg aat tct<br>Val Thr Met Asp Asn Val Gly Thr Trp Met Leu Thr Ser Met Asn Ser<br>625 630 635 640 | 1920 |
| agt cca aga agc aaa aag ctg agg ctg aaa ttc agg gat gtt aaa tgt<br>Ser Pro Arg Ser Lys Lys Leu Arg Leu Lys Phe Arg Asp Val Lys Cys<br>645 650 655 | 1968 |
| atc cca gat gat gat gaa gac tca tat gag att ttt gaa cct cca gaa<br>Ile Pro Asp Asp Asp Glu Asp Ser Tyr Glu Ile Phe Glu Pro Pro Glu<br>660 665 670 | 2016 |
| tct aca gtc atg gct aca cgg aaa atg cat gat cgt tta gaa cct gaa<br>Ser Thr Val Met Ala Thr Arg Lys Met His Asp Arg Leu Glu Pro Glu<br>675 680 685 | 2064 |
| gat gaa gag agt gat gct gac tat gat tac cag aac aga ctg gct gca<br>Asp Glu Glu Ser Asp Ala Asp Tyr Asp Tyr Gln Asn Arg Leu Ala Ala<br>690 695 700 | 2112 |
| gca tta gga att agg agg gaa aca gat att gaa gac tct gat gat att<br>Ala Leu Gly Ile Arg Arg Glu Thr Asp Ile Glu Asp Ser Asp Asp Ile | 2160 |

-continued

| | | | |
|---|---|---|---|
| | 705 | 710 | 715 | 720 | |
| cca gaa gat acc aca tat aag aaa gta gtt ttt cga aag tac ctc gac<br>Pro Glu Asp Thr Thr Tyr Lys Lys Val Val Phe Arg Lys Tyr Leu Asp<br>725 730 735 | 2208 |
| agc act ttt acc aaa cgt gat cct cga ggg gag tat gaa gag cat ctc<br>Ser Thr Phe Thr Lys Arg Asp Pro Arg Gly Glu Tyr Glu Glu His Leu<br>740 745 750 | 2256 |
| gga att ctt ggt cct atc atc aga gct gaa gtg gat gat gtt atc caa<br>Gly Ile Leu Gly Pro Ile Ile Arg Ala Glu Val Asp Asp Val Ile Gln<br>755 760 765 | 2304 |
| gtt cgt ttt aaa aat tta gca tcc aga ccg tat tct cta cat gcc cat<br>Val Arg Phe Lys Asn Leu Ala Ser Arg Pro Tyr Ser Leu His Ala His<br>770 775 780 | 2352 |
| gga ctt tcc tat gaa aaa tca tca gag gga aag act tat gaa gat gac<br>Gly Leu Ser Tyr Glu Lys Ser Ser Glu Gly Lys Thr Tyr Glu Asp Asp<br>785 790 795 800 | 2400 |
| tct cct gaa tgg ttt aag gaa gat aat gct gtt cag cca aat agc agt<br>Ser Pro Glu Trp Phe Lys Glu Asp Asn Ala Val Gln Pro Asn Ser Ser<br>805 810 815 | 2448 |
| tat acc tac gta tgg cat gcc act gag cga tca ggg cca gaa agt cct<br>Tyr Thr Tyr Val Trp His Ala Thr Glu Arg Ser Gly Pro Glu Ser Pro<br>820 825 830 | 2496 |
| ggc tct gcc tgt cgg gct tgg gcc tac tac tca gct gtg aac cca gaa<br>Gly Ser Ala Cys Arg Ala Trp Ala Tyr Tyr Ser Ala Val Asn Pro Glu<br>835 840 845 | 2544 |
| aaa gat att cac tca ggc ttg ata ggt ccc ctc cta atc tgc caa aaa<br>Lys Asp Ile His Ser Gly Leu Ile Gly Pro Leu Leu Ile Cys Gln Lys<br>850 855 860 | 2592 |
| gga ata cta cat aag gac agc aac atg cct gtg gac atg aga gaa ttt<br>Gly Ile Leu His Lys Asp Ser Asn Met Pro Val Asp Met Arg Glu Phe<br>865 870 875 880 | 2640 |
| gtc tta cta ttt atg acc ttt gat gaa aag aag agc tgg tac tat gaa<br>Val Leu Leu Phe Met Thr Phe Asp Glu Lys Lys Ser Trp Tyr Tyr Glu<br>885 890 895 | 2688 |
| aag aag tcc cga agt tct tgg aga ctc aca tcc tca gaa atg aaa aaa<br>Lys Lys Ser Arg Ser Ser Trp Arg Leu Thr Ser Ser Glu Met Lys Lys<br>900 905 910 | 2736 |
| tcc cat gag ttt cac gcc att aat ggg atg atc tac agc ttg cct ggc<br>Ser His Glu Phe His Ala Ile Asn Gly Met Ile Tyr Ser Leu Pro Gly<br>915 920 925 | 2784 |
| ctg aaa atg tat gag caa gag tgg gtg agg tta cac ctg ctg aac ata<br>Leu Lys Met Tyr Glu Gln Glu Trp Val Arg Leu His Leu Leu Asn Ile<br>930 935 940 | 2832 |
| ggc ggc tcc caa gac att cac gtg gtt cac ttt cac ggc cag acc ttg<br>Gly Gly Ser Gln Asp Ile His Val Val His Phe His Gly Gln Thr Leu<br>945 950 955 960 | 2880 |
| ctg gaa aat ggc aat aaa cag cac cag tta ggg gtc tgg ccc ctt ctg<br>Leu Glu Asn Gly Asn Lys Gln His Gln Leu Gly Val Trp Pro Leu Leu<br>965 970 975 | 2928 |
| cct ggt tca ttt aaa act ctt gaa atg aag gca tca aaa cct ggc tgg<br>Pro Gly Ser Phe Lys Thr Leu Glu Met Lys Ala Ser Lys Pro Gly Trp<br>980 985 990 | 2976 |
| tgg ctc cta aac aca gag gtt gga gaa aac cag aga gca ggg atg caa<br>Trp Leu Leu Asn Thr Glu Val Gly Glu Asn Gln Arg Ala Gly Met Gln<br>995 1000 1005 | 3024 |
| acg cca ttt ctt atc atg gac aga gac tgt agg atg cca atg gga cta<br>Thr Pro Phe Leu Ile Met Asp Arg Asp Cys Arg Met Pro Met Gly Leu<br>1010 1015 1020 | 3072 |
| agc act ggt atc ata tct gat tca cag atc aag gct tca gag ttt ctg<br> | 3120 |

```
Ser Thr Gly Ile Ile Ser Asp Ser Gln Ile Lys Ala Ser Glu Phe Leu
1025                1030                1035                1040 ggt tac tgg gag ccc aga tta gca aga tta aac aat ggt gga tct tat      3168
Gly Tyr Trp Glu Pro Arg Leu Ala Arg Leu Asn Asn Gly Gly Ser Tyr
        1045                1050                1055 aat gct tgg agt gta gaa aaa ctt gca gca gaa ttt gcc tct aaa cct      3216
Asn Ala Trp Ser Val Glu Lys Leu Ala Ala Glu Phe Ala Ser Lys Pro
    1060                1065                1070 tgg atc cag gtg gac atg caa aag gaa gtc ata atc aca ggg atc cag      3264
Trp Ile Gln Val Asp Met Gln Lys Glu Val Ile Ile Thr Gly Ile Gln
1075                1080                1085 acc caa ggt gcc aaa cac tac ctg aag tcc tgc tat acc aca gag ttc      3312
Thr Gln Gly Ala Lys His Tyr Leu Lys Ser Cys Tyr Thr Thr Glu Phe
 1090                1095                1100 tat gta gct tac agt tcc aac cag atc aac tgg cag atc ttc aaa ggg      3360
Tyr Val Ala Tyr Ser Ser Asn Gln Ile Asn Trp Gln Ile Phe Lys Gly
1105                1110                1115                1120 aac agc aca agg aat gtg atg tat ttt aat ggc aat tca gat gcc tct      3408
Asn Ser Thr Arg Asn Val Met Tyr Phe Asn Gly Asn Ser Asp Ala Ser
            1125                1130                1135 aca ata aaa gag aat cag ttt gac cca cct att gtg gct aga tat att      3456
Thr Ile Lys Glu Asn Gln Phe Asp Pro Pro Ile Val Ala Arg Tyr Ile
        1140                1145                1150 agg atc tct cca act cga gcc tat aac aga cct acc ctt cga ttg gaa      3504
Arg Ile Ser Pro Thr Arg Ala Tyr Asn Arg Pro Thr Leu Arg Leu Glu
    1155                1160                1165 ctg caa ggt tgt gag gta aat gga tgt tcc aca ccc ctg ggt atg gaa      3552
Leu Gln Gly Cys Glu Val Asn Gly Cys Ser Thr Pro Leu Gly Met Glu
1170                1175                1180 aat gga aag ata gaa aac aag caa atc aca gct tct tcg ttt aag aaa      3600
Asn Gly Lys Ile Glu Asn Lys Gln Ile Thr Ala Ser Ser Phe Lys Lys
1185                1190                1195                1200 tct tgg tgg gga gat tac tgg gaa ccc ttc cgt gcc cgt ctg aat gcc      3648
Ser Trp Trp Gly Asp Tyr Trp Glu Pro Phe Arg Ala Arg Leu Asn Ala
            1205                1210                1215 cag gga cgt gtg aat gcc tgg caa gcc aag gca aac aac aat aag cag      3696
Gln Gly Arg Val Asn Ala Trp Gln Ala Lys Ala Asn Asn Asn Lys Gln
        1220                1225                1230 tgg cta gaa att gat cta ctc aag atc aag aag ata acg gca att ata      3744
Trp Leu Glu Ile Asp Leu Leu Lys Ile Lys Lys Ile Thr Ala Ile Ile
    1235                1240                1245 aca cag ggc tgc aag tct ctg tcc tct gaa atg tat gta aag agc tat      3792
Thr Gln Gly Cys Lys Ser Leu Ser Ser Glu Met Tyr Val Lys Ser Tyr
1250                1255                1260 acc atc cac tac agt gag cag gga gtg gaa tgg aaa cca tac agg ctg      3840
Thr Ile His Tyr Ser Glu Gln Gly Val Glu Trp Lys Pro Tyr Arg Leu
1265                1270                1275                1280 aaa tcc tcc atg gtg gac aag att ttt gaa gga aat act aat acc aaa      3888
Lys Ser Ser Met Val Asp Lys Ile Phe Glu Gly Asn Thr Asn Thr Lys
            1285                1290                1295 gga cat gtg aag aac ttt ttc aac ccc cca atc att tcc agg ttt atc      3936
Gly His Val Lys Asn Phe Phe Asn Pro Pro Ile Ile Ser Arg Phe Ile
        1300                1305                1310 cgt gtc att cct aaa aca tgg aat caa agt att gca ctt cgc ctg gaa      3984
Arg Val Ile Pro Lys Thr Trp Asn Gln Ser Ile Ala Leu Arg Leu Glu
    1315                1320                1325 ctc ttt ggc tgt gat att tac tagaattgaa cattcaaaaa ccctggaag          4035
Leu Phe Gly Cys Asp Ile Tyr
1330                1335
```
agactcttta agacctcaaa ccatttagaa tgggcaatgt attttacgct gtgttaaatg    4095
ttaacagttt tccactattt ctctttcttt tctattagtg aataaaattt tatac         4150

<210> SEQ ID NO 10
<211> LENGTH: 1335
<212> TYPE: PRT
<213> ORGANISM: Homo sapiens

<400> SEQUENCE: 10

Ala Gln Leu Arg Gln Phe Tyr Val Ala Ala Gln Gly Ile Ser Trp Ser
 1               5                  10                  15

Tyr Arg Pro Glu Pro Thr Asn Ser Ser Leu Asn Leu Ser Val Thr Ser
            20                  25                  30

Phe Lys Lys Ile Val Tyr Arg Glu Tyr Glu Pro Tyr Phe Lys Lys Glu
        35                  40                  45

Lys Pro Gln Ser Thr Ile Ser Gly Leu Leu Gly Pro Thr Leu Tyr Ala
    50                  55                  60

Glu Val Gly Asp Ile Ile Lys Val His Phe Lys Asn Lys Ala Asp Lys
65                  70                  75                  80

Pro Leu Ser Ile His Pro Gln Gly Ile Arg Tyr Ser Lys Leu Ser Glu
                85                  90                  95

Gly Ala Ser Tyr Leu Asp His Thr Phe Pro Ala Glu Lys Met Asp Ala
           100                 105                 110

Ala Val Ala Pro Gly Arg Glu Tyr Thr Tyr Glu Trp Ser Ile Ser Glu
       115                 120                 125

Asp Ser Gly Pro Thr His Asp Asp Pro Pro Cys Leu Thr His Ile Tyr
   130                 135                 140

Tyr Ser His Glu Asn Leu Ile Glu Asp Phe Asn Ser Gly Leu Ile Gly
145                 150                 155                 160

Pro Leu Leu Ile Cys Lys Lys Gly Thr Leu Thr Glu Gly Gly Thr Gln
                165                 170                 175

Lys Thr Phe Asp Lys Gln Ile Val Leu Leu Phe Ala Val Phe Asp Glu
            180                 185                 190

Ser Lys Ser Trp Ser Gln Ser Ser Ser Leu Met Tyr Thr Val Asn Gly
        195                 200                 205

Tyr Val Asn Gly Thr Met Pro Asp Ile Thr Val Cys Ala His Asp His
    210                 215                 220

Ile Ser Trp His Leu Leu Gly Met Ser Ser Gly Pro Glu Leu Phe Ser
225                 230                 235                 240

Ile His Phe Asn Gly Gln Val Leu Glu Gln Asn His His Lys Val Ser
                245                 250                 255

Ala Ile Thr Leu Val Ser Ala Thr Ser Thr Thr Ala Asn Met Thr Val
            260                 265                 270

Gly Pro Glu Gly Lys Trp Ile Ile Ser Ser Leu Thr Pro Lys His Leu
        275                 280                 285

Gln Ala Gly Met Gln Ala Tyr Ile Asp Ile Lys Asn Cys Pro Lys Lys
    290                 295                 300

Thr Arg Asn Leu Lys Lys Ile Thr Arg Glu Gln Arg Arg His Met Lys
305                 310                 315                 320

Arg Trp Glu Tyr Phe Ile Ala Ala Glu Glu Val Ile Trp Asp Tyr Ala
                325                 330                 335

Pro Val Ile Pro Ala Asn Met Asp Lys Lys Tyr Arg Ser Gln His Leu
            340                 345                 350

Asp Asn Phe Ser Asn Gln Ile Gly Lys His Tyr Lys Lys Val Met Tyr

-continued

```
            355                 360                 365
Thr Gln Tyr Glu Asp Glu Ser Phe Thr Lys His Thr Val Asn Pro Asn
            370                 375                 380

Met Lys Glu Asp Gly Ile Leu Gly Pro Ile Ile Arg Ala Gln Val Arg
385                 390                 395                 400

Asp Thr Leu Lys Ile Val Phe Lys Asn Met Ala Ser Arg Pro Tyr Ser
            405                 410                 415

Ile Tyr Pro His Gly Val Thr Phe Ser Pro Tyr Glu Asp Glu Val Asn
            420                 425                 430

Ser Ser Phe Thr Ser Gly Arg Asn Asn Thr Met Ile Arg Ala Val Gln
            435                 440                 445

Pro Gly Glu Thr Tyr Thr Tyr Lys Trp Asn Ile Leu Glu Phe Asp Glu
450                 455                 460

Pro Thr Glu Asn Asp Ala Gln Cys Leu Thr Arg Pro Tyr Tyr Ser Asp
465                 470                 475                 480

Val Asp Ile Met Arg Asp Ile Ala Ser Gly Leu Ile Gly Leu Leu Leu
            485                 490                 495

Ile Cys Lys Ser Arg Ser Leu Asp Arg Arg Gly Ile Gln Arg Ala Ala
            500                 505                 510

Asp Ile Glu Gln Gln Ala Val Phe Ala Val Phe Asp Glu Asn Lys Ser
            515                 520                 525

Trp Tyr Leu Glu Asp Asn Ile Asn Lys Phe Cys Glu Asn Pro Asp Glu
            530                 535                 540

Val Lys Arg Asp Asp Pro Lys Phe Tyr Glu Ser Asn Ile Met Ser Thr
545                 550                 555                 560

Ile Asn Gly Tyr Val Pro Glu Ser Ile Thr Thr Leu Gly Phe Cys Phe
            565                 570                 575

Asp Asp Thr Val Gln Trp His Phe Cys Ser Val Gly Thr Gln Asn Glu
            580                 585                 590

Ile Leu Thr Ile His Phe Thr Gly His Ser Phe Ile Tyr Gly Lys Arg
            595                 600                 605

His Glu Asp Thr Leu Thr Leu Phe Pro Met Arg Gly Glu Ser Val Thr
            610                 615                 620

Val Thr Met Asp Asn Val Gly Thr Trp Met Leu Thr Ser Met Asn Ser
625                 630                 635                 640

Ser Pro Arg Ser Lys Lys Leu Arg Leu Lys Phe Arg Asp Val Lys Cys
            645                 650                 655

Ile Pro Asp Asp Glu Asp Ser Tyr Glu Ile Phe Glu Pro Pro Glu
            660                 665                 670

Ser Thr Val Met Ala Thr Arg Lys Met His Asp Arg Leu Glu Pro Glu
            675                 680                 685

Asp Glu Glu Ser Asp Ala Asp Tyr Asp Tyr Gln Asn Arg Leu Ala Ala
            690                 695                 700

Ala Leu Gly Ile Arg Arg Glu Thr Asp Ile Glu Asp Ser Asp Asp Ile
705                 710                 715                 720

Pro Glu Asp Thr Thr Tyr Lys Lys Val Val Phe Arg Lys Tyr Leu Asp
            725                 730                 735

Ser Thr Phe Thr Lys Arg Asp Pro Arg Gly Glu Tyr Glu Glu His Leu
            740                 745                 750

Gly Ile Leu Gly Pro Ile Ile Arg Ala Glu Val Asp Asp Val Ile Gln
            755                 760                 765

Val Arg Phe Lys Asn Leu Ala Ser Arg Pro Tyr Ser Leu His Ala His
770                 775                 780
```

-continued

```
Gly Leu Ser Tyr Glu Lys Ser Ser Glu Gly Lys Thr Tyr Glu Asp Asp
785                 790                 795                 800

Ser Pro Glu Trp Phe Lys Glu Asp Asn Ala Val Gln Pro Asn Ser Ser
                805                 810                 815

Tyr Thr Tyr Val Trp His Ala Thr Glu Arg Ser Gly Pro Glu Ser Pro
            820                 825                 830

Gly Ser Ala Cys Arg Ala Trp Ala Tyr Ser Ala Val Asn Pro Glu
        835                 840                 845

Lys Asp Ile His Ser Gly Leu Ile Gly Pro Leu Leu Ile Cys Gln Lys
    850                 855                 860

Gly Ile Leu His Lys Asp Ser Asn Met Pro Val Asp Met Arg Glu Phe
865                 870                 875                 880

Val Leu Leu Phe Met Thr Phe Asp Glu Lys Lys Ser Trp Tyr Tyr Glu
                885                 890                 895

Lys Lys Ser Arg Ser Ser Trp Arg Leu Thr Ser Ser Glu Met Lys Lys
                900                 905                 910

Ser His Glu Phe His Ala Ile Asn Gly Met Ile Tyr Ser Leu Pro Gly
            915                 920                 925

Leu Lys Met Tyr Glu Gln Glu Trp Val Arg Leu His Leu Leu Asn Ile
    930                 935                 940

Gly Gly Ser Gln Asp Ile His Val Val His Phe His Gly Gln Thr Leu
945                 950                 955                 960

Leu Glu Asn Gly Asn Lys Gln His Gln Leu Gly Val Trp Pro Leu Leu
                965                 970                 975

Pro Gly Ser Phe Lys Thr Leu Glu Met Lys Ala Ser Lys Pro Gly Trp
                980                 985                 990

Trp Leu Leu Asn Thr Glu Val Gly Glu Asn Gln Arg Ala Gly Met Gln
            995                 1000                1005

Thr Pro Phe Leu Ile Met Asp Arg Asp Cys Arg Met Pro Met Gly Leu
    1010                1015                1020

Ser Thr Gly Ile Ile Ser Asp Ser Gln Ile Lys Ala Ser Glu Phe Leu
1025                1030                1035                1040

Gly Tyr Trp Glu Pro Arg Leu Ala Arg Leu Asn Asn Gly Gly Ser Tyr
                1045                1050                1055

Asn Ala Trp Ser Val Glu Lys Leu Ala Ala Glu Phe Ala Ser Lys Pro
            1060                1065                1070

Trp Ile Gln Val Asp Met Gln Lys Glu Val Ile Ile Thr Gly Ile Gln
    1075                1080                1085

Thr Gln Gly Ala Lys His Tyr Leu Lys Ser Cys Tyr Thr Thr Glu Phe
    1090                1095                1100

Tyr Val Ala Tyr Ser Ser Asn Gln Ile Asn Trp Gln Ile Phe Lys Gly
1105                1110                1115                1120

Asn Ser Thr Arg Asn Val Met Tyr Phe Asn Gly Asn Ser Asp Ala Ser
            1125                1130                1135

Thr Ile Lys Glu Asn Gln Phe Asp Pro Pro Ile Val Ala Arg Tyr Ile
        1140                1145                1150

Arg Ile Ser Pro Thr Arg Ala Tyr Asn Arg Pro Thr Leu Arg Leu Glu
    1155                1160                1165

Leu Gln Gly Cys Glu Val Asn Gly Cys Ser Thr Pro Leu Gly Met Glu
    1170                1175                1180

Asn Gly Lys Ile Glu Asn Lys Gln Ile Thr Ala Ser Ser Phe Lys Lys
1185                1190                1195                1200
```

```
Ser Trp Trp Gly Asp Tyr Trp Glu Pro Phe Arg Ala Arg Leu Asn Ala
            1205                1210                1215

Gln Gly Arg Val Asn Ala Trp Gln Ala Lys Ala Asn Asn Lys Gln
        1220                1225                1230

Trp Leu Glu Ile Asp Leu Leu Lys Ile Lys Lys Ile Thr Ala Ile Ile
    1235                1240                1245

Thr Gln Gly Cys Lys Ser Leu Ser Ser Glu Met Tyr Val Lys Ser Tyr
    1250                1255                1260

Thr Ile His Tyr Ser Glu Gln Gly Val Glu Trp Lys Pro Tyr Arg Leu
1265                1270                1275                1280

Lys Ser Ser Met Val Asp Lys Ile Phe Glu Gly Asn Thr Asn Thr Lys
            1285                1290                1295

Gly His Val Lys Asn Phe Phe Asn Pro Pro Ile Ile Ser Arg Phe Ile
            1300                1305                1310

Arg Val Ile Pro Lys Thr Trp Asn Gln Ser Ile Ala Leu Arg Leu Glu
        1315                1320                1325

Leu Phe Gly Cys Asp Ile Tyr
    1330                1335

<210> SEQ ID NO 11
<211> LENGTH: 4150
<212> TYPE: DNA
<213> ORGANISM: Homo sapiens
<220> FEATURE:
<221> NAME/KEY: CDS
<222> LOCATION: (1)..(4005)

<400> SEQUENCE: 11
```

| | | | | | | | | | | | | | | | | |
|---|---|---|---|---|---|---|---|---|---|---|---|---|---|---|---|---|
| gca cag cta agg cag ttc tac gtg gct gct cag ggc atc agt tgg agc | | | | | | | | | | | | | | | | 48 |
| Ala Gln Leu Arg Gln Phe Tyr Val Ala Ala Gln Gly Ile Ser Trp Ser | | | | | | | | | | | | | | | | |
| 1 | | | | 5 | | | | | 10 | | | | | 15 | | |
| tac cga cct gag ccc aca aac tca agt ttg aat ctt tct gta act tcc | | | | | | | | | | | | | | | | 96 |
| Tyr Arg Pro Glu Pro Thr Asn Ser Ser Leu Asn Leu Ser Val Thr Ser | | | | | | | | | | | | | | | | |
| | | | | 20 | | | | | 25 | | | | | 30 | | |
| ttt aag aaa att gtc tac aga gag tat gaa cca tat ttt aag aaa gaa | | | | | | | | | | | | | | | | 144 |
| Phe Lys Lys Ile Val Tyr Arg Glu Tyr Glu Pro Tyr Phe Lys Lys Glu | | | | | | | | | | | | | | | | |
| | | 35 | | | | | 40 | | | | | 45 | | | | |
| aaa cca caa tct acc att tca gga ctt ctt ggg cct act tta tat gct | | | | | | | | | | | | | | | | 192 |
| Lys Pro Gln Ser Thr Ile Ser Gly Leu Leu Gly Pro Thr Leu Tyr Ala | | | | | | | | | | | | | | | | |
| | 50 | | | | | 55 | | | | | 60 | | | | | |
| gaa gtc gga gac atc ata aaa gtt cac ttt aaa aat aag gca gat aag | | | | | | | | | | | | | | | | 240 |
| Glu Val Gly Asp Ile Ile Lys Val His Phe Lys Asn Lys Ala Asp Lys | | | | | | | | | | | | | | | | |
| 65 | | | | | 70 | | | | | 75 | | | | | 80 | |
| ccc ttg agc atc cat cct caa gga att agg tac agt aaa tta tca gaa | | | | | | | | | | | | | | | | 288 |
| Pro Leu Ser Ile His Pro Gln Gly Ile Arg Tyr Ser Lys Leu Ser Glu | | | | | | | | | | | | | | | | |
| | | | | 85 | | | | | 90 | | | | | 95 | | |
| ggt gct tct tac ctt gac cac aca ttc cct gcg gcg aag atg gac gac | | | | | | | | | | | | | | | | 336 |
| Gly Ala Ser Tyr Leu Asp His Thr Phe Pro Ala Ala Lys Met Asp Asp | | | | | | | | | | | | | | | | |
| | | | 100 | | | | | 105 | | | | | 110 | | | |
| gct gtg gct cca ggc cga gaa tac acc tat gaa tgg agt atc agt gag | | | | | | | | | | | | | | | | 384 |
| Ala Val Ala Pro Gly Arg Glu Tyr Thr Tyr Glu Trp Ser Ile Ser Glu | | | | | | | | | | | | | | | | |
| | | 115 | | | | | 120 | | | | | 125 | | | | |
| gac agt gga ccc acc cat gat gac cct cca tgc ctc aca cac atc tat | | | | | | | | | | | | | | | | 432 |
| Asp Ser Gly Pro Thr His Asp Asp Pro Pro Cys Leu Thr His Ile Tyr | | | | | | | | | | | | | | | | |
| | 130 | | | | | 135 | | | | | 140 | | | | | |
| tac tcc cat gaa aat ctg atc gag gat ttc aac tct ggg ctg att ggg | | | | | | | | | | | | | | | | 480 |
| Tyr Ser His Glu Asn Leu Ile Glu Asp Phe Asn Ser Gly Leu Ile Gly | | | | | | | | | | | | | | | | |
| 145 | | | | | 150 | | | | | 155 | | | | | 160 | |
| ccc ctg ctt atc tgt aaa aaa ggg acc cta act gag ggt ggg aca cag | | | | | | | | | | | | | | | | 528 |

|  |  |
|---|---:|
| Pro Leu Leu Ile Cys Lys Lys Gly Thr Leu Thr Glu Gly Gly Thr Gln<br>             165                  170                175 |  |
| aag acg ttt gac aag caa atc gtg cta cta ttt gct gtg ttt gat gaa<br>Lys Thr Phe Asp Lys Gln Ile Val Leu Leu Phe Ala Val Phe Asp Glu<br>             180                  185                190 | 576 |
| agc aag agc tgg agc cag tca tca tcc cta atg tac aca gtc aat gga<br>Ser Lys Ser Trp Ser Gln Ser Ser Ser Leu Met Tyr Thr Val Asn Gly<br>             195                  200                205 | 624 |
| tat gtg aat ggg aca atg cca gat ata aca gtt tgt gcc cat gac cac<br>Tyr Val Asn Gly Thr Met Pro Asp Ile Thr Val Cys Ala His Asp His<br>             210                  215                220 | 672 |
| atc agc tgg cat ctg ctg gga atg agc tcg ggg cca gaa tta ttc tcc<br>Ile Ser Trp His Leu Leu Gly Met Ser Ser Gly Pro Glu Leu Phe Ser<br>225                  230                235                240 | 720 |
| att cat ttc aac ggc cag gtc ctg gag cag aac cat cat aag gtc tca<br>Ile His Phe Asn Gly Gln Val Leu Glu Gln Asn His His Lys Val Ser<br>             245                  250                255 | 768 |
| gcc atc acc ctt gtc agt gct aca tcc act acc gca aat atg act gtg<br>Ala Ile Thr Leu Val Ser Ala Thr Ser Thr Thr Ala Asn Met Thr Val<br>             260                  265                270 | 816 |
| ggc cca gag gga aag tgg atc ata tct tct ctc acc cca aaa cat ttg<br>Gly Pro Glu Gly Lys Trp Ile Ile Ser Ser Leu Thr Pro Lys His Leu<br>             275                  280                285 | 864 |
| caa gct ggg atg cag gct tac att gac att aaa aac tgc cca aag aaa<br>Gln Ala Gly Met Gln Ala Tyr Ile Asp Ile Lys Asn Cys Pro Lys Lys<br>             290                  295                300 | 912 |
| acc agg aat ctt aag aaa ata act cgt gag cag agg cgg cac atg aag<br>Thr Arg Asn Leu Lys Lys Ile Thr Arg Glu Gln Arg Arg His Met Lys<br>305                  310                315                320 | 960 |
| agg tgg gaa tac ttc att gct gca gag gaa gtc att tgg gac tat gca<br>Arg Trp Glu Tyr Phe Ile Ala Ala Glu Glu Val Ile Trp Asp Tyr Ala<br>             325                  330                335 | 1008 |
| cct gta ata cca gcg aat atg gac aaa aaa tac agg tct cag cat ttg<br>Pro Val Ile Pro Ala Asn Met Asp Lys Lys Tyr Arg Ser Gln His Leu<br>             340                  345                350 | 1056 |
| gat aat ttc tca aac caa att gga aaa cat tat aag aaa gtt atg tac<br>Asp Asn Phe Ser Asn Gln Ile Gly Lys His Tyr Lys Lys Val Met Tyr<br>             355                  360                365 | 1104 |
| aca cag tac gaa gat gag tcc ttc acc aaa cat aca gtg aat ccc aat<br>Thr Gln Tyr Glu Asp Glu Ser Phe Thr Lys His Thr Val Asn Pro Asn<br>             370                  375                380 | 1152 |
| atg aaa gaa gat ggg att ttg ggt cct att atc aga gcc cag gtc aga<br>Met Lys Glu Asp Gly Ile Leu Gly Pro Ile Ile Arg Ala Gln Val Arg<br>385                  390                395                400 | 1200 |
| gac aca ctc aaa atc gtg ttc aaa aat atg gcc agc cgc ccc tat agc<br>Asp Thr Leu Lys Ile Val Phe Lys Asn Met Ala Ser Arg Pro Tyr Ser<br>             405                  410                415 | 1248 |
| att tac cct cat gga gtg acc ttc tcg cct tat gaa gat gaa gtc aac<br>Ile Tyr Pro His Gly Val Thr Phe Ser Pro Tyr Glu Asp Glu Val Asn<br>             420                  425                430 | 1296 |
| tct tct ttc acc tca ggc agg aac aac acc atg atc aga gca gtt caa<br>Ser Ser Phe Thr Ser Gly Arg Asn Asn Thr Met Ile Arg Ala Val Gln<br>             435                  440                445 | 1344 |
| cca ggg gaa acc tat act tat aag tgg aac atc tta gag ttt gat gaa<br>Pro Gly Glu Thr Tyr Thr Tyr Lys Trp Asn Ile Leu Glu Phe Asp Glu<br>             450                  455                460 | 1392 |
| ccc aca gaa aat gat gcc cag tgc tta aca aga cca tac tac agt gac<br>Pro Thr Glu Asn Asp Ala Gln Cys Leu Thr Arg Pro Tyr Tyr Ser Asp<br>465                  470                475                480 | 1440 |

```
gtg gac atc atg aga gac atc gcc tct ggg cta ata gga cta ctt cta    1488
Val Asp Ile Met Arg Asp Ile Ala Ser Gly Leu Ile Gly Leu Leu Leu
                485                 490                 495 atc tgt aag agc aga tcc ctg gac agg cga gga ata cag agg gca gca    1536
Ile Cys Lys Ser Arg Ser Leu Asp Arg Arg Gly Ile Gln Arg Ala Ala
                500                 505                 510 gac atc gaa cag cag gct gtg ttt gct gtg ttt gat gag aac aaa agc    1584
Asp Ile Glu Gln Gln Ala Val Phe Ala Val Phe Asp Glu Asn Lys Ser
            515                 520                 525 tgg tac ctt gag gac aac atc aac aag ttt tgt gaa aat cct gat gag    1632
Trp Tyr Leu Glu Asp Asn Ile Asn Lys Phe Cys Glu Asn Pro Asp Glu
        530                 535                 540 gtg aaa cgt gat gac ccc aag ttt tat gaa tca aac atc atg agc act    1680
Val Lys Arg Asp Asp Pro Lys Phe Tyr Glu Ser Asn Ile Met Ser Thr
545                 550                 555                 560 atc aat ggc tat gtg cct gag agc ata act act ctt gga ttc tgc ttt    1728
Ile Asn Gly Tyr Val Pro Glu Ser Ile Thr Thr Leu Gly Phe Cys Phe
                565                 570                 575 gat gac act gtc cag tgg cac ttc tgt agt gtg ggg acc cag aat gaa    1776
Asp Asp Thr Val Gln Trp His Phe Cys Ser Val Gly Thr Gln Asn Glu
                580                 585                 590 att ttg acc atc cac ttc act ggg cac tca ttc atc tat gga aag agg    1824
Ile Leu Thr Ile His Phe Thr Gly His Ser Phe Ile Tyr Gly Lys Arg
            595                 600                 605 cat gag gac acc ttg acc ctc ttc ccc atg cgt gga gaa tct gtg acg    1872
His Glu Asp Thr Leu Thr Leu Phe Pro Met Arg Gly Glu Ser Val Thr
        610                 615                 620 gtc aca atg gat aat gtt gga act tgg atg tta act tcc atg aat tct    1920
Val Thr Met Asp Asn Val Gly Thr Trp Met Leu Thr Ser Met Asn Ser
625                 630                 635                 640 agt cca aga agc aaa aag ctg agg ctg aaa ttc agg gat gtt aaa tgt    1968
Ser Pro Arg Ser Lys Lys Leu Arg Leu Lys Phe Arg Asp Val Lys Cys
                645                 650                 655 atc cca gat gat gat gaa gac tca tat gag att ttt gaa cct cca gaa    2016
Ile Pro Asp Asp Asp Glu Asp Ser Tyr Glu Ile Phe Glu Pro Pro Glu
                660                 665                 670 tct aca gtc atg gct aca cgg aaa atg cat gat cgt tta gaa cct gaa    2064
Ser Thr Val Met Ala Thr Arg Lys Met His Asp Arg Leu Glu Pro Glu
            675                 680                 685 gat gaa gag agt gat gct gac tat gat tac cag aac aga ctg gct gca    2112
Asp Glu Glu Ser Asp Ala Asp Tyr Asp Tyr Gln Asn Arg Leu Ala Ala
        690                 695                 700 gca tta gga att agg agg gaa aca gat att gaa gac tct gat gat att    2160
Ala Leu Gly Ile Arg Arg Glu Thr Asp Ile Glu Asp Ser Asp Asp Ile
705                 710                 715                 720 cca gaa gat acc aca tat aag aaa gta gtt ttt cga aag tac ctc gac    2208
Pro Glu Asp Thr Thr Tyr Lys Lys Val Val Phe Arg Lys Tyr Leu Asp
                725                 730                 735 agc act ttt acc aaa cgt gat cct cga ggg gag tat gaa gag cat ctc    2256
Ser Thr Phe Thr Lys Arg Asp Pro Arg Gly Glu Tyr Glu Glu His Leu
                740                 745                 750 gga att ctt ggt cct att atc aga gct gaa gtg gat gat gtt atc caa    2304
Gly Ile Leu Gly Pro Ile Ile Arg Ala Glu Val Asp Asp Val Ile Gln
            755                 760                 765 gtt cgt ttt aaa aat tta gca tcc aga ccg tat tct cta cat gcc cat    2352
Val Arg Phe Lys Asn Leu Ala Ser Arg Pro Tyr Ser Leu His Ala His
        770                 775                 780 gga ctt tcc tat gaa aaa tca tca gag gga aag act tat gaa gat gac    2400
Gly Leu Ser Tyr Glu Lys Ser Ser Glu Gly Lys Thr Tyr Glu Asp Asp
785                 790                 795                 800
```

```
tct cct gaa tgg ttt aag gaa gat aat gct gtt cag cca aat agc agt      2448
Ser Pro Glu Trp Phe Lys Glu Asp Asn Ala Val Gln Pro Asn Ser Ser
            805                 810                 815 tat acc tac gta tgg cat gcc act gag cga tca ggg cca gaa agt cct      2496
Tyr Thr Tyr Val Trp His Ala Thr Glu Arg Ser Gly Pro Glu Ser Pro
            820                 825                 830 ggc tct gcc tgt cgg gct tgg gcc tac tac tca gct gtg aac cca gaa      2544
Gly Ser Ala Cys Arg Ala Trp Ala Tyr Tyr Ser Ala Val Asn Pro Glu
            835                 840                 845 aaa gat att cac tca ggc ttg ata ggt ccc ctc cta atc tgc caa aaa      2592
Lys Asp Ile His Ser Gly Leu Ile Gly Pro Leu Leu Ile Cys Gln Lys
        850                 855                 860 gga ata cta cat aag gac agc aac atg cct gtg gac atg aga gaa ttt      2640
Gly Ile Leu His Lys Asp Ser Asn Met Pro Val Asp Met Arg Glu Phe
865                 870                 875                 880 gtc tta cta ttt atg acc ttt gat gaa aag aag agc tgg tac tat gaa      2688
Val Leu Leu Phe Met Thr Phe Asp Glu Lys Lys Ser Trp Tyr Tyr Glu
                885                 890                 895 aag aag tcc cga agt tct tgg aga ctc aca tcc tca gaa atg aaa aaa      2736
Lys Lys Ser Arg Ser Ser Trp Arg Leu Thr Ser Ser Glu Met Lys Lys
            900                 905                 910 tcc cat gag ttt cac gcc att aat ggg atg atc tac agc ttg cct ggc      2784
Ser His Glu Phe His Ala Ile Asn Gly Met Ile Tyr Ser Leu Pro Gly
            915                 920                 925 ctg aaa atg tat gag caa gag tgg gtg agg tta cac ctg ctg aac ata      2832
Leu Lys Met Tyr Glu Gln Glu Trp Val Arg Leu His Leu Leu Asn Ile
        930                 935                 940 ggc ggc tcc caa gac att cac gtg gtt cac ttt cac ggc cag acc ttg      2880
Gly Gly Ser Gln Asp Ile His Val Val His Phe His Gly Gln Thr Leu
945                 950                 955                 960 ctg gaa aat ggc aat aaa cag cac cag tta ggg gtc tgg ccc ctt ctg      2928
Leu Glu Asn Gly Asn Lys Gln His Gln Leu Gly Val Trp Pro Leu Leu
                965                 970                 975 cct ggt tca ttt aaa act ctt gaa atg aag gca tca aaa cct ggc tgg      2976
Pro Gly Ser Phe Lys Thr Leu Glu Met Lys Ala Ser Lys Pro Gly Trp
            980                 985                 990 tgg ctc cta aac aca gag gtt gga gaa aac cag aga gca ggg atg caa      3024
Trp Leu Leu Asn Thr Glu Val Gly Glu Asn Gln Arg Ala Gly Met Gln
            995                 1000                1005 acg cca ttt ctt atc atg gac aga gac tgt agg atg cca atg gga cta      3072
Thr Pro Phe Leu Ile Met Asp Arg Asp Cys Arg Met Pro Met Gly Leu
        1010                1015                1020 agc act ggt atc ata tct gat tca cag atc aag gct tca gag ttt ctg      3120
Ser Thr Gly Ile Ile Ser Asp Ser Gln Ile Lys Ala Ser Glu Phe Leu
1025                1030                1035                1040 ggt tac tgg gag ccc aga tta gca aga tta aac aat ggt gga tct tat      3168
Gly Tyr Trp Glu Pro Arg Leu Ala Arg Leu Asn Asn Gly Gly Ser Tyr
                1045                1050                1055 aat gct tgg agt gta gaa aaa ctt gca gca gaa ttt gcc tct aaa cct      3216
Asn Ala Trp Ser Val Glu Lys Leu Ala Ala Glu Phe Ala Ser Lys Pro
            1060                1065                1070 tgg atc cag gtg gac atg caa aag gaa gtc ata atc aca ggg atc cag      3264
Trp Ile Gln Val Asp Met Gln Lys Glu Val Ile Ile Thr Gly Ile Gln
            1075                1080                1085 acc caa ggt gcc aaa cac tac ctg aag tcc tgc tat acc aca gag ttc      3312
Thr Gln Gly Ala Lys His Tyr Leu Lys Ser Cys Tyr Thr Thr Glu Phe
        1090                1095                1100 tat gta gct tac agt tcc aac cag atc aac tgg cag atc ttc aaa ggg      3360
Tyr Val Ala Tyr Ser Ser Asn Gln Ile Asn Trp Gln Ile Phe Lys Gly
```

-continued

| | | |
|---|---|---|
| 1105 | 1110 | 1115 | 1120 |

```
aac agc aca agg aat gtg atg tat ttt aat ggc aat tca gat gcc tct    3408
Asn Ser Thr Arg Asn Val Met Tyr Phe Asn Gly Asn Ser Asp Ala Ser
            1125                1130                1135 aca ata aaa gag aat cag ttt gac cca cct att gtg gct aga tat att    3456
Thr Ile Lys Glu Asn Gln Phe Asp Pro Pro Ile Val Ala Arg Tyr Ile
        1140                1145                1150 agg atc tct cca act cga gcc tat aac aga cct acc ctt cga ttg gaa    3504
Arg Ile Ser Pro Thr Arg Ala Tyr Asn Arg Pro Thr Leu Arg Leu Glu
    1155                1160                1165 ctg caa ggt tgt gag gta aat gga tgt tcc aca ccc tgg ggt atg gaa    3552
Leu Gln Gly Cys Glu Val Asn Gly Cys Ser Thr Pro Leu Gly Met Glu
1170                1175                1180 aat gga aag ata gaa aac aag caa atc aca gct tct tcg ttt aag aaa    3600
Asn Gly Lys Ile Glu Asn Lys Gln Ile Thr Ala Ser Ser Phe Lys Lys
1185                1190                1195                1200 tct tgg tgg gga gat tac tgg gaa ccc ttc cgt gcc cgt ctg aat gcc    3648
Ser Trp Trp Gly Asp Tyr Trp Glu Pro Phe Arg Ala Arg Leu Asn Ala
            1205                1210                1215 cag gga cgt gtg aat gcc tgg caa gcc aag gca aac aac aat aag cag    3696
Gln Gly Arg Val Asn Ala Trp Gln Ala Lys Ala Asn Asn Asn Lys Gln
        1220                1225                1230 tgg cta gaa att gat cta ctc aag atc aag aag ata acg gca att ata    3744
Trp Leu Glu Ile Asp Leu Leu Lys Ile Lys Lys Ile Thr Ala Ile Ile
    1235                1240                1245 aca cag ggc tgc aag tct ctg tcc tct gaa atg tat gta aag agc tat    3792
Thr Gln Gly Cys Lys Ser Leu Ser Ser Glu Met Tyr Val Lys Ser Tyr
1250                1255                1260 acc atc cac tac agt gag cag gga gtg gaa tgg aaa cca tac agg ctg    3840
Thr Ile His Tyr Ser Glu Gln Gly Val Glu Trp Lys Pro Tyr Arg Leu
1265                1270                1275                1280 aaa tcc tcc atg gtg gac aag att ttt gaa gga aat act aat acc aaa    3888
Lys Ser Ser Met Val Asp Lys Ile Phe Glu Gly Asn Thr Asn Thr Lys
            1285                1290                1295 gga cat gtg aag aac ttt ttc aac ccc cca atc att tcc agg ttt atc    3936
Gly His Val Lys Asn Phe Phe Asn Pro Pro Ile Ile Ser Arg Phe Ile
        1300                1305                1310 cgt gtc att cct aaa aca tgg aat caa agt att gca ctt cgc ctg gaa    3984
Arg Val Ile Pro Lys Thr Trp Asn Gln Ser Ile Ala Leu Arg Leu Glu
    1315                1320                1325 ctc ttt ggc tgt gat att tac tagaattgaa cattcaaaaa ccctggaag       4035
Leu Phe Gly Cys Asp Ile Tyr
1330                1335 agactcttta agacctcaaa ccatttagaa tgggcaatgt attttacgct gtgttaaatg    4095
ttaacagttt tccactattt ctctttcttt tctattagtg aataaattt tatac          4150

<210> SEQ ID NO 12
<211> LENGTH: 1335
<212> TYPE: PRT
<213> ORGANISM: Homo sapiens

<400> SEQUENCE: 12

Ala Gln Leu Arg Gln Phe Tyr Val Ala Ala Gln Gly Ile Ser Trp Ser
 1               5                  10                  15

Tyr Arg Pro Glu Pro Thr Asn Ser Ser Leu Asn Leu Ser Val Thr Ser
                20                  25                  30

Phe Lys Lys Ile Val Tyr Arg Glu Tyr Glu Pro Tyr Phe Lys Lys Glu
            35                  40                  45
```

```
Lys Pro Gln Ser Thr Ile Ser Gly Leu Leu Gly Pro Thr Leu Tyr Ala
     50                  55                  60

Glu Val Gly Asp Ile Ile Lys Val His Phe Lys Asn Lys Ala Asp Lys
 65                  70                  75                  80

Pro Leu Ser Ile His Pro Gln Gly Ile Arg Tyr Ser Lys Leu Ser Glu
                 85                  90                  95

Gly Ala Ser Tyr Leu Asp His Thr Phe Pro Ala Ala Lys Met Asp Asp
                100                 105                 110

Ala Val Ala Pro Gly Arg Glu Tyr Thr Tyr Glu Trp Ser Ile Ser Glu
            115                 120                 125

Asp Ser Gly Pro Thr His Asp Asp Pro Pro Cys Leu Thr His Ile Tyr
    130                 135                 140

Tyr Ser His Glu Asn Leu Ile Glu Asp Phe Asn Ser Gly Leu Ile Gly
145                 150                 155                 160

Pro Leu Leu Ile Cys Lys Lys Gly Thr Leu Thr Glu Gly Gly Thr Gln
                165                 170                 175

Lys Thr Phe Asp Lys Gln Ile Val Leu Leu Phe Ala Val Phe Asp Glu
                180                 185                 190

Ser Lys Ser Trp Ser Gln Ser Ser Ser Leu Met Tyr Thr Val Asn Gly
            195                 200                 205

Tyr Val Asn Gly Thr Met Pro Asp Ile Thr Val Cys Ala His Asp His
210                 215                 220

Ile Ser Trp His Leu Leu Gly Met Ser Ser Gly Pro Glu Leu Phe Ser
225                 230                 235                 240

Ile His Phe Asn Gly Gln Val Leu Glu Gln Asn His His Lys Val Ser
                245                 250                 255

Ala Ile Thr Leu Val Ser Ala Thr Ser Thr Thr Ala Asn Met Thr Val
                260                 265                 270

Gly Pro Glu Gly Lys Trp Ile Ile Ser Ser Leu Thr Pro Lys His Leu
            275                 280                 285

Gln Ala Gly Met Gln Ala Tyr Ile Asp Ile Lys Asn Cys Pro Lys Lys
    290                 295                 300

Thr Arg Asn Leu Lys Lys Ile Thr Arg Glu Gln Arg His Met Lys
305                 310                 315                 320

Arg Trp Glu Tyr Phe Ile Ala Ala Glu Glu Val Ile Trp Asp Tyr Ala
                325                 330                 335

Pro Val Ile Pro Ala Asn Met Asp Lys Lys Tyr Arg Ser Gln His Leu
            340                 345                 350

Asp Asn Phe Ser Asn Gln Ile Gly Lys His Tyr Lys Lys Val Met Tyr
    355                 360                 365

Thr Gln Tyr Glu Asp Glu Ser Phe Thr Lys His Thr Val Asn Pro Asn
370                 375                 380

Met Lys Glu Asp Gly Ile Leu Gly Pro Ile Ile Arg Ala Gln Val Arg
385                 390                 395                 400

Asp Thr Leu Lys Ile Val Phe Lys Asn Met Ala Ser Arg Pro Tyr Ser
                405                 410                 415

Ile Tyr Pro His Gly Val Thr Phe Ser Pro Tyr Glu Asp Glu Val Asn
            420                 425                 430

Ser Ser Phe Thr Ser Gly Arg Asn Asn Thr Met Ile Arg Ala Val Gln
    435                 440                 445

Pro Gly Glu Thr Tyr Thr Tyr Lys Trp Asn Ile Leu Glu Phe Asp Glu
    450                 455                 460

Pro Thr Glu Asn Asp Ala Gln Cys Leu Thr Arg Pro Tyr Tyr Ser Asp
```

```
            465                 470                 475                 480
Val Asp Ile Met Arg Asp Ile Ala Ser Gly Leu Ile Gly Leu Leu Leu
                    485                 490                 495
Ile Cys Lys Ser Arg Ser Leu Asp Arg Arg Gly Ile Gln Arg Ala Ala
                500                 505                 510
Asp Ile Glu Gln Gln Ala Val Phe Ala Val Phe Asp Glu Asn Lys Ser
            515                 520                 525
Trp Tyr Leu Glu Asp Asn Ile Asn Lys Phe Cys Glu Asn Pro Asp Glu
        530                 535                 540
Val Lys Arg Asp Asp Pro Lys Phe Tyr Glu Ser Asn Ile Met Ser Thr
545                 550                 555                 560
Ile Asn Gly Tyr Val Pro Glu Ser Ile Thr Thr Leu Gly Phe Cys Phe
                565                 570                 575
Asp Asp Thr Val Gln Trp His Phe Cys Ser Val Gly Thr Gln Asn Glu
            580                 585                 590
Ile Leu Thr Ile His Phe Thr Gly His Ser Phe Ile Tyr Gly Lys Arg
            595                 600                 605
His Glu Asp Thr Leu Thr Leu Phe Pro Met Arg Gly Glu Ser Val Thr
        610                 615                 620
Val Thr Met Asp Asn Val Gly Thr Trp Met Leu Thr Ser Met Asn Ser
625                 630                 635                 640
Ser Pro Arg Ser Lys Lys Leu Arg Leu Lys Phe Arg Asp Val Lys Cys
                645                 650                 655
Ile Pro Asp Asp Glu Asp Ser Tyr Glu Ile Phe Glu Pro Pro Glu
                660                 665                 670
Ser Thr Val Met Ala Thr Arg Lys Met His Asp Arg Leu Glu Pro Glu
            675                 680                 685
Asp Glu Glu Ser Asp Ala Asp Tyr Asp Tyr Gln Asn Arg Leu Ala Ala
            690                 695                 700
Ala Leu Gly Ile Arg Arg Glu Thr Asp Ile Glu Asp Ser Asp Asp Ile
705                 710                 715                 720
Pro Glu Asp Thr Thr Tyr Lys Lys Val Val Phe Arg Lys Tyr Leu Asp
                725                 730                 735
Ser Thr Phe Thr Lys Arg Asp Pro Arg Gly Glu Tyr Glu Glu His Leu
                740                 745                 750
Gly Ile Leu Gly Pro Ile Ile Arg Ala Glu Val Asp Asp Val Ile Gln
            755                 760                 765
Val Arg Phe Lys Asn Leu Ala Ser Arg Pro Tyr Ser Leu His Ala His
            770                 775                 780
Gly Leu Ser Tyr Glu Lys Ser Ser Glu Gly Lys Thr Tyr Glu Asp Asp
785                 790                 795                 800
Ser Pro Glu Trp Phe Lys Glu Asp Asn Ala Val Gln Pro Asn Ser Ser
                805                 810                 815
Tyr Thr Tyr Val Trp His Ala Thr Glu Arg Ser Gly Pro Glu Ser Pro
                820                 825                 830
Gly Ser Ala Cys Arg Ala Trp Ala Tyr Tyr Ser Ala Val Asn Pro Glu
            835                 840                 845
Lys Asp Ile His Ser Gly Leu Ile Gly Pro Leu Leu Ile Cys Gln Lys
        850                 855                 860
Gly Ile Leu His Lys Asp Ser Asn Met Pro Val Asp Met Arg Glu Phe
865                 870                 875                 880
Val Leu Leu Phe Met Thr Phe Asp Glu Lys Lys Ser Trp Tyr Tyr Glu
                885                 890                 895
```

-continued

```
Lys Lys Ser Arg Ser Ser Trp Arg Leu Thr Ser Ser Glu Met Lys Lys
            900                 905                 910

Ser His Glu Phe His Ala Ile Asn Gly Met Ile Tyr Ser Leu Pro Gly
        915                 920                 925

Leu Lys Met Tyr Glu Gln Glu Trp Val Arg Leu His Leu Leu Asn Ile
    930                 935                 940

Gly Gly Ser Gln Asp Ile His Val His Phe His Gly Gln Thr Leu
945                 950                 955                 960

Leu Glu Asn Gly Asn Lys Gln His Gln Leu Gly Val Trp Pro Leu Leu
                965                 970                 975

Pro Gly Ser Phe Lys Thr Leu Glu Met Lys Ala Ser Lys Pro Gly Trp
            980                 985                 990

Trp Leu Leu Asn Thr Glu Val Gly Glu Asn Gln Arg Ala Gly Met Gln
        995                1000                1005

Thr Pro Phe Leu Ile Met Asp Arg Asp Cys Arg Met Pro Met Gly Leu
    1010                1015                1020

Ser Thr Gly Ile Ile Ser Asp Ser Gln Ile Lys Ala Ser Glu Phe Leu
1025                1030                1035                1040

Gly Tyr Trp Glu Pro Arg Leu Ala Arg Leu Asn Asn Gly Gly Ser Tyr
                1045                1050                1055

Asn Ala Trp Ser Val Glu Lys Leu Ala Ala Glu Phe Ala Ser Lys Pro
            1060                1065                1070

Trp Ile Gln Val Asp Met Gln Lys Glu Val Ile Ile Thr Gly Ile Gln
        1075                1080                1085

Thr Gln Gly Ala Lys His Tyr Leu Lys Ser Cys Tyr Thr Thr Glu Phe
    1090                1095                1100

Tyr Val Ala Tyr Ser Ser Asn Gln Ile Asn Trp Gln Ile Phe Lys Gly
1105                1110                1115                1120

Asn Ser Thr Arg Asn Val Met Tyr Phe Asn Gly Asn Ser Asp Ala Ser
                1125                1130                1135

Thr Ile Lys Glu Asn Gln Phe Asp Pro Pro Ile Val Ala Arg Tyr Ile
            1140                1145                1150

Arg Ile Ser Pro Thr Arg Ala Tyr Asn Arg Pro Thr Leu Arg Leu Glu
        1155                1160                1165

Leu Gln Gly Cys Glu Val Asn Gly Cys Ser Thr Pro Leu Gly Met Glu
    1170                1175                1180

Asn Gly Lys Ile Glu Asn Lys Gln Ile Thr Ala Ser Ser Phe Lys Lys
1185                1190                1195                1200

Ser Trp Trp Gly Asp Tyr Trp Glu Pro Phe Arg Ala Arg Leu Asn Ala
                1205                1210                1215

Gln Gly Arg Val Asn Ala Trp Gln Ala Lys Ala Asn Asn Lys Gln
            1220                1225                1230

Trp Leu Glu Ile Asp Leu Leu Lys Ile Lys Ile Thr Ala Ile Ile
        1235                1240                1245

Thr Gln Gly Cys Lys Ser Leu Ser Ser Glu Met Tyr Val Lys Ser Tyr
    1250                1255                1260

Thr Ile His Tyr Ser Glu Gln Gly Val Glu Trp Lys Pro Tyr Arg Leu
1265                1270                1275                1280

Lys Ser Ser Met Val Asp Lys Ile Phe Glu Gly Asn Thr Asn Thr Lys
                1285                1290                1295

Gly His Val Lys Asn Phe Phe Asn Pro Pro Ile Ile Ser Arg Phe Ile
            1300                1305                1310
```

```
                    Arg Val Ile Pro Lys Thr Trp Asn Gln Ser Ile Ala Leu Arg Leu Glu
                                 1315                1320                1325

Leu Phe Gly Cys Asp Ile Tyr
                        1330                1335

<210> SEQ ID NO 13
<211> LENGTH: 4150
<212> TYPE: DNA
<213> ORGANISM: Homo sapiens
<220> FEATURE:
<221> NAME/KEY: CDS
<222> LOCATION: (1)..(4005)

<400> SEQUENCE: 13 gca cag cta agg cag ttc tac gtg gct gct cag ggc atc agt tgg agc         48
Ala Gln Leu Arg Gln Phe Tyr Val Ala Ala Gln Gly Ile Ser Trp Ser
 1               5                  10                  15 tac cga cct gag ccc aca aac tca agt ttg aat ctt tct gta act tcc         96
Tyr Arg Pro Glu Pro Thr Asn Ser Ser Leu Asn Leu Ser Val Thr Ser
             20                  25                  30 ttt aag aaa att gtc tac aga gag tat gaa cca tat ttt aag aaa gaa        144
Phe Lys Lys Ile Val Tyr Arg Glu Tyr Glu Pro Tyr Phe Lys Lys Glu
         35                  40                  45 aaa cca caa tct acc att tca gga ctt ctt ggg cct act tta tat gct        192
Lys Pro Gln Ser Thr Ile Ser Gly Leu Leu Gly Pro Thr Leu Tyr Ala
     50                  55                  60 gaa gtc gga gac atc ata aaa gtt cac ttt aaa aat aag gca gat aag        240
Glu Val Gly Asp Ile Ile Lys Val His Phe Lys Asn Lys Ala Asp Lys
 65                  70                  75                  80 ccc ttg agc atc cat cct caa gga att agg tac agt aaa tta tca gaa        288
Pro Leu Ser Ile His Pro Gln Gly Ile Arg Tyr Ser Lys Leu Ser Glu
                 85                  90                  95 ggt gct tct tac ctt gac cac gca ttc cct gcg gag aag atg gac gac        336
Gly Ala Ser Tyr Leu Asp His Ala Phe Pro Ala Glu Lys Met Asp Asp
            100                 105                 110 gct gtg gct cca ggc cga gaa tac acc tat gaa tgg agt atc agt gag        384
Ala Val Ala Pro Gly Arg Glu Tyr Thr Tyr Glu Trp Ser Ile Ser Glu
        115                 120                 125 gac agt gga ccc acc cat gat gac cct cca tgc ctc aca cac atc tat        432
Asp Ser Gly Pro Thr His Asp Asp Pro Pro Cys Leu Thr His Ile Tyr
    130                 135                 140 tac tcc cat gaa aat ctg atc gag gat ttc aac tct ggg ctg att ggg        480
Tyr Ser His Glu Asn Leu Ile Glu Asp Phe Asn Ser Gly Leu Ile Gly
145                 150                 155                 160 ccc ctg ctt atc tgt aaa aaa ggg acc cta act gag ggt ggg aca cag        528
Pro Leu Leu Ile Cys Lys Lys Gly Thr Leu Thr Glu Gly Gly Thr Gln
                165                 170                 175 aag acg ttt gac aag caa atc gtg cta cta ttt gct gtg ttt gat gaa        576
Lys Thr Phe Asp Lys Gln Ile Val Leu Leu Phe Ala Val Phe Asp Glu
            180                 185                 190 agc aag agc tgg agc cag tca tca tcc cta atg tac aca gtc aat gga        624
Ser Lys Ser Trp Ser Gln Ser Ser Ser Leu Met Tyr Thr Val Asn Gly
        195                 200                 205 tat gtg aat ggg aca atg cca gat ata aca gtt tgt gcc cat gac cac        672
Tyr Val Asn Gly Thr Met Pro Asp Ile Thr Val Cys Ala His Asp His
    210                 215                 220 atc agc tgg cat ctg ctg gga atg agc tcg ggg cca gaa tta ttc tcc        720
Ile Ser Trp His Leu Leu Gly Met Ser Ser Gly Pro Glu Leu Phe Ser
225                 230                 235                 240 att cat ttc aac ggc cag gtc ctg gag cag aac cat cat aag gtc tca        768
Ile His Phe Asn Gly Gln Val Leu Glu Gln Asn His His Lys Val Ser
```

```
                 245                 250                 255
gcc atc acc ctt gtc agt gct aca tcc act acc gca aat atg act gtg      816
Ala Ile Thr Leu Val Ser Ala Thr Ser Thr Thr Ala Asn Met Thr Val
            260                 265                 270 ggc cca gag gga aag tgg atc ata tct tct ctc acc cca aaa cat ttg      864
Gly Pro Glu Gly Lys Trp Ile Ile Ser Ser Leu Thr Pro Lys His Leu
        275                 280                 285 caa gct ggg atg cag gct tac att gac att aaa aac tgc cca aag aaa      912
Gln Ala Gly Met Gln Ala Tyr Ile Asp Ile Lys Asn Cys Pro Lys Lys
    290                 295                 300 acc agg aat ctt aag aaa ata act cgt gag cag agg cgg cac atg aag      960
Thr Arg Asn Leu Lys Lys Ile Thr Arg Glu Gln Arg Arg His Met Lys
305                 310                 315                 320 agg tgg gaa tac ttc att gct gca gag gaa gtc att tgg gac tat gca     1008
Arg Trp Glu Tyr Phe Ile Ala Ala Glu Glu Val Ile Trp Asp Tyr Ala
                325                 330                 335 cct gta ata cca gcg aat atg gac aaa aaa tac agg tct cag cat ttg     1056
Pro Val Ile Pro Ala Asn Met Asp Lys Lys Tyr Arg Ser Gln His Leu
            340                 345                 350 gat aat ttc tca aac caa att gga aaa cat tat aag aaa gtt atg tac     1104
Asp Asn Phe Ser Asn Gln Ile Gly Lys His Tyr Lys Lys Val Met Tyr
        355                 360                 365 aca cag tac gaa gat gag tcc ttc acc aaa cat aca gtg aat ccc aat     1152
Thr Gln Tyr Glu Asp Glu Ser Phe Thr Lys His Thr Val Asn Pro Asn
    370                 375                 380 atg aaa gaa gat ggg att ttg ggt cct att atc aga gcc cag gtc aga     1200
Met Lys Glu Asp Gly Ile Leu Gly Pro Ile Ile Arg Ala Gln Val Arg
385                 390                 395                 400 gac aca ctc aaa atc gtg ttc aaa aat atg gcc agc cgc ccc tat agc     1248
Asp Thr Leu Lys Ile Val Phe Lys Asn Met Ala Ser Arg Pro Tyr Ser
                405                 410                 415 att tac cct cat gga gtg acc ttc tcg cct tat gaa gat gaa gtc aac     1296
Ile Tyr Pro His Gly Val Thr Phe Ser Pro Tyr Glu Asp Glu Val Asn
            420                 425                 430 tct tct ttc acc tca ggc agg aac aac acc atg atc aga gca gtt caa     1344
Ser Ser Phe Thr Ser Gly Arg Asn Asn Thr Met Ile Arg Ala Val Gln
        435                 440                 445 cca ggg gaa acc tat act tat aag tgg aac atc tta gag ttt gat gaa     1392
Pro Gly Glu Thr Tyr Thr Tyr Lys Trp Asn Ile Leu Glu Phe Asp Glu
    450                 455                 460 ccc aca gaa aat gat gcc cag tgc tta aca aga cca tac tac agt gac     1440
Pro Thr Glu Asn Asp Ala Gln Cys Leu Thr Arg Pro Tyr Tyr Ser Asp
465                 470                 475                 480 gtg gac atc atg aga gac atc gcc tct ggg cta ata gga cta ctt cta     1488
Val Asp Ile Met Arg Asp Ile Ala Ser Gly Leu Ile Gly Leu Leu Leu
                485                 490                 495 atc tgt aag agc aga tcc ctg gac agg cga gga ata cag agg gca gca     1536
Ile Cys Lys Ser Arg Ser Leu Asp Arg Arg Gly Ile Gln Arg Ala Ala
            500                 505                 510 gac atc gaa cag cag gct gtg ttt gct gtg ttt gat gag aac aaa agc     1584
Asp Ile Glu Gln Gln Ala Val Phe Ala Val Phe Asp Glu Asn Lys Ser
        515                 520                 525 tgg tac ctt gag gac aac atc aac aag ttt tgt gaa aat cct gat gag     1632
Trp Tyr Leu Glu Asp Asn Ile Asn Lys Phe Cys Glu Asn Pro Asp Glu
    530                 535                 540 gtg aaa cgt gat gac ccc aag ttt tat gaa tca aac atc atg agc act     1680
Val Lys Arg Asp Asp Pro Lys Phe Tyr Glu Ser Asn Ile Met Ser Thr
545                 550                 555                 560 atc aat ggc tat gtg cct gag agc ata act act ctt gga ttc tgc ttt     1728
```

```
Ile Asn Gly Tyr Val Pro Glu Ser Ile Thr Thr Leu Gly Phe Cys Phe
                565             570             575 gat gac act gtc cag tgg cac ttc tgt agt gtg ggg acc cag aat gaa    1776
Asp Asp Thr Val Gln Trp His Phe Cys Ser Val Gly Thr Gln Asn Glu
            580             585             590 att ttg acc atc cac ttc act ggg cac tca ttc atc tat gga aag agg    1824
Ile Leu Thr Ile His Phe Thr Gly His Ser Phe Ile Tyr Gly Lys Arg
        595             600             605 cat gag gac acc ttg acc ctc ttc ccc atg cgt gga gaa tct gtg acg    1872
His Glu Asp Thr Leu Thr Leu Phe Pro Met Arg Gly Glu Ser Val Thr
    610             615             620 gtc aca atg gat aat gtt gga act tgg atg tta act tcc atg aat tct    1920
Val Thr Met Asp Asn Val Gly Thr Trp Met Leu Thr Ser Met Asn Ser
625             630             635             640 agt cca aga agc aaa aag ctg agg ctg aaa ttc agg gat gtt aaa tgt    1968
Ser Pro Arg Ser Lys Lys Leu Arg Leu Lys Phe Arg Asp Val Lys Cys
            645             650             655 atc cca gat gat gat gaa gac tca tat gag att ttt gaa cct cca gaa    2016
Ile Pro Asp Asp Asp Glu Asp Ser Tyr Glu Ile Phe Glu Pro Pro Glu
        660             665             670 tct aca gtc atg gct aca cgg aaa atg cat gat cgt tta gaa cct gaa    2064
Ser Thr Val Met Ala Thr Arg Lys Met His Asp Arg Leu Glu Pro Glu
    675             680             685 gat gaa gag agt gat gct gac tat gat tac cag aac aga ctg gct gca    2112
Asp Glu Glu Ser Asp Ala Asp Tyr Asp Tyr Gln Asn Arg Leu Ala Ala
690             695             700 gca tta gga att agg agg gaa aca gat att gaa gac tct gat gat att    2160
Ala Leu Gly Ile Arg Arg Glu Thr Asp Ile Glu Asp Ser Asp Asp Ile
705             710             715             720 cca gaa gat acc aca tat aag aaa gta gtt ttt cga aag tac ctc gac    2208
Pro Glu Asp Thr Thr Tyr Lys Lys Val Val Phe Arg Lys Tyr Leu Asp
            725             730             735 agc act ttt acc aaa cgt gat cct cga ggg gag tat gaa gag cat ctc    2256
Ser Thr Phe Thr Lys Arg Asp Pro Arg Gly Glu Tyr Glu Glu His Leu
        740             745             750 gga att ctt ggt cct att atc aga gct gaa gtg gat gat gtt atc caa    2304
Gly Ile Leu Gly Pro Ile Ile Arg Ala Glu Val Asp Asp Val Ile Gln
    755             760             765 gtt cgt ttt aaa aat tta gca tcc aga ccg tat tct cta cat gcc cat    2352
Val Arg Phe Lys Asn Leu Ala Ser Arg Pro Tyr Ser Leu His Ala His
770             775             780 gga ctt tcc tat gaa aaa tca tca gag gga aag act tat gaa gat gac    2400
Gly Leu Ser Tyr Glu Lys Ser Ser Glu Gly Lys Thr Tyr Glu Asp Asp
785             790             795             800 tct cct gaa tgg ttt aag gaa gat aat gct gtt cag cca aat agc agt    2448
Ser Pro Glu Trp Phe Lys Glu Asp Asn Ala Val Gln Pro Asn Ser Ser
            805             810             815 tat acc tac gta tgg cat gcc act gag cga tca ggg cca gaa agt cct    2496
Tyr Thr Tyr Val Trp His Ala Thr Glu Arg Ser Gly Pro Glu Ser Pro
        820             825             830 ggc tct gcc tgt cgg gct tgg gcc tac tac tca gct gtg aac cca gaa    2544
Gly Ser Ala Cys Arg Ala Trp Ala Tyr Tyr Ser Ala Val Asn Pro Glu
    835             840             845 aaa gat att cac tca ggc ttg ata ggt ccc ctc cta atc tgc caa aaa    2592
Lys Asp Ile His Ser Gly Leu Ile Gly Pro Leu Leu Ile Cys Gln Lys
850             855             860 gga ata cta cat aag gac agc aac atg cct gtg gac atg aga gaa ttt    2640
Gly Ile Leu His Lys Asp Ser Asn Met Pro Val Asp Met Arg Glu Phe
865             870             875             880
```

```
gtc tta cta ttt atg acc ttt gat gaa aag aag agc tgg tac tat gaa    2688
Val Leu Leu Phe Met Thr Phe Asp Glu Lys Lys Ser Trp Tyr Tyr Glu
                885                 890                 895 aag aag tcc cga agt tct tgg aga ctc aca tcc tca gaa atg aaa aaa    2736
Lys Lys Ser Arg Ser Ser Trp Arg Leu Thr Ser Ser Glu Met Lys Lys
        900                 905                 910 tcc cat gag ttt cac gcc att aat ggg atg atc tac agc ttg cct ggc    2784
Ser His Glu Phe His Ala Ile Asn Gly Met Ile Tyr Ser Leu Pro Gly
            915                 920                 925 ctg aaa atg tat gag caa gag tgg gtg agg tta cac ctg ctg aac ata    2832
Leu Lys Met Tyr Glu Gln Glu Trp Val Arg Leu His Leu Leu Asn Ile
        930                 935                 940 ggc ggc tcc caa gac att cac gtg gtt cac ttt cac ggc cag acc ttg    2880
Gly Gly Ser Gln Asp Ile His Val Val His Phe His Gly Gln Thr Leu
945                 950                 955                 960 ctg gaa aat ggc aat aaa cag cac cag tta ggg gtc tgg ccc ctt ctg    2928
Leu Glu Asn Gly Asn Lys Gln His Gln Leu Gly Val Trp Pro Leu Leu
                965                 970                 975 cct ggt tca ttt aaa act ctt gaa atg aag gca tca aaa cct ggc tgg    2976
Pro Gly Ser Phe Lys Thr Leu Glu Met Lys Ala Ser Lys Pro Gly Trp
            980                 985                 990 tgg ctc cta aac aca gag gtt gga gaa aac cag aga gca ggg atg caa    3024
Trp Leu Leu Asn Thr Glu Val Gly Glu Asn Gln Arg Ala Gly Met Gln
        995                 1000                1005 acg cca ttt ctt atc atg gac aga gac tgt agg atg cca atg gga cta    3072
Thr Pro Phe Leu Ile Met Asp Arg Asp Cys Arg Met Pro Met Gly Leu
    1010                1015                1020 agc act ggt atc ata tct gat tca cag atc aag gct tca gag ttt ctg    3120
Ser Thr Gly Ile Ile Ser Asp Ser Gln Ile Lys Ala Ser Glu Phe Leu
1025                1030                1035                1040 ggt tac tgg gag ccc aga tta gca aga tta aac aat ggt gga tct tat    3168
Gly Tyr Trp Glu Pro Arg Leu Ala Arg Leu Asn Asn Gly Gly Ser Tyr
                1045                1050                1055 aat gct tgg agt gta gaa aaa ctt gca gca gaa ttt gcc tct aaa cct    3216
Asn Ala Trp Ser Val Glu Lys Leu Ala Ala Glu Phe Ala Ser Lys Pro
            1060                1065                1070 tgg atc cag gtg gac atg caa aag gaa gtc ata atc aca ggg atc cag    3264
Trp Ile Gln Val Asp Met Gln Lys Glu Val Ile Ile Thr Gly Ile Gln
        1075                1080                1085 acc caa ggt gcc aaa cac tac ctg aag tcc tgc tat acc aca gag ttc    3312
Thr Gln Gly Ala Lys His Tyr Leu Lys Ser Cys Tyr Thr Thr Glu Phe
    1090                1095                1100 tat gta gct tac agt tcc aac cag atc aac tgg cag atc ttc aaa ggg    3360
Tyr Val Ala Tyr Ser Ser Asn Gln Ile Asn Trp Gln Ile Phe Lys Gly
1105                1110                1115                1120 aac agc aca agg aat gtg atg tat ttt aat ggc aat tca gat gcc tct    3408
Asn Ser Thr Arg Asn Val Met Tyr Phe Asn Gly Asn Ser Asp Ala Ser
                1125                1130                1135 aca ata aaa gag aat cag ttt gac cca cct att gtg gct aga tat att    3456
Thr Ile Lys Glu Asn Gln Phe Asp Pro Pro Ile Val Ala Arg Tyr Ile
            1140                1145                1150 agg atc tct cca act cga gcc tat aac aga cct acc ctt cga ttg gaa    3504
Arg Ile Ser Pro Thr Arg Ala Tyr Asn Arg Pro Thr Leu Arg Leu Glu
        1155                1160                1165 ctg caa ggt tgt gag gta aat gga tgt tcc aca ccc ctg ggt atg gaa    3552
Leu Gln Gly Cys Glu Val Asn Gly Cys Ser Thr Pro Leu Gly Met Glu
    1170                1175                1180 aat gga aag ata gaa aac aag caa atc aca gct tct tcg ttt aag aaa    3600
Asn Gly Lys Ile Glu Asn Lys Gln Ile Thr Ala Ser Ser Phe Lys Lys
1185                1190                1195                1200
```

```
tct tgg tgg gga gat tac tgg gaa ccc ttc cgt gcc cgt ctg aat gcc      3648
Ser Trp Trp Gly Asp Tyr Trp Glu Pro Phe Arg Ala Arg Leu Asn Ala
            1205                1210                1215 cag gga cgt gtg aat gcc tgg caa gcc aag gca aac aac aat aag cag      3696
Gln Gly Arg Val Asn Ala Trp Gln Ala Lys Ala Asn Asn Asn Lys Gln
        1220                1225                1230 tgg cta gaa att gat cta ctc aag atc aag aag ata acg gca att ata      3744
Trp Leu Glu Ile Asp Leu Leu Lys Ile Lys Lys Ile Thr Ala Ile Ile
    1235                1240                1245 aca cag ggc tgc aag tct ctg tcc tct gaa atg tat gta aag agc tat      3792
Thr Gln Gly Cys Lys Ser Leu Ser Ser Glu Met Tyr Val Lys Ser Tyr
1250                1255                1260 acc atc cac tac agt gag cag gga gtg gaa tgg aaa cca tac agg ctg      3840
Thr Ile His Tyr Ser Glu Gln Gly Val Glu Trp Lys Pro Tyr Arg Leu
1265                1270                1275                1280 aaa tcc tcc atg gtg gac aag att ttt gaa gga aat act aat acc aaa      3888
Lys Ser Ser Met Val Asp Lys Ile Phe Glu Gly Asn Thr Asn Thr Lys
            1285                1290                1295 gga cat gtg aag aac ttt ttc aac ccc cca atc att tcc agg ttt atc      3936
Gly His Val Lys Asn Phe Phe Asn Pro Pro Ile Ile Ser Arg Phe Ile
        1300                1305                1310 cgt gtc att cct aaa aca tgg aat caa agt att gca ctt cgc ctg gaa      3984
Arg Val Ile Pro Lys Thr Trp Asn Gln Ser Ile Ala Leu Arg Leu Glu
    1315                1320                1325 ctc ttt ggc tgt gat att tac tagaattgaa cattcaaaaa ccctggaag          4035
Leu Phe Gly Cys Asp Ile Tyr
1330                1335 agactcttta agacctcaaa ccatttagaa tgggcaatgt attttacgct gtgttaaatg    4095
ttaacagttt tccactattt ctctttcttt tctattagtg aataaatttt tatac         4150

<210> SEQ ID NO 14
<211> LENGTH: 1335
<212> TYPE: PRT
<213> ORGANISM: Homo sapiens

<400> SEQUENCE: 14

Ala Gln Leu Arg Gln Phe Tyr Val Ala Ala Gln Gly Ile Ser Trp Ser
1               5                   10                  15

Tyr Arg Pro Glu Pro Thr Asn Ser Ser Leu Asn Leu Ser Val Thr Ser
            20                  25                  30

Phe Lys Lys Ile Val Tyr Arg Glu Tyr Glu Pro Tyr Phe Lys Lys Glu
        35                  40                  45

Lys Pro Gln Ser Thr Ile Ser Gly Leu Leu Gly Pro Thr Leu Tyr Ala
    50                  55                  60

Glu Val Gly Asp Ile Ile Lys Val His Phe Lys Asn Lys Ala Asp Lys
65                  70                  75                  80

Pro Leu Ser Ile His Pro Gln Gly Ile Arg Tyr Ser Lys Leu Ser Glu
                85                  90                  95

Gly Ala Ser Tyr Leu Asp His Ala Phe Pro Ala Glu Lys Met Asp Asp
            100                 105                 110

Ala Val Ala Pro Gly Arg Glu Tyr Thr Tyr Glu Trp Ser Ile Ser Glu
        115                 120                 125

Asp Ser Gly Pro Thr His Asp Asp Pro Pro Cys Leu Thr His Ile Tyr
    130                 135                 140

Tyr Ser His Glu Asn Leu Ile Glu Asp Phe Asn Ser Gly Leu Ile Gly
145                 150                 155                 160
```

-continued

Pro Leu Leu Ile Cys Lys Lys Gly Thr Leu Thr Glu Gly Gly Thr Gln
            165                 170                 175

Lys Thr Phe Asp Lys Gln Ile Val Leu Leu Phe Ala Val Phe Asp Glu
            180                 185                 190

Ser Lys Ser Trp Ser Gln Ser Ser Leu Met Tyr Thr Val Asn Gly
            195                 200                 205

Tyr Val Asn Gly Thr Met Pro Asp Ile Thr Val Cys Ala His Asp His
        210                 215                 220

Ile Ser Trp His Leu Leu Gly Met Ser Ser Gly Pro Glu Leu Phe Ser
225                 230                 235                 240

Ile His Phe Asn Gly Gln Val Leu Glu Gln Asn His His Lys Val Ser
                245                 250                 255

Ala Ile Thr Leu Val Ser Ala Thr Ser Thr Ala Asn Met Thr Val
            260                 265                 270

Gly Pro Glu Gly Lys Trp Ile Ile Ser Ser Leu Thr Pro Lys His Leu
            275                 280                 285

Gln Ala Gly Met Gln Ala Tyr Ile Asp Ile Lys Asn Cys Pro Lys Lys
            290                 295                 300

Thr Arg Asn Leu Lys Lys Ile Thr Arg Glu Gln Arg His Met Lys
305                 310                 315                 320

Arg Trp Glu Tyr Phe Ile Ala Ala Glu Val Ile Trp Asp Tyr Ala
                325                 330                 335

Pro Val Ile Pro Ala Asn Met Asp Lys Lys Tyr Arg Ser Gln His Leu
            340                 345                 350

Asp Asn Phe Ser Asn Gln Ile Gly Lys His Tyr Lys Lys Val Met Tyr
            355                 360                 365

Thr Gln Tyr Glu Asp Glu Ser Phe Thr Lys His Thr Val Asn Pro Asn
        370                 375                 380

Met Lys Glu Asp Gly Ile Leu Gly Pro Ile Ile Arg Ala Gln Val Arg
385                 390                 395                 400

Asp Thr Leu Lys Ile Val Phe Lys Asn Met Ala Ser Arg Pro Tyr Ser
                405                 410                 415

Ile Tyr Pro His Gly Val Thr Phe Ser Pro Tyr Glu Asp Glu Val Asn
            420                 425                 430

Ser Ser Phe Thr Ser Gly Arg Asn Asn Thr Met Ile Arg Ala Val Gln
            435                 440                 445

Pro Gly Glu Thr Tyr Thr Tyr Lys Trp Asn Ile Leu Glu Phe Asp Glu
            450                 455                 460

Pro Thr Glu Asn Asp Ala Gln Cys Leu Thr Arg Pro Tyr Tyr Ser Asp
465                 470                 475                 480

Val Asp Ile Met Arg Asp Ile Ala Ser Gly Leu Ile Gly Leu Leu Leu
                485                 490                 495

Ile Cys Lys Ser Arg Ser Leu Asp Arg Arg Gly Ile Gln Arg Ala Ala
            500                 505                 510

Asp Ile Glu Gln Gln Ala Val Phe Ala Val Phe Asp Glu Asn Lys Ser
            515                 520                 525

Trp Tyr Leu Glu Asp Asn Ile Asn Lys Phe Cys Glu Asn Pro Asp Glu
            530                 535                 540

Val Lys Arg Asp Asp Pro Lys Phe Tyr Glu Ser Asn Ile Met Ser Thr
545                 550                 555                 560

Ile Asn Gly Tyr Val Pro Glu Ser Ile Thr Thr Leu Gly Phe Cys Phe
                565                 570                 575

Asp Asp Thr Val Gln Trp His Phe Cys Ser Val Gly Thr Gln Asn Glu

-continued

```
                580                 585                 590
Ile Leu Thr Ile His Phe Thr Gly His Ser Phe Ile Tyr Gly Lys Arg
            595                 600                 605

His Glu Asp Thr Leu Thr Leu Phe Pro Met Arg Gly Glu Ser Val Thr
            610                 615                 620

Val Thr Met Asp Asn Val Gly Thr Trp Met Leu Thr Ser Met Asn Ser
625                 630                 635                 640

Ser Pro Arg Ser Lys Lys Leu Arg Leu Lys Phe Arg Asp Val Lys Cys
                645                 650                 655

Ile Pro Asp Asp Asp Glu Asp Ser Tyr Glu Ile Phe Glu Pro Pro Glu
            660                 665                 670

Ser Thr Val Met Ala Thr Arg Lys Met His Asp Arg Leu Glu Pro Glu
            675                 680                 685

Asp Glu Glu Ser Asp Ala Asp Tyr Asp Tyr Gln Asn Arg Leu Ala Ala
            690                 695                 700

Ala Leu Gly Ile Arg Arg Glu Thr Asp Ile Glu Asp Ser Asp Asp Ile
705                 710                 715                 720

Pro Glu Asp Thr Thr Tyr Lys Lys Val Val Phe Arg Lys Tyr Leu Asp
                725                 730                 735

Ser Thr Phe Thr Lys Arg Asp Pro Arg Gly Glu Tyr Glu Glu His Leu
            740                 745                 750

Gly Ile Leu Gly Pro Ile Ile Arg Ala Glu Val Asp Asp Val Ile Gln
            755                 760                 765

Val Arg Phe Lys Asn Leu Ala Ser Arg Pro Tyr Ser Leu His Ala His
            770                 775                 780

Gly Leu Ser Tyr Glu Lys Ser Ser Glu Gly Lys Thr Tyr Glu Asp Asp
785                 790                 795                 800

Ser Pro Glu Trp Phe Lys Glu Asp Asn Ala Val Gln Pro Asn Ser Ser
                805                 810                 815

Tyr Thr Tyr Val Trp His Ala Thr Glu Arg Ser Gly Pro Glu Ser Pro
            820                 825                 830

Gly Ser Ala Cys Arg Ala Trp Ala Tyr Tyr Ser Ala Val Asn Pro Glu
            835                 840                 845

Lys Asp Ile His Ser Gly Leu Ile Gly Pro Leu Leu Ile Cys Gln Lys
            850                 855                 860

Gly Ile Leu His Lys Asp Ser Asn Met Pro Val Asp Met Arg Glu Phe
865                 870                 875                 880

Val Leu Leu Phe Met Thr Phe Asp Glu Lys Lys Ser Trp Tyr Tyr Glu
                885                 890                 895

Lys Lys Ser Arg Ser Ser Trp Arg Leu Thr Ser Ser Glu Met Lys Lys
            900                 905                 910

Ser His Glu Phe His Ala Ile Asn Gly Met Ile Tyr Ser Leu Pro Gly
            915                 920                 925

Leu Lys Met Tyr Glu Gln Glu Trp Val Arg Leu His Leu Leu Asn Ile
            930                 935                 940

Gly Gly Ser Gln Asp Ile His Val Val His Phe His Gly Gln Thr Leu
945                 950                 955                 960

Leu Glu Asn Gly Asn Lys Gln His Gln Leu Gly Val Trp Pro Leu Leu
                965                 970                 975

Pro Gly Ser Phe Lys Thr Leu Glu Met Lys Ala Ser Lys Pro Gly Trp
            980                 985                 990

Trp Leu Leu Asn Thr Glu Val Gly Glu Asn Gln Arg Ala Gly Met Gln
            995                 1000                1005
```

```
Thr Pro Phe Leu Ile Met Asp Arg Asp Cys Arg Met Pro Met Gly Leu
    1010                1015                1020

Ser Thr Gly Ile Ile Ser Asp Ser Gln Ile Lys Ala Ser Glu Phe Leu
1025                1030                1035                1040

Gly Tyr Trp Glu Pro Arg Leu Ala Arg Leu Asn Asn Gly Gly Ser Tyr
                1045                1050                1055

Asn Ala Trp Ser Val Glu Lys Leu Ala Ala Glu Phe Ala Ser Lys Pro
            1060                1065                1070

Trp Ile Gln Val Asp Met Gln Lys Glu Val Ile Ile Thr Gly Ile Gln
        1075                1080                1085

Thr Gln Gly Ala Lys His Tyr Leu Lys Ser Cys Tyr Thr Thr Glu Phe
    1090                1095                1100

Tyr Val Ala Tyr Ser Ser Asn Gln Ile Asn Trp Gln Ile Phe Lys Gly
1105                1110                1115                1120

Asn Ser Thr Arg Asn Val Met Tyr Phe Asn Gly Asn Ser Asp Ala Ser
                1125                1130                1135

Thr Ile Lys Glu Asn Gln Phe Asp Pro Pro Ile Val Ala Arg Tyr Ile
            1140                1145                1150

Arg Ile Ser Pro Thr Arg Ala Tyr Asn Arg Pro Thr Leu Arg Leu Glu
        1155                1160                1165

Leu Gln Gly Cys Glu Val Asn Gly Cys Ser Thr Pro Leu Gly Met Glu
    1170                1175                1180

Asn Gly Lys Ile Glu Asn Lys Gln Ile Thr Ala Ser Ser Phe Lys Lys
1185                1190                1195                1200

Ser Trp Trp Gly Asp Tyr Trp Glu Pro Phe Arg Ala Arg Leu Asn Ala
                1205                1210                1215

Gln Gly Arg Val Asn Ala Trp Gln Ala Lys Ala Asn Asn Asn Lys Gln
            1220                1225                1230

Trp Leu Glu Ile Asp Leu Leu Lys Ile Lys Lys Ile Thr Ala Ile Ile
        1235                1240                1245

Thr Gln Gly Cys Lys Ser Leu Ser Ser Glu Met Tyr Val Lys Ser Tyr
    1250                1255                1260

Thr Ile His Tyr Ser Glu Gln Gly Val Glu Trp Lys Pro Tyr Arg Leu
1265                1270                1275                1280

Lys Ser Ser Met Val Asp Lys Ile Phe Glu Gly Asn Thr Asn Thr Lys
                1285                1290                1295

Gly His Val Lys Asn Phe Phe Asn Pro Pro Ile Ile Ser Arg Phe Ile
            1300                1305                1310

Arg Val Ile Pro Lys Thr Trp Asn Gln Ser Ile Ala Leu Arg Leu Glu
        1315                1320                1325

Leu Phe Gly Cys Asp Ile Tyr
    1330                1335

<210> SEQ ID NO 15
<211> LENGTH: 4150
<212> TYPE: DNA
<213> ORGANISM: Homo sapiens
<220> FEATURE:
<221> NAME/KEY: CDS
<222> LOCATION: (1)..(4005)

<400> SEQUENCE: 15 gca cag cta agg cag ttc tac gtg gct gct cag ggc atc agt tgg agc        48
Ala Gln Leu Arg Gln Phe Tyr Val Ala Ala Gln Gly Ile Ser Trp Ser
 1               5                  10                  15
```

```
tac cga cct gag ccc aca aac tca agt ttg aat ctt tct gta act tcc      96
Tyr Arg Pro Glu Pro Thr Asn Ser Ser Leu Asn Leu Ser Val Thr Ser
            20                  25                  30 ttt aag aaa att gtc tac aga gag tat gaa cca tat ttt aag aaa gaa     144
Phe Lys Lys Ile Val Tyr Arg Glu Tyr Glu Pro Tyr Phe Lys Lys Glu
        35                  40                  45 aaa cca caa tct acc att tca gga ctt ctt ggg cct act tta tat gct     192
Lys Pro Gln Ser Thr Ile Ser Gly Leu Leu Gly Pro Thr Leu Tyr Ala
 50                  55                  60 gaa gtc gga gac atc ata aaa gtt cac ttt aaa aat aag gca gat aag     240
Glu Val Gly Asp Ile Ile Lys Val His Phe Lys Asn Lys Ala Asp Lys
 65                  70                  75                  80 ccc ttg agc atc cat cct caa gga att agg tac agt aaa tta tca gaa     288
Pro Leu Ser Ile His Pro Gln Gly Ile Arg Tyr Ser Lys Leu Ser Glu
                 85                  90                  95 ggt gct tct tac ctt gcc cac aca ttc cct gcg gag aag atg gac gac     336
Gly Ala Ser Tyr Leu Ala His Thr Phe Pro Ala Glu Lys Met Asp Asp
            100                 105                 110 gct gtg gct cca ggc cga gaa tac acc tat gaa tgg agt atc agt gag     384
Ala Val Ala Pro Gly Arg Glu Tyr Thr Tyr Glu Trp Ser Ile Ser Glu
        115                 120                 125 gac agt gga ccc acc cat gat gac cct cca tgc ctc aca cac atc tat     432
Asp Ser Gly Pro Thr His Asp Asp Pro Pro Cys Leu Thr His Ile Tyr
130                 135                 140 tac tcc cat gaa aat ctg atc gag gat ttc aac tct ggg ctg att ggg     480
Tyr Ser His Glu Asn Leu Ile Glu Asp Phe Asn Ser Gly Leu Ile Gly
145                 150                 155                 160 ccc ctg ctt atc tgt aaa aaa ggg acc cta act gag ggt ggg aca cag     528
Pro Leu Leu Ile Cys Lys Lys Gly Thr Leu Thr Glu Gly Gly Thr Gln
                165                 170                 175 aag acg ttt gac aag caa atc gtg cta cta ttt gct gtg ttt gat gaa     576
Lys Thr Phe Asp Lys Gln Ile Val Leu Leu Phe Ala Val Phe Asp Glu
            180                 185                 190 agc aag agc tgg agc cag tca tca tcc cta atg tac aca gtc aat gga     624
Ser Lys Ser Trp Ser Gln Ser Ser Ser Leu Met Tyr Thr Val Asn Gly
        195                 200                 205 tat gtg aat ggg aca atg cca gat ata aca gtt tgt gcc cat gac cac     672
Tyr Val Asn Gly Thr Met Pro Asp Ile Thr Val Cys Ala His Asp His
    210                 215                 220 atc agc tgg cat ctg ctg gga atg agc tcg ggg cca gaa tta ttc tcc     720
Ile Ser Trp His Leu Leu Gly Met Ser Ser Gly Pro Glu Leu Phe Ser
225                 230                 235                 240 att cat ttc aac ggc cag gtc ctg gag cag aac cat cat aag gtc tca     768
Ile His Phe Asn Gly Gln Val Leu Glu Gln Asn His His Lys Val Ser
                245                 250                 255 gcc atc acc ctt gtc agt gct aca tcc act acc gca aat atg act gtg     816
Ala Ile Thr Leu Val Ser Ala Thr Ser Thr Thr Ala Asn Met Thr Val
            260                 265                 270 ggc cca gag gga aag tgg atc ata tct tct ctc acc cca aaa cat ttg     864
Gly Pro Glu Gly Lys Trp Ile Ile Ser Ser Leu Thr Pro Lys His Leu
        275                 280                 285 caa gct ggg atg cag gct tac att gac att aaa aac tgc cca aag aaa     912
Gln Ala Gly Met Gln Ala Tyr Ile Asp Ile Lys Asn Cys Pro Lys Lys
    290                 295                 300 acc agg aat ctt aag aaa ata act cgt gag cag agg cgg cac atg aag     960
Thr Arg Asn Leu Lys Lys Ile Thr Arg Glu Gln Arg Arg His Met Lys
305                 310                 315                 320 agg tgg gaa tac ttc att gct gca gag gaa gtc att tgg gac tat gca    1008
Arg Trp Glu Tyr Phe Ile Ala Ala Glu Glu Val Ile Trp Asp Tyr Ala
                325                 330                 335
```

```
cct gta ata cca gcg aat atg gac aaa aaa tac agg tct cag cat ttg    1056
Pro Val Ile Pro Ala Asn Met Asp Lys Lys Tyr Arg Ser Gln His Leu
        340                 345                 350 gat aat ttc tca aac caa att gga aaa cat tat aag aaa gtt atg tac    1104
Asp Asn Phe Ser Asn Gln Ile Gly Lys His Tyr Lys Lys Val Met Tyr
            355                 360                 365 aca cag tac gaa gat gag tcc ttc acc aaa cat aca gtg aat ccc aat    1152
Thr Gln Tyr Glu Asp Glu Ser Phe Thr Lys His Thr Val Asn Pro Asn
    370                 375                 380 atg aaa gaa gat ggg att ttg ggt cct att atc aga gcc cag gtc aga    1200
Met Lys Glu Asp Gly Ile Leu Gly Pro Ile Ile Arg Ala Gln Val Arg
385                 390                 395                 400 gac aca ctc aaa atc gtg ttc aaa aat atg gcc agc cgc ccc tat agc    1248
Asp Thr Leu Lys Ile Val Phe Lys Asn Met Ala Ser Arg Pro Tyr Ser
                405                 410                 415 att tac cct cat gga gtg acc ttc tcg cct tat gaa gat gaa gtc aac    1296
Ile Tyr Pro His Gly Val Thr Phe Ser Pro Tyr Glu Asp Glu Val Asn
            420                 425                 430 tct tct ttc acc tca ggc agg aac aac acc atg atc aga gca gtt caa    1344
Ser Ser Phe Thr Ser Gly Arg Asn Asn Thr Met Ile Arg Ala Val Gln
    435                 440                 445 cca ggg gaa acc tat act tat aag tgg aac atc tta gag ttt gat gaa    1392
Pro Gly Glu Thr Tyr Thr Tyr Lys Trp Asn Ile Leu Glu Phe Asp Glu
450                 455                 460 ccc aca gaa aat gat gcc cag tgc tta aca aga cca tac tac agt gac    1440
Pro Thr Glu Asn Asp Ala Gln Cys Leu Thr Arg Pro Tyr Tyr Ser Asp
465                 470                 475                 480 gtg gac atc atg aga gac atc gcc tct ggg cta ata gga cta ctt cta    1488
Val Asp Ile Met Arg Asp Ile Ala Ser Gly Leu Ile Gly Leu Leu Leu
                485                 490                 495 atc tgt aag agc aga tcc ctg gac agg cga gga ata cag agg gca gca    1536
Ile Cys Lys Ser Arg Ser Leu Asp Arg Arg Gly Ile Gln Arg Ala Ala
            500                 505                 510 gac atc gaa cag cag gct gtg ttt gct gtg ttt gat gag aac aaa agc    1584
Asp Ile Glu Gln Gln Ala Val Phe Ala Val Phe Asp Glu Asn Lys Ser
    515                 520                 525 tgg tac ctt gag gac aac atc aac aag ttt tgt gaa aat cct gat gag    1632
Trp Tyr Leu Glu Asp Asn Ile Asn Lys Phe Cys Glu Asn Pro Asp Glu
530                 535                 540 gtg aaa cgt gat gac ccc aag ttt tat gaa tca aac atc atg agc act    1680
Val Lys Arg Asp Asp Pro Lys Phe Tyr Glu Ser Asn Ile Met Ser Thr
545                 550                 555                 560 atc aat ggc tat gtg cct gag agc ata act act ctt gga ttc tgc ttt    1728
Ile Asn Gly Tyr Val Pro Glu Ser Ile Thr Thr Leu Gly Phe Cys Phe
                565                 570                 575 gat gac act gtc cag tgg cac ttc tgt agt gtg ggg acc cag aat gaa    1776
Asp Asp Thr Val Gln Trp His Phe Cys Ser Val Gly Thr Gln Asn Glu
            580                 585                 590 att ttg acc atc cac ttc act ggg cac tca ttc atc tat gga aag agg    1824
Ile Leu Thr Ile His Phe Thr Gly His Ser Phe Ile Tyr Gly Lys Arg
    595                 600                 605 cat gag gac acc ttg acc ctc ttc ccc atg cgt gga gaa tct gtg acg    1872
His Glu Asp Thr Leu Thr Leu Phe Pro Met Arg Gly Glu Ser Val Thr
610                 615                 620 gtc aca atg gat aat gtt gga act tgg atg tta act tcc atg aat tct    1920
Val Thr Met Asp Asn Val Gly Thr Trp Met Leu Thr Ser Met Asn Ser
625                 630                 635                 640 agt cca aga agc aaa aag ctg agg ctg aaa ttc agg gat gtt aaa tgt    1968
Ser Pro Arg Ser Lys Lys Leu Arg Leu Lys Phe Arg Asp Val Lys Cys
```

-continued

```
                    645                 650                 655
atc cca gat gat gat gaa gac tca tat gag att ttt gaa cct cca gaa    2016
Ile Pro Asp Asp Asp Glu Asp Ser Tyr Glu Ile Phe Glu Pro Pro Glu
            660                 665                 670 tct aca gtc atg gct aca cgg aaa atg cat gat cgt tta gaa cct gaa    2064
Ser Thr Val Met Ala Thr Arg Lys Met His Asp Arg Leu Glu Pro Glu
            675                 680                 685 gat gaa gag agt gat gct gac tat gat tac cag aac aga ctg gct gca    2112
Asp Glu Glu Ser Asp Ala Asp Tyr Asp Tyr Gln Asn Arg Leu Ala Ala
        690                 695                 700 gca tta gga att agg agg gaa aca gat att gaa gac tct gat gat att    2160
Ala Leu Gly Ile Arg Arg Glu Thr Asp Ile Glu Asp Ser Asp Asp Ile
705                 710                 715                 720 cca gaa gat acc aca tat aag aaa gta gtt ttt cga aag tac ctc gac    2208
Pro Glu Asp Thr Thr Tyr Lys Lys Val Val Phe Arg Lys Tyr Leu Asp
                725                 730                 735 agc act ttt acc aaa cgt gat cct cga ggg gag tat gaa gag cat ctc    2256
Ser Thr Phe Thr Lys Arg Asp Pro Arg Gly Glu Tyr Glu Glu His Leu
            740                 745                 750 gga att ctt ggt cct atc atc aga gct gaa gtg gat gat gtt atc caa    2304
Gly Ile Leu Gly Pro Ile Ile Arg Ala Glu Val Asp Asp Val Ile Gln
        755                 760                 765 gtt cgt ttt aaa aat tta gca tcc aga ccg tat tct cta cat gcc cat    2352
Val Arg Phe Lys Asn Leu Ala Ser Arg Pro Tyr Ser Leu His Ala His
770                 775                 780 gga ctt tcc tat gaa aaa tca tca gag gga aag act tat gaa gat gac    2400
Gly Leu Ser Tyr Glu Lys Ser Ser Glu Gly Lys Thr Tyr Glu Asp Asp
785                 790                 795                 800 tct cct gaa tgg ttt aag gaa gat aat gct gtt cag cca aat agc agt    2448
Ser Pro Glu Trp Phe Lys Glu Asp Asn Ala Val Gln Pro Asn Ser Ser
                805                 810                 815 tat acc tac gta tgg cat gcc act gag cga tca ggg cca gaa agt cct    2496
Tyr Thr Tyr Val Trp His Ala Thr Glu Arg Ser Gly Pro Glu Ser Pro
            820                 825                 830 ggc tct gcc tgt cgg gct tgg gcc tac tac tca gct gtg aac cca gaa    2544
Gly Ser Ala Cys Arg Ala Trp Ala Tyr Tyr Ser Ala Val Asn Pro Glu
        835                 840                 845 aaa gat att cac tca ggc ttg ata ggt ccc ctc cta atc tgc caa aaa    2592
Lys Asp Ile His Ser Gly Leu Ile Gly Pro Leu Leu Ile Cys Gln Lys
850                 855                 860 gga ata cta cat aag gac agc aac atg cct gtg gac atg aga gaa ttt    2640
Gly Ile Leu His Lys Asp Ser Asn Met Pro Val Asp Met Arg Glu Phe
865                 870                 875                 880 gtc tta cta ttt atg acc ttt gat gaa aag aag agc tgg tac tat gaa    2688
Val Leu Leu Phe Met Thr Phe Asp Glu Lys Lys Ser Trp Tyr Tyr Glu
                885                 890                 895 aag aag tcc cga agt tct tgg aga ctc aca tcc tca gaa atg aaa aaa    2736
Lys Lys Ser Arg Ser Ser Trp Arg Leu Thr Ser Ser Glu Met Lys Lys
            900                 905                 910 tcc cat gag ttt cac gcc att aat ggg atg atc tac agc ttg cct ggc    2784
Ser His Glu Phe His Ala Ile Asn Gly Met Ile Tyr Ser Leu Pro Gly
        915                 920                 925 ctg aaa atg tat gag caa gag tgg gtg agg tta cac ctg ctg aac ata    2832
Leu Lys Met Tyr Glu Gln Glu Trp Val Arg Leu His Leu Leu Asn Ile
    930                 935                 940 ggc ggc tcc caa gac att cac gtg gtt cac ttt cac ggc cag acc ttg    2880
Gly Gly Ser Gln Asp Ile His Val Val His Phe His Gly Gln Thr Leu
945                 950                 955                 960 ctg gaa aat ggc aat aaa cag cac cag tta ggg gtc tgg ccc ctt ctg    2928
```

```
Leu Glu Asn Gly Asn Lys Gln His Gln Leu Gly Val Trp Pro Leu Leu
            965                 970                 975 cct ggt tca ttt aaa act ctt gaa atg aag gca tca aaa cct ggc tgg      2976
Pro Gly Ser Phe Lys Thr Leu Glu Met Lys Ala Ser Lys Pro Gly Trp
            980                 985                 990 tgg ctc cta aac aca gag gtt gga gaa aac cag aga gca ggg atg caa      3024
Trp Leu Leu Asn Thr Glu Val Gly Glu Asn Gln Arg Ala Gly Met Gln
            995                 1000                1005 acg cca ttt ctt atc atg gac aga gac tgt agg atg cca atg gga cta      3072
Thr Pro Phe Leu Ile Met Asp Arg Asp Cys Arg Met Pro Met Gly Leu
        1010                1015                1020 agc act ggt atc ata tct gat tca cag atc aag gct tca gag ttt ctg      3120
Ser Thr Gly Ile Ile Ser Asp Ser Gln Ile Lys Ala Ser Glu Phe Leu
    1025                1030                1035                1040 ggt tac tgg gag ccc aga tta gca aga tta aac aat ggt gga tct tat      3168
Gly Tyr Trp Glu Pro Arg Leu Ala Arg Leu Asn Asn Gly Gly Ser Tyr
            1045                1050                1055 aat gct tgg agt gta gaa aaa ctt gca gca gaa ttt gcc tct aaa cct      3216
Asn Ala Trp Ser Val Glu Lys Leu Ala Ala Glu Phe Ala Ser Lys Pro
            1060                1065                1070 tgg atc cag gtg gac atg caa aag gaa gtc ata atc aca ggg atc cag      3264
Trp Ile Gln Val Asp Met Gln Lys Glu Val Ile Ile Thr Gly Ile Gln
        1075                1080                1085 acc caa ggt gcc aaa cac tac ctg aag tcc tgc tat acc aca gag ttc      3312
Thr Gln Gly Ala Lys His Tyr Leu Lys Ser Cys Tyr Thr Thr Glu Phe
        1090                1095                1100 tat gta gct tac agt tcc aac cag atc aac tgg cag atc ttc aaa ggg      3360
Tyr Val Ala Tyr Ser Ser Asn Gln Ile Asn Trp Gln Ile Phe Lys Gly
1105                1110                1115                1120 aac agc aca agg aat gtg atg tat ttt aat ggc aat tca gat gcc tct      3408
Asn Ser Thr Arg Asn Val Met Tyr Phe Asn Gly Asn Ser Asp Ala Ser
            1125                1130                1135 aca ata aaa gag aat cag ttt gac cca cct att gtg gct aga tat att      3456
Thr Ile Lys Glu Asn Gln Phe Asp Pro Pro Ile Val Ala Arg Tyr Ile
        1140                1145                1150 agg atc tct cca act cga gcc tat aac aga cct acc ctt cga ttg gaa      3504
Arg Ile Ser Pro Thr Arg Ala Tyr Asn Arg Pro Thr Leu Arg Leu Glu
    1155                1160                1165 ctg caa ggt tgt gag gta aat gga tgt tcc aca ccc ctg ggt atg gaa      3552
Leu Gln Gly Cys Glu Val Asn Gly Cys Ser Thr Pro Leu Gly Met Glu
    1170                1175                1180 aat gga aag ata gaa aac aag caa atc aca gct tct tcg ttt aag aaa      3600
Asn Gly Lys Ile Glu Asn Lys Gln Ile Thr Ala Ser Ser Phe Lys Lys
1185                1190                1195                1200 tct tgg tgg gga gat tac tgg gaa ccc ttc cgt gcc cgt ctg aat gcc      3648
Ser Trp Trp Gly Asp Tyr Trp Glu Pro Phe Arg Ala Arg Leu Asn Ala
            1205                1210                1215 cag gga cgt gtg aat gcc tgg caa gcc aag gca aac aac aat aag cag      3696
Gln Gly Arg Val Asn Ala Trp Gln Ala Lys Ala Asn Asn Asn Lys Gln
        1220                1225                1230 tgg cta gaa att gat cta ctc aag atc aag aag ata acg gca att ata      3744
Trp Leu Glu Ile Asp Leu Leu Lys Ile Lys Lys Ile Thr Ala Ile Ile
    1235                1240                1245 aca cag ggc tgc aag tct ctg tcc tct gaa atg tat gta aag agc tat      3792
Thr Gln Gly Cys Lys Ser Leu Ser Ser Glu Met Tyr Val Lys Ser Tyr
    1250                1255                1260 acc atc cac tac agt gag cag gga gtg gaa tgg aaa cca tac agg ctg      3840
Thr Ile His Tyr Ser Glu Gln Gly Val Glu Trp Lys Pro Tyr Arg Leu
1265                1270                1275                1280
```

```
aaa tcc tcc atg gtg gac aag att ttt gaa gga aat act aat acc aaa    3888
Lys Ser Ser Met Val Asp Lys Ile Phe Glu Gly Asn Thr Asn Thr Lys
            1285                1290                1295 gga cat gtg aag aac ttt ttc aac ccc cca atc att tcc agg ttt atc    3936
Gly His Val Lys Asn Phe Phe Asn Pro Pro Ile Ile Ser Arg Phe Ile
        1300                1305                1310 cgt gtc att cct aaa aca tgg aat caa agt att gca ctt cgc ctg gaa    3984
Arg Val Ile Pro Lys Thr Trp Asn Gln Ser Ile Ala Leu Arg Leu Glu
    1315                1320                1325 ctc ttt ggc tgt gat att tac tagaattgaa cattcaaaaa ccctggaag        4035
Leu Phe Gly Cys Asp Ile Tyr
1330                1335 agactcttta agacctcaaa ccatttagaa tgggcaatgt attttacgct gtgttaaatg  4095
ttaacagttt tccactattt ctctttcttt tctattagtg aataaaattt tatac       4150

<210> SEQ ID NO 16
<211> LENGTH: 1335
<212> TYPE: PRT
<213> ORGANISM: Homo sapiens

<400> SEQUENCE: 16

Ala Gln Leu Arg Gln Phe Tyr Val Ala Ala Gln Gly Ile Ser Trp Ser
 1               5                  10                  15

Tyr Arg Pro Glu Pro Thr Asn Ser Ser Leu Asn Leu Ser Val Thr Ser
            20                  25                  30

Phe Lys Lys Ile Val Tyr Arg Glu Tyr Glu Pro Tyr Phe Lys Lys Glu
        35                  40                  45

Lys Pro Gln Ser Thr Ile Ser Gly Leu Leu Gly Pro Thr Leu Tyr Ala
    50                  55                  60

Glu Val Gly Asp Ile Ile Lys Val His Phe Lys Asn Lys Ala Asp Lys
65                  70                  75                  80

Pro Leu Ser Ile His Pro Gln Gly Ile Arg Tyr Ser Lys Leu Ser Glu
                85                  90                  95

Gly Ala Ser Tyr Leu Ala His Thr Phe Pro Ala Glu Lys Met Asp Asp
            100                 105                 110

Ala Val Ala Pro Gly Arg Glu Tyr Thr Tyr Glu Trp Ser Ile Ser Glu
        115                 120                 125

Asp Ser Gly Pro Thr His Asp Asp Pro Pro Cys Leu Thr His Ile Tyr
    130                 135                 140

Tyr Ser His Glu Asn Leu Ile Glu Asp Phe Asn Ser Gly Leu Ile Gly
145                 150                 155                 160

Pro Leu Leu Ile Cys Lys Lys Gly Thr Leu Thr Glu Gly Gly Thr Gln
                165                 170                 175

Lys Thr Phe Asp Lys Gln Ile Val Leu Leu Phe Ala Val Phe Asp Glu
            180                 185                 190

Ser Lys Ser Trp Ser Gln Ser Ser Ser Leu Met Tyr Thr Val Asn Gly
        195                 200                 205

Tyr Val Asn Gly Thr Met Pro Asp Ile Thr Val Cys Ala His Asp His
    210                 215                 220

Ile Ser Trp His Leu Leu Gly Met Ser Ser Gly Pro Glu Leu Phe Ser
225                 230                 235                 240

Ile His Phe Asn Gly Gln Val Leu Glu Gln Asn His His Lys Val Ser
                245                 250                 255

Ala Ile Thr Leu Val Ser Ala Thr Ser Thr Thr Ala Asn Met Thr Val
            260                 265                 270
```

```
Gly Pro Glu Gly Lys Trp Ile Ile Ser Ser Leu Thr Pro Lys His Leu
            275                 280                 285

Gln Ala Gly Met Gln Ala Tyr Ile Asp Ile Lys Asn Cys Pro Lys Lys
        290                 295                 300

Thr Arg Asn Leu Lys Lys Ile Thr Arg Glu Gln Arg His Met Lys
305                 310                 315                 320

Arg Trp Glu Tyr Phe Ile Ala Ala Glu Val Ile Trp Asp Tyr Ala
                325                 330                 335

Pro Val Ile Pro Ala Asn Met Asp Lys Lys Tyr Arg Ser Gln His Leu
            340                 345                 350

Asp Asn Phe Ser Asn Gln Ile Gly Lys His Tyr Lys Lys Val Met Tyr
        355                 360                 365

Thr Gln Tyr Glu Asp Glu Ser Phe Thr Lys His Thr Val Asn Pro Asn
    370                 375                 380

Met Lys Glu Asp Gly Ile Leu Gly Pro Ile Ile Arg Ala Gln Val Arg
385                 390                 395                 400

Asp Thr Leu Lys Ile Val Phe Lys Asn Met Ala Ser Arg Pro Tyr Ser
                405                 410                 415

Ile Tyr Pro His Gly Val Thr Phe Ser Pro Tyr Glu Asp Glu Val Asn
            420                 425                 430

Ser Ser Phe Thr Ser Gly Arg Asn Asn Thr Met Ile Arg Ala Val Gln
        435                 440                 445

Pro Gly Glu Thr Tyr Thr Tyr Lys Trp Asn Ile Leu Glu Phe Asp Glu
    450                 455                 460

Pro Thr Glu Asn Asp Ala Gln Cys Leu Thr Arg Pro Tyr Tyr Ser Asp
465                 470                 475                 480

Val Asp Ile Met Arg Asp Ile Ala Ser Gly Leu Ile Gly Leu Leu
                485                 490                 495

Ile Cys Lys Ser Arg Ser Leu Asp Arg Arg Gly Ile Gln Arg Ala Ala
        500                 505                 510

Asp Ile Glu Gln Gln Ala Val Phe Ala Val Phe Asp Glu Asn Lys Ser
    515                 520                 525

Trp Tyr Leu Glu Asp Asn Ile Asn Lys Phe Cys Glu Asn Pro Asp Glu
    530                 535                 540

Val Lys Arg Asp Asp Pro Lys Phe Tyr Glu Ser Asn Ile Met Ser Thr
545                 550                 555                 560

Ile Asn Gly Tyr Val Pro Glu Ser Ile Thr Thr Leu Gly Phe Cys Phe
                565                 570                 575

Asp Asp Thr Val Gln Trp His Phe Cys Ser Val Gly Thr Gln Asn Glu
        580                 585                 590

Ile Leu Thr Ile His Phe Thr Gly His Ser Phe Ile Tyr Gly Lys Arg
    595                 600                 605

His Glu Asp Thr Leu Thr Leu Phe Pro Met Arg Gly Glu Ser Val Thr
    610                 615                 620

Val Thr Met Asp Asn Val Gly Thr Trp Met Leu Thr Ser Met Asn Ser
625                 630                 635                 640

Ser Pro Arg Ser Lys Lys Leu Arg Leu Lys Phe Arg Asp Val Lys Cys
                645                 650                 655

Ile Pro Asp Asp Asp Glu Asp Ser Tyr Glu Ile Phe Glu Pro Pro Glu
            660                 665                 670

Ser Thr Val Met Ala Thr Arg Lys Met His Asp Arg Leu Glu Pro Glu
        675                 680                 685

Asp Glu Glu Ser Asp Ala Asp Tyr Asp Tyr Gln Asn Arg Leu Ala Ala
```

```
               690                 695                 700
Ala Leu Gly Ile Arg Arg Glu Thr Asp Ile Glu Ser Asp Asp Ile
705                 710                 715                 720

Pro Glu Asp Thr Thr Tyr Lys Lys Val Val Phe Arg Lys Tyr Leu Asp
                725                 730                 735

Ser Thr Phe Thr Lys Arg Asp Pro Arg Gly Glu Tyr Glu Glu His Leu
                740                 745                 750

Gly Ile Leu Gly Pro Ile Ile Arg Ala Glu Val Asp Asp Val Ile Gln
                755                 760                 765

Val Arg Phe Lys Asn Leu Ala Ser Arg Pro Tyr Ser Leu His Ala His
770                 775                 780

Gly Leu Ser Tyr Glu Lys Ser Ser Glu Gly Lys Thr Tyr Glu Asp Asp
785                 790                 795                 800

Ser Pro Glu Trp Phe Lys Glu Asp Asn Ala Val Gln Pro Asn Ser Ser
                805                 810                 815

Tyr Thr Tyr Val Trp His Ala Thr Glu Arg Ser Gly Pro Glu Ser Pro
                820                 825                 830

Gly Ser Ala Cys Arg Ala Trp Ala Tyr Tyr Ser Ala Val Asn Pro Glu
835                 840                 845

Lys Asp Ile His Ser Gly Leu Ile Gly Pro Leu Leu Ile Cys Gln Lys
850                 855                 860

Gly Ile Leu His Lys Asp Ser Asn Met Pro Val Asp Met Arg Glu Phe
865                 870                 875                 880

Val Leu Leu Phe Met Thr Phe Asp Glu Lys Lys Ser Trp Tyr Tyr Glu
                885                 890                 895

Lys Lys Ser Arg Ser Ser Trp Arg Leu Thr Ser Ser Glu Met Lys Lys
                900                 905                 910

Ser His Glu Phe His Ala Ile Asn Gly Met Ile Tyr Ser Leu Pro Gly
                915                 920                 925

Leu Lys Met Tyr Glu Gln Glu Trp Val Arg Leu His Leu Leu Asn Ile
930                 935                 940

Gly Gly Ser Gln Asp Ile His Val Val His Phe His Gly Gln Thr Leu
945                 950                 955                 960

Leu Glu Asn Gly Asn Lys Gln His Gln Leu Gly Val Trp Pro Leu Leu
                965                 970                 975

Pro Gly Ser Phe Lys Thr Leu Glu Met Lys Ala Ser Lys Pro Gly Trp
                980                 985                 990

Trp Leu Leu Asn Thr Glu Val Gly Glu Asn Gln Arg Ala Gly Met Gln
                995                 1000                1005

Thr Pro Phe Leu Ile Met Asp Arg Asp Cys Arg Met Pro Met Gly Leu
    1010                1015                1020

Ser Thr Gly Ile Ile Ser Asp Ser Gln Ile Lys Ala Ser Glu Phe Leu
1025                1030                1035                1040

Gly Tyr Trp Glu Pro Arg Leu Ala Arg Leu Asn Asn Gly Gly Ser Tyr
                1045                1050                1055

Asn Ala Trp Ser Val Glu Lys Leu Ala Ala Glu Phe Ala Ser Lys Pro
        1060                1065                1070

Trp Ile Gln Val Asp Met Gln Lys Glu Val Ile Ile Thr Gly Ile Gln
        1075                1080                1085

Thr Gln Gly Ala Lys His Tyr Leu Lys Ser Cys Tyr Thr Thr Glu Phe
    1090                1095                1100

Tyr Val Ala Tyr Ser Ser Asn Gln Ile Asn Trp Gln Ile Phe Lys Gly
1105                1110                1115                1120
```

-continued

```
Asn Ser Thr Arg Asn Val Met Tyr Phe Asn Gly Asn Ser Asp Ala Ser
            1125                1130                1135

Thr Ile Lys Glu Asn Gln Phe Asp Pro Pro Ile Val Ala Arg Tyr Ile
        1140                1145                1150

Arg Ile Ser Pro Thr Arg Ala Tyr Asn Arg Pro Thr Leu Arg Leu Glu
    1155                1160                1165

Leu Gln Gly Cys Glu Val Asn Gly Cys Ser Thr Pro Leu Gly Met Glu
    1170                1175                1180

Asn Gly Lys Ile Glu Asn Lys Gln Ile Thr Ala Ser Ser Phe Lys Lys
1185                1190                1195                1200

Ser Trp Trp Gly Asp Tyr Trp Glu Pro Phe Arg Ala Arg Leu Asn Ala
            1205                1210                1215

Gln Gly Arg Val Asn Ala Trp Gln Ala Lys Ala Asn Asn Lys Gln
        1220                1225                1230

Trp Leu Glu Ile Asp Leu Leu Lys Ile Lys Lys Ile Thr Ala Ile Ile
    1235                1240                1245

Thr Gln Gly Cys Lys Ser Leu Ser Ser Glu Met Tyr Val Lys Ser Tyr
    1250                1255                1260

Thr Ile His Tyr Ser Glu Gln Gly Val Glu Trp Lys Pro Tyr Arg Leu
1265                1270                1275                1280

Lys Ser Ser Met Val Asp Lys Ile Phe Glu Gly Asn Thr Asn Thr Lys
            1285                1290                1295

Gly His Val Lys Asn Phe Phe Asn Pro Pro Ile Ile Ser Arg Phe Ile
        1300                1305                1310

Arg Val Ile Pro Lys Thr Trp Asn Gln Ser Ile Ala Leu Arg Leu Glu
    1315                1320                1325

Leu Phe Gly Cys Asp Ile Tyr
    1330                1335

<210> SEQ ID NO 17
<211> LENGTH: 4150
<212> TYPE: DNA
<213> ORGANISM: Homo sapiens
<220> FEATURE:
<221> NAME/KEY: CDS
<222> LOCATION: (1)..(4005)

<400> SEQUENCE: 17 gca cag cta agg cag ttc tac gtg gct gct cag ggc atc agt tgg agc      48
Ala Gln Leu Arg Gln Phe Tyr Val Ala Ala Gln Gly Ile Ser Trp Ser
 1               5                  10                  15 tac cga cct gag ccc aca aac tca agt ttg aat ctt tct gta act tcc      96
Tyr Arg Pro Glu Pro Thr Asn Ser Ser Leu Asn Leu Ser Val Thr Ser
                20                  25                  30 ttt aag aaa att gtc tac aga gag tat gaa cca tat ttt aag aaa gaa     144
Phe Lys Lys Ile Val Tyr Arg Glu Tyr Glu Pro Tyr Phe Lys Lys Glu
            35                  40                  45 aaa cca caa tct acc att tca gga ctt ctt ggg cct act tta tat gct     192
Lys Pro Gln Ser Thr Ile Ser Gly Leu Leu Gly Pro Thr Leu Tyr Ala
        50                  55                  60 gaa gtc gga gac atc ata aaa gtt cac ttt aaa aat aag gca gat aag     240
Glu Val Gly Asp Ile Ile Lys Val His Phe Lys Asn Lys Ala Asp Lys
 65                  70                  75                  80 ccc ttg agc atc cat cct caa gga att agg tac agt aaa tta tca gaa     288
Pro Leu Ser Ile His Pro Gln Gly Ile Arg Tyr Ser Lys Leu Ser Glu
                85                  90                  95 ggt gct tct tac ctt gac cac aca ttc cct gcg gag aag atg gcc gac     336
```

```
                Gly Ala Ser Tyr Leu Asp His Thr Phe Pro Ala Glu Lys Met Ala Asp
                                100                 105                 110 gct gtg gct cca ggc cga gaa tac acc tat gaa tgg agt atc agt gag        384
Ala Val Ala Pro Gly Arg Glu Tyr Thr Tyr Glu Trp Ser Ile Ser Glu
            115                 120                 125 gac agt gga ccc acc cat gat gac cct cca tgc ctc aca cac atc tat        432
Asp Ser Gly Pro Thr His Asp Asp Pro Pro Cys Leu Thr His Ile Tyr
130                 135                 140 tac tcc cat gaa aat ctg atc gag gat ttc aac tct ggg ctg att ggg        480
Tyr Ser His Glu Asn Leu Ile Glu Asp Phe Asn Ser Gly Leu Ile Gly
145                 150                 155                 160 ccc ctg ctt atc tgt aaa aaa ggg acc cta act gag ggt ggg aca cag        528
Pro Leu Leu Ile Cys Lys Lys Gly Thr Leu Thr Glu Gly Gly Thr Gln
                165                 170                 175 aag acg ttt gac aag caa atc gta cta ttt gct gtg ttt gat gaa            576
Lys Thr Phe Asp Lys Gln Ile Val Leu Leu Phe Ala Val Phe Asp Glu
            180                 185                 190 agc aag agc tgg agc cag tca tca tcc cta atg tac aca gtc aat gga        624
Ser Lys Ser Trp Ser Gln Ser Ser Ser Leu Met Tyr Thr Val Asn Gly
        195                 200                 205 tat gtg aat ggg aca atg cca gat ata aca gtt tgt gcc cat gac cac        672
Tyr Val Asn Gly Thr Met Pro Asp Ile Thr Val Cys Ala His Asp His
210                 215                 220 atc agc tgg cat ctg ctg gga atg agc tcg ggg cca gaa tta ttc tcc        720
Ile Ser Trp His Leu Leu Gly Met Ser Ser Gly Pro Glu Leu Phe Ser
225                 230                 235                 240 att cat ttc aac ggc cag gtc ctg gag cag aac cat cat aag gtc tca        768
Ile His Phe Asn Gly Gln Val Leu Glu Gln Asn His His Lys Val Ser
                245                 250                 255 gcc atc acc ctt gtc agt gct aca tcc act acc gca aat atg act gtg        816
Ala Ile Thr Leu Val Ser Ala Thr Ser Thr Thr Ala Asn Met Thr Val
            260                 265                 270 ggc cca gag gga aag tgg atc ata tct tct ctc acc cca aaa cat ttg        864
Gly Pro Glu Gly Lys Trp Ile Ile Ser Ser Leu Thr Pro Lys His Leu
        275                 280                 285 caa gct ggg atg cag gct tac att gac att aaa aac tgc cca aag aaa        912
Gln Ala Gly Met Gln Ala Tyr Ile Asp Ile Lys Asn Cys Pro Lys Lys
290                 295                 300 acc agg aat ctt aag aaa ata act cgt gag cag agg cgg cac atg aag        960
Thr Arg Asn Leu Lys Lys Ile Thr Arg Glu Gln Arg Arg His Met Lys
305                 310                 315                 320 agg tgg gaa tac ttc att gct gca gag gaa gtc att tgg gac tat gca       1008
Arg Trp Glu Tyr Phe Ile Ala Ala Glu Glu Val Ile Trp Asp Tyr Ala
                325                 330                 335 cct gta ata cca gcg aat atg gac aaa aaa tac agg tct cag cat ttg       1056
Pro Val Ile Pro Ala Asn Met Asp Lys Lys Tyr Arg Ser Gln His Leu
            340                 345                 350 gat aat ttc tca aac caa att gga aaa cat tat aag aaa gtt atg tac       1104
Asp Asn Phe Ser Asn Gln Ile Gly Lys His Tyr Lys Lys Val Met Tyr
        355                 360                 365 aca cag tac gaa gat gag tcc ttc acc aaa cat aca gtg aat ccc aat       1152
Thr Gln Tyr Glu Asp Glu Ser Phe Thr Lys His Thr Val Asn Pro Asn
370                 375                 380 atg aaa gaa gat ggg att ttg ggt cct att atc aga gcc cag gtc aga       1200
Met Lys Glu Asp Gly Ile Leu Gly Pro Ile Ile Arg Ala Gln Val Arg
385                 390                 395                 400 gac aca ctc aaa atc gtg ttc aaa aat atg gcc agc cgc ccc tat agc       1248
Asp Thr Leu Lys Ile Val Phe Lys Asn Met Ala Ser Arg Pro Tyr Ser
                405                 410                 415
```

```
att tac cct cat gga gtg acc ttc tcg cct tat gaa gat gaa gtc aac      1296
Ile Tyr Pro His Gly Val Thr Phe Ser Pro Tyr Glu Asp Glu Val Asn
        420                 425                 430 tct tct ttc acc tca ggc agg aac aac acc atg atc aga gca gtt caa      1344
Ser Ser Phe Thr Ser Gly Arg Asn Asn Thr Met Ile Arg Ala Val Gln
                435                 440                 445 cca ggg gaa acc tat act tat aag tgg aac atc tta gag ttt gat gaa      1392
Pro Gly Glu Thr Tyr Thr Tyr Lys Trp Asn Ile Leu Glu Phe Asp Glu
    450                 455                 460 ccc aca gaa aat gat gcc cag tgc tta aca aga cca tac tac agt gac      1440
Pro Thr Glu Asn Asp Ala Gln Cys Leu Thr Arg Pro Tyr Tyr Ser Asp
465                 470                 475                 480 gtg gac atc atg aga gac atc gcc tct ggg cta ata gga cta ctt cta      1488
Val Asp Ile Met Arg Asp Ile Ala Ser Gly Leu Ile Gly Leu Leu Leu
                485                 490                 495 atc tgt aag agc aga tcc ctg gac agg cga gga ata cag agg gca gca      1536
Ile Cys Lys Ser Arg Ser Leu Asp Arg Arg Gly Ile Gln Arg Ala Ala
                500                 505                 510 gac atc gaa cag cag gct gtg ttt gct gtg ttt gat gag aac aaa agc      1584
Asp Ile Glu Gln Gln Ala Val Phe Ala Val Phe Asp Glu Asn Lys Ser
            515                 520                 525 tgg tac ctt gag gac aac atc aac aag ttt tgt gaa aat cct gat gag      1632
Trp Tyr Leu Glu Asp Asn Ile Asn Lys Phe Cys Glu Asn Pro Asp Glu
    530                 535                 540 gtg aaa cgt gat gac ccc aag ttt tat gaa tca aac atc atg agc act      1680
Val Lys Arg Asp Asp Pro Lys Phe Tyr Glu Ser Asn Ile Met Ser Thr
545                 550                 555                 560 atc aat ggc tat gtg cct gag agc ata act act ctt gga ttc tgc ttt      1728
Ile Asn Gly Tyr Val Pro Glu Ser Ile Thr Thr Leu Gly Phe Cys Phe
                565                 570                 575 gat gac act gtc cag tgg cac ttc tgt agt gtg ggg acc cag aat gaa      1776
Asp Asp Thr Val Gln Trp His Phe Cys Ser Val Gly Thr Gln Asn Glu
            580                 585                 590 att ttg acc atc cac ttc act ggg cac tca ttc atc tat gga aag agg      1824
Ile Leu Thr Ile His Phe Thr Gly His Ser Phe Ile Tyr Gly Lys Arg
    595                 600                 605 cat gag gac acc ttg acc ctc ttc ccc atg cgt gga gaa tct gtg acg      1872
His Glu Asp Thr Leu Thr Leu Phe Pro Met Arg Gly Glu Ser Val Thr
610                 615                 620 gtc aca atg gat aat gtt gga act tgg atg tta act tcc atg aat tct      1920
Val Thr Met Asp Asn Val Gly Thr Trp Met Leu Thr Ser Met Asn Ser
625                 630                 635                 640 agt cca aga agc aaa aag ctg agg ctg aaa ttc agg gat gtt aaa tgt      1968
Ser Pro Arg Ser Lys Lys Leu Arg Leu Lys Phe Arg Asp Val Lys Cys
                645                 650                 655 atc cca gat gat gat gaa gac tca tat gag att ttt gaa cct cca gaa      2016
Ile Pro Asp Asp Asp Glu Asp Ser Tyr Glu Ile Phe Glu Pro Pro Glu
            660                 665                 670 tct aca gtc atg gct aca cgg aaa atg cat gat cgt tta gaa cct gaa      2064
Ser Thr Val Met Ala Thr Arg Lys Met His Asp Arg Leu Glu Pro Glu
    675                 680                 685 gat gaa gag agt gat gct gac tat gat tac cag aac aga ctg gct gca      2112
Asp Glu Glu Ser Asp Ala Asp Tyr Asp Tyr Gln Asn Arg Leu Ala Ala
690                 695                 700 gca tta gga att agg agg gaa aca gat att gaa gac tct gat gat att      2160
Ala Leu Gly Ile Arg Arg Glu Thr Asp Ile Glu Asp Ser Asp Asp Ile
705                 710                 715                 720 cca gaa gat acc aca tat aag aaa gta gtt ttt cga aag tac ctc gac      2208
Pro Glu Asp Thr Thr Tyr Lys Lys Val Val Phe Arg Lys Tyr Leu Asp
                725                 730                 735
```

```
agc act ttt acc aaa cgt gat cct cga ggg gag tat gaa gag cat ctc    2256
Ser Thr Phe Thr Lys Arg Asp Pro Arg Gly Glu Tyr Glu Glu His Leu
        740                 745                 750 gga att ctt ggt cct att atc aga gct gaa gtg gat gat gtt atc caa    2304
Gly Ile Leu Gly Pro Ile Ile Arg Ala Glu Val Asp Asp Val Ile Gln
    755                 760                 765 gtt cgt ttt aaa aat tta gca tcc aga ccg tat tct cta cat gcc cat    2352
Val Arg Phe Lys Asn Leu Ala Ser Arg Pro Tyr Ser Leu His Ala His
770                 775                 780 gga ctt tcc tat gaa aaa tca tca gag gga aag act tat gaa gat gac    2400
Gly Leu Ser Tyr Glu Lys Ser Ser Glu Gly Lys Thr Tyr Glu Asp Asp
785                 790                 795                 800 tct cct gaa tgg ttt aag gaa gat aat gct gtt cag cca aat agc agt    2448
Ser Pro Glu Trp Phe Lys Glu Asp Asn Ala Val Gln Pro Asn Ser Ser
                805                 810                 815 tat acc tac gta tgg cat gcc act gag cga tca ggg cca gaa agt cct    2496
Tyr Thr Tyr Val Trp His Ala Thr Glu Arg Ser Gly Pro Glu Ser Pro
            820                 825                 830 ggc tct gcc tgt cgg gct tgg gcc tac tac tca gct gtg aac cca gaa    2544
Gly Ser Ala Cys Arg Ala Trp Ala Tyr Tyr Ser Ala Val Asn Pro Glu
        835                 840                 845 aaa gat att cac tca ggc ttg ata ggt ccc ctc cta atc tgc caa aaa    2592
Lys Asp Ile His Ser Gly Leu Ile Gly Pro Leu Leu Ile Cys Gln Lys
850                 855                 860 gga ata cta cat aag gac agc aac atg cct gtg gac atg aga gaa ttt    2640
Gly Ile Leu His Lys Asp Ser Asn Met Pro Val Asp Met Arg Glu Phe
865                 870                 875                 880 gtc tta cta ttt atg acc ttt gat gaa aag aag agc tgg tac tat gaa    2688
Val Leu Leu Phe Met Thr Phe Asp Glu Lys Lys Ser Trp Tyr Tyr Glu
                885                 890                 895 aag aag tcc cga agt tct tgg aga ctc aca tcc tca gaa atg aaa aaa    2736
Lys Lys Ser Arg Ser Ser Trp Arg Leu Thr Ser Ser Glu Met Lys Lys
            900                 905                 910 tcc cat gag ttt cac gcc att aat ggg atg atc tac agc ttg cct ggc    2784
Ser His Glu Phe His Ala Ile Asn Gly Met Ile Tyr Ser Leu Pro Gly
        915                 920                 925 ctg aaa atg tat gag caa gag tgg gtg agg tta cac ctg ctg aac ata    2832
Leu Lys Met Tyr Glu Gln Glu Trp Val Arg Leu His Leu Leu Asn Ile
    930                 935                 940 ggc ggc tcc caa gac att cac gtg gtt cac ttt cac ggc cag acc ttg    2880
Gly Gly Ser Gln Asp Ile His Val Val His Phe His Gly Gln Thr Leu
945                 950                 955                 960 ctg gaa aat ggc aat aaa cag cac cag tta ggg gtc tgg ccc ctt ctg    2928
Leu Glu Asn Gly Asn Lys Gln His Gln Leu Gly Val Trp Pro Leu Leu
                965                 970                 975 cct ggt tca ttt aaa act ctt gaa atg aag gca tca aaa cct ggc tgg    2976
Pro Gly Ser Phe Lys Thr Leu Glu Met Lys Ala Ser Lys Pro Gly Trp
            980                 985                 990 tgg ctc cta aac aca gag gtt gga gaa aac cag aga gca ggg atg caa    3024
Trp Leu Leu Asn Thr Glu Val Gly Glu Asn Gln Arg Ala Gly Met Gln
        995                 1000                1005 acg cca ttt ctt atc atg gac aga gac tgt agg atg cca atg gga cta    3072
Thr Pro Phe Leu Ile Met Asp Arg Asp Cys Arg Met Pro Met Gly Leu
    1010                1015                1020 agc act ggt atc ata tct gat tca cag atc aag gct tca gag ttt ctg    3120
Ser Thr Gly Ile Ile Ser Asp Ser Gln Ile Lys Ala Ser Glu Phe Leu
1025                1030                1035                1040 ggt tac tgg gag ccc aga tta gca aga tta aac aat ggt gga tct tat    3168
Gly Tyr Trp Glu Pro Arg Leu Ala Arg Leu Asn Asn Gly Gly Ser Tyr
```

-continued

```
                  1045                1050                1055
aat gct tgg agt gta gaa aaa ctt gca gca gaa ttt gcc tct aaa cct      3216
Asn Ala Trp Ser Val Glu Lys Leu Ala Ala Glu Phe Ala Ser Lys Pro
        1060                1065                1070 tgg atc cag gtg gac atg caa aag gaa gtc ata atc aca ggg atc cag      3264
Trp Ile Gln Val Asp Met Gln Lys Glu Val Ile Ile Thr Gly Ile Gln
    1075                1080                1085 acc caa ggt gcc aaa cac tac ctg aag tcc tgc tat acc aca gag ttc      3312
Thr Gln Gly Ala Lys His Tyr Leu Lys Ser Cys Tyr Thr Thr Glu Phe
    1090                1095                1100 tat gta gct tac agt tcc aac cag atc aac tgg cag atc ttc aaa ggg      3360
Tyr Val Ala Tyr Ser Ser Asn Gln Ile Asn Trp Gln Ile Phe Lys Gly
1105                1110                1115                1120 aac agc aca agg aat gtg atg tat ttt aat ggc aat tca gat gcc tct      3408
Asn Ser Thr Arg Asn Val Met Tyr Phe Asn Gly Asn Ser Asp Ala Ser
        1125                1130                1135 aca ata aaa gag aat cag ttt gac cca cct att gtg gct aga tat att      3456
Thr Ile Lys Glu Asn Gln Phe Asp Pro Pro Ile Val Ala Arg Tyr Ile
        1140                1145                1150 agg atc tct cca act cga gcc tat aac aga cct acc ctt cga ttg gaa      3504
Arg Ile Ser Pro Thr Arg Ala Tyr Asn Arg Pro Thr Leu Arg Leu Glu
        1155                1160                1165 ctg caa ggt tgt gag gta aat gga tgt tcc aca ccc ctg ggt atg gaa      3552
Leu Gln Gly Cys Glu Val Asn Gly Cys Ser Thr Pro Leu Gly Met Glu
    1170                1175                1180 aat gga aag ata gaa aac aag caa atc aca gct tct tcg ttt aag aaa      3600
Asn Gly Lys Ile Glu Asn Lys Gln Ile Thr Ala Ser Ser Phe Lys Lys
1185                1190                1195                1200 tct tgg tgg gga gat tac tgg gaa ccc ttc cgt gcc cgt ctg aat gcc      3648
Ser Trp Trp Gly Asp Tyr Trp Glu Pro Phe Arg Ala Arg Leu Asn Ala
        1205                1210                1215 cag gga cgt gtg aat gcc tgg caa gcc aag gca aac aac aat aag cag      3696
Gln Gly Arg Val Asn Ala Trp Gln Ala Lys Ala Asn Asn Asn Lys Gln
        1220                1225                1230 tgg cta gaa att gat cta ctc aag atc aag aag ata acg gca att ata      3744
Trp Leu Glu Ile Asp Leu Leu Lys Ile Lys Lys Ile Thr Ala Ile Ile
        1235                1240                1245 aca cag ggc tgc aag tct ctg tcc tct gaa atg tat gta aag agc tat      3792
Thr Gln Gly Cys Lys Ser Leu Ser Ser Glu Met Tyr Val Lys Ser Tyr
    1250                1255                1260 acc atc cac tac agt gag cag gga gtg gaa tgg aaa cca tac agg ctg      3840
Thr Ile His Tyr Ser Glu Gln Gly Val Glu Trp Lys Pro Tyr Arg Leu
1265                1270                1275                1280 aaa tcc tcc atg gtg gac aag att ttt gaa gga aat act aat acc aaa      3888
Lys Ser Ser Met Val Asp Lys Ile Phe Glu Gly Asn Thr Asn Thr Lys
        1285                1290                1295 gga cat gtg aag aac ttt ttc aac ccc cca atc att tcc agg ttt atc      3936
Gly His Val Lys Asn Phe Phe Asn Pro Pro Ile Ile Ser Arg Phe Ile
    1300                1305                1310 cgt gtc att cct aaa aca tgg aat caa agt att gca ctt cgc ctg gaa      3984
Arg Val Ile Pro Lys Thr Trp Asn Gln Ser Ile Ala Leu Arg Leu Glu
    1315                1320                1325 ctc ttt ggc tgt gat att tac tagaattgaa cattcaaaaa cccctggaag         4035
Leu Phe Gly Cys Asp Ile Tyr
    1330                1335 agactcttta agacctcaaa ccatttagaa tgggcaatgt attttacgct gtgttaaatg    4095
ttaacagttt tccactattt ctctttcttt tctattagtg aataaaattt tatac         4150
```

```
<210> SEQ ID NO 18
<211> LENGTH: 1335
<212> TYPE: PRT
<213> ORGANISM: Homo sapiens

<400> SEQUENCE: 18

Ala Gln Leu Arg Gln Phe Tyr Val Ala Ala Gln Gly Ile Ser Trp Ser
 1               5                  10                  15

Tyr Arg Pro Glu Pro Thr Asn Ser Ser Leu Asn Leu Ser Val Thr Ser
                20                  25                  30

Phe Lys Lys Ile Val Tyr Arg Glu Tyr Glu Pro Tyr Phe Lys Lys Glu
            35                  40                  45

Lys Pro Gln Ser Thr Ile Ser Gly Leu Leu Gly Pro Thr Leu Tyr Ala
        50                  55                  60

Glu Val Gly Asp Ile Ile Lys Val His Phe Lys Asn Lys Ala Asp Lys
65                  70                  75                  80

Pro Leu Ser Ile His Pro Gln Gly Ile Arg Tyr Ser Lys Leu Ser Glu
                85                  90                  95

Gly Ala Ser Tyr Leu Asp His Thr Phe Pro Ala Glu Lys Met Ala Asp
            100                 105                 110

Ala Val Ala Pro Gly Arg Glu Tyr Thr Tyr Glu Trp Ser Ile Ser Glu
        115                 120                 125

Asp Ser Gly Pro Thr His Asp Asp Pro Pro Cys Leu Thr His Ile Tyr
130                 135                 140

Tyr Ser His Glu Asn Leu Ile Glu Asp Phe Asn Ser Gly Leu Ile Gly
145                 150                 155                 160

Pro Leu Leu Ile Cys Lys Lys Gly Thr Leu Thr Glu Gly Gly Thr Gln
                165                 170                 175

Lys Thr Phe Asp Lys Gln Ile Val Leu Leu Phe Ala Val Phe Asp Glu
            180                 185                 190

Ser Lys Ser Trp Ser Gln Ser Ser Ser Leu Met Tyr Thr Val Asn Gly
        195                 200                 205

Tyr Val Asn Gly Thr Met Pro Asp Ile Thr Val Cys Ala His Asp His
    210                 215                 220

Ile Ser Trp His Leu Leu Gly Met Ser Ser Gly Pro Glu Leu Phe Ser
225                 230                 235                 240

Ile His Phe Asn Gly Gln Val Leu Glu Gln Asn His His Lys Val Ser
                245                 250                 255

Ala Ile Thr Leu Val Ser Ala Thr Ser Thr Thr Ala Asn Met Thr Val
            260                 265                 270

Gly Pro Glu Gly Lys Trp Ile Ile Ser Ser Leu Thr Pro Lys His Leu
        275                 280                 285

Gln Ala Gly Met Gln Ala Tyr Ile Asp Ile Lys Asn Cys Pro Lys Lys
    290                 295                 300

Thr Arg Asn Leu Lys Lys Ile Thr Arg Glu Gln Arg Arg His Met Lys
305                 310                 315                 320

Arg Trp Glu Tyr Phe Ile Ala Ala Glu Glu Val Ile Trp Asp Tyr Ala
                325                 330                 335

Pro Val Ile Pro Ala Asn Met Asp Lys Lys Tyr Arg Ser Gln His Leu
            340                 345                 350

Asp Asn Phe Ser Asn Gln Ile Gly Lys His Tyr Lys Lys Val Met Tyr
        355                 360                 365

Thr Gln Tyr Glu Asp Glu Ser Phe Thr Lys His Thr Val Asn Pro Asn
    370                 375                 380
```

-continued

```
Met Lys Glu Asp Gly Ile Leu Gly Pro Ile Ile Arg Ala Gln Val Arg
385                 390                 395                 400

Asp Thr Leu Lys Ile Val Phe Lys Asn Met Ala Ser Arg Pro Tyr Ser
            405                 410                 415

Ile Tyr Pro His Gly Val Thr Phe Ser Pro Tyr Glu Asp Glu Val Asn
        420                 425                 430

Ser Ser Phe Thr Ser Gly Arg Asn Asn Thr Met Ile Arg Ala Val Gln
        435                 440                 445

Pro Gly Glu Thr Tyr Thr Tyr Lys Trp Asn Ile Leu Glu Phe Asp Glu
        450                 455                 460

Pro Thr Glu Asn Asp Ala Gln Cys Leu Thr Arg Pro Tyr Tyr Ser Asp
465                 470                 475                 480

Val Asp Ile Met Arg Asp Ile Ala Ser Gly Leu Ile Gly Leu Leu Leu
                485                 490                 495

Ile Cys Lys Ser Arg Ser Leu Asp Arg Arg Gly Ile Gln Arg Ala Ala
            500                 505                 510

Asp Ile Glu Gln Gln Ala Val Phe Ala Val Phe Asp Glu Asn Lys Ser
            515                 520                 525

Trp Tyr Leu Glu Asp Asn Ile Asn Lys Phe Cys Glu Asn Pro Asp Glu
        530                 535                 540

Val Lys Arg Asp Asp Pro Lys Phe Tyr Glu Ser Asn Ile Met Ser Thr
545                 550                 555                 560

Ile Asn Gly Tyr Val Pro Glu Ser Ile Thr Thr Leu Gly Phe Cys Phe
                565                 570                 575

Asp Asp Thr Val Gln Trp His Phe Cys Ser Val Gly Thr Gln Asn Glu
            580                 585                 590

Ile Leu Thr Ile His Phe Thr Gly His Ser Phe Ile Tyr Gly Lys Arg
            595                 600                 605

His Glu Asp Thr Leu Thr Leu Phe Pro Met Arg Gly Glu Ser Val Thr
        610                 615                 620

Val Thr Met Asp Asn Val Gly Thr Trp Met Leu Thr Ser Met Asn Ser
625                 630                 635                 640

Ser Pro Arg Ser Lys Lys Leu Arg Leu Lys Phe Arg Asp Val Lys Cys
                645                 650                 655

Ile Pro Asp Asp Asp Glu Asp Ser Tyr Glu Ile Phe Glu Pro Pro Glu
            660                 665                 670

Ser Thr Val Met Ala Thr Arg Lys Met His Asp Arg Leu Glu Pro Glu
            675                 680                 685

Asp Glu Glu Ser Asp Ala Asp Tyr Asp Tyr Gln Asn Arg Leu Ala Ala
        690                 695                 700

Ala Leu Gly Ile Arg Arg Glu Thr Asp Ile Glu Asp Ser Asp Asp Ile
705                 710                 715                 720

Pro Glu Asp Thr Thr Tyr Lys Lys Val Val Phe Arg Lys Tyr Leu Asp
            725                 730                 735

Ser Thr Phe Thr Lys Arg Asp Pro Arg Gly Glu Tyr Glu Glu His Leu
            740                 745                 750

Gly Ile Leu Gly Pro Ile Ile Arg Ala Glu Val Asp Asp Val Ile Gln
        755                 760                 765

Val Arg Phe Lys Asn Leu Ala Ser Arg Pro Tyr Ser Leu His Ala His
        770                 775                 780

Gly Leu Ser Tyr Glu Lys Ser Ser Glu Gly Lys Thr Tyr Glu Asp Asp
785                 790                 795                 800

Ser Pro Glu Trp Phe Lys Glu Asp Asn Ala Val Gln Pro Asn Ser Ser
```

-continued

```
                805                 810                 815
Tyr Thr Tyr Val Trp His Ala Thr Glu Arg Ser Gly Pro Glu Ser Pro
            820                 825                 830
Gly Ser Ala Cys Arg Ala Trp Ala Tyr Tyr Ser Ala Val Asn Pro Glu
            835                 840                 845
Lys Asp Ile His Ser Gly Leu Ile Gly Pro Leu Leu Ile Cys Gln Lys
            850                 855                 860
Gly Ile Leu His Lys Asp Ser Asn Met Pro Val Asp Met Arg Glu Phe
865                 870                 875                 880
Val Leu Leu Phe Met Thr Phe Asp Glu Lys Lys Ser Trp Tyr Tyr Glu
                885                 890                 895
Lys Lys Ser Arg Ser Ser Trp Arg Leu Thr Ser Ser Glu Met Lys Lys
            900                 905                 910
Ser His Glu Phe His Ala Ile Asn Gly Met Ile Tyr Ser Leu Pro Gly
            915                 920                 925
Leu Lys Met Tyr Glu Gln Glu Trp Val Arg Leu His Leu Leu Asn Ile
            930                 935                 940
Gly Gly Ser Gln Asp Ile His Val Val His Phe His Gly Gln Thr Leu
945                 950                 955                 960
Leu Glu Asn Gly Asn Lys Gln His Gln Leu Gly Val Trp Pro Leu Leu
                965                 970                 975
Pro Gly Ser Phe Lys Thr Leu Glu Met Lys Ala Ser Lys Pro Gly Trp
            980                 985                 990
Trp Leu Leu Asn Thr Glu Val Gly Glu Asn Gln Arg Ala Gly Met Gln
            995                 1000                1005
Thr Pro Phe Leu Ile Met Asp Arg Asp Cys Arg Met Pro Met Gly Leu
    1010                1015                1020
Ser Thr Gly Ile Ile Ser Asp Ser Gln Ile Lys Ala Ser Glu Phe Leu
1025                1030                1035                1040
Gly Tyr Trp Glu Pro Arg Leu Ala Arg Leu Asn Asn Gly Gly Ser Tyr
                1045                1050                1055
Asn Ala Trp Ser Val Glu Lys Leu Ala Ala Glu Phe Ala Ser Lys Pro
            1060                1065                1070
Trp Ile Gln Val Asp Met Gln Lys Glu Val Ile Ile Thr Gly Ile Gln
    1075                1080                1085
Thr Gln Gly Ala Lys His Tyr Leu Lys Ser Cys Tyr Thr Thr Glu Phe
    1090                1095                1100
Tyr Val Ala Tyr Ser Ser Asn Gln Ile Asn Trp Gln Ile Phe Lys Gly
1105                1110                1115                1120
Asn Ser Thr Arg Asn Val Met Tyr Phe Asn Gly Asn Ser Asp Ala Ser
                1125                1130                1135
Thr Ile Lys Glu Asn Gln Phe Asp Pro Pro Ile Val Ala Arg Tyr Ile
            1140                1145                1150
Arg Ile Ser Pro Thr Arg Ala Tyr Asn Arg Pro Thr Leu Arg Leu Glu
    1155                1160                1165
Leu Gln Gly Cys Glu Val Asn Gly Cys Ser Thr Pro Leu Gly Met Glu
    1170                1175                1180
Asn Gly Lys Ile Glu Asn Lys Gln Ile Thr Ala Ser Ser Phe Lys Lys
1185                1190                1195                1200
Ser Trp Trp Gly Asp Tyr Trp Glu Pro Phe Arg Ala Arg Leu Asn Ala
                1205                1210                1215
Gln Gly Arg Val Asn Ala Trp Gln Ala Lys Ala Asn Asn Asn Lys Gln
            1220                1225                1230
```

```
Trp Leu Glu Ile Asp Leu Leu Lys Ile Lys Lys Ile Thr Ala Ile Ile
         1235                1240                1245

Thr Gln Gly Cys Lys Ser Leu Ser Ser Glu Met Tyr Val Lys Ser Tyr
    1250                1255                1260

Thr Ile His Tyr Ser Glu Gln Gly Val Glu Trp Lys Pro Tyr Arg Leu
1265                1270                1275                1280

Lys Ser Ser Met Val Asp Lys Ile Phe Glu Gly Asn Thr Asn Thr Lys
                1285                1290                1295

Gly His Val Lys Asn Phe Phe Asn Pro Ile Ile Ser Arg Phe Ile
            1300                1305                1310

Arg Val Ile Pro Lys Thr Trp Asn Gln Ser Ile Ala Leu Arg Leu Glu
        1315                1320                1325

Leu Phe Gly Cys Asp Ile Tyr
    1330                1335

<210> SEQ ID NO 19
<211> LENGTH: 4150
<212> TYPE: DNA
<213> ORGANISM: Homo sapiens
<220> FEATURE:
<221> NAME/KEY: CDS
<222> LOCATION: (1)..(4005)

<400> SEQUENCE: 19 gca cag cta agg cag ttc tac gtg gct gct cag ggc atc agt tgg agc       48
Ala Gln Leu Arg Gln Phe Tyr Val Ala Ala Gln Gly Ile Ser Trp Ser
1               5                   10                  15 tac cga cct gag ccc aca aac tca agt ttg aat ctt tct gta act tcc       96
Tyr Arg Pro Glu Pro Thr Asn Ser Ser Leu Asn Leu Ser Val Thr Ser
            20                  25                  30 ttt aag aaa att gtc tac aga gag tat gaa cca tat ttt aag aaa gaa      144
Phe Lys Lys Ile Val Tyr Arg Glu Tyr Glu Pro Tyr Phe Lys Lys Glu
        35                  40                  45 aaa cca caa tct acc att tca gga ctt ctt ggg cct act tta tat gct      192
Lys Pro Gln Ser Thr Ile Ser Gly Leu Leu Gly Pro Thr Leu Tyr Ala
    50                  55                  60 gaa gtc gga gac atc ata aaa gtt cac ttt aaa aat aag gca gat aag      240
Glu Val Gly Asp Ile Ile Lys Val His Phe Lys Asn Lys Ala Asp Lys
65                  70                  75                  80 ccc ttg agc atc cat cct caa gga att agg tac agt aaa tta tca gca      288
Pro Leu Ser Ile His Pro Gln Gly Ile Arg Tyr Ser Lys Leu Ser Ala
                85                  90                  95 ggt gct tct tac ctt gac cac aca ttc cct gca gag aag atg gac gac      336
Gly Ala Ser Tyr Leu Asp His Thr Phe Pro Ala Glu Lys Met Asp Asp
            100                 105                 110 gct gtg gct cca ggc cga gaa tac acc tat gaa tgg agt atc agt gag      384
Ala Val Ala Pro Gly Arg Glu Tyr Thr Tyr Glu Trp Ser Ile Ser Glu
        115                 120                 125 gac agt gga ccc acc cat gat gac cct cca tgc ctc aca cac atc tat      432
Asp Ser Gly Pro Thr His Asp Asp Pro Pro Cys Leu Thr His Ile Tyr
    130                 135                 140 tac tcc cat gaa aat ctg atc gag gat ttc aac tct ggg ctg att ggg      480
Tyr Ser His Glu Asn Leu Ile Glu Asp Phe Asn Ser Gly Leu Ile Gly
145                 150                 155                 160 ccc ctg ctt atc tgt aaa aaa ggg acc cta act gag ggt ggg aca cag      528
Pro Leu Leu Ile Cys Lys Lys Gly Thr Leu Thr Glu Gly Gly Thr Gln
                165                 170                 175 aag acg ttt gac aag caa atc gtg cta cta ttt gct gtg ttt gat gaa      576
Lys Thr Phe Asp Lys Gln Ile Val Leu Leu Phe Ala Val Phe Asp Glu
```

```
                      180              185              190
agc aag agc tgg agc cag tca tca tcc cta atg tac aca gtc aat gga    624
Ser Lys Ser Trp Ser Gln Ser Ser Ser Leu Met Tyr Thr Val Asn Gly
        195              200              205 tat gtg aat ggg aca atg cca gat ata aca gtt tgt gcc cat gac cac    672
Tyr Val Asn Gly Thr Met Pro Asp Ile Thr Val Cys Ala His Asp His
210              215              220 atc agc tgg cat ctg ctg gga atg agc tcg ggg cca gaa tta ttc tcc    720
Ile Ser Trp His Leu Leu Gly Met Ser Ser Gly Pro Glu Leu Phe Ser
225              230              235              240 att cat ttc aac ggc cag gtc ctg gag cag aac cat cat aag gtc tca    768
Ile His Phe Asn Gly Gln Val Leu Glu Gln Asn His His Lys Val Ser
                245              250              255 gcc atc acc ctt gtc agt gct aca tcc act acc gca aat atg act gtg    816
Ala Ile Thr Leu Val Ser Ala Thr Ser Thr Thr Ala Asn Met Thr Val
            260              265              270 ggc cca gag gga aag tgg atc ata tct tct ctc acc cca aaa cat ttg    864
Gly Pro Glu Gly Lys Trp Ile Ile Ser Ser Leu Thr Pro Lys His Leu
        275              280              285 caa gct ggg atg cag gct tac att gac att aaa aac tgc cca aag aaa    912
Gln Ala Gly Met Gln Ala Tyr Ile Asp Ile Lys Asn Cys Pro Lys Lys
    290              295              300 acc agg aat ctt aag aaa ata act cgt gag cag agg cgg cac atg aag    960
Thr Arg Asn Leu Lys Lys Ile Thr Arg Glu Gln Arg Arg His Met Lys
305              310              315              320 agg tgg gaa tac ttc att gct gca gag gaa gtc att tgg gac tat gca   1008
Arg Trp Glu Tyr Phe Ile Ala Ala Glu Glu Val Ile Trp Asp Tyr Ala
                325              330              335 cct gta ata cca gcg aat atg gac aaa aaa tac agg tct cag cat ttg   1056
Pro Val Ile Pro Ala Asn Met Asp Lys Lys Tyr Arg Ser Gln His Leu
            340              345              350 gat aat ttc tca aac caa att gga aaa cat tat aag aaa gtt atg tac   1104
Asp Asn Phe Ser Asn Gln Ile Gly Lys His Tyr Lys Lys Val Met Tyr
        355              360              365 aca cag tac gaa gat gag tcc ttc acc aaa cat aca gtg aat ccc aat   1152
Thr Gln Tyr Glu Asp Glu Ser Phe Thr Lys His Thr Val Asn Pro Asn
    370              375              380 atg aaa gaa gat ggg att ttg ggt cct att atc aga gcc cag gtc aga   1200
Met Lys Glu Asp Gly Ile Leu Gly Pro Ile Ile Arg Ala Gln Val Arg
385              390              395              400 gac aca ctc aaa atc gtg ttc aaa aat atg gcc agc cgc ccc tat agc   1248
Asp Thr Leu Lys Ile Val Phe Lys Asn Met Ala Ser Arg Pro Tyr Ser
                405              410              415 att tac cct cat gga gtg acc ttc tcg cct tat gaa gat gaa gtc aac   1296
Ile Tyr Pro His Gly Val Thr Phe Ser Pro Tyr Glu Asp Glu Val Asn
            420              425              430 tct tct ttc acc tca ggc agg aac aac acc atg atc aga gca gtt caa   1344
Ser Ser Phe Thr Ser Gly Arg Asn Asn Thr Met Ile Arg Ala Val Gln
        435              440              445 cca ggg gaa acc tat act tat aag tgg aac atc tta gag ttt gat gaa   1392
Pro Gly Glu Thr Tyr Thr Tyr Lys Trp Asn Ile Leu Glu Phe Asp Glu
    450              455              460 ccc aca gaa aat gat gcc cag tgc tta aca aga cca tac tac agt gac   1440
Pro Thr Glu Asn Asp Ala Gln Cys Leu Thr Arg Pro Tyr Tyr Ser Asp
465              470              475              480 gtg gac atc atg aga gac atc gcc tct ggg cta ata gga cta ctt cta   1488
Val Asp Ile Met Arg Asp Ile Ala Ser Gly Leu Ile Gly Leu Leu Leu
                485              490              495 atc tgt aag agc aga tcc ctg gac agg cga gga ata cag agg gca gca   1536
```

```
Ile Cys Lys Ser Arg Ser Leu Asp Arg Arg Gly Ile Gln Arg Ala Ala
            500                 505                 510 gac atc gaa cag cag gct gtg ttt gct gtg ttt gat gag aac aaa agc      1584
Asp Ile Glu Gln Gln Ala Val Phe Ala Val Phe Asp Glu Asn Lys Ser
            515                 520                 525 tgg tac ctt gag gac aac atc aac aag ttt tgt gaa aat cct gat gag      1632
Trp Tyr Leu Glu Asp Asn Ile Asn Lys Phe Cys Glu Asn Pro Asp Glu
        530                 535                 540 gtg aaa cgt gat gac ccc aag ttt tat gaa tca aac atc atg agc act      1680
Val Lys Arg Asp Asp Pro Lys Phe Tyr Glu Ser Asn Ile Met Ser Thr
545                 550                 555                 560 atc aat ggc tat gtg cct gag agc ata act act ctt gga ttc tgc ttt      1728
Ile Asn Gly Tyr Val Pro Glu Ser Ile Thr Thr Leu Gly Phe Cys Phe
                565                 570                 575 gat gac act gtc cag tgg cac ttc tgt agt gtg ggg acc cag aat gaa      1776
Asp Asp Thr Val Gln Trp His Phe Cys Ser Val Gly Thr Gln Asn Glu
            580                 585                 590 att ttg acc atc cac ttc act ggg cac tca ttc atc tat gga aag agg      1824
Ile Leu Thr Ile His Phe Thr Gly His Ser Phe Ile Tyr Gly Lys Arg
        595                 600                 605 cat gag gac acc ttg acc ctc ttc ccc atg cgt gga gaa tct gtg acg      1872
His Glu Asp Thr Leu Thr Leu Phe Pro Met Arg Gly Glu Ser Val Thr
    610                 615                 620 gtc aca atg gat aat gtt gga act tgg atg tta act tcc atg aat tct      1920
Val Thr Met Asp Asn Val Gly Thr Trp Met Leu Thr Ser Met Asn Ser
625                 630                 635                 640 agt cca aga agc aaa aag ctg agg ctg aaa ttc agg gat gtt aaa tgt      1968
Ser Pro Arg Ser Lys Lys Leu Arg Leu Lys Phe Arg Asp Val Lys Cys
                645                 650                 655 atc cca gat gat gat gaa gac tca tat gag att ttt gaa cct cca gaa      2016
Ile Pro Asp Asp Asp Glu Asp Ser Tyr Glu Ile Phe Glu Pro Pro Glu
            660                 665                 670 tct aca gtc atg gct aca cgg aaa atg cat gat cgt tta gaa cct gaa      2064
Ser Thr Val Met Ala Thr Arg Lys Met His Asp Arg Leu Glu Pro Glu
        675                 680                 685 gat gaa gag agt gat gct gac tat gat tac cag aac aga ctg gct gca      2112
Asp Glu Glu Ser Asp Ala Asp Tyr Asp Tyr Gln Asn Arg Leu Ala Ala
    690                 695                 700 gca tta gga att agg agg gaa aca gat att gaa gac tct gat gat att      2160
Ala Leu Gly Ile Arg Arg Glu Thr Asp Ile Glu Asp Ser Asp Asp Ile
705                 710                 715                 720 cca gaa gat acc aca tat aag aaa gta gtt ttt cga aag tac ctc gac      2208
Pro Glu Asp Thr Thr Tyr Lys Lys Val Val Phe Arg Lys Tyr Leu Asp
                725                 730                 735 agc act ttt acc aaa cgt gat cct cga ggg gag tat gaa gag cat ctc      2256
Ser Thr Phe Thr Lys Arg Asp Pro Arg Gly Glu Tyr Glu Glu His Leu
            740                 745                 750 gga att ctt ggt cct att atc aga gct gaa gtg gat gat gtt atc caa      2304
Gly Ile Leu Gly Pro Ile Ile Arg Ala Glu Val Asp Asp Val Ile Gln
        755                 760                 765 gtt cgt ttt aaa aat tta gca tcc aga ccg tat tct cta cat gcc cat      2352
Val Arg Phe Lys Asn Leu Ala Ser Arg Pro Tyr Ser Leu His Ala His
    770                 775                 780 gga ctt tcc tat gaa aaa tca tca gag gga aag act tat gaa gat gac      2400
Gly Leu Ser Tyr Glu Lys Ser Ser Glu Gly Lys Thr Tyr Glu Asp Asp
785                 790                 795                 800 tct cct gaa tgg ttt aag gaa gat aat gct gtt cag cca aat agc agt      2448
Ser Pro Glu Trp Phe Lys Glu Asp Asn Ala Val Gln Pro Asn Ser Ser
                805                 810                 815
```

```
tat acc tac gta tgg cat gcc act gag cga tca ggg cca gaa agt cct    2496
Tyr Thr Tyr Val Trp His Ala Thr Glu Arg Ser Gly Pro Glu Ser Pro
            820                 825                 830 ggc tct gcc tgt cgg gct tgg gcc tac tac tca gct gtg aac cca gaa    2544
Gly Ser Ala Cys Arg Ala Trp Ala Tyr Tyr Ser Ala Val Asn Pro Glu
        835                 840                 845 aaa gat att cac tca ggc ttg ata ggt ccc ctc cta atc tgc caa aaa    2592
Lys Asp Ile His Ser Gly Leu Ile Gly Pro Leu Leu Ile Cys Gln Lys
    850                 855                 860 gga ata cta cat aag gac agc aac atg cct gtg gac atg aga gaa ttt    2640
Gly Ile Leu His Lys Asp Ser Asn Met Pro Val Asp Met Arg Glu Phe
865                 870                 875                 880 gtc tta cta ttt atg acc ttt gat gaa aag aag agc tgg tac tat gaa    2688
Val Leu Leu Phe Met Thr Phe Asp Glu Lys Lys Ser Trp Tyr Tyr Glu
                885                 890                 895 aag aag tcc cga agt tct tgg aga ctc aca tcc tca gaa atg aaa aaa    2736
Lys Lys Ser Arg Ser Ser Trp Arg Leu Thr Ser Ser Glu Met Lys Lys
            900                 905                 910 tcc cat gag ttt cac gcc att aat ggg atg atc tac agc ttg cct ggc    2784
Ser His Glu Phe His Ala Ile Asn Gly Met Ile Tyr Ser Leu Pro Gly
        915                 920                 925 ctg aaa atg tat gag caa gag tgg gtg agg tta cac ctg ctg aac ata    2832
Leu Lys Met Tyr Glu Gln Glu Trp Val Arg Leu His Leu Leu Asn Ile
    930                 935                 940 ggc ggc tcc caa gac att cac gtg gtt cac ttt cac ggc cag acc ttg    2880
Gly Gly Ser Gln Asp Ile His Val Val His Phe His Gly Gln Thr Leu
945                 950                 955                 960 ctg gaa aat ggc aat aaa cag cac cag tta ggg gtc tgg ccc ctt ctg    2928
Leu Glu Asn Gly Asn Lys Gln His Gln Leu Gly Val Trp Pro Leu Leu
                965                 970                 975 cct ggt tca ttt aaa act ctt gaa atg aag gca tca aaa cct ggc tgg    2976
Pro Gly Ser Phe Lys Thr Leu Glu Met Lys Ala Ser Lys Pro Gly Trp
            980                 985                 990 tgg ctc cta aac aca gag gtt gga gaa aac cag aga gca ggg atg caa    3024
Trp Leu Leu Asn Thr Glu Val Gly Glu Asn Gln Arg Ala Gly Met Gln
        995                 1000                1005 acg cca ttt ctt atc atg gac aga gac tgt agg atg cca atg gga cta    3072
Thr Pro Phe Leu Ile Met Asp Arg Asp Cys Arg Met Pro Met Gly Leu
    1010                1015                1020 agc act ggt atc ata tct gat tca cag atc aag gct tca gag ttt ctg    3120
Ser Thr Gly Ile Ile Ser Asp Ser Gln Ile Lys Ala Ser Glu Phe Leu
1025                1030                1035                1040 ggt tac tgg gag ccc aga tta gca aga tta aac aat ggt gga tct tat    3168
Gly Tyr Trp Glu Pro Arg Leu Ala Arg Leu Asn Asn Gly Gly Ser Tyr
                1045                1050                1055 aat gct tgg agt gta gaa aaa ctt gca gca gaa ttt gcc tct aaa cct    3216
Asn Ala Trp Ser Val Glu Lys Leu Ala Ala Glu Phe Ala Ser Lys Pro
            1060                1065                1070 tgg atc cag gtg gac atg caa aag gaa gtc ata atc aca ggg atc cag    3264
Trp Ile Gln Val Asp Met Gln Lys Glu Val Ile Ile Thr Gly Ile Gln
        1075                1080                1085 acc caa ggt gcc aaa cac tac ctg aag tcc tgc tat acc aca gag ttc    3312
Thr Gln Gly Ala Lys His Tyr Leu Lys Ser Cys Tyr Thr Thr Glu Phe
    1090                1095                1100 tat gta gct tac agt tcc aac cag atc aac tgg cag atc ttc aaa ggg    3360
Tyr Val Ala Tyr Ser Ser Asn Gln Ile Asn Trp Gln Ile Phe Lys Gly
1105                1110                1115                1120 aac agc aca agg aat gtg atg tat ttt aat ggc aat tca gat gcc tct    3408
Asn Ser Thr Arg Asn Val Met Tyr Phe Asn Gly Asn Ser Asp Ala Ser
                1125                1130                1135
```

-continued

```
aca ata aaa gag aat cag ttt gac cca cct att gtg gct aga tat att    3456
Thr Ile Lys Glu Asn Gln Phe Asp Pro Pro Ile Val Ala Arg Tyr Ile
        1140                1145                1150 agg atc tct cca act cga gcc tat aac aga cct acc ctt cga ttg gaa    3504
Arg Ile Ser Pro Thr Arg Ala Tyr Asn Arg Pro Thr Leu Arg Leu Glu
    1155                1160                1165 ctg caa ggt tgt gag gta aat gga tgt tcc aca ccc ctg ggt atg gaa    3552
Leu Gln Gly Cys Glu Val Asn Gly Cys Ser Thr Pro Leu Gly Met Glu
1170                1175                1180 aat gga aag ata gaa aac aag caa atc aca gct tct tcg ttt aag aaa    3600
Asn Gly Lys Ile Glu Asn Lys Gln Ile Thr Ala Ser Ser Phe Lys Lys
1185                1190                1195                1200 tct tgg tgg gga gat tac tgg gaa ccc ttc cgt gcc cgt ctg aat gcc    3648
Ser Trp Trp Gly Asp Tyr Trp Glu Pro Phe Arg Ala Arg Leu Asn Ala
            1205                1210                1215 cag gga cgt gtg aat gcc tgg caa gcc aag gca aac aac aat aag cag    3696
Gln Gly Arg Val Asn Ala Trp Gln Ala Lys Ala Asn Asn Asn Lys Gln
        1220                1225                1230 tgg cta gaa att gat cta ctc aag atc aag aag ata acg gca att ata    3744
Trp Leu Glu Ile Asp Leu Leu Lys Ile Lys Lys Ile Thr Ala Ile Ile
    1235                1240                1245 aca cag ggc tgc aag tct ctg tcc tct gaa atg tat gta aag agc tat    3792
Thr Gln Gly Cys Lys Ser Leu Ser Ser Glu Met Tyr Val Lys Ser Tyr
1250                1255                1260 acc atc cac tac agt gag cag gga gtg gaa tgg aaa cca tac agg ctg    3840
Thr Ile His Tyr Ser Glu Gln Gly Val Glu Trp Lys Pro Tyr Arg Leu
1265                1270                1275                1280 aaa tcc tcc atg gtg gac aag att ttt gaa gga aat act aat acc aaa    3888
Lys Ser Ser Met Val Asp Lys Ile Phe Glu Gly Asn Thr Asn Thr Lys
            1285                1290                1295 gga cat gtg aag aac ttt ttc aac ccc cca atc att tcc agg ttt atc    3936
Gly His Val Lys Asn Phe Phe Asn Pro Pro Ile Ile Ser Arg Phe Ile
        1300                1305                1310 cgt gtc att cct aaa aca tgg aat caa agt att gca ctt cgc ctg gaa    3984
Arg Val Ile Pro Lys Thr Trp Asn Gln Ser Ile Ala Leu Arg Leu Glu
    1315                1320                1325 ctc ttt ggc tgt gat att tac tagaattgaa cattcaaaaa ccoctggaag       4035
Leu Phe Gly Cys Asp Ile Tyr
1330                1335 agactcttta agacctcaaa ccatttagaa tgggcaatgt attttacgct gtgttaaatg  4095
ttaacagttt tccactattt ctctttcttt tctattagtg aataaaattt tatac       4150
```

<210> SEQ ID NO 20
<211> LENGTH: 1335
<212> TYPE: PRT
<213> ORGANISM: Homo sapiens

<400> SEQUENCE: 20

```
Ala Gln Leu Arg Gln Phe Tyr Val Ala Ala Gln Gly Ile Ser Trp Ser
1               5                   10                  15

Tyr Arg Pro Glu Pro Thr Asn Ser Ser Leu Asn Leu Ser Val Thr Ser
            20                  25                  30

Phe Lys Lys Ile Val Tyr Arg Glu Tyr Glu Pro Tyr Phe Lys Lys Glu
        35                  40                  45

Lys Pro Gln Ser Thr Ile Ser Gly Leu Leu Gly Pro Thr Leu Tyr Ala
    50                  55                  60

Glu Val Gly Asp Ile Ile Lys Val His Phe Lys Asn Lys Ala Asp Lys
65                  70                  75                  80
```

-continued

```
Pro Leu Ser Ile His Pro Gln Gly Ile Arg Tyr Ser Lys Leu Ser Ala
                85                  90                  95

Gly Ala Ser Tyr Leu Asp His Thr Phe Pro Ala Glu Lys Met Asp Asp
            100                 105                 110

Ala Val Ala Pro Gly Arg Glu Tyr Thr Tyr Glu Trp Ser Ile Ser Glu
        115                 120                 125

Asp Ser Gly Pro Thr His Asp Asp Pro Cys Leu Thr His Ile Tyr
    130                 135                 140

Tyr Ser His Glu Asn Leu Ile Glu Asp Phe Asn Ser Gly Leu Ile Gly
145                 150                 155                 160

Pro Leu Leu Ile Cys Lys Lys Gly Thr Leu Thr Glu Gly Gly Thr Gln
                165                 170                 175

Lys Thr Phe Asp Lys Gln Ile Val Leu Phe Ala Val Phe Asp Glu
            180                 185                 190

Ser Lys Ser Trp Ser Gln Ser Ser Leu Met Tyr Thr Val Asn Gly
        195                 200                 205

Tyr Val Asn Gly Thr Met Pro Asp Ile Thr Val Cys Ala His Asp His
    210                 215                 220

Ile Ser Trp His Leu Leu Gly Met Ser Ser Gly Pro Glu Leu Phe Ser
225                 230                 235                 240

Ile His Phe Asn Gly Gln Val Leu Glu Gln Asn His His Lys Val Ser
                245                 250                 255

Ala Ile Thr Leu Val Ser Ala Thr Ser Thr Ala Asn Met Thr Val
            260                 265                 270

Gly Pro Glu Gly Lys Trp Ile Ile Ser Ser Leu Thr Pro Lys His Leu
        275                 280                 285

Gln Ala Gly Met Gln Ala Tyr Ile Asp Ile Lys Asn Cys Pro Lys Lys
    290                 295                 300

Thr Arg Asn Leu Lys Lys Ile Thr Arg Glu Gln Arg His Met Lys
305                 310                 315                 320

Arg Trp Glu Tyr Phe Ile Ala Ala Glu Glu Val Ile Trp Asp Tyr Ala
                325                 330                 335

Pro Val Ile Pro Ala Asn Met Asp Lys Lys Tyr Arg Ser Gln His Leu
            340                 345                 350

Asp Asn Phe Ser Asn Gln Ile Gly Lys His Tyr Lys Lys Val Met Tyr
        355                 360                 365

Thr Gln Tyr Glu Asp Glu Ser Phe Thr Lys His Thr Val Asn Pro Asn
    370                 375                 380

Met Lys Glu Asp Gly Ile Leu Gly Pro Ile Ile Arg Ala Gln Val Arg
385                 390                 395                 400

Asp Thr Leu Lys Ile Val Phe Lys Asn Met Ala Ser Arg Pro Tyr Ser
                405                 410                 415

Ile Tyr Pro His Gly Val Thr Phe Ser Pro Tyr Glu Asp Glu Val Asn
            420                 425                 430

Ser Ser Phe Thr Ser Gly Arg Asn Asn Thr Met Ile Arg Ala Val Gln
        435                 440                 445

Pro Gly Glu Thr Tyr Thr Tyr Lys Trp Asn Ile Leu Glu Phe Asp Glu
    450                 455                 460

Pro Thr Glu Asn Asp Ala Gln Cys Leu Thr Arg Pro Tyr Tyr Ser Asp
465                 470                 475                 480

Val Asp Ile Met Arg Asp Ile Ala Ser Gly Leu Ile Gly Leu Leu Leu
                485                 490                 495
```

```
Ile Cys Lys Ser Arg Ser Leu Asp Arg Arg Gly Ile Gln Arg Ala Ala
            500                 505                 510

Asp Ile Glu Gln Gln Ala Val Phe Ala Val Phe Asp Glu Asn Lys Ser
            515                 520                 525

Trp Tyr Leu Glu Asp Asn Ile Asn Lys Phe Cys Glu Asn Pro Asp Glu
            530                 535                 540

Val Lys Arg Asp Asp Pro Lys Phe Tyr Glu Ser Asn Ile Met Ser Thr
545                 550                 555                 560

Ile Asn Gly Tyr Val Pro Glu Ser Ile Thr Thr Leu Gly Phe Cys Phe
                565                 570                 575

Asp Asp Thr Val Gln Trp His Phe Cys Ser Val Gly Thr Gln Asn Glu
            580                 585                 590

Ile Leu Thr Ile His Phe Thr Gly His Ser Phe Ile Tyr Gly Lys Arg
            595                 600                 605

His Glu Asp Thr Leu Thr Leu Phe Pro Met Arg Gly Glu Ser Val Thr
            610                 615                 620

Val Thr Met Asp Asn Val Gly Thr Trp Met Leu Thr Ser Met Asn Ser
625                 630                 635                 640

Ser Pro Arg Ser Lys Lys Leu Arg Leu Lys Phe Arg Asp Val Lys Cys
                645                 650                 655

Ile Pro Asp Asp Asp Glu Asp Ser Tyr Glu Ile Phe Glu Pro Pro Glu
            660                 665                 670

Ser Thr Val Met Ala Thr Arg Lys Met His Asp Arg Leu Glu Pro Glu
            675                 680                 685

Asp Glu Glu Ser Asp Ala Asp Tyr Asp Tyr Gln Asn Arg Leu Ala Ala
            690                 695                 700

Ala Leu Gly Ile Arg Arg Glu Thr Asp Ile Glu Asp Ser Asp Asp Ile
705                 710                 715                 720

Pro Glu Asp Thr Thr Tyr Lys Lys Val Val Phe Arg Lys Tyr Leu Asp
                725                 730                 735

Ser Thr Phe Thr Lys Arg Asp Pro Arg Gly Glu Tyr Glu Glu His Leu
            740                 745                 750

Gly Ile Leu Gly Pro Ile Ile Arg Ala Glu Val Asp Asp Val Ile Gln
            755                 760                 765

Val Arg Phe Lys Asn Leu Ala Ser Arg Pro Tyr Ser Leu His Ala His
770                 775                 780

Gly Leu Ser Tyr Glu Lys Ser Ser Glu Gly Lys Thr Tyr Glu Asp Asp
785                 790                 795                 800

Ser Pro Glu Trp Phe Lys Glu Asp Asn Ala Val Gln Pro Asn Ser Ser
                805                 810                 815

Tyr Thr Tyr Val Trp His Ala Thr Glu Arg Ser Gly Pro Glu Ser Pro
            820                 825                 830

Gly Ser Ala Cys Arg Ala Trp Ala Tyr Tyr Ser Ala Val Asn Pro Glu
            835                 840                 845

Lys Asp Ile His Ser Gly Leu Ile Gly Pro Leu Leu Ile Cys Gln Lys
850                 855                 860

Gly Ile Leu His Lys Asp Ser Asn Met Pro Val Asp Met Arg Glu Phe
865                 870                 875                 880

Val Leu Leu Phe Met Thr Phe Asp Glu Lys Lys Ser Trp Tyr Tyr Glu
                885                 890                 895

Lys Lys Ser Arg Ser Ser Trp Arg Leu Thr Ser Ser Glu Met Lys Lys
            900                 905                 910

Ser His Glu Phe His Ala Ile Asn Gly Met Ile Tyr Ser Leu Pro Gly
```

-continued

```
                915                 920                 925
Leu Lys Met Tyr Glu Gln Glu Trp Val Arg Leu His Leu Leu Asn Ile
        930                 935                 940
Gly Gly Ser Gln Asp Ile His Val Val His Phe His Gly Gln Thr Leu
945                 950                 955                 960
Leu Glu Asn Gly Asn Lys Gln His Gln Leu Gly Val Trp Pro Leu Leu
                965                 970                 975
Pro Gly Ser Phe Lys Thr Leu Glu Met Lys Ala Ser Lys Pro Gly Trp
            980                 985                 990
Trp Leu Leu Asn Thr Glu Val Gly Glu Asn Gln Arg Ala Gly Met Gln
        995                 1000                1005
Thr Pro Phe Leu Ile Met Asp Arg Asp Cys Arg Met Pro Met Gly Leu
    1010                1015                1020
Ser Thr Gly Ile Ile Ser Asp Ser Gln Ile Lys Ala Ser Glu Phe Leu
1025                1030                1035                1040
Gly Tyr Trp Glu Pro Arg Leu Ala Arg Leu Asn Asn Gly Gly Ser Tyr
                1045                1050                1055
Asn Ala Trp Ser Val Glu Lys Leu Ala Ala Glu Phe Ala Ser Lys Pro
            1060                1065                1070
Trp Ile Gln Val Asp Met Gln Lys Glu Val Ile Ile Thr Gly Ile Gln
        1075                1080                1085
Thr Gln Gly Ala Lys His Tyr Leu Lys Ser Cys Tyr Thr Thr Glu Phe
    1090                1095                1100
Tyr Val Ala Tyr Ser Ser Asn Gln Ile Asn Trp Gln Ile Phe Lys Gly
1105                1110                1115                1120
Asn Ser Thr Arg Asn Val Met Tyr Phe Asn Gly Asn Ser Asp Ala Ser
                1125                1130                1135
Thr Ile Lys Glu Asn Gln Phe Asp Pro Pro Ile Val Ala Arg Tyr Ile
            1140                1145                1150
Arg Ile Ser Pro Thr Arg Ala Tyr Asn Arg Pro Thr Leu Arg Leu Glu
        1155                1160                1165
Leu Gln Gly Cys Glu Val Asn Gly Cys Ser Thr Pro Leu Gly Met Glu
    1170                1175                1180
Asn Gly Lys Ile Glu Asn Lys Gln Ile Thr Ala Ser Ser Phe Lys Lys
1185                1190                1195                1200
Ser Trp Trp Gly Asp Tyr Trp Glu Pro Phe Arg Ala Arg Leu Asn Ala
                1205                1210                1215
Gln Gly Arg Val Asn Ala Trp Gln Ala Lys Ala Asn Asn Asn Lys Gln
            1220                1225                1230
Trp Leu Glu Ile Asp Leu Leu Lys Ile Lys Ile Thr Ala Ile Ile
        1235                1240                1245
Thr Gln Gly Cys Lys Ser Leu Ser Ser Glu Met Tyr Val Lys Ser Tyr
    1250                1255                1260
Thr Ile His Tyr Ser Glu Gln Gly Val Glu Trp Lys Pro Tyr Arg Leu
1265                1270                1275                1280
Lys Ser Ser Met Val Asp Lys Ile Phe Glu Gly Asn Thr Asn Thr Lys
                1285                1290                1295
Gly His Val Lys Asn Phe Phe Asn Pro Pro Ile Ile Ser Arg Phe Ile
            1300                1305                1310
Arg Val Ile Pro Lys Thr Trp Asn Gln Ser Ile Ala Leu Arg Leu Glu
        1315                1320                1325
Leu Phe Gly Cys Asp Ile Tyr
    1330                1335
```

<210> SEQ ID NO 21
<211> LENGTH: 4150
<212> TYPE: DNA
<213> ORGANISM: Homo sapiens
<220> FEATURE:
<221> NAME/KEY: CDS
<222> LOCATION: (1)..(4005)

<400> SEQUENCE: 21

| | | | | | | | | | | | | | | | | |
|---|---|---|---|---|---|---|---|---|---|---|---|---|---|---|---|---|
| gca | cag | cta | agg | cag | ttc | tac | gtg | gct | gct | cag | ggc | atc | agt | tgg | agc | 48 |
| Ala | Gln | Leu | Arg | Gln | Phe | Tyr | Val | Ala | Ala | Gln | Gly | Ile | Ser | Trp | Ser | |
| 1 | | | | 5 | | | | | 10 | | | | | 15 | | |
| tac | cga | cct | gag | ccc | aca | aac | tca | agt | ttg | aat | ctt | tct | gta | act | tcc | 96 |
| Tyr | Arg | Pro | Glu | Pro | Thr | Asn | Ser | Ser | Leu | Asn | Leu | Ser | Val | Thr | Ser | |
| | | | 20 | | | | | 25 | | | | | 30 | | | |
| ttt | aag | aaa | att | gtc | tac | aga | gag | tat | gaa | cca | tat | ttt | aag | aaa | gaa | 144 |
| Phe | Lys | Lys | Ile | Val | Tyr | Arg | Glu | Tyr | Glu | Pro | Tyr | Phe | Lys | Lys | Glu | |
| | 35 | | | | | 40 | | | | | 45 | | | | | |
| aaa | cca | caa | tct | acc | att | tca | gga | ctt | ctt | ggg | cct | act | tta | tat | gct | 192 |
| Lys | Pro | Gln | Ser | Thr | Ile | Ser | Gly | Leu | Leu | Gly | Pro | Thr | Leu | Tyr | Ala | |
| | 50 | | | | | 55 | | | | | 60 | | | | | |
| gaa | gtc | gga | gac | atc | ata | aaa | gtt | cac | ttt | aaa | aat | aag | gca | gat | aag | 240 |
| Glu | Val | Gly | Asp | Ile | Ile | Lys | Val | His | Phe | Lys | Asn | Lys | Ala | Asp | Lys | |
| 65 | | | | | 70 | | | | | 75 | | | | | 80 | |
| ccc | ttg | agc | atc | cat | cct | caa | gga | att | agg | tac | agt | aaa | tta | tca | gca | 288 |
| Pro | Leu | Ser | Ile | His | Pro | Gln | Gly | Ile | Arg | Tyr | Ser | Lys | Leu | Ser | Ala | |
| | | | | 85 | | | | | 90 | | | | | 95 | | |
| ggt | gct | tct | tac | ctt | gcc | cac | aca | ttc | cct | gca | gcg | aag | atg | gcc | gcc | 336 |
| Gly | Ala | Ser | Tyr | Leu | Ala | His | Thr | Phe | Pro | Ala | Ala | Lys | Met | Ala | Ala | |
| | | | 100 | | | | | 105 | | | | | 110 | | | |
| gct | gtg | gct | cca | ggc | cga | gaa | tac | acc | tat | gaa | tgg | agt | atc | agt | gag | 384 |
| Ala | Val | Ala | Pro | Gly | Arg | Glu | Tyr | Thr | Tyr | Glu | Trp | Ser | Ile | Ser | Glu | |
| | | 115 | | | | | 120 | | | | | 125 | | | | |
| gac | agt | gga | ccc | acc | cat | gat | gac | cct | cca | tgc | ctc | aca | cac | atc | tat | 432 |
| Asp | Ser | Gly | Pro | Thr | His | Asp | Asp | Pro | Pro | Cys | Leu | Thr | His | Ile | Tyr | |
| | 130 | | | | | 135 | | | | | 140 | | | | | |
| tac | tcc | cat | gaa | aat | ctg | atc | gag | gat | ttc | aac | tct | ggg | ctg | att | ggg | 480 |
| Tyr | Ser | His | Glu | Asn | Leu | Ile | Glu | Asp | Phe | Asn | Ser | Gly | Leu | Ile | Gly | |
| 145 | | | | | 150 | | | | | 155 | | | | | 160 | |
| ccc | ctg | ctt | atc | tgt | aaa | aaa | ggg | acc | cta | act | gag | ggt | ggg | aca | cag | 528 |
| Pro | Leu | Leu | Ile | Cys | Lys | Lys | Gly | Thr | Leu | Thr | Glu | Gly | Gly | Thr | Gln | |
| | | | | 165 | | | | | 170 | | | | | 175 | | |
| aag | acg | ttt | gac | aag | caa | atc | gtg | cta | cta | ttt | gct | gtg | ttt | gat | gaa | 576 |
| Lys | Thr | Phe | Asp | Lys | Gln | Ile | Val | Leu | Leu | Phe | Ala | Val | Phe | Asp | Glu | |
| | | | 180 | | | | | 185 | | | | | 190 | | | |
| agc | aag | agc | tgg | agc | cag | tca | tca | tcc | cta | atg | tac | aca | gtc | aat | gga | 624 |
| Ser | Lys | Ser | Trp | Ser | Gln | Ser | Ser | Ser | Leu | Met | Tyr | Thr | Val | Asn | Gly | |
| | | 195 | | | | | 200 | | | | | 205 | | | | |
| tat | gtg | aat | ggg | aca | atg | cca | gat | ata | aca | gtt | tgt | gcc | cat | gac | cac | 672 |
| Tyr | Val | Asn | Gly | Thr | Met | Pro | Asp | Ile | Thr | Val | Cys | Ala | His | Asp | His | |
| | 210 | | | | | 215 | | | | | 220 | | | | | |
| atc | agc | tgg | cat | ctg | ctg | gga | atg | agc | tcg | ggg | cca | gaa | tta | ttc | tcc | 720 |
| Ile | Ser | Trp | His | Leu | Leu | Gly | Met | Ser | Ser | Gly | Pro | Glu | Leu | Phe | Ser | |
| 225 | | | | | 230 | | | | | 235 | | | | | 240 | |
| att | cat | ttc | aac | ggc | cag | gtc | ctg | gag | cag | aac | cat | cat | aag | gtc | tca | 768 |
| Ile | His | Phe | Asn | Gly | Gln | Val | Leu | Glu | Gln | Asn | His | His | Lys | Val | Ser | |
| | | | | 245 | | | | | 250 | | | | | 255 | | |
| gcc | atc | acc | ctt | gtc | agt | gct | aca | tcc | act | acc | gca | aat | atg | act | gtg | 816 |
| Ala | Ile | Thr | Leu | Val | Ser | Ala | Thr | Ser | Thr | Thr | Ala | Asn | Met | Thr | Val | |
| | | | 260 | | | | | 265 | | | | | 270 | | | |

| | | |
|---|---|---|
| ggc cca gag gga aag tgg atc ata tct tct ctc acc cca aaa cat ttg<br>Gly Pro Glu Gly Lys Trp Ile Ile Ser Ser Leu Thr Pro Lys His Leu<br>275 280 285 | | 864 |
| caa gct ggg atg cag gct tac att gac att aaa aac tgc cca aag aaa<br>Gln Ala Gly Met Gln Ala Tyr Ile Asp Ile Lys Asn Cys Pro Lys Lys<br>290 295 300 | | 912 |
| acc agg aat ctt aag aaa ata act cgt gag cag agg cgg cac atg aag<br>Thr Arg Asn Leu Lys Lys Ile Thr Arg Glu Gln Arg Arg His Met Lys<br>305 310 315 320 | | 960 |
| agg tgg gaa tac ttc att gct gca gag gaa gtc att tgg gac tat gca<br>Arg Trp Glu Tyr Phe Ile Ala Ala Glu Glu Val Ile Trp Asp Tyr Ala<br>325 330 335 | | 1008 |
| cct gta ata cca gcg aat atg gac aaa aaa tac agg tct cag cat ttg<br>Pro Val Ile Pro Ala Asn Met Asp Lys Lys Tyr Arg Ser Gln His Leu<br>340 345 350 | | 1056 |
| gat aat ttc tca aac caa att gga aaa cat tat aag aaa gtt atg tac<br>Asp Asn Phe Ser Asn Gln Ile Gly Lys His Tyr Lys Lys Val Met Tyr<br>355 360 365 | | 1104 |
| aca cag tac gaa gat gag tcc ttc acc aaa cat aca gtg aat ccc aat<br>Thr Gln Tyr Glu Asp Glu Ser Phe Thr Lys His Thr Val Asn Pro Asn<br>370 375 380 | | 1152 |
| atg aaa gaa gat ggg att ttg ggt cct att atc aga gcc cag gtc aga<br>Met Lys Glu Asp Gly Ile Leu Gly Pro Ile Ile Arg Ala Gln Val Arg<br>385 390 395 400 | | 1200 |
| gac aca ctc aaa atc gtg ttc aaa aat atg gcc agc cgc ccc tat agc<br>Asp Thr Leu Lys Ile Val Phe Lys Asn Met Ala Ser Arg Pro Tyr Ser<br>405 410 415 | | 1248 |
| att tac cct cat gga gtg acc ttc tcg cct tat gaa gat gaa gtc aac<br>Ile Tyr Pro His Gly Val Thr Phe Ser Pro Tyr Glu Asp Glu Val Asn<br>420 425 430 | | 1296 |
| tct tct ttc acc tca ggc agg aac aac acc atg atc aga gca gtt caa<br>Ser Ser Phe Thr Ser Gly Arg Asn Asn Thr Met Ile Arg Ala Val Gln<br>435 440 445 | | 1344 |
| cca ggg gaa acc tat act tat aag tgg aac atc tta gag ttt gat gaa<br>Pro Gly Glu Thr Tyr Thr Tyr Lys Trp Asn Ile Leu Glu Phe Asp Glu<br>450 455 460 | | 1392 |
| ccc aca gaa aat gat gcc cag tgc tta aca aga cca tac tac agt gac<br>Pro Thr Glu Asn Asp Ala Gln Cys Leu Thr Arg Pro Tyr Tyr Ser Asp<br>465 470 475 480 | | 1440 |
| gtg gac atc atg aga gac atc gcc tct ggg cta ata gga cta ctt cta<br>Val Asp Ile Met Arg Asp Ile Ala Ser Gly Leu Ile Gly Leu Leu Leu<br>485 490 495 | | 1488 |
| atc tgt aag agc aga tcc ctg gac agg cga gga ata cag agg gca gca<br>Ile Cys Lys Ser Arg Ser Leu Asp Arg Arg Gly Ile Gln Arg Ala Ala<br>500 505 510 | | 1536 |
| gac atc gaa cag cag gct gtg ttt gct gtg ttt gat gag aac aaa agc<br>Asp Ile Glu Gln Gln Ala Val Phe Ala Val Phe Asp Glu Asn Lys Ser<br>515 520 525 | | 1584 |
| tgg tac ctt gag gac aac atc aac aag ttt tgt gaa aat cct gat gag<br>Trp Tyr Leu Glu Asp Asn Ile Asn Lys Phe Cys Glu Asn Pro Asp Glu<br>530 535 540 | | 1632 |
| gtg aaa cgt gat gac ccc aag ttt tat gaa tca aac atc atg agc act<br>Val Lys Arg Asp Asp Pro Lys Phe Tyr Glu Ser Asn Ile Met Ser Thr<br>545 550 555 560 | | 1680 |
| atc aat ggc tat gtg cct gag agc ata act act ctt gga ttc tgc ttt<br>Ile Asn Gly Tyr Val Pro Glu Ser Ile Thr Thr Leu Gly Phe Cys Phe<br>565 570 575 | | 1728 |
| gat gac act gtc cag tgg cac ttc tgt agt gtg ggg acc cag aat gaa<br>Asp Asp Thr Val Gln Trp His Phe Cys Ser Val Gly Thr Gln Asn Glu | | 1776 |

-continued

```
                 580                 585                 590
att ttg acc atc cac ttc act ggg cac tca ttc atc tat gga aag agg         1824
Ile Leu Thr Ile His Phe Thr Gly His Ser Phe Ile Tyr Gly Lys Arg
            595                 600                 605 cat gag gac acc ttg acc ctc ttc ccc atg cgt gga gaa tct gtg acg         1872
His Glu Asp Thr Leu Thr Leu Phe Pro Met Arg Gly Glu Ser Val Thr
610                 615                 620 gtc aca atg gat aat gtt gga act tgg atg tta act tcc atg aat tct         1920
Val Thr Met Asp Asn Val Gly Thr Trp Met Leu Thr Ser Met Asn Ser
625                 630                 635                 640 agt cca aga agc aaa aag ctg agg ctg aaa ttc agg gat gtt aaa tgt         1968
Ser Pro Arg Ser Lys Lys Leu Arg Leu Lys Phe Arg Asp Val Lys Cys
            645                 650                 655 atc cca gat gat gat gaa gac tca tat gag att ttt gaa cct cca gaa         2016
Ile Pro Asp Asp Asp Glu Asp Ser Tyr Glu Ile Phe Glu Pro Pro Glu
                660                 665                 670 tct aca gtc atg gct aca cgg aaa atg cat gat cgt tta gaa cct gaa         2064
Ser Thr Val Met Ala Thr Arg Lys Met His Asp Arg Leu Glu Pro Glu
            675                 680                 685 gat gaa gag agt gat gct gac tat gat tac cag aac aga ctg gct gca         2112
Asp Glu Glu Ser Asp Ala Asp Tyr Asp Tyr Gln Asn Arg Leu Ala Ala
690                 695                 700 gca tta gga att agg agg gaa aca gat att gaa gac tct gat gat att         2160
Ala Leu Gly Ile Arg Arg Glu Thr Asp Ile Glu Asp Ser Asp Asp Ile
705                 710                 715                 720 cca gaa gat acc aca tat aag aaa gta gtt ttt cga aag tac ctc gac         2208
Pro Glu Asp Thr Thr Tyr Lys Lys Val Val Phe Arg Lys Tyr Leu Asp
            725                 730                 735 agc act ttt acc aaa cgt gat cct cga ggg gag tat gaa gag cat ctc         2256
Ser Thr Phe Thr Lys Arg Asp Pro Arg Gly Glu Tyr Glu Glu His Leu
                740                 745                 750 gga att ctt ggt cct att atc aga gct gaa gtg gat gat gtt atc caa         2304
Gly Ile Leu Gly Pro Ile Ile Arg Ala Glu Val Asp Asp Val Ile Gln
            755                 760                 765 gtt cgt ttt aaa aat tta gca tcc aga ccg tat tct cta cat gcc cat         2352
Val Arg Phe Lys Asn Leu Ala Ser Arg Pro Tyr Ser Leu His Ala His
770                 775                 780 gga ctt tcc tat gaa aaa tca tca gag gga aag act tat gaa gat gac         2400
Gly Leu Ser Tyr Glu Lys Ser Ser Glu Gly Lys Thr Tyr Glu Asp Asp
785                 790                 795                 800 tct cct gaa tgg ttt aag gaa gat aat gct gtt cag cca aat agc agt         2448
Ser Pro Glu Trp Phe Lys Glu Asp Asn Ala Val Gln Pro Asn Ser Ser
            805                 810                 815 tat acc tac gta tgg cat gcc act gag cga tca ggg cca gaa agt cct         2496
Tyr Thr Tyr Val Trp His Ala Thr Glu Arg Ser Gly Pro Glu Ser Pro
                820                 825                 830 ggc tct gcc tgt cgg gct tgg gcc tac tac tca gct gtg aac cca gaa         2544
Gly Ser Ala Cys Arg Ala Trp Ala Tyr Tyr Ser Ala Val Asn Pro Glu
            835                 840                 845 aaa gat att cac tca ggc ttg ata ggt ccc ctc cta atc tgc caa aaa         2592
Lys Asp Ile His Ser Gly Leu Ile Gly Pro Leu Leu Ile Cys Gln Lys
850                 855                 860 gga ata cta cat aag gac agc aac atg cct gtg gac atg aga gaa ttt         2640
Gly Ile Leu His Lys Asp Ser Asn Met Pro Val Asp Met Arg Glu Phe
865                 870                 875                 880 gtc tta cta ttt atg acc ttt gat gaa aag aag agc tgg tac tat gaa         2688
Val Leu Leu Phe Met Thr Phe Asp Glu Lys Lys Ser Trp Tyr Tyr Glu
                885                 890                 895 aag aag tcc cga agt tct tgg aga ctc aca tcc tca gaa atg aaa aaa         2736
```

```
Lys Lys Ser Arg Ser Ser Trp Arg Leu Thr Ser Ser Glu Met Lys Lys
            900                 905                 910 tcc cat gag ttt cac gcc att aat ggg atg atc tac agc ttg cct ggc    2784
Ser His Glu Phe His Ala Ile Asn Gly Met Ile Tyr Ser Leu Pro Gly
        915                 920                 925 ctg aaa atg tat gag caa gag tgg gtg agg tta cac ctg ctg aac ata    2832
Leu Lys Met Tyr Glu Gln Glu Trp Val Arg Leu His Leu Leu Asn Ile
    930                 935                 940 ggc ggc tcc caa gac att cac gtg gtt cac ttt cac ggc cag acc ttg    2880
Gly Gly Ser Gln Asp Ile His Val Val His Phe His Gly Gln Thr Leu
945                 950                 955                 960 ctg gaa aat ggc aat aaa cag cac cag tta ggg gtc tgg ccc ctt ctg    2928
Leu Glu Asn Gly Asn Lys Gln His Gln Leu Gly Val Trp Pro Leu Leu
                965                 970                 975 cct ggt tca ttt aaa act ctt gaa atg aag gca tca aaa cct ggc tgg    2976
Pro Gly Ser Phe Lys Thr Leu Glu Met Lys Ala Ser Lys Pro Gly Trp
            980                 985                 990 tgg ctc cta aac aca gag gtt gga gaa aac cag aga gca ggg atg caa    3024
Trp Leu Leu Asn Thr Glu Val Gly Glu Asn Gln Arg Ala Gly Met Gln
        995                 1000                1005 acg cca ttt ctt atc atg gac aga gac tgt agg atg cca atg gga cta    3072
Thr Pro Phe Leu Ile Met Asp Arg Asp Cys Arg Met Pro Met Gly Leu
    1010                1015                1020 agc act ggt atc ata tct gat tca cag atc aag gct tca gag ttt ctg    3120
Ser Thr Gly Ile Ile Ser Asp Ser Gln Ile Lys Ala Ser Glu Phe Leu
1025                1030                1035                1040 ggt tac tgg gag ccc aga tta gca aga tta aac aat ggt gga tct tat    3168
Gly Tyr Trp Glu Pro Arg Leu Ala Arg Leu Asn Asn Gly Gly Ser Tyr
                1045                1050                1055 aat gct tgg agt gta gaa aaa ctt gca gca gaa ttt gcc tct aaa cct    3216
Asn Ala Trp Ser Val Glu Lys Leu Ala Ala Glu Phe Ala Ser Lys Pro
            1060                1065                1070 tgg atc cag gtg gac atg caa aag gaa gtc ata atc aca ggg atc cag    3264
Trp Ile Gln Val Asp Met Gln Lys Glu Val Ile Ile Thr Gly Ile Gln
        1075                1080                1085 acc caa ggt gcc aaa cac tac ctg aag tcc tgc tat acc aca gag ttc    3312
Thr Gln Gly Ala Lys His Tyr Leu Lys Ser Cys Tyr Thr Thr Glu Phe
    1090                1095                1100 tat gta gct tac agt tcc aac cag atc aac tgg cag atc ttc aaa ggg    3360
Tyr Val Ala Tyr Ser Ser Asn Gln Ile Asn Trp Gln Ile Phe Lys Gly
1105                1110                1115                1120 aac agc aca agg aat gtg atg tat ttt aat ggc aat tca gat gcc tct    3408
Asn Ser Thr Arg Asn Val Met Tyr Phe Asn Gly Asn Ser Asp Ala Ser
                1125                1130                1135 aca ata aaa gag aat cag ttt gac cca cct att gtg gct aga tat att    3456
Thr Ile Lys Glu Asn Gln Phe Asp Pro Pro Ile Val Ala Arg Tyr Ile
            1140                1145                1150 agg atc tct cca act cga gcc tat aac aga cct acc ctt cga ttg gaa    3504
Arg Ile Ser Pro Thr Arg Ala Tyr Asn Arg Pro Thr Leu Arg Leu Glu
        1155                1160                1165 ctg caa ggt tgt gag gta aat gga tgt tcc aca ccc ctg ggt atg gaa    3552
Leu Gln Gly Cys Glu Val Asn Gly Cys Ser Thr Pro Leu Gly Met Glu
    1170                1175                1180 aat gga aag ata gaa aac aag caa atc aca gct tct tcg ttt aag aaa    3600
Asn Gly Lys Ile Glu Asn Lys Gln Ile Thr Ala Ser Ser Phe Lys Lys
1185                1190                1195                1200 tct tgg tgg gga gat tac tgg gaa ccc ttc cgt gcc cgt ctg aat gcc    3648
Ser Trp Trp Gly Asp Tyr Trp Glu Pro Phe Arg Ala Arg Leu Asn Ala
                1205                1210                1215
```

```
cag gga cgt gtg aat gcc tgg caa gcc aag gca aac aac aat aag cag    3696
Gln Gly Arg Val Asn Ala Trp Gln Ala Lys Ala Asn Asn Asn Lys Gln
        1220                1225                1230 tgg cta gaa att gat cta ctc aag atc aag aag ata acg gca att ata    3744
Trp Leu Glu Ile Asp Leu Leu Lys Ile Lys Lys Ile Thr Ala Ile Ile
    1235                1240                1245 aca cag ggc tgc aag tct ctg tcc tct gaa atg tat gta aag agc tat    3792
Thr Gln Gly Cys Lys Ser Leu Ser Ser Glu Met Tyr Val Lys Ser Tyr
1250                1255                1260 acc atc cac tac agt gag cag gga gtg gaa tgg aaa cca tac agg ctg    3840
Thr Ile His Tyr Ser Glu Gln Gly Val Glu Trp Lys Pro Tyr Arg Leu
    1265                1270                1275                1280 aaa tcc tcc atg gtg gac aag att ttt gaa gga aat act aat acc aaa    3888
Lys Ser Ser Met Val Asp Lys Ile Phe Glu Gly Asn Thr Asn Thr Lys
            1285                1290                1295 gga cat gtg aag aac ttt ttc aac ccc cca atc att tcc agg ttt atc    3936
Gly His Val Lys Asn Phe Phe Asn Pro Pro Ile Ile Ser Arg Phe Ile
        1300                1305                1310 cgt gtc att cct aaa aca tgg aat caa agt att gca ctt cgc ctg gaa    3984
Arg Val Ile Pro Lys Thr Trp Asn Gln Ser Ile Ala Leu Arg Leu Glu
    1315                1320                1325 ctc ttt ggc tgt gat att tac tagaattgaa cattcaaaaa cccctggaag       4035
Leu Phe Gly Cys Asp Ile Tyr
1330                1335 agactcttta agacctcaaa ccatttagaa tgggcaatgt attttacgct gtgttaaatg  4095
ttaacagttt tccactattt ctctttcttt tctattagtg aataaaattt tatac       4150

<210> SEQ ID NO 22
<211> LENGTH: 1335
<212> TYPE: PRT
<213> ORGANISM: Homo sapiens

<400> SEQUENCE: 22

Ala Gln Leu Arg Gln Phe Tyr Val Ala Ala Gln Gly Ile Ser Trp Ser
1               5                   10                  15

Tyr Arg Pro Glu Pro Thr Asn Ser Ser Leu Asn Leu Ser Val Thr Ser
            20                  25                  30

Phe Lys Lys Ile Val Tyr Arg Glu Tyr Glu Pro Tyr Phe Lys Lys Glu
        35                  40                  45

Lys Pro Gln Ser Thr Ile Ser Gly Leu Leu Gly Pro Thr Leu Tyr Ala
    50                  55                  60

Glu Val Gly Asp Ile Ile Lys Val His Phe Lys Asn Lys Ala Asp Lys
65                  70                  75                  80

Pro Leu Ser Ile His Pro Gln Gly Ile Arg Tyr Ser Lys Leu Ser Ala
                85                  90                  95

Gly Ala Ser Tyr Leu Ala His Thr Phe Pro Ala Ala Lys Met Ala Ala
            100                 105                 110

Ala Val Ala Pro Gly Arg Glu Tyr Thr Tyr Glu Trp Ser Ile Ser Glu
        115                 120                 125

Asp Ser Gly Pro Thr His Asp Asp Pro Pro Cys Leu Thr His Ile Tyr
    130                 135                 140

Tyr Ser His Glu Asn Leu Ile Glu Asp Phe Asn Ser Gly Leu Ile Gly
145                 150                 155                 160

Pro Leu Leu Ile Cys Lys Lys Gly Thr Leu Thr Glu Gly Gly Thr Gln
                165                 170                 175

Lys Thr Phe Asp Lys Gln Ile Val Leu Leu Phe Ala Val Phe Asp Glu
            180                 185                 190
```

-continued

Ser Lys Ser Trp Ser Gln Ser Ser Leu Met Tyr Thr Val Asn Gly
        195                 200                 205

Tyr Val Asn Gly Thr Met Pro Asp Ile Thr Val Cys Ala His Asp His
210                 215                 220

Ile Ser Trp His Leu Leu Gly Met Ser Ser Gly Pro Glu Leu Phe Ser
225                 230                 235                 240

Ile His Phe Asn Gly Gln Val Leu Glu Gln Asn His His Lys Val Ser
                245                 250                 255

Ala Ile Thr Leu Val Ser Ala Thr Ser Thr Ala Asn Met Thr Val
            260                 265                 270

Gly Pro Glu Gly Lys Trp Ile Ile Ser Ser Leu Thr Pro Lys His Leu
        275                 280                 285

Gln Ala Gly Met Gln Ala Tyr Ile Asp Ile Lys Asn Cys Pro Lys Lys
        290                 295                 300

Thr Arg Asn Leu Lys Lys Ile Thr Arg Glu Gln Arg His Met Lys
305                 310                 315                 320

Arg Trp Glu Tyr Phe Ile Ala Ala Glu Glu Val Ile Trp Asp Tyr Ala
                325                 330                 335

Pro Val Ile Pro Ala Asn Met Asp Lys Lys Tyr Arg Ser Gln His Leu
            340                 345                 350

Asp Asn Phe Ser Asn Gln Ile Gly Lys His Tyr Lys Lys Val Met Tyr
        355                 360                 365

Thr Gln Tyr Glu Asp Glu Ser Phe Thr Lys His Thr Val Asn Pro Asn
        370                 375                 380

Met Lys Glu Asp Gly Ile Leu Gly Pro Ile Ile Arg Ala Gln Val Arg
385                 390                 395                 400

Asp Thr Leu Lys Ile Val Phe Lys Asn Met Ala Ser Arg Pro Tyr Ser
                405                 410                 415

Ile Tyr Pro His Gly Val Thr Phe Ser Pro Tyr Glu Asp Glu Val Asn
            420                 425                 430

Ser Ser Phe Thr Ser Gly Arg Asn Asn Thr Met Ile Arg Ala Val Gln
        435                 440                 445

Pro Gly Glu Thr Tyr Thr Tyr Lys Trp Asn Ile Leu Glu Phe Asp Glu
450                 455                 460

Pro Thr Glu Asn Asp Ala Gln Cys Leu Thr Arg Pro Tyr Tyr Ser Asp
465                 470                 475                 480

Val Asp Ile Met Arg Asp Ile Ala Ser Gly Leu Ile Gly Leu Leu Leu
            485                 490                 495

Ile Cys Lys Ser Arg Ser Leu Asp Arg Arg Gly Ile Gln Arg Ala Ala
        500                 505                 510

Asp Ile Glu Gln Gln Ala Val Phe Ala Val Phe Asp Glu Asn Lys Ser
        515                 520                 525

Trp Tyr Leu Glu Asp Asn Ile Asn Lys Phe Cys Glu Asn Pro Asp Glu
        530                 535                 540

Val Lys Arg Asp Asp Pro Lys Phe Tyr Glu Ser Asn Ile Met Ser Thr
545                 550                 555                 560

Ile Asn Gly Tyr Val Pro Glu Ser Ile Thr Thr Leu Gly Phe Cys Phe
            565                 570                 575

Asp Asp Thr Val Gln Trp His Phe Cys Ser Val Gly Thr Gln Asn Glu
        580                 585                 590

Ile Leu Thr Ile His Phe Thr Gly His Ser Phe Ile Tyr Gly Lys Arg
        595                 600                 605

-continued

```
His Glu Asp Thr Leu Thr Leu Phe Pro Met Arg Gly Glu Ser Val Thr
    610                 615                 620
Val Thr Met Asp Asn Val Gly Thr Trp Met Leu Thr Ser Met Asn Ser
625                 630                 635                 640
Ser Pro Arg Ser Lys Lys Leu Arg Leu Lys Phe Arg Asp Val Lys Cys
                645                 650                 655
Ile Pro Asp Asp Glu Asp Ser Tyr Glu Ile Phe Glu Pro Pro Glu
            660                 665                 670
Ser Thr Val Met Ala Thr Arg Lys Met His Asp Arg Leu Glu Pro Glu
            675                 680                 685
Asp Glu Glu Ser Asp Ala Asp Tyr Asp Tyr Gln Asn Arg Leu Ala Ala
690                 695                 700
Ala Leu Gly Ile Arg Arg Glu Thr Asp Ile Glu Asp Ser Asp Asp Ile
705                 710                 715                 720
Pro Glu Asp Thr Thr Tyr Lys Lys Val Val Phe Arg Lys Tyr Leu Asp
                725                 730                 735
Ser Thr Phe Thr Lys Arg Asp Pro Arg Gly Glu Tyr Glu Glu His Leu
            740                 745                 750
Gly Ile Leu Gly Pro Ile Ile Arg Ala Glu Val Asp Asp Val Ile Gln
        755                 760                 765
Val Arg Phe Lys Asn Leu Ala Ser Arg Pro Tyr Ser Leu His Ala His
770                 775                 780
Gly Leu Ser Tyr Glu Lys Ser Ser Glu Gly Lys Thr Tyr Glu Asp Asp
785                 790                 795                 800
Ser Pro Glu Trp Phe Lys Glu Asp Asn Ala Val Gln Pro Asn Ser Ser
                805                 810                 815
Tyr Thr Tyr Val Trp His Ala Thr Glu Arg Ser Gly Pro Glu Ser Pro
            820                 825                 830
Gly Ser Ala Cys Arg Ala Trp Ala Tyr Tyr Ser Ala Val Asn Pro Glu
            835                 840                 845
Lys Asp Ile His Ser Gly Leu Ile Gly Pro Leu Leu Ile Cys Gln Lys
850                 855                 860
Gly Ile Leu His Lys Asp Ser Asn Met Pro Val Asp Met Arg Glu Phe
865                 870                 875                 880
Val Leu Leu Phe Met Thr Phe Asp Glu Lys Lys Ser Trp Tyr Tyr Glu
                885                 890                 895
Lys Lys Ser Arg Ser Ser Trp Arg Leu Thr Ser Ser Glu Met Lys Lys
            900                 905                 910
Ser His Glu Phe His Ala Ile Asn Gly Met Ile Tyr Ser Leu Pro Gly
        915                 920                 925
Leu Lys Met Tyr Glu Gln Glu Trp Val Arg Leu His Leu Leu Asn Ile
    930                 935                 940
Gly Gly Ser Gln Asp Ile His Val Val His Phe His Gly Gln Thr Leu
945                 950                 955                 960
Leu Glu Asn Gly Asn Lys Gln His Gln Leu Gly Val Trp Pro Leu Leu
                965                 970                 975
Pro Gly Ser Phe Lys Thr Leu Glu Met Lys Ala Ser Lys Pro Gly Trp
            980                 985                 990
Trp Leu Leu Asn Thr Glu Val Gly Glu Asn Gln Arg Ala Gly Met Gln
            995                 1000                1005
Thr Pro Phe Leu Ile Met Asp Arg Asp Cys Arg Met Pro Met Gly Leu
    1010                1015                1020
Ser Thr Gly Ile Ile Ser Asp Ser Gln Ile Lys Ala Ser Glu Phe Leu
```

-continued

```
1025                1030                1035                1040

Gly Tyr Trp Glu Pro Arg Leu Ala Arg Leu Asn Asn Gly Gly Ser Tyr
            1045                1050                1055

Asn Ala Trp Ser Val Glu Lys Leu Ala Ala Glu Phe Ala Ser Lys Pro
        1060                1065                1070

Trp Ile Gln Val Asp Met Gln Lys Glu Val Ile Ile Thr Gly Ile Gln
    1075                1080                1085

Thr Gln Gly Ala Lys His Tyr Leu Lys Ser Cys Tyr Thr Thr Glu Phe
    1090                1095                1100

Tyr Val Ala Tyr Ser Ser Asn Gln Ile Asn Trp Gln Ile Phe Lys Gly
1105                1110                1115                1120

Asn Ser Thr Arg Asn Val Met Tyr Phe Asn Gly Asn Ser Asp Ala Ser
            1125                1130                1135

Thr Ile Lys Glu Asn Gln Phe Asp Pro Pro Ile Val Ala Arg Tyr Ile
        1140                1145                1150

Arg Ile Ser Pro Thr Arg Ala Tyr Asn Arg Pro Thr Leu Arg Leu Glu
    1155                1160                1165

Leu Gln Gly Cys Glu Val Asn Gly Cys Ser Thr Pro Leu Gly Met Glu
    1170                1175                1180

Asn Gly Lys Ile Glu Asn Lys Gln Ile Thr Ala Ser Ser Phe Lys Lys
1185                1190                1195                1200

Ser Trp Trp Gly Asp Tyr Trp Glu Pro Phe Arg Ala Arg Leu Asn Ala
            1205                1210                1215

Gln Gly Arg Val Asn Ala Trp Gln Ala Lys Ala Asn Asn Asn Lys Gln
        1220                1225                1230

Trp Leu Glu Ile Asp Leu Leu Lys Ile Lys Lys Ile Thr Ala Ile Ile
    1235                1240                1245

Thr Gln Gly Cys Lys Ser Leu Ser Ser Glu Met Tyr Val Lys Ser Tyr
    1250                1255                1260

Thr Ile His Tyr Ser Glu Gln Gly Val Glu Trp Lys Pro Tyr Arg Leu
1265                1270                1275                1280

Lys Ser Ser Met Val Asp Lys Ile Phe Glu Gly Asn Thr Asn Thr Lys
            1285                1290                1295

Gly His Val Lys Asn Phe Phe Asn Pro Pro Ile Ile Ser Arg Phe Ile
        1300                1305                1310

Arg Val Ile Pro Lys Thr Trp Asn Gln Ser Ile Ala Leu Arg Leu Glu
    1315                1320                1325

Leu Phe Gly Cys Asp Ile Tyr
    1330                1335

<210> SEQ ID NO 23
<211> LENGTH: 4150
<212> TYPE: DNA
<213> ORGANISM: Homo sapiens
<220> FEATURE:
<221> NAME/KEY: CDS
<222> LOCATION: (1)..(4005)

<400> SEQUENCE: 23 gca cag cta agg cag ttc tac gtg gct gct cag ggc atc agt tgg agc      48
Ala Gln Leu Arg Gln Phe Tyr Val Ala Ala Gln Gly Ile Ser Trp Ser
  1               5                  10                  15 tac cga cct gag ccc aca aac tca agt ttg aat ctt tct gta act tcc      96
Tyr Arg Pro Glu Pro Thr Asn Ser Ser Leu Asn Leu Ser Val Thr Ser
                 20                  25                  30 ttt aag aaa att gtc tac aga gag tat gaa cca tat ttt aag aaa gaa     144
```

```
                Phe Lys Lys Ile Val Tyr Arg Glu Tyr Glu Pro Tyr Phe Lys Lys Glu
                         35                  40                  45 aaa cca caa tct acc att tca gga ctt ctt ggg cct act tta tat gct        192
Lys Pro Gln Ser Thr Ile Ser Gly Leu Leu Gly Pro Thr Leu Tyr Ala
 50                  55                  60 gaa gtc gga gac atc ata aaa gtt cac ttt aaa aat aag gca gat aag        240
Glu Val Gly Asp Ile Ile Lys Val His Phe Lys Asn Lys Ala Asp Lys
 65                  70                  75                  80 ccc ttg agc atc cat cct caa gga att agg tac agt aaa tta tca gaa        288
Pro Leu Ser Ile His Pro Gln Gly Ile Arg Tyr Ser Lys Leu Ser Glu
                 85                  90                  95 ggt gct tct gcc ctt gac cac gca ttc cct gcg gag aag atg gac gac        336
Gly Ala Ser Ala Leu Asp His Ala Phe Pro Ala Glu Lys Met Asp Asp
                100                 105                 110 gct gtg gct cca ggc cga gaa tac acc tat gaa tgg agt atc agt gag        384
Ala Val Ala Pro Gly Arg Glu Tyr Thr Tyr Glu Trp Ser Ile Ser Glu
            115                 120                 125 gac agt gga ccc acc cat gat gac cct cca tgc ctc aca cac atc tat        432
Asp Ser Gly Pro Thr His Asp Asp Pro Pro Cys Leu Thr His Ile Tyr
        130                 135                 140 tac tcc cat gaa aat ctg atc gag gat ttc aac tct ggg ctg att ggg        480
Tyr Ser His Glu Asn Leu Ile Glu Asp Phe Asn Ser Gly Leu Ile Gly
145                 150                 155                 160 ccc ctg ctt atc tgt aaa aaa ggg acc cta act gag ggt ggg aca cag        528
Pro Leu Leu Ile Cys Lys Lys Gly Thr Leu Thr Glu Gly Gly Thr Gln
                165                 170                 175 aag acg ttt gac aag caa atc gtg cta cta ttt gct gtg ttt gat gaa        576
Lys Thr Phe Asp Lys Gln Ile Val Leu Leu Phe Ala Val Phe Asp Glu
                180                 185                 190 agc aag agc tgg agc cag tca tca tcc cta atg tac aca gtc aat gga        624
Ser Lys Ser Trp Ser Gln Ser Ser Leu Met Tyr Thr Val Asn Gly
            195                 200                 205 tat gtg aat ggg aca atg cca gat ata aca gtt tgt gcc cat gac cac        672
Tyr Val Asn Gly Thr Met Pro Asp Ile Thr Val Cys Ala His Asp His
        210                 215                 220 atc agc tgg cat ctg ctg gga atg agc tcg ggg cca gaa tta ttc tcc        720
Ile Ser Trp His Leu Leu Gly Met Ser Ser Gly Pro Glu Leu Phe Ser
225                 230                 235                 240 att cat ttc aac ggc cag gtc ctg gag cag aac cat cat aag gtc tca        768
Ile His Phe Asn Gly Gln Val Leu Glu Gln Asn His His Lys Val Ser
                245                 250                 255 gcc atc acc ctt gtc agt gct aca tcc act acc gca aat atg act gtg        816
Ala Ile Thr Leu Val Ser Ala Thr Ser Thr Thr Ala Asn Met Thr Val
                260                 265                 270 ggc cca gag gga aag tgg atc ata tct tct ctc acc cca aaa cat ttg        864
Gly Pro Glu Gly Lys Trp Ile Ile Ser Ser Leu Thr Pro Lys His Leu
            275                 280                 285 caa gct ggg atg cag gct tac att gac att aaa aac tgc cca aag aaa        912
Gln Ala Gly Met Gln Ala Tyr Ile Asp Ile Lys Asn Cys Pro Lys Lys
        290                 295                 300 acc agg aat ctt aag aaa ata act cgt gag cag agg cgg cac atg aag        960
Thr Arg Asn Leu Lys Lys Ile Thr Arg Glu Gln Arg Arg His Met Lys
305                 310                 315                 320 agg tgg gaa tac ttc att gct gca gag gaa gtc att tgg gac tat gca       1008
Arg Trp Glu Tyr Phe Ile Ala Ala Glu Glu Val Ile Trp Asp Tyr Ala
                325                 330                 335 cct gta ata cca gcg aat atg gac aaa aaa tac agg tct cag cat ttg       1056
Pro Val Ile Pro Ala Asn Met Asp Lys Lys Tyr Arg Ser Gln His Leu
                340                 345                 350
```

```
gat aat ttc tca aac caa att gga aaa cat tat aag aaa gtt atg tac    1104
Asp Asn Phe Ser Asn Gln Ile Gly Lys His Tyr Lys Lys Val Met Tyr
        355                 360                 365 aca cag tac gaa gat gag tcc ttc acc aaa cat aca gtg aat ccc aat    1152
Thr Gln Tyr Glu Asp Glu Ser Phe Thr Lys His Thr Val Asn Pro Asn
    370                 375                 380 atg aaa gaa gat ggg att ttg ggt cct att atc aga gcc cag gtc aga    1200
Met Lys Glu Asp Gly Ile Leu Gly Pro Ile Ile Arg Ala Gln Val Arg
385                 390                 395                 400 gac aca ctc aaa atc gtg ttc aaa aat atg gcc agc cgc ccc tat agc    1248
Asp Thr Leu Lys Ile Val Phe Lys Asn Met Ala Ser Arg Pro Tyr Ser
            405                 410                 415 att tac cct cat gga gtg acc ttc tcg cct tat gaa gat gaa gtc aac    1296
Ile Tyr Pro His Gly Val Thr Phe Ser Pro Tyr Glu Asp Glu Val Asn
        420                 425                 430 tct tct ttc acc tca ggc agg aac aac acc atg atc aga gca gtt caa    1344
Ser Ser Phe Thr Ser Gly Arg Asn Asn Thr Met Ile Arg Ala Val Gln
    435                 440                 445 cca ggg gaa acc tat act tat aag tgg aac atc tta gag ttt gat gaa    1392
Pro Gly Glu Thr Tyr Thr Tyr Lys Trp Asn Ile Leu Glu Phe Asp Glu
450                 455                 460 ccc aca gaa aat gat gcc cag tgc tta aca aga cca tac tac agt gac    1440
Pro Thr Glu Asn Asp Ala Gln Cys Leu Thr Arg Pro Tyr Tyr Ser Asp
465                 470                 475                 480 gtg gac atc atg aga gac atc gcc tct ggg cta ata gga cta ctt cta    1488
Val Asp Ile Met Arg Asp Ile Ala Ser Gly Leu Ile Gly Leu Leu Leu
            485                 490                 495 atc tgt aag agc aga tcc ctg gac agg cga gga ata cag agg gca gca    1536
Ile Cys Lys Ser Arg Ser Leu Asp Arg Arg Gly Ile Gln Arg Ala Ala
    500                 505                 510 gac atc gaa cag cag gct gtg ttt gct gtg ttt gat gag aac aaa agc    1584
Asp Ile Glu Gln Gln Ala Val Phe Ala Val Phe Asp Glu Asn Lys Ser
        515                 520                 525 tgg tac ctt gag gac aac atc aac aag ttt tgt gaa aat cct gat gag    1632
Trp Tyr Leu Glu Asp Asn Ile Asn Lys Phe Cys Glu Asn Pro Asp Glu
    530                 535                 540 gtg aaa cgt gat gac ccc aag ttt tat gaa tca aac atc atg agc act    1680
Val Lys Arg Asp Asp Pro Lys Phe Tyr Glu Ser Asn Ile Met Ser Thr
545                 550                 555                 560 atc aat ggc tat gtg cct gag agc ata act act ctt gga ttc tgc ttt    1728
Ile Asn Gly Tyr Val Pro Glu Ser Ile Thr Thr Leu Gly Phe Cys Phe
            565                 570                 575 gat gac act gtc cag tgg cac ttc tgt agt gtg ggg acc cag aat gaa    1776
Asp Asp Thr Val Gln Trp His Phe Cys Ser Val Gly Thr Gln Asn Glu
    580                 585                 590 att ttg acc atc cac ttc act ggg cac tca ttc atc tat gga aag agg    1824
Ile Leu Thr Ile His Phe Thr Gly His Ser Phe Ile Tyr Gly Lys Arg
        595                 600                 605 cat gag gac acc ttg acc ctc ttc ccc atg cgt gga gaa tct gtg acg    1872
His Glu Asp Thr Leu Thr Leu Phe Pro Met Arg Gly Glu Ser Val Thr
    610                 615                 620 gtc aca atg gat aat gtt gga act tgg atg tta act tcc atg aat tct    1920
Val Thr Met Asp Asn Val Gly Thr Trp Met Leu Thr Ser Met Asn Ser
625                 630                 635                 640 agt cca aga agc aaa aag ctg agg ctg aaa ttc agg gat gtt aaa tgt    1968
Ser Pro Arg Ser Lys Lys Leu Arg Leu Lys Phe Arg Asp Val Lys Cys
            645                 650                 655 atc cca gat gat gat gaa gac tca tat gag att ttt gaa cct cca gaa    2016
Ile Pro Asp Asp Asp Glu Asp Ser Tyr Glu Ile Phe Glu Pro Pro Glu
        660                 665                 670
```

```
tct aca gtc atg gct aca cgg aaa atg cat gat cgt tta gaa cct gaa    2064
Ser Thr Val Met Ala Thr Arg Lys Met His Asp Arg Leu Glu Pro Glu
            675                 680                 685 gat gaa gag agt gat gct gac tat gat tac cag aac aga ctg gct gca    2112
Asp Glu Glu Ser Asp Ala Asp Tyr Asp Tyr Gln Asn Arg Leu Ala Ala
690                 695                 700 gca tta gga att agg agg gaa aca gat att gaa gac tct gat gat att    2160
Ala Leu Gly Ile Arg Arg Glu Thr Asp Ile Glu Asp Ser Asp Asp Ile
705                 710                 715                 720 cca gaa gat acc aca tat aag aaa gta gtt ttt cga aag tac ctc gac    2208
Pro Glu Asp Thr Thr Tyr Lys Lys Val Val Phe Arg Lys Tyr Leu Asp
                725                 730                 735 agc act ttt acc aaa cgt gat cct cga ggg gag tat gaa gag cat ctc    2256
Ser Thr Phe Thr Lys Arg Asp Pro Arg Gly Glu Tyr Glu Glu His Leu
            740                 745                 750 gga att ctt ggt cct att atc aga gct gaa gtg gat gat gtt atc caa    2304
Gly Ile Leu Gly Pro Ile Ile Arg Ala Glu Val Asp Asp Val Ile Gln
            755                 760                 765 gtt cgt ttt aaa aat tta gca tcc aga ccg tat tct cta cat gcc cat    2352
Val Arg Phe Lys Asn Leu Ala Ser Arg Pro Tyr Ser Leu His Ala His
770                 775                 780 gga ctt tcc tat gaa aaa tca tca gag gga aag act tat gaa gat gac    2400
Gly Leu Ser Tyr Glu Lys Ser Ser Glu Gly Lys Thr Tyr Glu Asp Asp
785                 790                 795                 800 tct cct gaa tgg ttt aag gaa gat aat gct gtt cag cca aat agc agt    2448
Ser Pro Glu Trp Phe Lys Glu Asp Asn Ala Val Gln Pro Asn Ser Ser
                805                 810                 815 tat acc tac gta tgg cat gcc act gag cga tca ggg cca gaa agt cct    2496
Tyr Thr Tyr Val Trp His Ala Thr Glu Arg Ser Gly Pro Glu Ser Pro
            820                 825                 830 ggc tct gcc tgt cgg gct tgg gcc tac tac tca gct gtg aac cca gaa    2544
Gly Ser Ala Cys Arg Ala Trp Ala Tyr Tyr Ser Ala Val Asn Pro Glu
            835                 840                 845 aaa gat att cac tca ggc ttg ata ggt ccc ctc cta atc tgc caa aaa    2592
Lys Asp Ile His Ser Gly Leu Ile Gly Pro Leu Leu Ile Cys Gln Lys
850                 855                 860 gga ata cta cat aag gac agc aac atg cct gtg gac atg aga gaa ttt    2640
Gly Ile Leu His Lys Asp Ser Asn Met Pro Val Asp Met Arg Glu Phe
865                 870                 875                 880 gtc tta cta ttt atg acc ttt gat gaa aag aag agc tgg tac tat gaa    2688
Val Leu Leu Phe Met Thr Phe Asp Glu Lys Lys Ser Trp Tyr Tyr Glu
                885                 890                 895 aag aag tcc cga agt tct tgg aga ctc aca tcc tca gaa atg aaa aaa    2736
Lys Lys Ser Arg Ser Ser Trp Arg Leu Thr Ser Ser Glu Met Lys Lys
            900                 905                 910 tcc cat gag ttt cac gcc att aat ggg atg atc tac agc ttg cct ggc    2784
Ser His Glu Phe His Ala Ile Asn Gly Met Ile Tyr Ser Leu Pro Gly
            915                 920                 925 ctg aaa atg tat gag caa gag tgg gtg agg tta cac ctg ctg aac ata    2832
Leu Lys Met Tyr Glu Gln Glu Trp Val Arg Leu His Leu Leu Asn Ile
930                 935                 940 ggc ggc tcc caa gac att cac gtg gtt cac ttt cac ggc cag acc ttg    2880
Gly Gly Ser Gln Asp Ile His Val Val His Phe His Gly Gln Thr Leu
945                 950                 955                 960 ctg gaa aat ggc aat aaa cag cac cag tta ggg gtc tgg ccc ctt ctg    2928
Leu Glu Asn Gly Asn Lys Gln His Gln Leu Gly Val Trp Pro Leu Leu
                965                 970                 975 cct ggt tca ttt aaa act ctt gaa atg aag gca tca aaa cct ggc tgg    2976
Pro Gly Ser Phe Lys Thr Leu Glu Met Lys Ala Ser Lys Pro Gly Trp
```

|  |  |
|---|---|
| 980 985 990 | |
| tgg ctc cta aac aca gag gtt gga gaa aac cag aga gca ggg atg caa<br>Trp Leu Leu Asn Thr Glu Val Gly Glu Asn Gln Arg Ala Gly Met Gln<br>        995                      1000                    1005 | 3024 |
| acg cca ttt ctt atc atg gac aga gac tgt agg atg cca atg gga cta<br>Thr Pro Phe Leu Ile Met Asp Arg Asp Cys Arg Met Pro Met Gly Leu<br>  1010                      1015                    1020 | 3072 |
| agc act ggt atc ata tct gat tca cag atc aag gct tca gag ttt ctg<br>Ser Thr Gly Ile Ile Ser Asp Ser Gln Ile Lys Ala Ser Glu Phe Leu<br>1025                    1030                    1035                    1040 | 3120 |
| ggt tac tgg gag ccc aga tta gca aga tta aac aat ggt gga tct tat<br>Gly Tyr Trp Glu Pro Arg Leu Ala Arg Leu Asn Asn Gly Gly Ser Tyr<br>                1045                    1050                    1055 | 3168 |
| aat gct tgg agt gta gaa aaa ctt gca gca gaa ttt gcc tct aaa cct<br>Asn Ala Trp Ser Val Glu Lys Leu Ala Ala Glu Phe Ala Ser Lys Pro<br>                    1060                    1065                    1070 | 3216 |
| tgg atc cag gtg gac atg caa aag gaa gtc ata atc aca ggg atc cag<br>Trp Ile Gln Val Asp Met Gln Lys Glu Val Ile Ile Thr Gly Ile Gln<br>            1075                    1080                    1085 | 3264 |
| acc caa ggt gcc aaa cac tac ctg aag tcc tgc tat acc aca gag ttc<br>Thr Gln Gly Ala Lys His Tyr Leu Lys Ser Cys Tyr Thr Thr Glu Phe<br>  1090                      1095                    1100 | 3312 |
| tat gta gct tac agt tcc aac cag atc aac tgg cag atc ttc aaa ggg<br>Tyr Val Ala Tyr Ser Ser Asn Gln Ile Asn Trp Gln Ile Phe Lys Gly<br>1105                    1110                    1115                    1120 | 3360 |
| aac agc aca agg aat gtg atg tat ttt aat ggc aat tca gat gcc tct<br>Asn Ser Thr Arg Asn Val Met Tyr Phe Asn Gly Asn Ser Asp Ala Ser<br>                1125                    1130                    1135 | 3408 |
| aca ata aaa gag aat cag ttt gac cca cct att gtg gct aga tat att<br>Thr Ile Lys Glu Asn Gln Phe Asp Pro Pro Ile Val Ala Arg Tyr Ile<br>                    1140                    1145                    1150 | 3456 |
| agg atc tct cca act cga gcc tat aac aga cct acc ctt cga ttg gaa<br>Arg Ile Ser Pro Thr Arg Ala Tyr Asn Arg Pro Thr Leu Arg Leu Glu<br>            1155                    1160                    1165 | 3504 |
| ctg caa ggt tgt gag gta aat gga tgt tcc aca ccc ctg ggt atg gaa<br>Leu Gln Gly Cys Glu Val Asn Gly Cys Ser Thr Pro Leu Gly Met Glu<br>  1170                      1175                    1180 | 3552 |
| aat gga aag ata gaa aac aag caa atc aca gct tct tcg ttt aag aaa<br>Asn Gly Lys Ile Glu Asn Lys Gln Ile Thr Ala Ser Ser Phe Lys Lys<br>1185                    1190                    1195                    1200 | 3600 |
| tct tgg tgg gga gat tac tgg gaa ccc ttc cgt gcc cgt ctg aat gcc<br>Ser Trp Trp Gly Asp Tyr Trp Glu Pro Phe Arg Ala Arg Leu Asn Ala<br>                1205                    1210                    1215 | 3648 |
| cag gga cgt gtg aat gcc tgg caa gcc aag gca aac aac aat aag cag<br>Gln Gly Arg Val Asn Ala Trp Gln Ala Lys Ala Asn Asn Asn Lys Gln<br>            1220                    1225                    1230 | 3696 |
| tgg cta gaa att gat cta ctc aag atc aag aag ata acg gca att ata<br>Trp Leu Glu Ile Asp Leu Leu Lys Ile Lys Lys Ile Thr Ala Ile Ile<br>                    1235                    1240                    1245 | 3744 |
| aca cag ggc tgc aag tct ctg tcc tct gaa atg tat gta aag agc tat<br>Thr Gln Gly Cys Lys Ser Leu Ser Ser Glu Met Tyr Val Lys Ser Tyr<br>        1250                    1255                    1260 | 3792 |
| acc atc cac tac agt gag cag gga gtg gaa tgg aaa cca tac agg ctg<br>Thr Ile His Tyr Ser Glu Gln Gly Val Glu Trp Lys Pro Tyr Arg Leu<br>1265                    1270                    1275                    1280 | 3840 |
| aaa tcc tcc atg gtg gac aag att ttt gaa gga aat act aat acc aaa<br>Lys Ser Ser Met Val Asp Lys Ile Phe Glu Gly Asn Thr Asn Thr Lys<br>                    1285                    1290                    1295 | 3888 |
| gga cat gtg aag aac ttt ttc aac ccc cca atc att tcc agg ttt atc | 3936 |

```
Gly His Val Lys Asn Phe Phe Asn Pro Pro Ile Ile Ser Arg Phe Ile
            1300                1305                1310 cgt gtc att cct aaa aca tgg aat caa agt att gca ctt cgc ctg gaa    3984
Arg Val Ile Pro Lys Thr Trp Asn Gln Ser Ile Ala Leu Arg Leu Glu
        1315                1320                1325 ctc ttt ggc tgt gat att tac tagaattgaa cattcaaaaa ccctggaag        4035
Leu Phe Gly Cys Asp Ile Tyr
    1330            1335 agactcttta agacctcaaa ccatttagaa tgggcaatgt attttacgct gtgttaaatg  4095
ttaacagttt tccactattt ctctttcttt tctattagtg aataaaattt tatac       4150

<210> SEQ ID NO 24
<211> LENGTH: 1335
<212> TYPE: PRT
<213> ORGANISM: Homo sapiens

<400> SEQUENCE: 24

Ala Gln Leu Arg Gln Phe Tyr Val Ala Ala Gln Gly Ile Ser Trp Ser
 1               5                  10                  15

Tyr Arg Pro Glu Pro Thr Asn Ser Ser Leu Asn Leu Ser Val Thr Ser
            20                  25                  30

Phe Lys Lys Ile Val Tyr Arg Glu Tyr Glu Pro Tyr Phe Lys Lys Glu
        35                  40                  45

Lys Pro Gln Ser Thr Ile Ser Gly Leu Leu Gly Pro Thr Leu Tyr Ala
    50                  55                  60

Glu Val Gly Asp Ile Ile Lys Val His Phe Lys Asn Lys Ala Asp Lys
65                  70                  75                  80

Pro Leu Ser Ile His Pro Gln Gly Ile Arg Tyr Ser Lys Leu Ser Glu
                85                  90                  95

Gly Ala Ser Ala Leu Asp His Ala Phe Pro Ala Glu Lys Met Asp Asp
            100                 105                 110

Ala Val Ala Pro Gly Arg Glu Tyr Thr Tyr Glu Trp Ser Ile Ser Glu
        115                 120                 125

Asp Ser Gly Pro Thr His Asp Asp Pro Pro Cys Leu Thr His Ile Tyr
    130                 135                 140

Tyr Ser His Glu Asn Leu Ile Glu Asp Phe Asn Ser Gly Leu Ile Gly
145                 150                 155                 160

Pro Leu Leu Ile Cys Lys Lys Gly Thr Leu Thr Glu Gly Gly Thr Gln
                165                 170                 175

Lys Thr Phe Asp Lys Gln Ile Val Leu Leu Phe Ala Val Phe Asp Glu
            180                 185                 190

Ser Lys Ser Trp Ser Gln Ser Ser Ser Leu Met Tyr Thr Val Asn Gly
        195                 200                 205

Tyr Val Asn Gly Thr Met Pro Asp Ile Thr Val Cys Ala His Asp His
    210                 215                 220

Ile Ser Trp His Leu Leu Gly Met Ser Ser Gly Pro Glu Leu Phe Ser
225                 230                 235                 240

Ile His Phe Asn Gly Gln Val Leu Glu Gln Asn His His Lys Val Ser
                245                 250                 255

Ala Ile Thr Leu Val Ser Ala Thr Ser Thr Ala Asn Met Thr Val
            260                 265                 270

Gly Pro Glu Gly Lys Trp Ile Ile Ser Ser Leu Thr Pro Lys His Leu
        275                 280                 285

Gln Ala Gly Met Gln Ala Tyr Ile Asp Ile Lys Asn Cys Pro Lys Lys
    290                 295                 300
```

```
Thr Arg Asn Leu Lys Lys Ile Thr Arg Glu Gln Arg His Met Lys
305                 310                 315                 320

Arg Trp Glu Tyr Phe Ile Ala Ala Glu Val Ile Trp Asp Tyr Ala
                325                 330                 335

Pro Val Ile Pro Ala Asn Met Asp Lys Lys Tyr Arg Ser Gln His Leu
                340                 345                 350

Asp Asn Phe Ser Asn Gln Ile Gly Lys His Tyr Lys Lys Val Met Tyr
            355                 360                 365

Thr Gln Tyr Glu Asp Glu Ser Phe Thr Lys His Thr Val Asn Pro Asn
370                 375                 380

Met Lys Glu Asp Gly Ile Leu Gly Pro Ile Ile Arg Ala Gln Val Arg
385                 390                 395                 400

Asp Thr Leu Lys Ile Val Phe Lys Asn Met Ala Ser Arg Pro Tyr Ser
                405                 410                 415

Ile Tyr Pro His Gly Val Thr Phe Ser Pro Tyr Glu Asp Glu Val Asn
                420                 425                 430

Ser Ser Phe Thr Ser Gly Arg Asn Asn Thr Met Ile Arg Ala Val Gln
            435                 440                 445

Pro Gly Glu Thr Tyr Thr Tyr Lys Trp Asn Ile Leu Glu Phe Asp Glu
            450                 455                 460

Pro Thr Glu Asn Asp Ala Gln Cys Leu Thr Arg Pro Tyr Tyr Ser Asp
465                 470                 475                 480

Val Asp Ile Met Arg Asp Ile Ala Ser Gly Leu Ile Gly Leu Leu Leu
                485                 490                 495

Ile Cys Lys Ser Arg Ser Leu Asp Arg Arg Gly Ile Gln Arg Ala Ala
                500                 505                 510

Asp Ile Glu Gln Gln Ala Val Phe Ala Val Phe Asp Glu Asn Lys Ser
            515                 520                 525

Trp Tyr Leu Glu Asp Asn Ile Asn Lys Phe Cys Glu Asn Pro Asp Glu
            530                 535                 540

Val Lys Arg Asp Asp Pro Lys Phe Tyr Glu Ser Asn Ile Met Ser Thr
545                 550                 555                 560

Ile Asn Gly Tyr Val Pro Glu Ser Ile Thr Thr Leu Gly Phe Cys Phe
                565                 570                 575

Asp Asp Thr Val Gln Trp His Phe Cys Ser Val Gly Thr Gln Asn Glu
            580                 585                 590

Ile Leu Thr Ile His Phe Thr Gly His Ser Phe Ile Tyr Gly Lys Arg
            595                 600                 605

His Glu Asp Thr Leu Thr Leu Phe Pro Met Arg Gly Glu Ser Val Thr
610                 615                 620

Val Thr Met Asp Asn Val Gly Thr Trp Met Leu Thr Ser Met Asn Ser
625                 630                 635                 640

Ser Pro Arg Ser Lys Lys Leu Arg Leu Lys Phe Arg Asp Val Lys Cys
                645                 650                 655

Ile Pro Asp Asp Asp Glu Asp Ser Tyr Glu Ile Phe Glu Pro Pro Glu
                660                 665                 670

Ser Thr Val Met Ala Thr Arg Lys Met His Asp Arg Leu Glu Pro Glu
            675                 680                 685

Asp Glu Glu Ser Asp Ala Asp Tyr Asp Tyr Gln Asn Arg Leu Ala Ala
            690                 695                 700

Ala Leu Gly Ile Arg Arg Glu Thr Asp Ile Glu Asp Ser Asp Asp Ile
705                 710                 715                 720
```

-continued

Pro Glu Asp Thr Thr Tyr Lys Lys Val Val Phe Arg Lys Tyr Leu Asp
            725                 730                 735

Ser Thr Phe Thr Lys Arg Asp Pro Arg Gly Glu Tyr Glu Glu His Leu
            740                 745                 750

Gly Ile Leu Gly Pro Ile Ile Arg Ala Glu Val Asp Asp Val Ile Gln
            755                 760                 765

Val Arg Phe Lys Asn Leu Ala Ser Arg Pro Tyr Ser Leu His Ala His
        770                 775                 780

Gly Leu Ser Tyr Glu Lys Ser Ser Glu Gly Lys Thr Tyr Glu Asp Asp
785                 790                 795                 800

Ser Pro Glu Trp Phe Lys Glu Asp Asn Ala Val Gln Pro Asn Ser Ser
                805                 810                 815

Tyr Thr Tyr Val Trp His Ala Thr Glu Arg Ser Gly Pro Glu Ser Pro
                820                 825                 830

Gly Ser Ala Cys Arg Ala Trp Ala Tyr Tyr Ser Ala Val Asn Pro Glu
            835                 840                 845

Lys Asp Ile His Ser Gly Leu Ile Gly Pro Leu Leu Ile Cys Gln Lys
        850                 855                 860

Gly Ile Leu His Lys Asp Ser Asn Met Pro Val Asp Met Arg Glu Phe
865                 870                 875                 880

Val Leu Leu Phe Met Thr Phe Asp Glu Lys Lys Ser Trp Tyr Tyr Glu
                885                 890                 895

Lys Lys Ser Arg Ser Ser Trp Arg Leu Thr Ser Ser Glu Met Lys Lys
            900                 905                 910

Ser His Glu Phe His Ala Ile Asn Gly Met Ile Tyr Ser Leu Pro Gly
        915                 920                 925

Leu Lys Met Tyr Glu Gln Glu Trp Val Arg Leu His Leu Leu Asn Ile
        930                 935                 940

Gly Gly Ser Gln Asp Ile His Val Val His Phe His Gly Gln Thr Leu
945                 950                 955                 960

Leu Glu Asn Gly Asn Lys Gln His Gln Leu Gly Val Trp Pro Leu Leu
                965                 970                 975

Pro Gly Ser Phe Lys Thr Leu Glu Met Lys Ala Ser Lys Pro Gly Trp
            980                 985                 990

Trp Leu Leu Asn Thr Glu Val Gly Glu Asn Gln Arg Ala Gly Met Gln
            995                 1000                1005

Thr Pro Phe Leu Ile Met Asp Arg Asp Cys Arg Met Pro Met Gly Leu
    1010                1015                1020

Ser Thr Gly Ile Ile Ser Asp Ser Gln Ile Lys Ala Ser Glu Phe Leu
1025                1030                1035                1040

Gly Tyr Trp Glu Pro Arg Leu Ala Arg Leu Asn Asn Gly Gly Ser Tyr
                1045                1050                1055

Asn Ala Trp Ser Val Glu Lys Leu Ala Ala Glu Phe Ala Ser Lys Pro
        1060                1065                1070

Trp Ile Gln Val Asp Met Gln Lys Glu Val Ile Ile Thr Gly Ile Gln
    1075                1080                1085

Thr Gln Gly Ala Lys His Tyr Leu Lys Ser Cys Tyr Thr Thr Glu Phe
    1090                1095                1100

Tyr Val Ala Tyr Ser Ser Asn Gln Ile Asn Trp Gln Ile Phe Lys Gly
1105                1110                1115                1120

Asn Ser Thr Arg Asn Val Met Tyr Phe Asn Gly Asn Ser Asp Ala Ser
        1125                1130                1135

Thr Ile Lys Glu Asn Gln Phe Asp Pro Pro Ile Val Ala Arg Tyr Ile

```
                        1140                1145                1150
            Arg Ile Ser Pro Thr Arg Ala Tyr Asn Arg Pro Thr Leu Arg Leu Glu
                1155                1160                1165

Leu Gln Gly Cys Glu Val Asn Gly Cys Ser Thr Pro Leu Gly Met Glu
                1170                1175                1180

Asn Gly Lys Ile Glu Asn Lys Gln Ile Thr Ala Ser Ser Phe Lys Lys
            1185                1190                1195                1200

Ser Trp Trp Gly Asp Tyr Trp Glu Pro Phe Arg Ala Arg Leu Asn Ala
                        1205                1210                1215

Gln Gly Arg Val Asn Ala Trp Gln Ala Lys Ala Asn Asn Asn Lys Gln
                    1220                1225                1230

Trp Leu Glu Ile Asp Leu Leu Lys Ile Lys Lys Ile Thr Ala Ile Ile
                    1235                1240                1245

Thr Gln Gly Cys Lys Ser Leu Ser Ser Glu Met Tyr Val Lys Ser Tyr
                    1250                1255                1260

Thr Ile His Tyr Ser Glu Gln Gly Val Glu Trp Lys Pro Tyr Arg Leu
            1265                1270                1275                1280

Lys Ser Ser Met Val Asp Lys Ile Phe Glu Gly Asn Thr Asn Thr Lys
                        1285                1290                1295

Gly His Val Lys Asn Phe Phe Asn Pro Pro Ile Ile Ser Arg Phe Ile
                    1300                1305                1310

Arg Val Ile Pro Lys Thr Trp Asn Gln Ser Ile Ala Leu Arg Leu Glu
                1315                1320                1325

Leu Phe Gly Cys Asp Ile Tyr
                1330                1335

<210> SEQ ID NO 25
<211> LENGTH: 4150
<212> TYPE: DNA
<213> ORGANISM: Homo sapiens
<220> FEATURE:
<221> NAME/KEY: CDS
<222> LOCATION: (1)..(4005)

<400> SEQUENCE: 25 gca cag cta agg cag ttc tac gtg gct gct cag ggc atc agt tgg agc         48
Ala Gln Leu Arg Gln Phe Tyr Val Ala Ala Gln Gly Ile Ser Trp Ser
  1               5                  10                  15 tac cga cct gag ccc aca aac tca agt ttg aat ctt tct gta act tcc         96
Tyr Arg Pro Glu Pro Thr Asn Ser Ser Leu Asn Leu Ser Val Thr Ser
                 20                  25                  30 ttt aag aaa att gtc tac aga gag tat gaa cca tat ttt aag aaa gaa        144
Phe Lys Lys Ile Val Tyr Arg Glu Tyr Glu Pro Tyr Phe Lys Lys Glu
             35                  40                  45 aaa cca caa tct acc att tca gga ctt ctt ggg cct act tta tat gct        192
Lys Pro Gln Ser Thr Ile Ser Gly Leu Leu Gly Pro Thr Leu Tyr Ala
         50                  55                  60 gaa gtc gga gac atc ata aaa gtt cac ttt aaa aat aag gca gat aag        240
Glu Val Gly Asp Ile Ile Lys Val His Phe Lys Asn Lys Ala Asp Lys
 65                  70                  75                  80 ccc ttg agc atc cat cct caa gga att agg tac agt aaa tta tca gaa        288
Pro Leu Ser Ile His Pro Gln Gly Ile Arg Tyr Ser Lys Leu Ser Glu
                 85                  90                  95 ggt gct tct tac ctt gac cac aca ttc cct gcg gcg aag atg gcc gcc        336
Gly Ala Ser Tyr Leu Asp His Thr Phe Pro Ala Ala Lys Met Ala Ala
                100                 105                 110 gct gtg gct cca ggc cga gaa tac acc tat gaa tgg agt atc agt gag        384
Ala Val Ala Pro Gly Arg Glu Tyr Thr Tyr Glu Trp Ser Ile Ser Glu
```

-continued

```
              115                 120                 125
gac agt gga ccc acc cat gat gac cct cca tgc ctc aca cac atc tat      432
Asp Ser Gly Pro Thr His Asp Asp Pro Pro Cys Leu Thr His Ile Tyr
    130                 135                 140 tac tcc cat gaa aat ctg atc gag gat ttc aac tct ggg ctg att ggg      480
Tyr Ser His Glu Asn Leu Ile Glu Asp Phe Asn Ser Gly Leu Ile Gly
145                 150                 155                 160 ccc ctg ctt atc tgt aaa aaa ggg acc cta act gag ggt ggg aca cag      528
Pro Leu Leu Ile Cys Lys Lys Gly Thr Leu Thr Glu Gly Gly Thr Gln
                165                 170                 175 aag acg ttt gac aag caa atc gtg cta cta ttt gct gtg ttt gat gaa      576
Lys Thr Phe Asp Lys Gln Ile Val Leu Leu Phe Ala Val Phe Asp Glu
            180                 185                 190 agc aag agc tgg agc cag tca tca tcc cta atg tac aca gtc aat gga      624
Ser Lys Ser Trp Ser Gln Ser Ser Leu Met Tyr Thr Val Asn Gly
        195                 200                 205 tat gtg aat ggg aca atg cca gat ata aca gtt tgt gcc cat gac cac      672
Tyr Val Asn Gly Thr Met Pro Asp Ile Thr Val Cys Ala His Asp His
    210                 215                 220 atc agc tgg cat ctg ctg gga atg agc tcg ggg cca gaa tta ttc tcc      720
Ile Ser Trp His Leu Leu Gly Met Ser Ser Gly Pro Glu Leu Phe Ser
225                 230                 235                 240 att cat ttc aac ggc cag gtc ctg gag cag aac cat cat aag gtc tca      768
Ile His Phe Asn Gly Gln Val Leu Glu Gln Asn His His Lys Val Ser
                245                 250                 255 gcc atc acc ctt gtc agt gct aca tcc act acc gca aat atg act gtg      816
Ala Ile Thr Leu Val Ser Ala Thr Ser Thr Thr Ala Asn Met Thr Val
            260                 265                 270 ggc cca gag gga aag tgg atc ata tct tct ctc acc cca aaa cat ttg      864
Gly Pro Glu Gly Lys Trp Ile Ile Ser Ser Leu Thr Pro Lys His Leu
        275                 280                 285 caa gct ggg atg cag gct tac att gac att aaa aac tgc cca aag aaa      912
Gln Ala Gly Met Gln Ala Tyr Ile Asp Ile Lys Asn Cys Pro Lys Lys
    290                 295                 300 acc agg aat ctt aag aaa ata act cgt gag cag agg cgg cac atg aag      960
Thr Arg Asn Leu Lys Lys Ile Thr Arg Glu Gln Arg Arg His Met Lys
305                 310                 315                 320 agg tgg gaa tac ttc att gct gca gag gaa gtc att tgg gac tat gca     1008
Arg Trp Glu Tyr Phe Ile Ala Ala Glu Glu Val Ile Trp Asp Tyr Ala
                325                 330                 335 cct gta ata cca gcg aat atg gac aaa aaa tac agg tct cag cat ttg     1056
Pro Val Ile Pro Ala Asn Met Asp Lys Lys Tyr Arg Ser Gln His Leu
            340                 345                 350 gat aat ttc tca aac caa att gga aaa cat tat aag aaa gtt atg tac     1104
Asp Asn Phe Ser Asn Gln Ile Gly Lys His Tyr Lys Lys Val Met Tyr
        355                 360                 365 aca cag tac gaa gat gag tcc ttc acc aaa cat aca gtg aat ccc aat     1152
Thr Gln Tyr Glu Asp Glu Ser Phe Thr Lys His Thr Val Asn Pro Asn
    370                 375                 380 atg aaa gaa gat ggg att ttg ggt cct att atc aga gcc cag gtc aga     1200
Met Lys Glu Asp Gly Ile Leu Gly Pro Ile Ile Arg Ala Gln Val Arg
385                 390                 395                 400 gac aca ctc aaa atc gtg ttc aaa aat atg gcc agc cgc ccc tat agc     1248
Asp Thr Leu Lys Ile Val Phe Lys Asn Met Ala Ser Arg Pro Tyr Ser
                405                 410                 415 att tac cct cat gga gtg acc ttc tcg cct tat gaa gat gaa gtc aac     1296
Ile Tyr Pro His Gly Val Thr Phe Ser Pro Tyr Glu Asp Glu Val Asn
            420                 425                 430 tct tct ttc acc tca ggc agg aac aac acc atg atc aga gca gtt caa     1344
```

```
                Ser Ser Phe Thr Ser Gly Arg Asn Asn Thr Met Ile Arg Ala Val Gln
                        435                 440                 445 cca ggg gaa acc tat act tat aag tgg aac atc tta gag ttt gat gaa      1392
Pro Gly Glu Thr Tyr Thr Tyr Lys Trp Asn Ile Leu Glu Phe Asp Glu
    450                 455                 460 ccc aca gaa aat gat gcc cag tgc tta aca aga cca tac tac agt gac      1440
Pro Thr Glu Asn Asp Ala Gln Cys Leu Thr Arg Pro Tyr Tyr Ser Asp
465                 470                 475                 480 gtg gac atc atg aga gac atc gcc tct ggg cta ata gga cta ctt cta      1488
Val Asp Ile Met Arg Asp Ile Ala Ser Gly Leu Ile Gly Leu Leu Leu
                485                 490                 495 atc tgt aag agc aga tcc ctg gac agg cga gga ata cag agg gca gca      1536
Ile Cys Lys Ser Arg Ser Leu Asp Arg Arg Gly Ile Gln Arg Ala Ala
            500                 505                 510 gac atc gaa cag cag gct gtg ttt gct gtg ttt gat gag aac aaa agc      1584
Asp Ile Glu Gln Gln Ala Val Phe Ala Val Phe Asp Glu Asn Lys Ser
        515                 520                 525 tgg tac ctt gag gac aac atc aac aag ttt tgt gaa aat cct gat gag      1632
Trp Tyr Leu Glu Asp Asn Ile Asn Lys Phe Cys Glu Asn Pro Asp Glu
    530                 535                 540 gtg aaa cgt gat gac ccc aag ttt tat gaa tca aac atc atg agc act      1680
Val Lys Arg Asp Asp Pro Lys Phe Tyr Glu Ser Asn Ile Met Ser Thr
545                 550                 555                 560 atc aat ggc tat gtg cct gag agc ata act act ctt gga ttc tgc ttt      1728
Ile Asn Gly Tyr Val Pro Glu Ser Ile Thr Thr Leu Gly Phe Cys Phe
                565                 570                 575 gat gac act gtc cag tgg cac ttc tgt agt gtg ggg acc cag aat gaa      1776
Asp Asp Thr Val Gln Trp His Phe Cys Ser Val Gly Thr Gln Asn Glu
            580                 585                 590 att ttg acc atc cac ttc act ggg cac tca ttc atc tat gga aag agg      1824
Ile Leu Thr Ile His Phe Thr Gly His Ser Phe Ile Tyr Gly Lys Arg
        595                 600                 605 cat gag gac acc ttg acc ctc ttc ccc atg cgt gga gaa tct gtg acg      1872
His Glu Asp Thr Leu Thr Leu Phe Pro Met Arg Gly Glu Ser Val Thr
    610                 615                 620 gtc aca atg gat aat gtt gga act tgg atg tta act tcc atg aat tct      1920
Val Thr Met Asp Asn Val Gly Thr Trp Met Leu Thr Ser Met Asn Ser
625                 630                 635                 640 agt cca aga agc aaa aag ctg agg ctg aaa ttc agg gat gtt aaa tgt      1968
Ser Pro Arg Ser Lys Lys Leu Arg Leu Lys Phe Arg Asp Val Lys Cys
                645                 650                 655 atc cca gat gat gat gaa gac tca tat gag att ttt gaa cct cca gaa      2016
Ile Pro Asp Asp Asp Glu Asp Ser Tyr Glu Ile Phe Glu Pro Pro Glu
            660                 665                 670 tct aca gtc atg gct aca cgg aaa atg cat gat cgt tta gaa cct gaa      2064
Ser Thr Val Met Ala Thr Arg Lys Met His Asp Arg Leu Glu Pro Glu
        675                 680                 685 gat gaa gag agt gat gct gac tat gat tac cag aac aga ctg gct gca      2112
Asp Glu Glu Ser Asp Ala Asp Tyr Asp Tyr Gln Asn Arg Leu Ala Ala
    690                 695                 700 gca tta gga att agg agg gaa aca gat att gaa gac tct gat gat att      2160
Ala Leu Gly Ile Arg Arg Glu Thr Asp Ile Glu Asp Ser Asp Asp Ile
705                 710                 715                 720 cca gaa gat acc aca tat aag aaa gta gtt ttt cga aag tac ctc gac      2208
Pro Glu Asp Thr Thr Tyr Lys Lys Val Val Phe Arg Lys Tyr Leu Asp
                725                 730                 735 agc act ttt acc aaa cgt gat cct cga ggg gag tat gaa gag cat ctc      2256
Ser Thr Phe Thr Lys Arg Asp Pro Arg Gly Glu Tyr Glu Glu His Leu
            740                 745                 750
```

```
gga att ctt ggt cct att atc aga gct gaa gtg gat gat gtt atc caa    2304
Gly Ile Leu Gly Pro Ile Ile Arg Ala Glu Val Asp Asp Val Ile Gln
            755                 760                 765 gtt cgt ttt aaa aat tta gca tcc aga ccg tat tct cta cat gcc cat    2352
Val Arg Phe Lys Asn Leu Ala Ser Arg Pro Tyr Ser Leu His Ala His
        770                 775                 780 gga ctt tcc tat gaa aaa tca tca gag gga aag act tat gaa gat gac    2400
Gly Leu Ser Tyr Glu Lys Ser Ser Glu Gly Lys Thr Tyr Glu Asp Asp
785                 790                 795                 800 tct cct gaa tgg ttt aag gaa gat aat gct gtt cag cca aat agc agt    2448
Ser Pro Glu Trp Phe Lys Glu Asp Asn Ala Val Gln Pro Asn Ser Ser
                805                 810                 815 tat acc tac gta tgg cat gcc act gag cga tca ggg cca gaa agt cct    2496
Tyr Thr Tyr Val Trp His Ala Thr Glu Arg Ser Gly Pro Glu Ser Pro
            820                 825                 830 ggc tct gcc tgt cgg gct tgg gcc tac tac tca gct gtg aac cca gaa    2544
Gly Ser Ala Cys Arg Ala Trp Ala Tyr Tyr Ser Ala Val Asn Pro Glu
        835                 840                 845 aaa gat att cac tca ggc ttg ata ggt ccc ctc cta atc tgc caa aaa    2592
Lys Asp Ile His Ser Gly Leu Ile Gly Pro Leu Leu Ile Cys Gln Lys
    850                 855                 860 gga ata cta cat aag gac agc aac atg cct gtg gac atg aga gaa ttt    2640
Gly Ile Leu His Lys Asp Ser Asn Met Pro Val Asp Met Arg Glu Phe
865                 870                 875                 880 gtc tta cta ttt atg acc ttt gat gaa aag aag agc tgg tac tat gaa    2688
Val Leu Leu Phe Met Thr Phe Asp Glu Lys Lys Ser Trp Tyr Tyr Glu
                885                 890                 895 aag aag tcc cga agt tct tgg aga ctc aca tcc tca gaa atg aaa aaa    2736
Lys Lys Ser Arg Ser Ser Trp Arg Leu Thr Ser Ser Glu Met Lys Lys
            900                 905                 910 tcc cat gag ttt cac gcc att aat ggg atg atc tac agc ttg cct ggc    2784
Ser His Glu Phe His Ala Ile Asn Gly Met Ile Tyr Ser Leu Pro Gly
        915                 920                 925 ctg aaa atg tat gag caa gag tgg gtg agg tta cac ctg ctg aac ata    2832
Leu Lys Met Tyr Glu Gln Glu Trp Val Arg Leu His Leu Leu Asn Ile
    930                 935                 940 ggc ggc tcc caa gac att cac gtg gtt cac ttt cac ggc cag acc ttg    2880
Gly Gly Ser Gln Asp Ile His Val Val His Phe His Gly Gln Thr Leu
945                 950                 955                 960 ctg gaa aat ggc aat aaa cag cac cag tta ggg gtc tgg ccc ctt ctg    2928
Leu Glu Asn Gly Asn Lys Gln His Gln Leu Gly Val Trp Pro Leu Leu
                965                 970                 975 cct ggt tca ttt aaa act ctt gaa atg aag gca tca aaa cct ggc tgg    2976
Pro Gly Ser Phe Lys Thr Leu Glu Met Lys Ala Ser Lys Pro Gly Trp
            980                 985                 990 tgg ctc cta aac aca gag gtt gga gaa aac cag aga gca ggg atg caa    3024
Trp Leu Leu Asn Thr Glu Val Gly Glu Asn Gln Arg Ala Gly Met Gln
        995                 1000                1005 acg cca ttt ctt atc atg gac aga gac tgt agg atg cca atg gga cta    3072
Thr Pro Phe Leu Ile Met Asp Arg Asp Cys Arg Met Pro Met Gly Leu
    1010                1015                1020 agc act ggt atc ata tct gat tca cag atc aag gct tca gag ttt ctg    3120
Ser Thr Gly Ile Ile Ser Asp Ser Gln Ile Lys Ala Ser Glu Phe Leu
1025                1030                1035                1040 ggt tac tgg gag ccc aga tta gca aga tta aac aat ggt gga tct tat    3168
Gly Tyr Trp Glu Pro Arg Leu Ala Arg Leu Asn Asn Gly Gly Ser Tyr
                1045                1050                1055 aat gct tgg agt gta gaa aaa ctt gca gca gaa ttt gcc tct aaa cct    3216
Asn Ala Trp Ser Val Glu Lys Leu Ala Ala Glu Phe Ala Ser Lys Pro
            1060                1065                1070
```

-continued

| | |
|---|---|
| tgg atc cag gtg gac atg caa aag gaa gtc ata atc aca ggg atc cag<br>Trp Ile Gln Val Asp Met Gln Lys Glu Val Ile Ile Thr Gly Ile Gln<br>    1075                1080                1085 | 3264 |
| acc caa ggt gcc aaa cac tac ctg aag tcc tgc tat acc aca gag ttc<br>Thr Gln Gly Ala Lys His Tyr Leu Lys Ser Cys Tyr Thr Thr Glu Phe<br>1090                1095                1100 | 3312 |
| tat gta gct tac agt tcc aac cag atc aac tgg cag atc ttc aaa ggg<br>Tyr Val Ala Tyr Ser Ser Asn Gln Ile Asn Trp Gln Ile Phe Lys Gly<br>1105                1110                1115                1120 | 3360 |
| aac agc aca agg aat gtg atg tat ttt aat ggc aat tca gat gcc tct<br>Asn Ser Thr Arg Asn Val Met Tyr Phe Asn Gly Asn Ser Asp Ala Ser<br>            1125                1130                1135 | 3408 |
| aca ata aaa gag aat cag ttt gac cca cct att gtg gct aga tat att<br>Thr Ile Lys Glu Asn Gln Phe Asp Pro Pro Ile Val Ala Arg Tyr Ile<br>        1140                1145                1150 | 3456 |
| agg atc tct cca act cga gcc tat aac aga cct acc ctt cga ttg gaa<br>Arg Ile Ser Pro Thr Arg Ala Tyr Asn Arg Pro Thr Leu Arg Leu Glu<br>    1155                1160                1165 | 3504 |
| ctg caa ggt tgt gag gta aat gga tgt tcc aca ccc ctg ggt atg gaa<br>Leu Gln Gly Cys Glu Val Asn Gly Cys Ser Thr Pro Leu Gly Met Glu<br>1170                1175                1180 | 3552 |
| aat gga aag ata gaa aac aag caa atc aca gct tct tcg ttt aag aaa<br>Asn Gly Lys Ile Glu Asn Lys Gln Ile Thr Ala Ser Ser Phe Lys Lys<br>1185                1190                1195                1200 | 3600 |
| tct tgg tgg gga gat tac tgg gaa ccc ttc cgt gcc cgt ctg aat gcc<br>Ser Trp Trp Gly Asp Tyr Trp Glu Pro Phe Arg Ala Arg Leu Asn Ala<br>            1205                1210                1215 | 3648 |
| cag gga cgt gtg aat gcc tgg caa gcc aag gca aac aac aat aag cag<br>Gln Gly Arg Val Asn Ala Trp Gln Ala Lys Ala Asn Asn Asn Lys Gln<br>        1220                1225                1230 | 3696 |
| tgg cta gaa att gat cta ctc aag atc aag aag ata acg gca att ata<br>Trp Leu Glu Ile Asp Leu Leu Lys Ile Lys Lys Ile Thr Ala Ile Ile<br>    1235                1240                1245 | 3744 |
| aca cag ggc tgc aag tct ctg tcc tct gaa atg tat gta aag agc tat<br>Thr Gln Gly Cys Lys Ser Leu Ser Ser Glu Met Tyr Val Lys Ser Tyr<br>1250                1255                1260 | 3792 |
| acc atc cac tac agt gag cag gga gtg gaa tgg aaa cca tac agg ctg<br>Thr Ile His Tyr Ser Glu Gln Gly Val Glu Trp Lys Pro Tyr Arg Leu<br>1265                1270                1275                1280 | 3840 |
| aaa tcc tcc atg gtg gac aag att ttt gaa gga aat act aat acc aaa<br>Lys Ser Ser Met Val Asp Lys Ile Phe Glu Gly Asn Thr Asn Thr Lys<br>            1285                1290                1295 | 3888 |
| gga cat gtg aag aac ttt ttc aac ccc cca atc att tcc agg ttt atc<br>Gly His Val Lys Asn Phe Phe Asn Pro Pro Ile Ile Ser Arg Phe Ile<br>        1300                1305                1310 | 3936 |
| cgt gtc att cct aaa aca tgg aat caa agt att gca ctt cgc ctg gaa<br>Arg Val Ile Pro Lys Thr Trp Asn Gln Ser Ile Ala Leu Arg Leu Glu<br>    1315                1320                1325 | 3984 |
| ctc ttt ggc tgt gat att tac tagaattgaa cattcaaaaa cccctggaag<br>Leu Phe Gly Cys Asp Ile Tyr<br>    1330            1335 | 4035 |
| agactcttta agacctcaaa ccatttagaa tgggcaatgt attttacgct gtgttaaatg | 4095 |
| ttaacagttt tccactattt ctctttcttt tctattagtg aataaaattt tatac | 4150 |

<210> SEQ ID NO 26
<211> LENGTH: 1335
<212> TYPE: PRT
<213> ORGANISM: Homo sapiens -continued

```
<400> SEQUENCE: 26

Ala Gln Leu Arg Gln Phe Tyr Val Ala Ala Gln Gly Ile Ser Trp Ser
  1               5                  10                  15

Tyr Arg Pro Glu Pro Thr Asn Ser Ser Leu Asn Leu Ser Val Thr Ser
             20                  25                  30

Phe Lys Lys Ile Val Tyr Arg Glu Tyr Glu Pro Tyr Phe Lys Lys Glu
         35                  40                  45

Lys Pro Gln Ser Thr Ile Ser Gly Leu Leu Gly Pro Thr Leu Tyr Ala
     50                  55                  60

Glu Val Gly Asp Ile Ile Lys Val His Phe Lys Asn Lys Ala Asp Lys
 65                  70                  75                  80

Pro Leu Ser Ile His Pro Gln Gly Ile Arg Tyr Ser Lys Leu Ser Glu
                 85                  90                  95

Gly Ala Ser Tyr Leu Asp His Thr Phe Pro Ala Ala Lys Met Ala Ala
            100                 105                 110

Ala Val Ala Pro Gly Arg Glu Tyr Thr Tyr Glu Trp Ser Ile Ser Glu
        115                 120                 125

Asp Ser Gly Pro Thr His Asp Asp Pro Pro Cys Leu Thr His Ile Tyr
    130                 135                 140

Tyr Ser His Glu Asn Leu Ile Glu Asp Phe Asn Ser Gly Leu Ile Gly
145                 150                 155                 160

Pro Leu Leu Ile Cys Lys Lys Gly Thr Leu Thr Glu Gly Gly Thr Gln
                165                 170                 175

Lys Thr Phe Asp Lys Gln Ile Val Leu Leu Phe Ala Val Phe Asp Glu
            180                 185                 190

Ser Lys Ser Trp Ser Gln Ser Ser Ser Leu Met Tyr Thr Val Asn Gly
        195                 200                 205

Tyr Val Asn Gly Thr Met Pro Asp Ile Thr Val Cys Ala His Asp His
    210                 215                 220

Ile Ser Trp His Leu Leu Gly Met Ser Ser Gly Pro Glu Leu Phe Ser
225                 230                 235                 240

Ile His Phe Asn Gly Gln Val Leu Glu Gln Asn His His Lys Val Ser
                245                 250                 255

Ala Ile Thr Leu Val Ser Ala Thr Ser Thr Thr Ala Asn Met Thr Val
            260                 265                 270

Gly Pro Glu Gly Lys Trp Ile Ile Ser Ser Leu Thr Pro Lys His Leu
        275                 280                 285

Gln Ala Gly Met Gln Ala Tyr Ile Asp Ile Lys Asn Cys Pro Lys Lys
    290                 295                 300

Thr Arg Asn Leu Lys Lys Ile Thr Arg Glu Gln Arg His Met Lys
305                 310                 315                 320

Arg Trp Glu Tyr Phe Ile Ala Ala Glu Glu Val Ile Trp Asp Tyr Ala
                325                 330                 335

Pro Val Ile Pro Ala Asn Met Asp Lys Lys Tyr Arg Ser Gln His Leu
            340                 345                 350

Asp Asn Phe Ser Asn Gln Ile Gly Lys His Tyr Lys Lys Val Met Tyr
        355                 360                 365

Thr Gln Tyr Glu Asp Glu Ser Phe Thr Lys His Thr Val Asn Pro Asn
    370                 375                 380

Met Lys Glu Asp Gly Ile Leu Gly Pro Ile Ile Arg Ala Gln Val Arg
385                 390                 395                 400

Asp Thr Leu Lys Ile Val Phe Lys Asn Met Ala Ser Arg Pro Tyr Ser
                405                 410                 415
```

```
Ile Tyr Pro His Gly Val Thr Phe Ser Pro Tyr Glu Asp Glu Val Asn
            420                 425                 430

Ser Ser Phe Thr Ser Gly Arg Asn Asn Thr Met Ile Arg Ala Val Gln
        435                 440                 445

Pro Gly Glu Thr Tyr Thr Tyr Lys Trp Asn Ile Leu Glu Phe Asp Glu
    450                 455                 460

Pro Thr Glu Asn Asp Ala Gln Cys Leu Thr Arg Pro Tyr Tyr Ser Asp
465                 470                 475                 480

Val Asp Ile Met Arg Asp Ile Ala Ser Gly Leu Ile Gly Leu Leu Leu
                485                 490                 495

Ile Cys Lys Ser Arg Ser Leu Asp Arg Arg Gly Ile Gln Arg Ala Ala
            500                 505                 510

Asp Ile Glu Gln Gln Ala Val Phe Ala Val Phe Asp Glu Asn Lys Ser
        515                 520                 525

Trp Tyr Leu Glu Asp Asn Ile Asn Lys Phe Cys Glu Asn Pro Asp Glu
    530                 535                 540

Val Lys Arg Asp Asp Pro Lys Phe Tyr Glu Ser Asn Ile Met Ser Thr
545                 550                 555                 560

Ile Asn Gly Tyr Val Pro Glu Ser Ile Thr Thr Leu Gly Phe Cys Phe
                565                 570                 575

Asp Asp Thr Val Gln Trp His Phe Cys Ser Val Gly Thr Gln Asn Glu
            580                 585                 590

Ile Leu Thr Ile His Phe Thr Gly His Ser Phe Ile Tyr Gly Lys Arg
        595                 600                 605

His Glu Asp Thr Leu Thr Leu Phe Pro Met Arg Gly Glu Ser Val Thr
    610                 615                 620

Val Thr Met Asp Asn Val Gly Thr Trp Met Leu Thr Ser Met Asn Ser
625                 630                 635                 640

Ser Pro Arg Ser Lys Lys Leu Arg Leu Lys Phe Arg Asp Val Lys Cys
                645                 650                 655

Ile Pro Asp Asp Asp Glu Asp Ser Tyr Glu Ile Phe Glu Pro Pro Glu
            660                 665                 670

Ser Thr Val Met Ala Thr Arg Lys Met His Asp Arg Leu Glu Pro Glu
        675                 680                 685

Asp Glu Glu Ser Asp Ala Asp Tyr Asp Tyr Gln Asn Arg Leu Ala Ala
    690                 695                 700

Ala Leu Gly Ile Arg Arg Glu Thr Asp Ile Glu Asp Ser Asp Asp Ile
705                 710                 715                 720

Pro Glu Asp Thr Thr Tyr Lys Lys Val Val Phe Arg Lys Tyr Leu Asp
                725                 730                 735

Ser Thr Phe Thr Lys Arg Asp Pro Arg Gly Glu Tyr Glu Glu His Leu
            740                 745                 750

Gly Ile Leu Gly Pro Ile Ile Arg Ala Glu Val Asp Asp Val Ile Gln
        755                 760                 765

Val Arg Phe Lys Asn Leu Ala Ser Arg Pro Tyr Ser Leu His Ala His
    770                 775                 780

Gly Leu Ser Tyr Glu Lys Ser Ser Glu Gly Lys Thr Tyr Glu Asp Asp
785                 790                 795                 800

Ser Pro Glu Trp Phe Lys Glu Asp Asn Ala Val Gln Pro Asn Ser Ser
                805                 810                 815

Tyr Thr Tyr Val Trp His Ala Thr Glu Arg Ser Gly Pro Glu Ser Pro
            820                 825                 830
```

-continued

```
Gly Ser Ala Cys Arg Ala Trp Ala Tyr Tyr Ser Ala Val Asn Pro Glu
        835                 840                 845

Lys Asp Ile His Ser Gly Leu Ile Gly Pro Leu Leu Ile Cys Gln Lys
    850                 855                 860

Gly Ile Leu His Lys Asp Ser Asn Met Pro Val Asp Met Arg Glu Phe
865                 870                 875                 880

Val Leu Leu Phe Met Thr Phe Asp Glu Lys Ser Trp Tyr Tyr Glu
                885                 890                 895

Lys Lys Ser Arg Ser Ser Trp Arg Leu Thr Ser Ser Glu Met Lys Lys
            900                 905                 910

Ser His Glu Phe His Ala Ile Asn Gly Met Ile Tyr Ser Leu Pro Gly
        915                 920                 925

Leu Lys Met Tyr Glu Gln Glu Trp Val Arg Leu His Leu Leu Asn Ile
    930                 935                 940

Gly Gly Ser Gln Asp Ile His Val Val His Phe His Gly Gln Thr Leu
945                 950                 955                 960

Leu Glu Asn Gly Asn Lys Gln His Gln Leu Gly Val Trp Pro Leu Leu
                965                 970                 975

Pro Gly Ser Phe Lys Thr Leu Glu Met Lys Ala Ser Lys Pro Gly Trp
            980                 985                 990

Trp Leu Leu Asn Thr Glu Val Gly Glu Asn Gln Arg Ala Gly Met Gln
        995                 1000                1005

Thr Pro Phe Leu Ile Met Asp Arg Asp Cys Arg Met Pro Met Gly Leu
    1010                1015                1020

Ser Thr Gly Ile Ile Ser Asp Ser Gln Ile Lys Ala Ser Glu Phe Leu
1025                1030                1035                1040

Gly Tyr Trp Glu Pro Arg Leu Ala Arg Leu Asn Asn Gly Gly Ser Tyr
                1045                1050                1055

Asn Ala Trp Ser Val Glu Lys Leu Ala Ala Glu Phe Ala Ser Lys Pro
            1060                1065                1070

Trp Ile Gln Val Asp Met Gln Lys Glu Val Ile Ile Thr Gly Ile Gln
        1075                1080                1085

Thr Gln Gly Ala Lys His Tyr Leu Lys Ser Cys Tyr Thr Thr Glu Phe
    1090                1095                1100

Tyr Val Ala Tyr Ser Ser Asn Gln Ile Asn Trp Gln Ile Phe Lys Gly
1105                1110                1115                1120

Asn Ser Thr Arg Asn Val Met Tyr Phe Asn Gly Asn Ser Asp Ala Ser
                1125                1130                1135

Thr Ile Lys Glu Asn Gln Phe Asp Pro Pro Ile Val Ala Arg Tyr Ile
            1140                1145                1150

Arg Ile Ser Pro Thr Arg Ala Tyr Asn Arg Pro Thr Leu Arg Leu Glu
        1155                1160                1165

Leu Gln Gly Cys Glu Val Asn Gly Cys Ser Thr Pro Leu Gly Met Glu
    1170                1175                1180

Asn Gly Lys Ile Glu Asn Lys Gln Ile Thr Ala Ser Ser Phe Lys Lys
1185                1190                1195                1200

Ser Trp Trp Gly Asp Tyr Trp Glu Pro Phe Arg Ala Arg Leu Asn Ala
                1205                1210                1215

Gln Gly Arg Val Asn Ala Trp Gln Ala Lys Ala Asn Asn Asn Lys Gln
            1220                1225                1230

Trp Leu Glu Ile Asp Leu Leu Lys Ile Lys Lys Ile Thr Ala Ile Ile
        1235                1240                1245

Thr Gln Gly Cys Lys Ser Leu Ser Ser Glu Met Tyr Val Lys Ser Tyr
```

```
                  1250              1255              1260
Thr Ile His Tyr Ser Glu Gln Gly Val Glu Trp Lys Pro Tyr Arg Leu
1265              1270              1275              1280

Lys Ser Ser Met Val Asp Lys Ile Phe Glu Gly Asn Thr Asn Thr Lys
              1285              1290              1295

Gly His Val Lys Asn Phe Phe Asn Pro Ile Ile Ser Arg Phe Ile
          1300              1305              1310

Arg Val Ile Pro Lys Thr Trp Asn Gln Ser Ile Ala Leu Arg Leu Glu
      1315              1320              1325

Leu Phe Gly Cys Asp Ile Tyr
    1330              1335

<210> SEQ ID NO 27
<211> LENGTH: 4150
<212> TYPE: DNA
<213> ORGANISM: Homo sapiens
<220> FEATURE:
<221> NAME/KEY: CDS
<222> LOCATION: (1)..(4005)

<400> SEQUENCE: 27 gca cag cta agg cag ttc tac gtg gct gct cag ggc atc agt tgg agc    48
Ala Gln Leu Arg Gln Phe Tyr Val Ala Ala Gln Gly Ile Ser Trp Ser
 1               5                  10                  15 tac cga cct gag ccc aca aac tca agt ttg aat ctt tct gta act tcc    96
Tyr Arg Pro Glu Pro Thr Asn Ser Ser Leu Asn Leu Ser Val Thr Ser
                20                  25                  30 ttt aag aaa att gtc tac aga gag tat gaa cca tat ttt aag aaa gaa   144
Phe Lys Lys Ile Val Tyr Arg Glu Tyr Glu Pro Tyr Phe Lys Lys Glu
            35                  40                  45 aaa cca caa tct acc att tca gga ctt ctt ggg cct act tta tat gct   192
Lys Pro Gln Ser Thr Ile Ser Gly Leu Leu Gly Pro Thr Leu Tyr Ala
        50                  55                  60 gaa gtc gga gac atc ata aaa gtt cac ttt aaa aat aag gca gat aag   240
Glu Val Gly Asp Ile Ile Lys Val His Phe Lys Asn Lys Ala Asp Lys
 65                  70                  75                  80 ccc ttg agc atc cat cct caa gga att agg tac agt aaa tta tca gca   288
Pro Leu Ser Ile His Pro Gln Gly Ile Arg Tyr Ser Lys Leu Ser Ala
                 85                  90                  95 ggt gct tct tac ctt gcc cac aca ttc cct gca gag aag atg gac gac   336
Gly Ala Ser Tyr Leu Ala His Thr Phe Pro Ala Glu Lys Met Asp Asp
                100                 105                 110 gct gtg gct cca ggc cga gaa tac acc tat gaa tgg agt atc agt gag   384
Ala Val Ala Pro Gly Arg Glu Tyr Thr Tyr Glu Trp Ser Ile Ser Glu
            115                 120                 125 gac agt gga ccc acc cat gat gac cct cca tgc ctc aca cac atc tat   432
Asp Ser Gly Pro Thr His Asp Asp Pro Pro Cys Leu Thr His Ile Tyr
        130                 135                 140 tac tcc cat gaa aat ctg atc gag gat ttc aac tct ggg ctg att ggg   480
Tyr Ser His Glu Asn Leu Ile Glu Asp Phe Asn Ser Gly Leu Ile Gly
145                 150                 155                 160 ccc ctg ctt atc tgt aaa aaa ggg acc cta act gag ggt ggg aca cag   528
Pro Leu Leu Ile Cys Lys Lys Gly Thr Leu Thr Glu Gly Gly Thr Gln
                165                 170                 175 aag acg ttt gac aag caa atc gtg cta cta ttt gct gtg ttt gat gaa   576
Lys Thr Phe Asp Lys Gln Ile Val Leu Leu Phe Ala Val Phe Asp Glu
                180                 185                 190 agc aag agc tgg agc cag tca tca tcc cta atg tac aca gtc aat gga   624
Ser Lys Ser Trp Ser Gln Ser Ser Ser Leu Met Tyr Thr Val Asn Gly
            195                 200                 205
```

```
tat gtg aat ggg aca atg cca gat ata aca gtt tgt gcc cat gac cac      672
Tyr Val Asn Gly Thr Met Pro Asp Ile Thr Val Cys Ala His Asp His
210                 215                 220 atc agc tgg cat ctg ctg gga atg agc tcg ggg cca gaa tta ttc tcc      720
Ile Ser Trp His Leu Leu Gly Met Ser Ser Gly Pro Glu Leu Phe Ser
225                 230                 235                 240 att cat ttc aac ggc cag gtc ctg gag cag aac cat cat aag gtc tca      768
Ile His Phe Asn Gly Gln Val Leu Glu Gln Asn His His Lys Val Ser
            245                 250                 255 gcc atc acc ctt gtc agt gct aca tcc act acc gca aat atg act gtg      816
Ala Ile Thr Leu Val Ser Ala Thr Ser Thr Thr Ala Asn Met Thr Val
        260                 265                 270 ggc cca gag gga aag tgg atc ata tct tct ctc acc cca aaa cat ttg      864
Gly Pro Glu Gly Lys Trp Ile Ile Ser Ser Leu Thr Pro Lys His Leu
    275                 280                 285 caa gct ggg atg cag gct tac att gac att aaa aac tgc cca aag aaa      912
Gln Ala Gly Met Gln Ala Tyr Ile Asp Ile Lys Asn Cys Pro Lys Lys
290                 295                 300 acc agg aat ctt aag aaa ata act cgt gag cag agg cgg cac atg aag      960
Thr Arg Asn Leu Lys Lys Ile Thr Arg Glu Gln Arg Arg His Met Lys
305                 310                 315                 320 agg tgg gaa tac ttc att gct gca gag gaa gtc att tgg gac tat gca     1008
Arg Trp Glu Tyr Phe Ile Ala Ala Glu Glu Val Ile Trp Asp Tyr Ala
            325                 330                 335 cct gta ata cca gcg aat atg gac aaa aaa tac agg tct cag cat ttg     1056
Pro Val Ile Pro Ala Asn Met Asp Lys Lys Tyr Arg Ser Gln His Leu
        340                 345                 350 gat aat ttc tca aac caa att gga aaa cat tat aag aaa gtt atg tac     1104
Asp Asn Phe Ser Asn Gln Ile Gly Lys His Tyr Lys Lys Val Met Tyr
    355                 360                 365 aca cag tac gaa gat gag tcc ttc acc aaa cat aca gtg aat ccc aat     1152
Thr Gln Tyr Glu Asp Glu Ser Phe Thr Lys His Thr Val Asn Pro Asn
370                 375                 380 atg aaa gaa gat ggg att ttg ggt cct att atc aga gcc cag gtc aga     1200
Met Lys Glu Asp Gly Ile Leu Gly Pro Ile Ile Arg Ala Gln Val Arg
385                 390                 395                 400 gac aca ctc aaa atc gtg ttc aaa aat atg gcc agc cgc ccc tat agc     1248
Asp Thr Leu Lys Ile Val Phe Lys Asn Met Ala Ser Arg Pro Tyr Ser
            405                 410                 415 att tac cct cat gga gtg acc ttc tcg cct tat gaa gat gaa gtc aac     1296
Ile Tyr Pro His Gly Val Thr Phe Ser Pro Tyr Glu Asp Glu Val Asn
        420                 425                 430 tct tct ttc acc tca ggc agg aac aac acc atg atc aga gca gtt caa     1344
Ser Ser Phe Thr Ser Gly Arg Asn Asn Thr Met Ile Arg Ala Val Gln
    435                 440                 445 cca ggg gaa acc tat act tat aag tgg aac atc tta gag ttt gat gaa     1392
Pro Gly Glu Thr Tyr Thr Tyr Lys Trp Asn Ile Leu Glu Phe Asp Glu
450                 455                 460 ccc aca gaa aat gat gcc cag tgc tta aca aga cca tac tac agt gac     1440
Pro Thr Glu Asn Asp Ala Gln Cys Leu Thr Arg Pro Tyr Tyr Ser Asp
465                 470                 475                 480 gtg gac atc atg aga gac atc gcc tct ggg cta ata gga cta ctt cta     1488
Val Asp Ile Met Arg Asp Ile Ala Ser Gly Leu Ile Gly Leu Leu Leu
            485                 490                 495 atc tgt aag agc aga tcc ctg gac agg cga gga ata cag agg gca gca     1536
Ile Cys Lys Ser Arg Ser Leu Asp Arg Arg Gly Ile Gln Arg Ala Ala
        500                 505                 510 gac atc gaa cag cag gct gtg ttt gct gtg ttt gat gag aac aaa agc     1584
Asp Ile Glu Gln Gln Ala Val Phe Ala Val Phe Asp Glu Asn Lys Ser
```

-continued

```
         515                 520                 525
tgg tac ctt gag gac aac atc aac aag ttt tgt gaa aat cct gat gag    1632
Trp Tyr Leu Glu Asp Asn Ile Asn Lys Phe Cys Glu Asn Pro Asp Glu
        530                 535                 540 gtg aaa cgt gat gac ccc aag ttt tat gaa tca aac atc atg agc act    1680
Val Lys Arg Asp Asp Pro Lys Phe Tyr Glu Ser Asn Ile Met Ser Thr
545                 550                 555                 560 atc aat ggc tat gtg cct gag agc ata act act ctt gga ttc tgc ttt    1728
Ile Asn Gly Tyr Val Pro Glu Ser Ile Thr Thr Leu Gly Phe Cys Phe
                565                 570                 575 gat gac act gtc cag tgg cac ttc tgt agt gtg ggg acc cag aat gaa    1776
Asp Asp Thr Val Gln Trp His Phe Cys Ser Val Gly Thr Gln Asn Glu
            580                 585                 590 att ttg acc atc cac ttc act ggg cac tca ttc atc tat gga aag agg    1824
Ile Leu Thr Ile His Phe Thr Gly His Ser Phe Ile Tyr Gly Lys Arg
        595                 600                 605 cat gag gac acc ttg acc ctc ttc ccc atg cgt gga gaa tct gtg acg    1872
His Glu Asp Thr Leu Thr Leu Phe Pro Met Arg Gly Glu Ser Val Thr
    610                 615                 620 gtc aca atg gat aat gtt gga act tgg atg tta act tcc atg aat tct    1920
Val Thr Met Asp Asn Val Gly Thr Trp Met Leu Thr Ser Met Asn Ser
625                 630                 635                 640 agt cca aga agc aaa aag ctg agg ctg aaa ttc agg gat gtt aaa tgt    1968
Ser Pro Arg Ser Lys Lys Leu Arg Leu Lys Phe Arg Asp Val Lys Cys
                645                 650                 655 atc cca gat gat gat gaa gac tca tat gag att ttt gaa cct cca gaa    2016
Ile Pro Asp Asp Asp Glu Asp Ser Tyr Glu Ile Phe Glu Pro Pro Glu
            660                 665                 670 tct aca gtc atg gct aca cgg aaa atg cat gat cgt tta gaa cct gaa    2064
Ser Thr Val Met Ala Thr Arg Lys Met His Asp Arg Leu Glu Pro Glu
        675                 680                 685 gat gaa gag agt gat gct gac tat gat tac cag aac aga ctg gct gca    2112
Asp Glu Glu Ser Asp Ala Asp Tyr Asp Tyr Gln Asn Arg Leu Ala Ala
    690                 695                 700 gca tta gga att agg agg gaa aca gat att gaa gac tct gat gat att    2160
Ala Leu Gly Ile Arg Arg Glu Thr Asp Ile Glu Asp Ser Asp Asp Ile
705                 710                 715                 720 cca gaa gat acc aca tat aag aaa gta gtt ttt cga aag tac ctc gac    2208
Pro Glu Asp Thr Thr Tyr Lys Lys Val Val Phe Arg Lys Tyr Leu Asp
                725                 730                 735 agc act ttt acc aaa cgt gat cct cga ggg gag tat gaa gag cat ctc    2256
Ser Thr Phe Thr Lys Arg Asp Pro Arg Gly Glu Tyr Glu Glu His Leu
            740                 745                 750 gga att ctt ggt cct att atc aga gct gaa gtg gat gat gtt atc caa    2304
Gly Ile Leu Gly Pro Ile Ile Arg Ala Glu Val Asp Asp Val Ile Gln
        755                 760                 765 gtt cgt ttt aaa aat tta gca tcc aga ccg tat tct cta cat gcc cat    2352
Val Arg Phe Lys Asn Leu Ala Ser Arg Pro Tyr Ser Leu His Ala His
    770                 775                 780 gga ctt tcc tat gaa aaa tca tca gag gga aag act tat gaa gat gac    2400
Gly Leu Ser Tyr Glu Lys Ser Ser Glu Gly Lys Thr Tyr Glu Asp Asp
785                 790                 795                 800 tct cct gaa tgg ttt aag gaa gat aat gct gtt cag cca aat agc agt    2448
Ser Pro Glu Trp Phe Lys Glu Asp Asn Ala Val Gln Pro Asn Ser Ser
                805                 810                 815 tat acc tac gta tgg cat gcc act gag cga tca ggg cca gaa agt cct    2496
Tyr Thr Tyr Val Trp His Ala Thr Glu Arg Ser Gly Pro Glu Ser Pro
            820                 825                 830 ggc tct gcc tgt cgg gct tgg gcc tac tac tca gct gtg aac cca gaa    2544
Gly Ser Ala Cys Arg Ala Trp Ala Tyr Tyr Ser Ala Val Asn Pro Glu
```

```
                Gly Ser Ala Cys Arg Ala Trp Ala Tyr Tyr Ser Ala Val Asn Pro Glu
                    835                 840                 845 aaa gat att cac tca ggc ttg ata ggt ccc ctc cta atc tgc caa aaa           2592
Lys Asp Ile His Ser Gly Leu Ile Gly Pro Leu Leu Ile Cys Gln Lys
850                 855                 860 gga ata cta cat aag gac agc aac atg cct gtg gac atg aga gaa ttt           2640
Gly Ile Leu His Lys Asp Ser Asn Met Pro Val Asp Met Arg Glu Phe
865                 870                 875                 880 gtc tta cta ttt atg acc ttt gat gaa aag aag agc tgg tac tat gaa           2688
Val Leu Leu Phe Met Thr Phe Asp Glu Lys Lys Ser Trp Tyr Tyr Glu
                885                 890                 895 aag aag tcc cga agt tct tgg aga ctc aca tcc tca gaa atg aaa aaa           2736
Lys Lys Ser Arg Ser Ser Trp Arg Leu Thr Ser Ser Glu Met Lys Lys
            900                 905                 910 tcc cat gag ttt cac gcc att aat ggg atg atc tac agc ttg cct ggc           2784
Ser His Glu Phe His Ala Ile Asn Gly Met Ile Tyr Ser Leu Pro Gly
        915                 920                 925 ctg aaa atg tat gag caa gag tgg gtg agg tta cac ctg ctg aac ata           2832
Leu Lys Met Tyr Glu Gln Glu Trp Val Arg Leu His Leu Leu Asn Ile
    930                 935                 940 ggc ggc tcc caa gac att cac gtg gtt cac ttt cac ggc cag acc ttg           2880
Gly Gly Ser Gln Asp Ile His Val Val His Phe His Gly Gln Thr Leu
945                 950                 955                 960 ctg gaa aat ggc aat aaa cag cac cag tta ggg gtc tgg ccc ctt ctg           2928
Leu Glu Asn Gly Asn Lys Gln His Gln Leu Gly Val Trp Pro Leu Leu
                965                 970                 975 cct ggt tca ttt aaa act ctt gaa atg aag gca tca aaa cct ggc tgg           2976
Pro Gly Ser Phe Lys Thr Leu Glu Met Lys Ala Ser Lys Pro Gly Trp
            980                 985                 990 tgg ctc cta aac aca gag gtt gga gaa aac cag aga gca ggg atg caa           3024
Trp Leu Leu Asn Thr Glu Val Gly Glu Asn Gln Arg Ala Gly Met Gln
        995                 1000                1005 acg cca ttt ctt atc atg gac aga gac tgt agg atg cca atg gga cta           3072
Thr Pro Phe Leu Ile Met Asp Arg Asp Cys Arg Met Pro Met Gly Leu
    1010                1015                1020 agc act ggt atc ata tct gat tca cag atc aag gct tca gag ttt ctg           3120
Ser Thr Gly Ile Ile Ser Asp Ser Gln Ile Lys Ala Ser Glu Phe Leu
1025                1030                1035                1040 ggt tac tgg gag ccc aga tta gca aga tta aac aat ggt gga tct tat           3168
Gly Tyr Trp Glu Pro Arg Leu Ala Arg Leu Asn Asn Gly Gly Ser Tyr
                1045                1050                1055 aat gct tgg agt gta gaa aaa ctt gca gca gaa ttt gcc tct aaa cct           3216
Asn Ala Trp Ser Val Glu Lys Leu Ala Ala Glu Phe Ala Ser Lys Pro
            1060                1065                1070 tgg atc cag gtg gac atg caa aag gaa gtc ata atc aca ggg atc cag           3264
Trp Ile Gln Val Asp Met Gln Lys Glu Val Ile Ile Thr Gly Ile Gln
        1075                1080                1085 acc caa ggt gcc aaa cac tac ctg aag tcc tgc tat acc aca gag ttc           3312
Thr Gln Gly Ala Lys His Tyr Leu Lys Ser Cys Tyr Thr Thr Glu Phe
    1090                1095                1100 tat gta gct tac agt tcc aac cag atc aac tgg cag atc ttc aaa ggg           3360
Tyr Val Ala Tyr Ser Ser Asn Gln Ile Asn Trp Gln Ile Phe Lys Gly
1105                1110                1115                1120 aac agc aca agg aat gtg atg tat ttt aat ggc aat tca gat gcc tct           3408
Asn Ser Thr Arg Asn Val Met Tyr Phe Asn Gly Asn Ser Asp Ala Ser
                1125                1130                1135 aca ata aaa gag aat cag ttt gac cca cct att gtg gct aga tat att           3456
Thr Ile Lys Glu Asn Gln Phe Asp Pro Pro Ile Val Ala Arg Tyr Ile
            1140                1145                1150
```

```
agg atc tct cca act cga gcc tat aac aga cct acc ctt cga ttg gaa      3504
Arg Ile Ser Pro Thr Arg Ala Tyr Asn Arg Pro Thr Leu Arg Leu Glu
    1155                1160                1165 ctg caa ggt tgt gag gta aat gga tgt tcc aca ccc ctg ggt atg gaa      3552
Leu Gln Gly Cys Glu Val Asn Gly Cys Ser Thr Pro Leu Gly Met Glu
1170                1175                1180 aat gga aag ata gaa aac aag caa atc aca gct tct tcg ttt aag aaa      3600
Asn Gly Lys Ile Glu Asn Lys Gln Ile Thr Ala Ser Ser Phe Lys Lys
1185                1190                1195                1200 tct tgg tgg gga gat tac tgg gaa ccc ttc cgt gcc cgt ctg aat gcc      3648
Ser Trp Trp Gly Asp Tyr Trp Glu Pro Phe Arg Ala Arg Leu Asn Ala
            1205                1210                1215 cag gga cgt gtg aat gcc tgg caa gcc aag gca aac aac aat aag cag      3696
Gln Gly Arg Val Asn Ala Trp Gln Ala Lys Ala Asn Asn Asn Lys Gln
        1220                1225                1230 tgg cta gaa att gat cta ctc aag atc aag aag ata acg gca att ata      3744
Trp Leu Glu Ile Asp Leu Leu Lys Ile Lys Lys Ile Thr Ala Ile Ile
    1235                1240                1245 aca cag ggc tgc aag tct ctg tcc tct gaa atg tat gta aag agc tat      3792
Thr Gln Gly Cys Lys Ser Leu Ser Ser Glu Met Tyr Val Lys Ser Tyr
1250                1255                1260 acc atc cac tac agt gag cag gga gtg gaa tgg aaa cca tac agg ctg      3840
Thr Ile His Tyr Ser Glu Gln Gly Val Glu Trp Lys Pro Tyr Arg Leu
1265                1270                1275                1280 aaa tcc tcc atg gtg gac aag att ttt gaa gga aat act aat acc aaa      3888
Lys Ser Ser Met Val Asp Lys Ile Phe Glu Gly Asn Thr Asn Thr Lys
            1285                1290                1295 gga cat gtg aag aac ttt ttc aac ccc cca atc att tcc agg ttt atc      3936
Gly His Val Lys Asn Phe Phe Asn Pro Pro Ile Ile Ser Arg Phe Ile
        1300                1305                1310 cgt gtc att cct aaa aca tgg aat caa agt att gca ctt cgc ctg gaa      3984
Arg Val Ile Pro Lys Thr Trp Asn Gln Ser Ile Ala Leu Arg Leu Glu
    1315                1320                1325 ctc ttt ggc tgt gat att tac tagaattgaa cattcaaaaa ccctggaag          4035
Leu Phe Gly Cys Asp Ile Tyr
    1330                1335 agactcttta agacctcaaa ccatttagaa tgggcaatgt attttacgct gtgttaaatg    4095
ttaacagttt tccactattt ctctttcttt tctattagtg aataaaattt tatac         4150

<210> SEQ ID NO 28
<211> LENGTH: 1335
<212> TYPE: PRT
<213> ORGANISM: Homo sapiens

<400> SEQUENCE: 28

Ala Gln Leu Arg Gln Phe Tyr Val Ala Ala Gln Gly Ile Ser Trp Ser
 1               5                  10                  15

Tyr Arg Pro Glu Pro Thr Asn Ser Ser Leu Asn Leu Ser Val Thr Ser
            20                  25                  30

Phe Lys Lys Ile Val Tyr Arg Glu Tyr Glu Pro Tyr Phe Lys Lys Glu
        35                  40                  45

Lys Pro Gln Ser Thr Ile Ser Gly Leu Leu Gly Pro Thr Leu Tyr Ala
    50                  55                  60

Glu Val Gly Asp Ile Ile Lys Val His Phe Lys Asn Lys Ala Asp Lys
65                  70                  75                  80

Pro Leu Ser Ile His Pro Gln Gly Ile Arg Tyr Ser Lys Leu Ser Ala
                85                  90                  95

Gly Ala Ser Tyr Leu Ala His Thr Phe Pro Ala Glu Lys Met Asp Asp
```

-continued

```
                100                 105                 110
Ala Val Ala Pro Gly Arg Glu Tyr Thr Tyr Glu Trp Ser Ile Ser Glu
            115                 120                 125
Asp Ser Gly Pro Thr His Asp Asp Pro Cys Leu Thr His Ile Tyr
        130                 135                 140
Tyr Ser His Glu Asn Leu Ile Glu Asp Phe Asn Ser Gly Leu Ile Gly
145                 150                 155                 160
Pro Leu Leu Ile Cys Lys Lys Gly Thr Leu Thr Glu Gly Thr Gln
                165                 170                 175
Lys Thr Phe Asp Lys Gln Ile Val Leu Leu Phe Ala Val Phe Asp Glu
            180                 185                 190
Ser Lys Ser Trp Ser Gln Ser Ser Leu Met Tyr Thr Val Asn Gly
        195                 200                 205
Tyr Val Asn Gly Thr Met Pro Asp Ile Thr Val Cys Ala His Asp His
    210                 215                 220
Ile Ser Trp His Leu Leu Gly Met Ser Ser Gly Pro Glu Leu Phe Ser
225                 230                 235                 240
Ile His Phe Asn Gly Gln Val Leu Glu Gln Asn His His Lys Val Ser
                245                 250                 255
Ala Ile Thr Leu Val Ser Ala Thr Ser Thr Ala Asn Met Thr Val
            260                 265                 270
Gly Pro Glu Gly Lys Trp Ile Ile Ser Ser Leu Thr Pro Lys His Leu
        275                 280                 285
Gln Ala Gly Met Gln Ala Tyr Ile Asp Ile Lys Asn Cys Pro Lys Lys
    290                 295                 300
Thr Arg Asn Leu Lys Lys Ile Thr Arg Glu Gln Arg Arg His Met Lys
305                 310                 315                 320
Arg Trp Glu Tyr Phe Ile Ala Ala Glu Glu Val Ile Trp Asp Tyr Ala
                325                 330                 335
Pro Val Ile Pro Ala Asn Met Asp Lys Lys Tyr Arg Ser Gln His Leu
            340                 345                 350
Asp Asn Phe Ser Asn Gln Ile Gly Lys His Tyr Lys Lys Val Met Tyr
        355                 360                 365
Thr Gln Tyr Glu Asp Glu Ser Phe Thr Lys His Thr Val Asn Pro Asn
    370                 375                 380
Met Lys Glu Asp Gly Ile Leu Gly Pro Ile Ile Arg Ala Gln Val Arg
385                 390                 395                 400
Asp Thr Leu Lys Ile Val Phe Lys Asn Met Ala Ser Arg Pro Tyr Ser
                405                 410                 415
Ile Tyr Pro His Gly Val Thr Phe Ser Pro Tyr Glu Asp Glu Val Asn
            420                 425                 430
Ser Ser Phe Thr Ser Gly Arg Asn Asn Thr Met Ile Arg Ala Val Gln
        435                 440                 445
Pro Gly Glu Thr Tyr Thr Tyr Lys Trp Asn Ile Leu Glu Phe Asp Glu
    450                 455                 460
Pro Thr Glu Asn Asp Ala Gln Cys Leu Thr Arg Pro Tyr Tyr Ser Asp
465                 470                 475                 480
Val Asp Ile Met Arg Asp Ile Ala Ser Gly Leu Ile Gly Leu Leu Leu
                485                 490                 495
Ile Cys Lys Ser Arg Ser Leu Asp Arg Arg Gly Ile Gln Arg Ala Ala
            500                 505                 510
Asp Ile Glu Gln Gln Ala Val Phe Ala Val Phe Asp Glu Asn Lys Ser
        515                 520                 525
```

```
Trp Tyr Leu Glu Asp Asn Ile Asn Lys Phe Cys Glu Asn Pro Asp Glu
    530                 535                 540

Val Lys Arg Asp Asp Pro Lys Phe Tyr Glu Ser Asn Ile Met Ser Thr
545                 550                 555                 560

Ile Asn Gly Tyr Val Pro Glu Ser Ile Thr Thr Leu Gly Phe Cys Phe
                565                 570                 575

Asp Asp Thr Val Gln Trp His Phe Cys Ser Val Gly Thr Gln Asn Glu
            580                 585                 590

Ile Leu Thr Ile His Phe Thr Gly His Ser Phe Ile Tyr Gly Lys Arg
        595                 600                 605

His Glu Asp Thr Leu Thr Leu Phe Pro Met Arg Gly Glu Ser Val Thr
    610                 615                 620

Val Thr Met Asp Asn Val Gly Thr Trp Met Leu Thr Ser Met Asn Ser
625                 630                 635                 640

Ser Pro Arg Ser Lys Lys Leu Arg Leu Lys Phe Arg Asp Val Lys Cys
                645                 650                 655

Ile Pro Asp Asp Asp Glu Asp Ser Tyr Glu Ile Phe Glu Pro Pro Glu
            660                 665                 670

Ser Thr Val Met Ala Thr Arg Lys Met His Asp Arg Leu Glu Pro Glu
        675                 680                 685

Asp Glu Glu Ser Asp Ala Asp Tyr Asp Tyr Gln Asn Arg Leu Ala Ala
    690                 695                 700

Ala Leu Gly Ile Arg Arg Glu Thr Asp Ile Glu Asp Ser Asp Asp Ile
705                 710                 715                 720

Pro Glu Asp Thr Thr Tyr Lys Lys Val Val Phe Arg Lys Tyr Leu Asp
                725                 730                 735

Ser Thr Phe Thr Lys Arg Asp Pro Arg Gly Glu Tyr Glu Glu His Leu
            740                 745                 750

Gly Ile Leu Gly Pro Ile Ile Arg Ala Glu Val Asp Asp Val Ile Gln
        755                 760                 765

Val Arg Phe Lys Asn Leu Ala Ser Arg Pro Tyr Ser Leu His Ala His
    770                 775                 780

Gly Leu Ser Tyr Glu Lys Ser Ser Glu Gly Lys Thr Tyr Glu Asp Asp
785                 790                 795                 800

Ser Pro Glu Trp Phe Lys Glu Asp Asn Ala Val Gln Pro Asn Ser Ser
                805                 810                 815

Tyr Thr Tyr Val Trp His Ala Thr Glu Arg Ser Gly Pro Glu Ser Pro
            820                 825                 830

Gly Ser Ala Cys Arg Ala Trp Ala Tyr Tyr Ser Ala Val Asn Pro Glu
        835                 840                 845

Lys Asp Ile His Ser Gly Leu Ile Gly Pro Leu Leu Ile Cys Gln Lys
    850                 855                 860

Gly Ile Leu His Lys Asp Ser Asn Met Pro Val Asp Met Arg Glu Phe
865                 870                 875                 880

Val Leu Leu Phe Met Thr Phe Asp Glu Lys Lys Ser Trp Tyr Tyr Glu
                885                 890                 895

Lys Lys Ser Arg Ser Ser Trp Arg Leu Thr Ser Ser Glu Met Lys Lys
            900                 905                 910

Ser His Glu Phe His Ala Ile Asn Gly Met Ile Tyr Ser Leu Pro Gly
        915                 920                 925

Leu Lys Met Tyr Glu Gln Glu Trp Val Arg Leu His Leu Leu Asn Ile
    930                 935                 940
```

```
Gly Gly Ser Gln Asp Ile His Val Val His Phe His Gly Gln Thr Leu
945                 950                 955                 960

Leu Glu Asn Gly Asn Lys Gln His Gln Leu Gly Val Trp Pro Leu Leu
            965                 970                 975

Pro Gly Ser Phe Lys Thr Leu Glu Met Lys Ala Ser Lys Pro Gly Trp
        980                 985                 990

Trp Leu Leu Asn Thr Glu Val Gly Glu Asn Gln Arg Ala Gly Met Gln
    995                 1000                1005

Thr Pro Phe Leu Ile Met Asp Arg Asp Cys Arg Met Pro Met Gly Leu
   1010                 1015                1020

Ser Thr Gly Ile Ile Ser Asp Ser Gln Ile Lys Ala Ser Glu Phe Leu
1025                1030                1035                1040

Gly Tyr Trp Glu Pro Arg Leu Ala Arg Leu Asn Asn Gly Gly Ser Tyr
            1045                1050                1055

Asn Ala Trp Ser Val Glu Lys Leu Ala Ala Glu Phe Ala Ser Lys Pro
        1060                1065                1070

Trp Ile Gln Val Asp Met Gln Lys Glu Val Ile Ile Thr Gly Ile Gln
    1075                1080                1085

Thr Gln Gly Ala Lys His Tyr Leu Lys Ser Cys Tyr Thr Thr Glu Phe
   1090                 1095                1100

Tyr Val Ala Tyr Ser Ser Asn Gln Ile Asn Trp Gln Ile Phe Lys Gly
1105                1110                1115                1120

Asn Ser Thr Arg Asn Val Met Tyr Phe Asn Gly Asn Ser Asp Ala Ser
            1125                1130                1135

Thr Ile Lys Glu Asn Gln Phe Asp Pro Pro Ile Val Ala Arg Tyr Ile
        1140                1145                1150

Arg Ile Ser Pro Thr Arg Ala Tyr Asn Arg Pro Thr Leu Arg Leu Glu
    1155                1160                1165

Leu Gln Gly Cys Glu Val Asn Gly Cys Ser Thr Pro Leu Gly Met Glu
   1170                 1175                1180

Asn Gly Lys Ile Glu Asn Lys Gln Ile Thr Ala Ser Ser Phe Lys Lys
1185                1190                1195                1200

Ser Trp Trp Gly Asp Tyr Trp Glu Pro Phe Arg Ala Arg Leu Asn Ala
            1205                1210                1215

Gln Gly Arg Val Asn Ala Trp Gln Ala Lys Ala Asn Asn Asn Lys Gln
            1220                1225                1230

Trp Leu Glu Ile Asp Leu Leu Lys Ile Lys Lys Ile Thr Ala Ile Ile
        1235                1240                1245

Thr Gln Gly Cys Lys Ser Leu Ser Ser Glu Met Tyr Val Lys Ser Tyr
   1250                 1255                1260

Thr Ile His Tyr Ser Glu Gln Gly Val Glu Trp Lys Pro Tyr Arg Leu
1265                1270                1275                1280

Lys Ser Ser Met Val Asp Lys Ile Phe Glu Gly Asn Thr Asn Thr Lys
            1285                1290                1295

Gly His Val Lys Asn Phe Phe Asn Pro Pro Ile Ile Ser Arg Phe Ile
            1300                1305                1310

Arg Val Ile Pro Lys Thr Trp Asn Gln Ser Ile Ala Leu Arg Leu Glu
        1315                1320                1325

Leu Phe Gly Cys Asp Ile Tyr
   1330                 1335

<210> SEQ ID NO 29
<211> LENGTH: 4162
<212> TYPE: DNA
```

<213> ORGANISM: Homo sapiens
<220> FEATURE:
<221> NAME/KEY: CDS
<222> LOCATION: (1)..(4017)

<400> SEQUENCE: 29

| | | |
|---|---|---|
| gca cag cta agg cag ttc tac gtg gct gct cag ggc atc agt tgg agc<br>Ala Gln Leu Arg Gln Phe Tyr Val Ala Ala Gln Gly Ile Ser Trp Ser<br>1               5                  10                  15 | 48 |
| tac cga cct gag ccc aca aac tca agt ttg aat ctt tct gta act tcc<br>Tyr Arg Pro Glu Pro Thr Asn Ser Ser Leu Asn Leu Ser Val Thr Ser<br>            20                  25                  30 | 96 |
| ttt aag aaa att gtc tac aga gag tat gaa cca tat ttt aag aaa gaa<br>Phe Lys Lys Ile Val Tyr Arg Glu Tyr Glu Pro Tyr Phe Lys Lys Glu<br>        35                  40                  45 | 144 |
| aaa cca caa tct acc att tca gga ctt ctt ggg cct act tta tat gct<br>Lys Pro Gln Ser Thr Ile Ser Gly Leu Leu Gly Pro Thr Leu Tyr Ala<br>    50                  55                  60 | 192 |
| gaa gtc gga gac atc ata aaa gtt cac ttt aaa aat aag gca gat aag<br>Glu Val Gly Asp Ile Ile Lys Val His Phe Lys Asn Lys Ala Asp Lys<br>65                  70                  75                  80 | 240 |
| ccc ttg agc atc cat cct caa gga att agg tac agt aaa tta tca gaa<br>Pro Leu Ser Ile His Pro Gln Gly Ile Arg Tyr Ser Lys Leu Ser Glu<br>                85                  90                  95 | 288 |
| ggt gct tct tac ctt gac cac gca gct gct gca aca ttc cct gcg gag<br>Gly Ala Ser Tyr Leu Asp His Ala Ala Ala Thr Phe Pro Ala Glu<br>            100                 105                 110 | 336 |
| aag atg gac gac gct gtg gct cca ggc cga gaa tac acc tat gaa tgg<br>Lys Met Asp Asp Ala Val Ala Pro Gly Arg Glu Tyr Thr Tyr Glu Trp<br>        115                 120                 125 | 384 |
| agt atc agt gag gac agt gga ccc acc cat gat gac cct cca tgc ctc<br>Ser Ile Ser Glu Asp Ser Gly Pro Thr His Asp Asp Pro Pro Cys Leu<br>    130                 135                 140 | 432 |
| aca cac atc tat tac tcc cat gaa aat ctg atc gag gat ttc aac tct<br>Thr His Ile Tyr Tyr Ser His Glu Asn Leu Ile Glu Asp Phe Asn Ser<br>145                 150                 155                 160 | 480 |
| ggg ctg att ggg ccc ctg ctt atc tgt aaa aaa ggg acc cta act gag<br>Gly Leu Ile Gly Pro Leu Leu Ile Cys Lys Lys Gly Thr Leu Thr Glu<br>                165                 170                 175 | 528 |
| ggt ggg aca cag aag acg ttt gac aag caa atc gtg cta cta ttt gct<br>Gly Gly Thr Gln Lys Thr Phe Asp Lys Gln Ile Val Leu Leu Phe Ala<br>            180                 185                 190 | 576 |
| gtg ttt gat gaa agc aag agc tgg agc cag tca tca tcc cta atg tac<br>Val Phe Asp Glu Ser Lys Ser Trp Ser Gln Ser Ser Ser Leu Met Tyr<br>        195                 200                 205 | 624 |
| aca gtc aat gga tat gtg aat ggg aca atg cca gat ata aca gtt tgt<br>Thr Val Asn Gly Tyr Val Asn Gly Thr Met Pro Asp Ile Thr Val Cys<br>    210                 215                 220 | 672 |
| gcc cat gac cac atc agc tgg cat ctg ctg gga atg agc tcg ggg cca<br>Ala His Asp His Ile Ser Trp His Leu Leu Gly Met Ser Ser Gly Pro<br>225                 230                 235                 240 | 720 |
| gaa tta ttc tcc att cat ttc aac ggc cag gtc ctg gag cag aac cat<br>Glu Leu Phe Ser Ile His Phe Asn Gly Gln Val Leu Glu Gln Asn His<br>                245                 250                 255 | 768 |
| cat aag gtc tca gcc atc acc ctt gtc agt gct aca tcc act acc gca<br>His Lys Val Ser Ala Ile Thr Leu Val Ser Ala Thr Ser Thr Thr Ala<br>            260                 265                 270 | 816 |
| aat atg act gtg ggc cca gag gga aag tgg atc ata tct tct ctc acc<br>Asn Met Thr Val Gly Pro Glu Gly Lys Trp Ile Ile Ser Ser Leu Thr<br>        275                 280                 285 | 864 |

```
cca aaa cat ttg caa gct ggg atg cag gct tac att gac att aaa aac    912
Pro Lys His Leu Gln Ala Gly Met Gln Ala Tyr Ile Asp Ile Lys Asn
    290             295                 300 tgc cca aag aaa acc agg aat ctt aag aaa ata act cgt gag cag agg    960
Cys Pro Lys Lys Thr Arg Asn Leu Lys Lys Ile Thr Arg Glu Gln Arg
305             310                 315                 320 cgg cac atg aag agg tgg gaa tac ttc att gct gca gag gaa gtc att   1008
Arg His Met Lys Arg Trp Glu Tyr Phe Ile Ala Ala Glu Glu Val Ile
                325                 330                 335 tgg gac tat gca cct gta ata cca gcg aat atg gac aaa aaa tac agg   1056
Trp Asp Tyr Ala Pro Val Ile Pro Ala Asn Met Asp Lys Lys Tyr Arg
            340                 345                 350 tct cag cat ttg gat aat ttc tca aac caa att gga aaa cat tat aag   1104
Ser Gln His Leu Asp Asn Phe Ser Asn Gln Ile Gly Lys His Tyr Lys
        355                 360                 365 aaa gtt atg tac aca cag tac gaa gat gag tcc ttc acc aaa cat aca   1152
Lys Val Met Tyr Thr Gln Tyr Glu Asp Glu Ser Phe Thr Lys His Thr
    370                 375                 380 gtg aat ccc aat atg aaa gaa gat ggg att ttg ggt cct att atc aga   1200
Val Asn Pro Asn Met Lys Glu Asp Gly Ile Leu Gly Pro Ile Ile Arg
385             390                 395                 400 gcc cag gtc aga gac aca ctc aaa atc gtg ttc aaa aat atg gcc agc   1248
Ala Gln Val Arg Asp Thr Leu Lys Ile Val Phe Lys Asn Met Ala Ser
                405                 410                 415 cgc ccc tat agc att tac cct cat gga gtg acc ttc tcg cct tat gaa   1296
Arg Pro Tyr Ser Ile Tyr Pro His Gly Val Thr Phe Ser Pro Tyr Glu
            420                 425                 430 gat gaa gtc aac tct tct ttc acc tca ggc agg aac aac acc atg atc   1344
Asp Glu Val Asn Ser Ser Phe Thr Ser Gly Arg Asn Asn Thr Met Ile
        435                 440                 445 aga gca gtt caa cca ggg gaa acc tat act tat aag tgg aac atc tta   1392
Arg Ala Val Gln Pro Gly Glu Thr Tyr Thr Tyr Lys Trp Asn Ile Leu
    450                 455                 460 gag ttt gat gaa ccc aca gaa aat gat gcc cag tgc tta aca aga cca   1440
Glu Phe Asp Glu Pro Thr Glu Asn Asp Ala Gln Cys Leu Thr Arg Pro
465             470                 475                 480 tac tac agt gac gtg gac atc atg aga gac atc gcc tct ggg cta ata   1488
Tyr Tyr Ser Asp Val Asp Ile Met Arg Asp Ile Ala Ser Gly Leu Ile
                485                 490                 495 gga cta ctt cta atc tgt aag agc aga tcc ctg gac agg cga gga ata   1536
Gly Leu Leu Leu Ile Cys Lys Ser Arg Ser Leu Asp Arg Arg Gly Ile
            500                 505                 510 cag agg gca gca gac atc gaa cag cag gct gtg ttt gct gtg ttt gat   1584
Gln Arg Ala Ala Asp Ile Glu Gln Gln Ala Val Phe Ala Val Phe Asp
        515                 520                 525 gag aac aaa agc tgg tac ctt gag gac aac atc aac aag ttt tgt gaa   1632
Glu Asn Lys Ser Trp Tyr Leu Glu Asp Asn Ile Asn Lys Phe Cys Glu
    530                 535                 540 aat cct gat gag gtg aaa cgt gat gac ccc aag ttt tat gaa tca aac   1680
Asn Pro Asp Glu Val Lys Arg Asp Asp Pro Lys Phe Tyr Glu Ser Asn
545             550                 555                 560 atc atg agc act atc aat ggc tat gtg cct gag agc ata act act ctt   1728
Ile Met Ser Thr Ile Asn Gly Tyr Val Pro Glu Ser Ile Thr Thr Leu
                565                 570                 575 gga ttc tgc ttt gat gac act gtc cag tgg cac ttc tgt agt gtg ggg   1776
Gly Phe Cys Phe Asp Asp Thr Val Gln Trp His Phe Cys Ser Val Gly
            580                 585                 590 acc cag aat gaa att ttg acc atc cac ttc act ggg cac tca ttc atc   1824
Thr Gln Asn Glu Ile Leu Thr Ile His Phe Thr Gly His Ser Phe Ile
        595                 600                 605
```

-continued

```
tat gga aag agg cat gag gac acc ttg acc ctc ttc ccc atg cgt gga         1872
Tyr Gly Lys Arg His Glu Asp Thr Leu Thr Leu Phe Pro Met Arg Gly
        610                 615                 620 gaa tct gtg acg gtc aca atg gat aat gtt gga act tgg atg tta act         1920
Glu Ser Val Thr Val Thr Met Asp Asn Val Gly Thr Trp Met Leu Thr
625                 630                 635                 640 tcc atg aat tct agt cca aga agc aaa aag ctg agg ctg aaa ttc agg         1968
Ser Met Asn Ser Ser Pro Arg Ser Lys Lys Leu Arg Leu Lys Phe Arg
                645                 650                 655 gat gtt aaa tgt atc cca gat gat gat gaa gac tca tat gag att ttt         2016
Asp Val Lys Cys Ile Pro Asp Asp Asp Glu Asp Ser Tyr Glu Ile Phe
            660                 665                 670 gaa cct cca gaa tct aca gtc atg gct aca cgg aaa atg cat gat cgt         2064
Glu Pro Pro Glu Ser Thr Val Met Ala Thr Arg Lys Met His Asp Arg
        675                 680                 685 tta gaa cct gaa gat gaa gag agt gat gct gac tat gat tac cag aac         2112
Leu Glu Pro Glu Asp Glu Glu Ser Asp Ala Asp Tyr Asp Tyr Gln Asn
    690                 695                 700 aga ctg gct gca gca tta gga att agg agg gaa aca gat att gaa gac         2160
Arg Leu Ala Ala Ala Leu Gly Ile Arg Arg Glu Thr Asp Ile Glu Asp
705                 710                 715                 720 tct gat gat att cca gaa gat acc aca tat aag aaa gta gtt ttt cga         2208
Ser Asp Asp Ile Pro Glu Asp Thr Thr Tyr Lys Lys Val Val Phe Arg
                725                 730                 735 aag tac ctc gac agc act ttt acc aaa cgt gat cct cga ggg gag tat         2256
Lys Tyr Leu Asp Ser Thr Phe Thr Lys Arg Asp Pro Arg Gly Glu Tyr
            740                 745                 750 gaa gag cat ctc gga att ctt ggt cct att atc aga gct gaa gtg gat         2304
Glu Glu His Leu Gly Ile Leu Gly Pro Ile Ile Arg Ala Glu Val Asp
        755                 760                 765 gat gtt atc caa gtt cgt ttt aaa aat tta gca tcc aga ccg tat tct         2352
Asp Val Ile Gln Val Arg Phe Lys Asn Leu Ala Ser Arg Pro Tyr Ser
    770                 775                 780 cta cat gcc cat gga ctt tcc tat gaa aaa tca tca gag gga aag act         2400
Leu His Ala His Gly Leu Ser Tyr Glu Lys Ser Ser Glu Gly Lys Thr
785                 790                 795                 800 tat gaa gat gac tct cct gaa tgg ttt aag gaa gat aat gct gtt cag         2448
Tyr Glu Asp Asp Ser Pro Glu Trp Phe Lys Glu Asp Asn Ala Val Gln
                805                 810                 815 cca aat agc agt tat acc tac gta tgg cat gcc act gag cga tca ggg         2496
Pro Asn Ser Ser Tyr Thr Tyr Val Trp His Ala Thr Glu Arg Ser Gly
            820                 825                 830 cca gaa agt cct ggc tct gcc tgt cgg gct tgg gcc tac tac tca gct         2544
Pro Glu Ser Pro Gly Ser Ala Cys Arg Ala Trp Ala Tyr Tyr Ser Ala
        835                 840                 845 gtg aac cca gaa aaa gat att cac tca ggc ttg ata ggt ccc ctc cta         2592
Val Asn Pro Glu Lys Asp Ile His Ser Gly Leu Ile Gly Pro Leu Leu
    850                 855                 860 atc tgc caa aaa gga ata cta cat aag gac agc aac atg cct gtg gac         2640
Ile Cys Gln Lys Gly Ile Leu His Lys Asp Ser Asn Met Pro Val Asp
865                 870                 875                 880 atg aga gaa ttt gtc tta cta ttt atg acc ttt gat gaa aag aag agc         2688
Met Arg Glu Phe Val Leu Leu Phe Met Thr Phe Asp Glu Lys Lys Ser
                885                 890                 895 tgg tac tat gaa aag aag tcc cga agt tct tgg aga ctc aca tcc tca         2736
Trp Tyr Tyr Glu Lys Lys Ser Arg Ser Ser Trp Arg Leu Thr Ser Ser
            900                 905                 910 gaa atg aaa aaa tcc cat gag ttt cac gcc att aat ggg atg atc tac         2784
Glu Met Lys Lys Ser His Glu Phe His Ala Ile Asn Gly Met Ile Tyr
```

```
                915                 920                 925
agc ttg cct ggc ctg aaa atg tat gag caa gag tgg gtg agg tta cac      2832
Ser Leu Pro Gly Leu Lys Met Tyr Glu Gln Glu Trp Val Arg Leu His
        930                 935                 940 ctg ctg aac ata ggc ggc tcc caa gac att cac gtg gtt cac ttt cac      2880
Leu Leu Asn Ile Gly Gly Ser Gln Asp Ile His Val Val His Phe His
945                 950                 955                 960 ggc cag acc ttg ctg gaa aat ggc aat aaa cag cac cag tta ggg gtc      2928
Gly Gln Thr Leu Leu Glu Asn Gly Asn Lys Gln His Gln Leu Gly Val
            965                 970                 975 tgg ccc ctt ctg cct ggt tca ttt aaa act ctt gaa atg aag gca tca      2976
Trp Pro Leu Leu Pro Gly Ser Phe Lys Thr Leu Glu Met Lys Ala Ser
        980                 985                 990 aaa cct ggc tgg tgg ctc cta aac aca gag gtt gga gaa aac cag aga      3024
Lys Pro Gly Trp Trp Leu Leu Asn Thr Glu Val Gly Glu Asn Gln Arg
    995                 1000                1005 gca ggg atg caa acg cca ttt ctt atc atg gac aga gac tgt agg atg      3072
Ala Gly Met Gln Thr Pro Phe Leu Ile Met Asp Arg Asp Cys Arg Met
    1010                1015                1020 cca atg gga cta agc act ggt atc ata tct gat tca cag atc aag gct      3120
Pro Met Gly Leu Ser Thr Gly Ile Ile Ser Asp Ser Gln Ile Lys Ala
1025                1030                1035                1040 tca gag ttt ctg ggt tac tgg gag ccc aga tta gca aga tta aac aat      3168
Ser Glu Phe Leu Gly Tyr Trp Glu Pro Arg Leu Ala Arg Leu Asn Asn
            1045                1050                1055 ggt gga tct tat aat gct tgg agt gta gaa aaa ctt gca gca gaa ttt      3216
Gly Gly Ser Tyr Asn Ala Trp Ser Val Glu Lys Leu Ala Ala Glu Phe
        1060                1065                1070 gcc tct aaa cct tgg atc cag gtg gac atg caa aag gaa gtc ata atc      3264
Ala Ser Lys Pro Trp Ile Gln Val Asp Met Gln Lys Glu Val Ile Ile
    1075                1080                1085 aca ggg atc cag acc caa ggt gcc aaa cac tac ctg aag tcc tgc tat      3312
Thr Gly Ile Gln Thr Gln Gly Ala Lys His Tyr Leu Lys Ser Cys Tyr
    1090                1095                1100 acc aca gag ttc tat gta gct tac agt tcc aac cag atc aac tgg cag      3360
Thr Thr Glu Phe Tyr Val Ala Tyr Ser Ser Asn Gln Ile Asn Trp Gln
1105                1110                1115                1120 atc ttc aaa ggg aac agc aca agg aat gtg atg tat ttt aat ggc aat      3408
Ile Phe Lys Gly Asn Ser Thr Arg Asn Val Met Tyr Phe Asn Gly Asn
            1125                1130                1135 tca gat gcc tct aca ata aaa gag aat cag ttt gac cca cct att gtg      3456
Ser Asp Ala Ser Thr Ile Lys Glu Asn Gln Phe Asp Pro Pro Ile Val
        1140                1145                1150 gct aga tat att agg atc tct cca act cga gcc tat aac aga cct acc      3504
Ala Arg Tyr Ile Arg Ile Ser Pro Thr Arg Ala Tyr Asn Arg Pro Thr
    1155                1160                1165 ctt cga ttg gaa ctg caa ggt tgt gag gta aat gga tgt tcc aca ccc      3552
Leu Arg Leu Glu Leu Gln Gly Cys Glu Val Asn Gly Cys Ser Thr Pro
    1170                1175                1180 ctg ggt atg gaa aat gga aag ata gaa aac aag caa atc aca gct tct      3600
Leu Gly Met Glu Asn Gly Lys Ile Glu Asn Lys Gln Ile Thr Ala Ser
1185                1190                1195                1200 tcg ttt aag aaa tct tgg tgg gga gat tac tgg gaa ccc ttc cgt gcc      3648
Ser Phe Lys Lys Ser Trp Trp Gly Asp Tyr Trp Glu Pro Phe Arg Ala
            1205                1210                1215 cgt ctg aat gcc cag gga cgt gtg aat gcc tgg caa gcc aag gca aac      3696
Arg Leu Asn Ala Gln Gly Arg Val Asn Ala Trp Gln Ala Lys Ala Asn
        1220                1225                1230 aac aat aag cag tgg cta gaa att gat cta ctc aag atc aag aag ata      3744
```

-continued

| | | | | | | | | | | | | |
|---|---|---|---|---|---|---|---|---|---|---|---|---|
|Asn|Asn|Lys|Gln|Trp|Leu|Glu|Ile|Asp|Leu|Leu|Lys|Ile|Lys|Lys|Ile|
| |1235| | | |1240| | | | |1245| | |

```
acg gca att ata aca cag ggc tgc aag tct ctg tcc tct gaa atg tat    3792
Thr Ala Ile Ile Thr Gln Gly Cys Lys Ser Leu Ser Ser Glu Met Tyr
    1250                1255                1260 gta aag agc tat acc atc cac tac agt gag cag gga gtg gaa tgg aaa    3840
Val Lys Ser Tyr Thr Ile His Tyr Ser Glu Gln Gly Val Glu Trp Lys
1265            1270                1275                1280 cca tac agg ctg aaa tcc tcc atg gtg gac aag att ttt gaa gga aat    3888
Pro Tyr Arg Leu Lys Ser Ser Met Val Asp Lys Ile Phe Glu Gly Asn
                1285                1290                1295 act aat acc aaa gga cat gtg aag aac ttt ttc aac ccc cca atc att    3936
Thr Asn Thr Lys Gly His Val Lys Asn Phe Phe Asn Pro Pro Ile Ile
            1300                1305                1310 tcc agg ttt atc cgt gtc att cct aaa aca tgg aat caa agt att gca    3984
Ser Arg Phe Ile Arg Val Ile Pro Lys Thr Trp Asn Gln Ser Ile Ala
        1315                1320                1325 ctt cgc ctg gaa ctc ttt ggc tgt gat att tac tagaattgaa cattcaaaaa    4037
Leu Arg Leu Glu Leu Phe Gly Cys Asp Ile Tyr
    1330                1335 cccctggaag agactcttta agacctcaaa ccatttagaa tgggcaatgt attttacgct    4097
gtgttaaatg ttaacagttt tccactattt ctctttcttt tctattagtg aataaaattt    4157
tatac                                                                4162

<210> SEQ ID NO 30
<211> LENGTH: 1339
<212> TYPE: PRT
<213> ORGANISM: Homo sapiens

<400> SEQUENCE: 30
```

| | | | | | | | | | | | | | | | |
|---|---|---|---|---|---|---|---|---|---|---|---|---|---|---|---|
|Ala|Gln|Leu|Arg|Gln|Phe|Tyr|Val|Ala|Ala|Gln|Gly|Ile|Ser|Trp|Ser|
|1| | | |5| | | | |10| | | | |15| |

| | | | | | | | | | | | | |
|---|---|---|---|---|---|---|---|---|---|---|---|---|
|Tyr|Arg|Pro|Glu|Pro|Thr|Asn|Ser|Ser|Leu|Asn|Leu|Ser|Val|Thr|Ser|
| | | | |20| | | | |25| | | | |30| |

| | | | | | | | | | | | | | | | |
|---|---|---|---|---|---|---|---|---|---|---|---|---|---|---|---|
|Phe|Lys|Lys|Ile|Val|Tyr|Arg|Glu|Tyr|Glu|Pro|Tyr|Phe|Lys|Lys|Glu|
| | | | |35| | | | |40| | | | |45| |

| | | | | | | | | | | | | | | | |
|---|---|---|---|---|---|---|---|---|---|---|---|---|---|---|---|
|Lys|Pro|Gln|Ser|Thr|Ile|Ser|Gly|Leu|Leu|Gly|Pro|Thr|Leu|Tyr|Ala|
| | | | |50| | | | |55| | | | |60| |

| | | | | | | | | | | | | | | | |
|---|---|---|---|---|---|---|---|---|---|---|---|---|---|---|---|
|Glu|Val|Gly|Asp|Ile|Ile|Lys|Val|His|Phe|Lys|Asn|Lys|Ala|Asp|Lys|
|65| | | | |70| | | | |75| | | | |80|

| | | | | | | | | | | | | | | | |
|---|---|---|---|---|---|---|---|---|---|---|---|---|---|---|---|
|Pro|Leu|Ser|Ile|His|Pro|Gln|Gly|Ile|Arg|Tyr|Ser|Lys|Leu|Ser|Glu|
| | | | |85| | | | |90| | | | |95| |

| | | | | | | | | | | | | | | | |
|---|---|---|---|---|---|---|---|---|---|---|---|---|---|---|---|
|Gly|Ala|Ser|Tyr|Leu|Asp|His|Ala|Ala|Ala|Thr|Phe|Pro|Ala|Glu|
| | | | |100| | | | |105| | | | |110|

| | | | | | | | | | | | | | | | |
|---|---|---|---|---|---|---|---|---|---|---|---|---|---|---|---|
|Lys|Met|Asp|Asp|Ala|Val|Ala|Pro|Gly|Arg|Glu|Tyr|Thr|Tyr|Glu|Trp|
| | | | |115| | | | |120| | | | |125| |

| | | | | | | | | | | | | | | | |
|---|---|---|---|---|---|---|---|---|---|---|---|---|---|---|---|
|Ser|Ile|Ser|Glu|Asp|Ser|Gly|Pro|Thr|His|Asp|Asp|Pro|Pro|Cys|Leu|
| | | | |130| | | | |135| | | | |140| |

| | | | | | | | | | | | | | | | |
|---|---|---|---|---|---|---|---|---|---|---|---|---|---|---|---|
|Thr|His|Ile|Tyr|Tyr|Ser|His|Glu|Asn|Leu|Ile|Glu|Asp|Phe|Asn|Ser|
|145| | | | |150| | | | |155| | | | |160|

| | | | | | | | | | | | | | | | |
|---|---|---|---|---|---|---|---|---|---|---|---|---|---|---|---|
|Gly|Leu|Ile|Gly|Pro|Leu|Leu|Ile|Cys|Lys|Lys|Gly|Thr|Leu|Thr|Glu|
| | | | |165| | | | |170| | | | |175| |

| | | | | | | | | | | | | | | | |
|---|---|---|---|---|---|---|---|---|---|---|---|---|---|---|---|
|Gly|Gly|Thr|Gln|Lys|Thr|Phe|Asp|Lys|Gln|Ile|Val|Leu|Leu|Phe|Ala|
| | | | |180| | | | |185| | | | |190| |

| | | | | | | | | | | | | | | | |
|---|---|---|---|---|---|---|---|---|---|---|---|---|---|---|---|
|Val|Phe|Asp|Glu|Ser|Lys|Ser|Trp|Ser|Gln|Ser|Ser|Ser|Leu|Met|Tyr|
| | | | |195| | | | |200| | | | |205| |

```
Thr Val Asn Gly Tyr Val Asn Gly Thr Met Pro Asp Ile Thr Val Cys
    210                 215                 220
Ala His Asp His Ile Ser Trp His Leu Leu Gly Met Ser Ser Gly Pro
225                 230                 235                 240
Glu Leu Phe Ser Ile His Phe Asn Gly Gln Val Leu Glu Gln Asn His
                245                 250                 255
His Lys Val Ser Ala Ile Thr Leu Val Ser Ala Thr Ser Thr Thr Ala
            260                 265                 270
Asn Met Thr Val Gly Pro Glu Gly Lys Trp Ile Ile Ser Ser Leu Thr
        275                 280                 285
Pro Lys His Leu Gln Ala Gly Met Gln Ala Tyr Ile Asp Ile Lys Asn
    290                 295                 300
Cys Pro Lys Lys Thr Arg Asn Leu Lys Lys Ile Thr Arg Glu Gln Arg
305                 310                 315                 320
Arg His Met Lys Arg Trp Glu Tyr Phe Ile Ala Ala Glu Glu Val Ile
                325                 330                 335
Trp Asp Tyr Ala Pro Val Ile Pro Ala Asn Met Asp Lys Lys Tyr Arg
            340                 345                 350
Ser Gln His Leu Asp Asn Phe Ser Asn Gln Ile Gly Lys His Tyr Lys
        355                 360                 365
Lys Val Met Tyr Thr Gln Tyr Glu Asp Glu Ser Phe Thr Lys His Thr
    370                 375                 380
Val Asn Pro Asn Met Lys Glu Asp Gly Ile Leu Gly Pro Ile Ile Arg
385                 390                 395                 400
Ala Gln Val Arg Asp Thr Leu Lys Ile Val Phe Lys Asn Met Ala Ser
                405                 410                 415
Arg Pro Tyr Ser Ile Tyr Pro His Gly Val Thr Phe Ser Pro Tyr Glu
            420                 425                 430
Asp Glu Val Asn Ser Ser Phe Thr Ser Gly Arg Asn Asn Thr Met Ile
        435                 440                 445
Arg Ala Val Gln Pro Gly Glu Thr Tyr Thr Tyr Lys Trp Asn Ile Leu
    450                 455                 460
Glu Phe Asp Glu Pro Thr Glu Asn Asp Ala Gln Cys Leu Thr Arg Pro
465                 470                 475                 480
Tyr Tyr Ser Asp Val Asp Ile Met Arg Asp Ile Ala Ser Gly Leu Ile
                485                 490                 495
Gly Leu Leu Leu Ile Cys Lys Ser Arg Ser Leu Asp Arg Arg Gly Ile
            500                 505                 510
Gln Arg Ala Ala Asp Ile Glu Gln Gln Ala Val Phe Ala Val Phe Asp
        515                 520                 525
Glu Asn Lys Ser Trp Tyr Leu Glu Asp Asn Ile Asn Lys Phe Cys Glu
    530                 535                 540
Asn Pro Asp Glu Val Lys Arg Asp Asp Pro Lys Phe Tyr Glu Ser Asn
545                 550                 555                 560
Ile Met Ser Thr Ile Asn Gly Tyr Val Pro Glu Ser Ile Thr Thr Leu
                565                 570                 575
Gly Phe Cys Phe Asp Asp Thr Val Gln Trp His Phe Cys Ser Val Gly
            580                 585                 590
Thr Gln Asn Glu Ile Leu Thr Ile His Phe Thr Gly His Ser Phe Ile
        595                 600                 605
Tyr Gly Lys Arg His Glu Asp Thr Leu Thr Leu Phe Pro Met Arg Gly
    610                 615                 620
```

-continued

```
Glu Ser Val Thr Val Thr Met Asp Asn Val Gly Thr Trp Met Leu Thr
625                 630                 635                 640

Ser Met Asn Ser Ser Pro Arg Ser Lys Lys Leu Arg Leu Lys Phe Arg
                645                 650                 655

Asp Val Lys Cys Ile Pro Asp Asp Glu Asp Ser Tyr Glu Ile Phe
            660                 665                 670

Glu Pro Pro Glu Ser Thr Val Met Ala Thr Arg Lys Met His Asp Arg
        675                 680                 685

Leu Glu Pro Glu Asp Glu Ser Asp Ala Asp Tyr Asp Tyr Gln Asn
    690                 695                 700

Arg Leu Ala Ala Ala Leu Gly Ile Arg Arg Glu Thr Asp Ile Glu Asp
705                 710                 715                 720

Ser Asp Asp Ile Pro Glu Asp Thr Thr Tyr Lys Lys Val Val Phe Arg
                725                 730                 735

Lys Tyr Leu Asp Ser Thr Phe Thr Lys Arg Asp Pro Arg Gly Glu Tyr
            740                 745                 750

Glu Glu His Leu Gly Ile Leu Gly Pro Ile Ile Arg Ala Glu Val Asp
        755                 760                 765

Asp Val Ile Gln Val Arg Phe Lys Asn Leu Ala Ser Arg Pro Tyr Ser
    770                 775                 780

Leu His Ala His Gly Leu Ser Tyr Glu Lys Ser Ser Glu Gly Lys Thr
785                 790                 795                 800

Tyr Glu Asp Asp Ser Pro Glu Trp Phe Lys Glu Asp Asn Ala Val Gln
                805                 810                 815

Pro Asn Ser Ser Tyr Thr Tyr Val Trp His Ala Thr Glu Arg Ser Gly
            820                 825                 830

Pro Glu Ser Pro Gly Ser Ala Cys Arg Ala Trp Ala Tyr Tyr Ser Ala
        835                 840                 845

Val Asn Pro Glu Lys Asp Ile His Ser Gly Leu Ile Gly Pro Leu Leu
    850                 855                 860

Ile Cys Gln Lys Gly Ile Leu His Lys Asp Ser Asn Met Pro Val Asp
865                 870                 875                 880

Met Arg Glu Phe Val Leu Leu Phe Met Thr Phe Asp Glu Lys Lys Ser
                885                 890                 895

Trp Tyr Tyr Glu Lys Lys Ser Arg Ser Ser Trp Arg Leu Thr Ser Ser
            900                 905                 910

Glu Met Lys Lys Ser His Glu Phe His Ala Ile Asn Gly Met Ile Tyr
        915                 920                 925

Ser Leu Pro Gly Leu Lys Met Tyr Glu Gln Glu Trp Val Arg Leu His
    930                 935                 940

Leu Leu Asn Ile Gly Gly Ser Gln Asp Ile His Val Val His Phe His
945                 950                 955                 960

Gly Gln Thr Leu Leu Glu Asn Gly Asn Lys Gln His Gln Leu Gly Val
                965                 970                 975

Trp Pro Leu Leu Pro Gly Ser Phe Lys Thr Leu Glu Met Lys Ala Ser
            980                 985                 990

Lys Pro Gly Trp Trp Leu Leu Asn Thr Glu Val Gly Glu Asn Gln Arg
        995                 1000                1005

Ala Gly Met Gln Thr Pro Phe Leu Ile Met Asp Arg Asp Cys Arg Met
    1010                1015                1020

Pro Met Gly Leu Ser Thr Gly Ile Ile Ser Asp Ser Gln Ile Lys Ala
1025                1030                1035                1040

Ser Glu Phe Leu Gly Tyr Trp Glu Pro Arg Leu Ala Arg Leu Asn Asn
```

-continued

```
                    1045                1050                1055
Gly Gly Ser Tyr Asn Ala Trp Ser Val Glu Lys Leu Ala Ala Glu Phe
                1060                1065                1070
Ala Ser Lys Pro Trp Ile Gln Val Asp Met Gln Lys Glu Val Ile Ile
            1075                1080                1085
Thr Gly Ile Gln Thr Gln Gly Ala Lys His Tyr Leu Lys Ser Cys Tyr
        1090                1095                1100
Thr Thr Glu Phe Tyr Val Ala Tyr Ser Ser Asn Gln Ile Asn Trp Gln
1105                1110                1115                1120
Ile Phe Lys Gly Asn Ser Thr Arg Asn Val Met Tyr Phe Asn Gly Asn
                1125                1130                1135
Ser Asp Ala Ser Thr Ile Lys Glu Asn Gln Phe Asp Pro Pro Ile Val
            1140                1145                1150
Ala Arg Tyr Ile Arg Ile Ser Pro Thr Arg Ala Tyr Asn Arg Pro Thr
        1155                1160                1165
Leu Arg Leu Glu Leu Gln Gly Cys Glu Val Asn Gly Cys Ser Thr Pro
    1170                1175                1180
Leu Gly Met Glu Asn Gly Lys Ile Glu Asn Lys Gln Ile Thr Ala Ser
1185                1190                1195                1200
Ser Phe Lys Lys Ser Trp Trp Gly Asp Tyr Trp Glu Pro Phe Arg Ala
                1205                1210                1215
Arg Leu Asn Ala Gln Gly Arg Val Asn Ala Trp Gln Ala Lys Ala Asn
            1220                1225                1230
Asn Asn Lys Gln Trp Leu Glu Ile Asp Leu Leu Lys Ile Lys Lys Ile
        1235                1240                1245
Thr Ala Ile Ile Thr Gln Gly Cys Lys Ser Leu Ser Ser Glu Met Tyr
    1250                1255                1260
Val Lys Ser Tyr Thr Ile His Tyr Ser Glu Gln Gly Val Glu Trp Lys
1265                1270                1275                1280
Pro Tyr Arg Leu Lys Ser Ser Met Val Asp Lys Ile Phe Glu Gly Asn
                1285                1290                1295
Thr Asn Thr Lys Gly His Val Lys Asn Phe Phe Asn Pro Pro Ile Ile
            1300                1305                1310
Ser Arg Phe Ile Arg Val Ile Pro Lys Thr Trp Asn Gln Ser Ile Ala
        1315                1320                1325
Leu Arg Leu Glu Leu Phe Gly Cys Asp Ile Tyr
    1330                1335
```

AMINO ACID-SUBSTITUTED COAGULATION FACTOR V

CROSS-REFERENCE TO RELATED APPLICATIONS

This application is a continuation application of co-pending International Application PCT/CA2004/001089, filed Jul. 23, 2004, which designated the U.S. and which claims the benefit under 35 U.S.C. § 119(e) of U.S. Provisional Application 60/489,124, filed Jul. 23, 2003; the contents of which are herewith incorporated by reference in their entirety.

This application relates to provisional application Ser. No. 60/459,647, filed on Apr. 3, 2003, and entitled USE OF COAGULATION PROTEINS TO LYSE CLOTS, which is incorporated herein by reference.

The present invention relates to the therapeutic use of coagulation proteins to control blood clot formation and more specifically, the invention relates to the therapeutic use of coagulation Factor V (FV).

BACKGROUND OF THE INVENTION

The ability of the body to control the flow of blood is paramount to healthy cardiovascular functions. The process of blood clotting and the subsequent dissolution of the clot, following repair of injured tissue, is termed hemostasis and comprises the clotting cascade. Several coagulation factors are involved in the cascade that results in the activation of thrombin and ultimately in the formation the fibrin clot.

Among these factors, the pivotal function of the blood coagulation proteins, Factor Va (FVa) and Factor Xa (FXa), is to activate prothrombin (II) to thrombin (IIa), which is directly responsible for producing fibrin clot (FIG. 1).

As the inactive precursor of coagulation FVa, FV is an essential clotting protein. FVa functions to accelerate the factor Xa-dependent production of thrombin by five orders of magnitude. The generation of both FVa and FVa activity is strictly regulated by physiological anticoagulants. Too much activity increases the risk of thrombotic disease, whereas too little results in severe hemophilia. An example of the former is the most prevalent inherited coagulation mutation (arginine 506 to glutamine) resulting in a form of Va, termed Va Leiden, that is protected from the key anticoagulant, activated protein C. Transfusion with normal plasma to ameliorate the effect of V Leiden leads to even more clotting activity. Therefore prevention of further thrombosis in these patients is controlled indirectly by use of therapeutics that lead to reduction in the activity of other clotting proteins.

Part of the molecular mechanism by which FV and FVa ultimately activate prothrombin (II) and thrombin (IIa) is understood. FVa and factor Xa must simultaneously associate with anionic phospholipid in the presence of Ca 2+ to form the physiologically relevant enzyme-cofactor complex, prothrombinase. Using plasma-derived human FVa, we recently reported (Zeibdawi, A. R. et al. (2001) *J. Biol. Chem.* 276 (23), 19929-19936) that leucine 94-lysine 109 (L94-K109) within the A1 domain appears to play a critical part in the FVa light chain (FVaL) and FVa heavy chain (FVaH) $Ca^{2+}$-dependent association. However, other structure-function relationships for the L94-K109 region remain to be elucidated to more fully understand their role in thrombin formation. Furthermore, it will be appreciated that further understanding of this structure-function relationship is needed to devise new therapeutic strategies for the various known coagulation diseases.

SUMMARY OF THE INVENTION

In one aspect of this invention, there is provided a human FV derivative that reduces blood clotting activity, by reducing thrombin generation, when compared to wild-type human FV. In one embodiment, the human FV of the present invention comprises single-point and multi-point mutations, encompassed by aspartic acid 79 to glutamic acid 119.

In another embodiment, there is also provided a human FV derivative, which reduces blood clotting activity, produced by the process comprising the steps of transforming a whole cell with a vector containing a nucleic acid encoding a human FV derivative, culturing said whole cell in a medium appropriate for expression of said human FV derivative and collecting the human factor derivative from the culture medium.

In a further embodiment of the present invention, there is provided a method for treating thrombotic diseases comprising the administration to a subject in need thereof of a human FV derivative having a reduced blood clotting activity compared to wild-type human FV.

In yet a further embodiment of the present invention, there is provided a method for purifying human FVaL which comprise providing a recombinant human FV, incorporating the recombinant in a solution to generate a dissociated human FVaH and human FVaL peptides, and isolating the human FVaL.

There is also provided a method for measuring physiological changes in cells comprising contacting the cells with human FVaL and detecting the human FVaL chain bound to the cells as a measure of the presence of anionic phospholipids.

In another aspect of the invention, the FV derivative can be used to modulate physiological responses of cells affected by thrombin.

BRIEF DESCRIPTION OF THE DRAWINGS

Further features and advantages of the present invention will become apparent from the following detailed description, taken in combination with the appended drawings, in which:

FIG. 4 is a gel electrophoresis of an incubation mixture comprising anionic phospholipids-containing large vesicles, thrombin and ΔFV or single-point mutant, wherein the FVa subunits remaining bound to the vesicles was probed with either FVaH or FVaL specific antibody at one hour intervals in the presence of calcium, with or without EDTA;

DETAILED DESCRIPTION OF THE PREFERRED EMBODIMENT

Prior to setting forth the invention in detail, it may be helpful to the understanding thereof to define the following terms:

The term "degenerate variant" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

"Operably linked" means that two or more entities are joined together such that they function in concert for their intended purposes. When referring to DNA segments, the phrase indicates, for example, that coding sequences are joined in the correct reading frame, and transcription initiates in the promoter and proceeds through the coding segment(s) to the terminator.

All references cited herein are incorporated by reference in their entirety.

Figure 1:
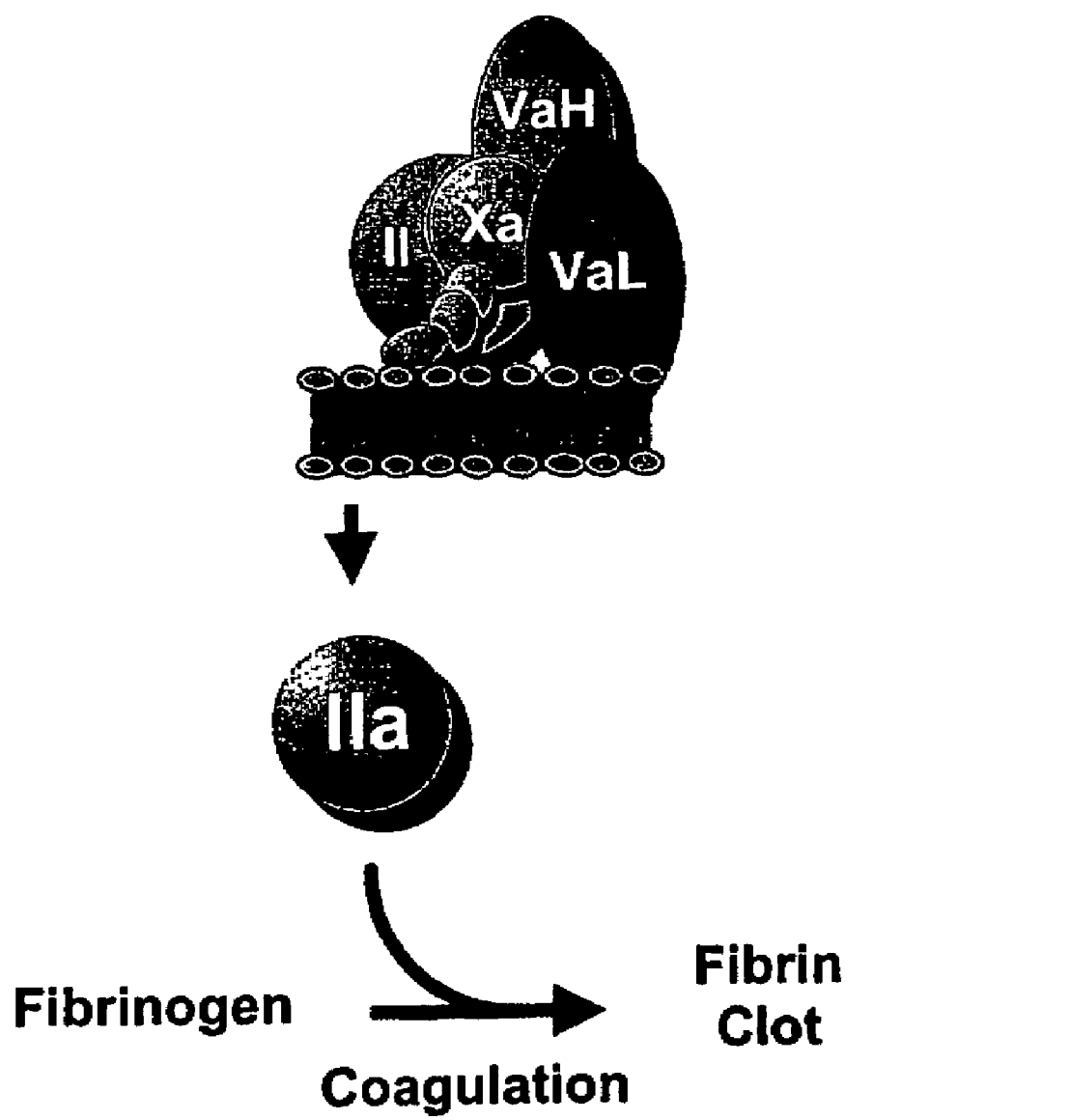
FIG. 1 is a diagram showing the coagulation proteins involved in the formation of blood clot.
Figure 2:
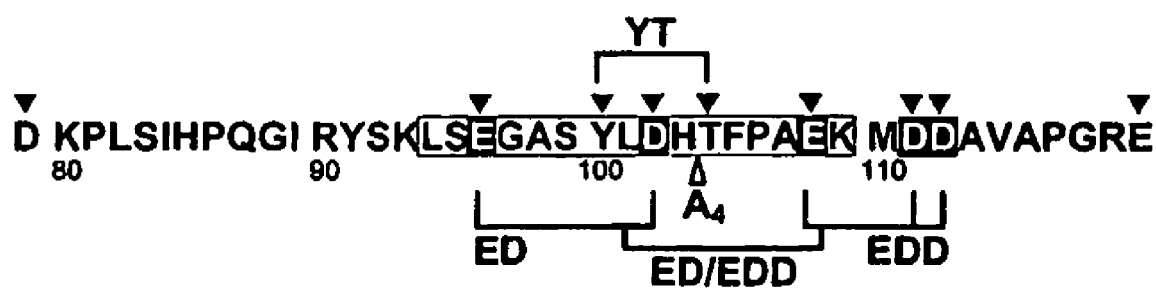
FIG. 2 is a partial sequence from FV showing amino acids 79-119 of SEQ ID NO:2.

To investigate the role of acidic amino acids within the D79-E119 and more specifically the L94-K109 region and the overlapping region predicted to be involved in the $Ca^{2+}$-dependent FVa subunit association, nine amino acids in ΔFV (amino acid SEQ ID NO:2 and corresponding nucleic acid SEQ ID NO:1) (a FV clone containing the secretory peptide of FV, the heavy subunit up to the thrombin-mediated activation site and the entire light subunit, but not containing the B-domain), were individually changed to Ala (FIG. 2, triangles). Through ceruloplasmin homology modeling, five of the amino acids we selected for mutation, E96, D102, E108, D111 and D112, were previously suggested to have an appropriate orientation to bind $Ca^{2+}$ (Villoutreix, B. O. et al. (1998) *Protein Science* 7, 1317-1325). Y100 and T104 were also mutated because they are highly conserved for unknown reasons in the A1-domains of ceruloplasmin, FVIII and FV from all species of known sequence. As specificity controls, the first acidic amino acid on either side of the implicated 94-112 segment, E119 and D79, were substituted with Ala to produce peptides of SEQ ID NO:4 and SEQ ID NO:6 respectively. The combined functional effects of these single residues were also investigated by producing four multipoint mutants also depicted in FIG. 2. The functional effect of a large disruption in the 94-112 region was evaluated by inserting four alanines ($A_4$) between H103 and T104 in a final mutant (SEQ ID NO:30). ΔFV and the 14 mutants secreted into serum-free culture medium were used for all studies. In each case, Western blots revealed a non-reducible protein with estimated molecular mass of ~170 kDa consistent with the expected $M_r$ of ΔFV. No anti-FV-reactive band was observed in the supernatant of cells transfected with the null expression vector devoid of the ΔFV sequence (mock).

Figure 3:
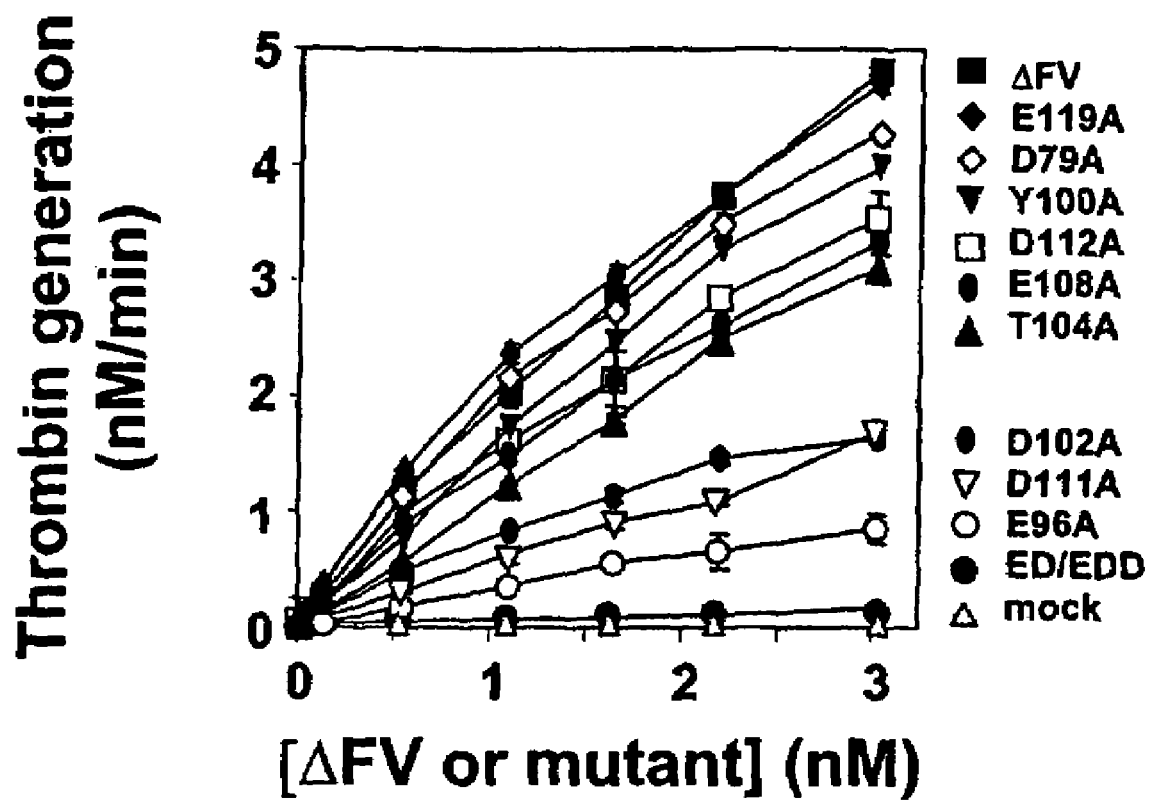
FIG. 3 is a graphic of thrombin generation as a function of recombinant FV engineered to be deficient in the central B-domain (ΔFV) or ΔFV single-point mutant concentrations.

To investigate a potential role for FV residues E96, D102, E108, D111 and D112 in prothrombinase function, the effect of substituting each to Ala (SEQ ID NO:20, SEQ ID NO:16, SEQ ID NO:12, SEQ ID NO:18 and SEQ ID NO:10 respectively) was evaluated and compared to ΔFV (SEQ ID NO:2). Prothrombinase function was assayed by measuring thrombin generation. It will be appreciated that measurement of thrombin generation is a reliable end point to measure blood clotting activity in view of the direct role of thrombin in the production of fibrin clots. The simultaneous substitution of all five acidic residues to Ala (ED/EDD, SEQ ID NO:22) resulted in nearly complete inhibition (98%) of ΔFV activity, which strongly supported a functional role for this region of FV (FIG. 3). To minimize allosteric changes that may accompany the large variation of charge due to the five mutations in ED/EDD and to localize individual residues contributing to function, the respective single point mutants were assayed. When compared to ΔFV, the largest effects on prothrombinase activity occurred when E96>D111>D102 were mutated. At 2.2 nM (the concentration where differences appeared to be maximal), substitution to Ala resulted in 81, 70 and 60% inhibition, respectively. Moderate reductions in activity were observed for T104 (SEQ ID NO:14) (35%), E108 (30%), and D112 (25%). In contrast, relatively small inhibitory effects were observed for substitution of Y100 (SEQ ID NO:8) (16%), D79 (SEQ ID NO:6) (7%) and E119 (SEQ ID NO:4) (0%) by Ala. The latter two mutations (D79 and E119) are the nearest acidic residues neighboring the predicted $Ca^{2+}$-sensitive region in the A1 domain (i.e. L94-D112). The finding that these have limited or no involvement in ΔFV function serves as a negative control for mutagenesis and supports the specific contribution of select residues.

Thus in one embodiment of the present invention there is provided a human FV derivative that comprises an amino acid sequence incorporating one or more of the mutants described above and that exhibit a reduced thrombin generation and therefore a reduced blood clotting activity when compared to wild-type human FV. In a preferred embodiment the amino acid sequence is selected from SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, and SEQ ID NO:30. Multiple mutants Y100/T104 (SEQ ID NO:24), E108/D111/D112 (SEQ ID NO:26) and E96/D102 (SEQ ID NO:28) also exhibit a reduced blood clotting activity as will be described below.

In another embodiment of the present invention there is also provided polynucleotides (SEQ ID NO:3, SEQ ID NO:5, SEQ ID NO:7, SEQ ID NO:9, SEQ ID NO: 11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, and SEQ ID NO:29) encoding human FV derivatives comprising amino acid sequences SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, and SEQ ID NO:30 respectively as well as nucleic acid sequences complementary to polynucleotides encoding human FV derivatives. It will be appreciated that a complementary sequence may include an anti-sense nucleotide.

The FV derivatives of the present invention also comprise derivatives with amino acid substitutions that do not substantially affect their reduced blood clotting activity. The polynucleotide sequences encoding the FV derivatives may similarly comprise base substitutions giving rise to the above mentioned amino acid substitutions. Furthermore, the polynucleotide sequences of the present invention comprise degenerate variants thereof.

It will be appreciated that the A1 domain of human FV may share a significant degree of homology with FV of other species (Yang TL et al. (1998) Blood, 91(12):4593-9). Accordingly, its structure and function are highly conserved and therefore the FV derivative and methods of the present invention also encompass other mammalian species.

DNA sequences encoding human FV derivatives can be expressed in vitro by DNA transfer into a suitable host cell in which a vector comprising the DNA sequences can be propagated and its DNA expressed. Host cells include prokaryotic and eukaryotic cells that may be cultured in a medium appropriate for expression of FV derivatives. In one embodiment of the present invention, the FV derivatives thus obtained can be isolated from the medium by techniques that are well known in the art such as by liquid chromatography for example. It will be appreciated that constructs comprising DNA sequences encoding human FV derivatives can be placed under the control of suitable expression control regulatory sequences.

Thus in a further embodiment of the invention there is provided a method for treating patients with conditions necessitating a reduced blood clotting activity. The method involves the administration of a FV derivative having a reduced blood clotting activity compared to wild-type human FV.

The effectiveness of the treatment method can be assessed by monitoring the patient for known signs or symptoms of the disorder. Tests for coagulation disorders are well known in the art. A non-limiting example is the prothrombin time assay.

Conditions that can be treated in accordance with this method comprise conditions in which a slower rate of clot formation is desirable. Such conditions may comprise but are not limited to: thrombosis, FV Leiden, or other hypercoagulable state based on excess FVa activity. It will be appreciated that administration of FV derivatives may be prophylactic to patients susceptible to the above mentioned conditions.

Preferred routes of administration are intravenous, intramuscular, subcutaneous, intraperitoneous, and intraarterial. It will be appreciated that other methods of administration may be used such as, for example, local administration at the site of a clot using a catheter.

The FV derivatives are preferably administered as part of a pharmaceutical composition which may also comprise a pharmaceutically acceptable carrier as would be obvious to one skilled in the art.

It will be appreciated that the FV derivatives of the present invention may be administered concurrently with one or more drugs that lead to reduction in the activity of other clotting proteins such as but not limited to heparin, aspirin, hirudin, tissue plasminogen activator and the like.

In another aspect of the invention, the FV derivatives can be used to modulate the function of cells, such as platelets, white blood cells, endothelial cells, smooth muscle cells and the like, which are affected by thrombin in normal physiological and pathological hemostasis, immunity, tissue remodelling or other processes.

Figure 4:
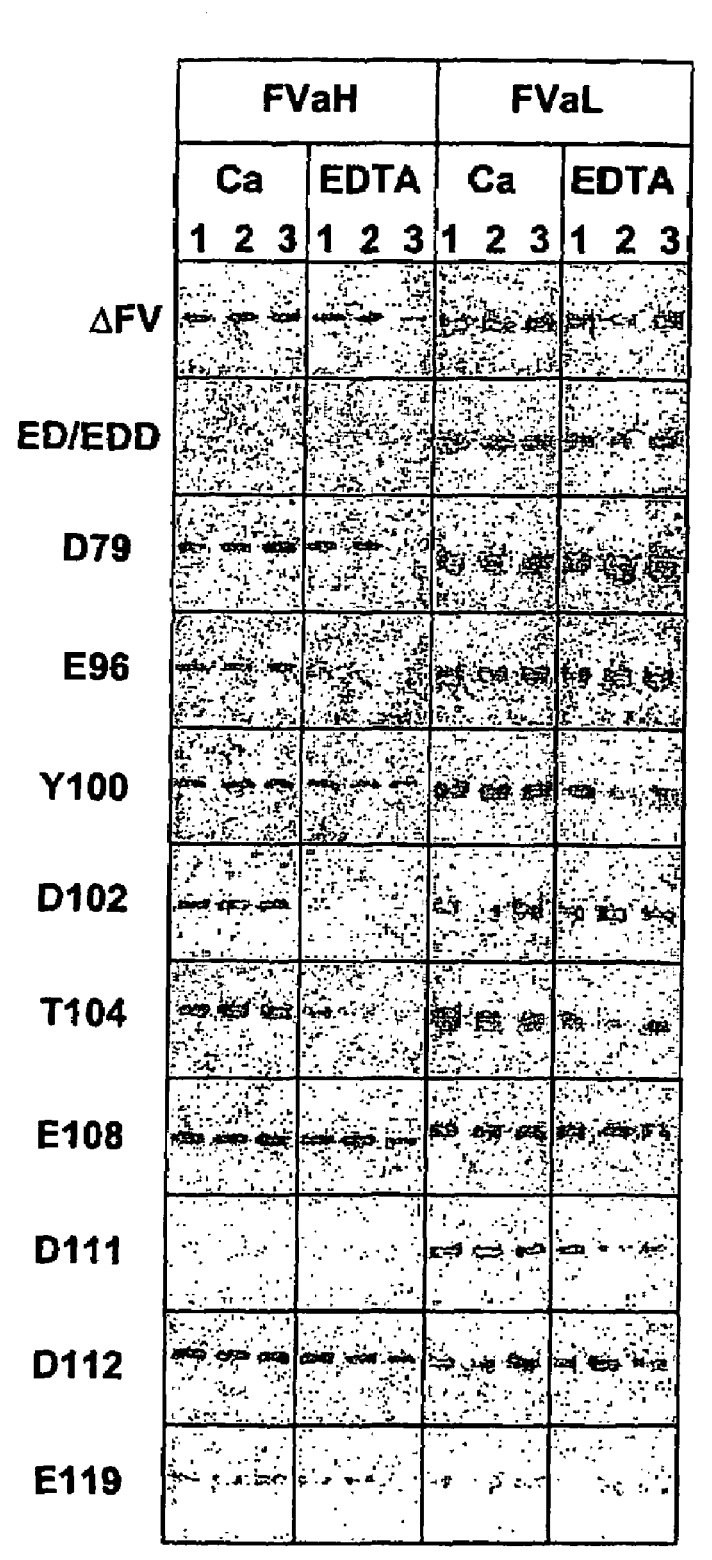

Having observed that at least E96, D102 and D111 play a significant part in ΔFV function, the present inventors next investigated whether the $Ca^{2+}$-dependent non-covalent interaction between FVaH and FVaL was affected. An experiment was designed to take advantage of the requirement for FVaL to anchor FVaH to anionic phospholipids (aPL). Equal antigenic concentrations of the ΔFV mutants were equilibrated with excess aPL-containing large vesicles (LV), which sediment easily. Each mixture was treated with thrombin to achieve complete conversion to FVa and the amount of each subunit bound to washed LV was probed with either a FVaH- or FVaL-specific antibody at one hour intervals. FVaL has been well established as the exclusive aPL-binding subunit and is expected to remain associated with aPL for the duration of the experiment regardless of the presence of $Ca^{2+}$. As shown in FIG. 4, the amount of FVaL generated from each mutant that remained bound to the aPL-containing LV was constant throughout the experiment and was independent of divalent cations. This observation confirmed that approximately the same number of molecules of FVa are generated for each ΔFV mutant and that the efficiency of LV sedimentation does not change over the 3 hour course of the experiment.

In the presence of $Ca^{2+}$, FVaH derived from ΔFV did not dissociate from its FVaL anchor to aPL, which was expected (Krishnaswamy, S. et al. (1988) *J Biol. Chem.* 263, 5714-5723; Ortel, T. L. et al. (1992) *J Biol. Chem.* 267 (6), 4189-4198) Consistent with observations made with FVa purified from human plasma (Zeibdawi A. R. et al. (2001) *J Biol. Chem.* 276 (23), 19929-19936), inclusion of an excess of chelator (EDTA) in the incubation mixture resulted in a relatively slow dissociation of ΔFV FVaH from the aPL-containing LV.

In sharp contrast, simultaneous substitution of all five acidic amino acids in the ED/EDD mutant caused complete dissociation of FVaH from FVaL prior to the first sampling at 1 hour, regardless of the presence of $Ca^{2+}$. Like all of the mutants evaluated, the amount of FVaL bound to aPL did not change, which further confirmed that membrane interactions were not grossly influenced by mutations in the A1-domain. The observed spontaneous and rapid dissociation of FVa subunits provides an explanation for the nearly complete loss of prothrombinase function observed for the ED/EDD mutant (FIG. 3).

The specific amino acids contributing to the spontaneous dissociation of FVaH from FVaL due to ED/EDD mutation were assigned using our panel of 9 single point mutants. FIG. 4 shows the amount of FVaH and FVaL remaining bound to aPL-containing LV after treatment of the respective ΔFV mutant with thrombin. These data revealed that substitution of only D111 by Ala was sufficient to give rise to the phenotype observed for ED/EDD. In the presence of 2 mM supplemented $Ca^{2+}$ and the absence of chelator, the FVaH derived from all other single point ΔFV mutants behaved exactly like ΔFV, exhibiting no dissociation from FVaL over the duration of the experiment. This is interesting because at least mutation of E96 or D102 caused significant (i.e. >50%) functional inhibition measured by prothrombinase assays (FIG. 3), which are conducted at identical divalent cation concentrations. Therefore a property of FVa that is required for FXa cofactor activity, other than subunit association, must be affected. A partial explanation for the difference is provided by following subunit dissociation in the presence of chelator. Although FVaH-FVaL association appeared to be identical to ΔFV in the presence of divalent cations, mutation of E96 or D102 resulted in comparatively rapid FVaH dissociation when EDTA was included in the incubation mixture. FVaH dissociation similar to that of ΔFV in the presence of chelator was observed for Ala substitution of D79, Y100, T104, E108, D112 or E119. Thus, despite being very close in proximity, mutation of D111 or either E96 or D102 causes inhibition of FVa cofactor function by two distinguishable mechanisms.

Figures 5A, 5B:
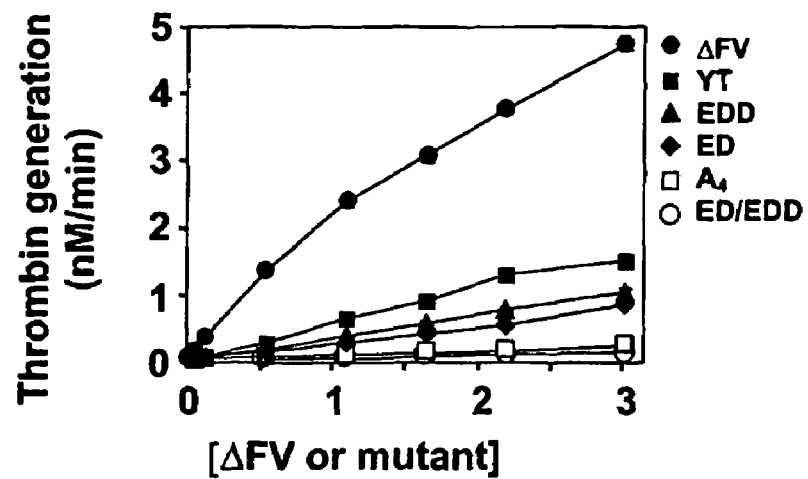
FIG. 5A is a graphic of thrombin generation as a function of recombinant FV engineered to be deficient in the central B-domain (ΔFV) or ΔFV multi-point mutant concentrations.
FIG. 5B is a gel electrophoresis of an incubation mixture comprising anionic phospholipids-containing large vesicles, thrombin and ΔFV or multi-point mutant, wherein the FVa subunits remaining bound to the vesicles was probed with either FVaH or FVaL specific antibody at one hour intervals in the presence of calcium, with or without EDTA.

The functional contribution of FV residues spanning 94-112 was further mapped by generating several multipoint mutants, which were evaluated for effects on prothrombinase function and FVa subunit association. Experiments that probed function by single point mutation suggested that the profound inhibition caused by simultaneously mutating all five acidic amino acids, E96, D102, E108, D111 and D112, may involve two discernible mechanisms. Mutation of D111 appeared to be required to induce the spontaneous dissociation of FVaL and FVaH, whereas mutation of the N terminal residues, E96 or D102, resulted in inhibition without subunit dissociation in the presence of $Ca^{2+}$. We therefore constructed mutants consisting of Ala substitutions at adjacent acidic residues, E108, D111 and D112 (EDD, SEQ ID NO:26) or E96 and D102 (ED, SEQ ID NO:28), to ask whether the two functional phenotypes observed for the single point mutants persisted. FIG. 5A showed that EDD and ED were significantly inhibited compared to ΔFV by approximately 78 and 85% respectively at an antigenic concentration of 2.2 nM. In comparison, the inhibitory effect of the combined mutant, ED/EDD, was even greater (98%) which would be expected for an aggregate of distinct effects. The result of EDD or ED mutation on FVa subunit dissociation was similar to the single point mutant findings.

Upon conversion of the EDD mutant of ΔFV to FVa by thrombin, a rapid loss of FVaH from FVaL bound to aPL-containing LV was observed in the absence or presence of chelator (FIG. 5B). The same experiment showed that dissociation of FVaH derived from the ED mutant was intermediate between that observed for ΔFV and ED/EDD in the presence of $Ca^{2+}$. Chelator-mediated dissociation observed for ED was commensurate with that of E96A, D102A, D111A or ED/EDD. Like the single point mutants, FIG. 5B showed that the amount of FVaL remaining bound to the LV was invariant for all multipoint mutants, confirming that the same amount of LV-bound FVa was initially generated and that the sedimentation properties of the LV were not changing during the experiment. These data supported the conclusion drawn from experiments with single point mutants that the L94-D112 region participates in two FVa functions loosely divisible according to C-terminal and N-terminal effects.

To further explore the functional contribution of the conserved neutral amino acids within L94-D112, a combined mutant consisting of Y100 and T104 was produced (YT, SEQ ID NO:24). Individual substitution of these residues by Ala was moderately or negligibly inhibitory, respectively (FIG. 5). However, their simultaneous mutation resulted in 65% inhibition of prothrombinase activity at 2.2 nM (FIG. 5A). Western blot analysis of FVaH and FVaL derived from the YT ΔFV remaining bound to LV after thrombin activation was characteristic of that observed for mutation of E96 or D102 with an arguably slower dissociation of FVaH in the presence of chelator (FIG. 5B). Since single mutation of either Y100 or T104 more closely resembled ΔFV, we investigated whether a general multipoint mutation of the N-terminal half of L94-D112 was sufficient to confer the rapid chelator-dependent dissociation of FVaH characteristic of a sole mutation at E96 or D102. Four alanines ($A_4$) were consequently inserted on the N-terminal side of T104 (SEQ ID NO:30). This resulted in 94% inhibition of prothrombinase function (FIG. 5A). Like the single point E96 and D102 mutants, rapid FVaH dissociation from FVaL was observed after conversion to FVa in the presence of chelator, while in the presence of divalent cations the subunit interaction was stable over the three hour duration of the experiment. Thus, a substantial insertion causing nearly complete loss of cofactor function was insufficient to mediate spontaneous FVa subunit dissociation. This observation adds further support for a specific contribution of D111 to the association of FVaH and FVaL, and a different contribution of at least the region spanning E96-T104 to FVa function.

The above observations provide the basis for a method for purifying human FVaL by preparing a solution comprising a human FV comprising an amino acid sequence selected from SEQ ID NO:18, SEQ ID NO:22, SEQ ID NO:26 or SEQ ID NO:28 to generate a dissociated FVaH and FVaL. The dissociated FVaL may then be isolated from the solution by protein isolation methods that are well known in the art.

Furthermore the results also support the fact that these FV derivatives (i.e. SEQ ID NO:18, SEQ ID NO:22, SEQ ID or SEQ ID NO:28) can also bind to aPL in a calcium-independent manner. Thus, in one embodiment of the present invention, physiological changes in cells characterized by the presence of anionic phospholipids at their surface can be assessed by detecting the presence of FVaL bound on cells. In a preferred embodiment the binding of FVaL on cells is performed in a calcium-free medium.

The embodiment(s) of the invention described above is(are) intended to be exemplary only. The scope of the invention is therefore intended to be limited solely by the scope of the appended claims.

We claim:

1. An isolated human Factor V (FV) protein comprising the amino acid sequence of SEQ ID NO: 2 with: (i) an amino acid substitution at a position selected from the group consisting of E96, Y100, D102, T104, E108, D111, and D112 of SEQ ID NO:2, or (ii) an insertion of 4 alanine residues between amino acid residues H103 and T104 of SEQ ID NO: 2, wherein said isolated human Factor V protein has reduced blood clotting activity compared to wild type human FV.

2. An isolated human Factor V (FV) protein selected from the group consisting of SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28 and SEQ ID NO:30, wherein said isolated human FV has reduced blood clotting activity compared to wild type human FV.

3. The isolated human FV protein of claim 2 selected from the group consisting of SEQ ID NO:20, SEQ ID NO:18, SEQ ID NO:16, SEQ ID NO:22, SEQ ID NO:26 and SEQ ID NO:28.

4. A pharmaceutical composition comprising the isolated FV protein of claim 1 and a pharmaceutically acceptable carrier.

5. An isolated human Factor V (FV) protein selected from the group consisting of SEQ ID NO:16, SEQ ID NO:18, SEQ ID NO:20, SEQ ID NO:22, SEQ ID NO: 24, SEQ ID NO:26 and SEQ ID NO: 28, SEQ ID NO: 30, wherein said isolated human FV has reduced blood clotting activity compared to wild type human FV.

6. A pharmaceutical composition comprising the isolated human FV protein of claim 2 and a pharmaceutically acceptable carrier.

7. A pharmaceutical composition comprising the isolated human FV of claim 5 and a pharmaceutically acceptable carrier.

8. An isolated human Factor V (FV) protein comprising the amino acid sequence of SEQ ID NO:30, wherein said isolated human FV protein has reduced blood clotting activity compared to wild type human FV.

\* \* \* \* \*